US006372153B1

(12) United States Patent
Tamura et al.

(10) Patent No.: US 6,372,153 B1
(45) Date of Patent: Apr. 16, 2002

(54) FLUOROALKOXYBENZENE DERIVATIVES HAVING ETHER BOND, LIQUID-CRYSTAL COMPOSITION, AND LIQUID-CRYSTAL DISPLAY ELEMENT

(75) Inventors: Norio Tamura; Hiroyuki Takeuchi; Shuichi Matsui; Kazutoshi Miyazawa; Yasusuke Hisatsune; Fusayuki Takeshita; Etsuo Nakagawa, all of Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/508,541

(22) PCT Filed: Sep. 8, 1998

(86) PCT No.: PCT/JP98/04028

§ 371 Date: Mar. 13, 2000

§ 102(e) Date: Mar. 13, 2000

(87) PCT Pub. No.: WO99/12879

PCT Pub. Date: Mar. 18, 1999

(30) Foreign Application Priority Data

Sep. 11, 1997 (JP) .......................................... 9-264843

(51) Int. Cl.[7] ...................... C09K 19/30; C09K 19/12; C07C 25/13

(52) U.S. Cl. .......................... 252/299.63; 252/299.66; 252/299.01; 570/127; 570/129; 570/144

(58) Field of Search ............................... 570/144, 127, 570/129; 252/299.63, 299.66, 299.01

(56) References Cited

U.S. PATENT DOCUMENTS

| | | | | | |
|---|---|---|---|---|---|
| 5,356,562 | A | * | 10/1994 | Greenfield et al. | 252/299.63 |
| 5,562,858 | A | * | 10/1996 | Bartmann et al. | 252/299.66 |
| 5,641,430 | A | * | 6/1997 | Nakashima et al. | 252/299.61 |
| 5,718,840 | A | * | 2/1998 | Plach et al. | 252/299.66 |
| 5,730,904 | A | * | 3/1998 | Bartmann et al. | 252/299.63 |
| 5,762,826 | A | * | 6/1998 | Shimizu et al. | 252/299.61 |
| 5,807,500 | A | * | 9/1998 | Bremer et al. | 252/299.66 |
| 5,811,029 | A | * | 9/1998 | Wachtler et al. | 252/299.63 |
| 5,932,138 | A | * | 8/1999 | Plach et al. | 252/299.66 |
| 5,951,913 | A | * | 9/1999 | Shimizu et al. | 252/299.61 |
| 6,057,006 | A | * | 5/2000 | Kirsch et al. | 428/1 |
| 6,083,573 | A | * | 7/2000 | Tarumi et al. | 428/1.1 |
| 6,146,720 | A | * | 11/2000 | Pausch et al. | 428/1.1 |

FOREIGN PATENT DOCUMENTS

| | | |
|---|---|---|
| JP | 8-239388 | 9/1996 |
| JP | 8-269069 | 10/1996 |
| JP | 9-31024 | 2/1997 |

* cited by examiner

*Primary Examiner*—Shean C. Wu
(74) *Attorney, Agent, or Firm*—Wenderoth, Lind & Ponack, L.L.P.

(57) ABSTRACT

Liquid crystalline compounds superior in having an eminent dielectric anisotropy, being stable against environment and having improved miscibility with other liquid crystalline compounds, as well as a liquid crystal composition with driving-ability at a low voltage and responsibility at a high-speed comprising the compounds as a constituting component, and a liquid crystal display element comprising the composition are provided, said compounds are fluoroalkoxybenzene derivatives expressed by the general formula (1)

(1)

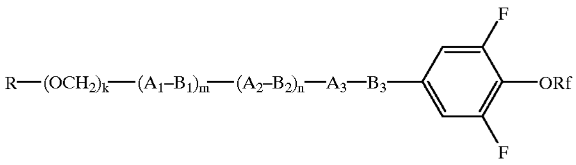

wherein $A_1$, $A_2$ and $A_3$ each independently denote trans-1,4-cyclohexylene,1,4-phenylene or so; B, $B_2$ and $B_3$ each independently denote a single bond, 1,2-ethylene or so; R denotes an alkyl group having 1 to 15 carbon atoms optionally substitutable with a halogen atom(s); Rf denotes a fluoroalkyl group having 1 to 3 carbon; k, m, and n each independently denote 0 or 1; with the proviso that when k=0 is a case, then one of $B_1$, $B_2$ and $B_3$ is a methyleneoxy bond or so, and that when $m+n\geqq 1$ is a case, then dependency of $A_1$, $A_2$ and $A_3$ is partly restricted and content of Rf is partly limited when $B_1$ or/and $B_2$ and $B_3$ are all single bonds.

17 Claims, No Drawings

FLUOROALKOXYBENZENE DERIVATIVES HAVING ETHER BOND, LIQUID-CRYSTAL COMPOSITION, AND LIQUID-CRYSTAL DISPLAY ELEMENT

This application is a 371 application of PCT/JP98/04028 filed Sep. 8, 1998.

TECHNICAL FIELD

The present invention relates to a liquid crystalline compound and a liquid crystal composition. In more detail, the invention relates to a fluoroalkoxybenzene derivative having an ether linkage and being preferable as a component of liquid crystal composition, a liquid crystal composition comprising the derivative, and a liquid crystal display element fabricated by using the liquid crystal composition.

BACKGROUND ART

Liquid crystal display elements utilize optical anisotropy and dielectric anisotropy of liquid crystalline compounds. They are divided into modes such as twisted nematic (TN), super twisted nematic (STN), dynamic scattering (DS), guest-host (GH) and DAP type mode or so depending on their display modes on the electric optical effects, and also divided into driving modes such as static, time sharing addressing, active matrix and two-frequency addressing scheme.

Recently, particularly high quality display elements are required, and needs for display elements of active matrix types exemplified by a thin film transistor (TFT) type is increased. Furthermore, in order to improve response time against a change of an electric field or in order to lower a driving voltage, there are particularly required liquid crystal materials having higher dielectric anisotropy values ($\Delta\epsilon$) and lower viscosity values. Liquid crystal materials used in said liquid crystal, display elements are required to exhibit a liquid crystal phase at temperatures in a wide range and to be stable against heat, light, moisture, air, electric field and electromagnetic radiation or so. However, no compounds are found at present which satisfy such requirements by a single compound, and thus it is a current situation that a plurality, often as much of 20 or more, of liquid crystalline compounds are mixed and used. In particular, since there are recently many cases that liquid crystal display elements are used under such severe conditions as a quite low temperature or so, improvement in miscibility at a low temperature is also required.

Since TFT type liquid crystal display element needs a holding of electric charge stored between electrodes of pixels during a flame period, liquid crystal materials therefor are required to have a particularly high voltage holding ratio. Liquid crystalline compounds having fluorine atoms in their molecules have been used hitherto as liquid crystal materials which satisfy such requirements and have relatively high $\Delta\epsilon$.

For example, fluoroalkoxybenzene derivatives shown by the formulae (10) to (18)

(10)

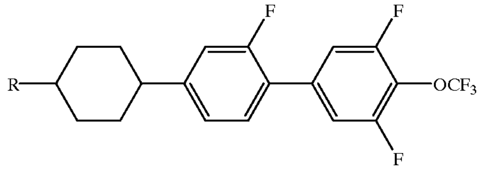

(11)

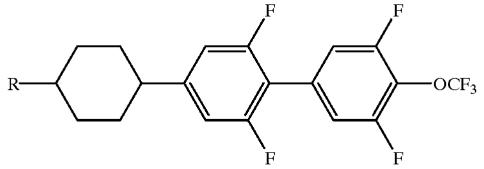

(12)

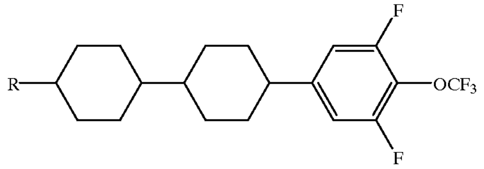

(13)

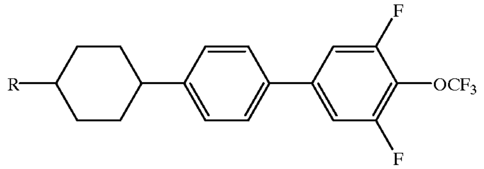

(14)

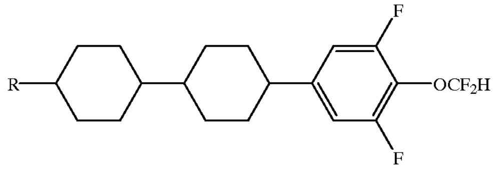

(15)

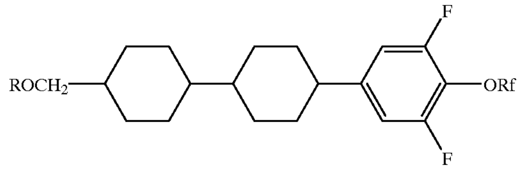

(16)

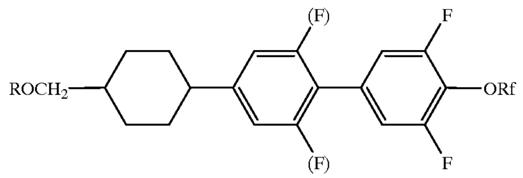

(17)

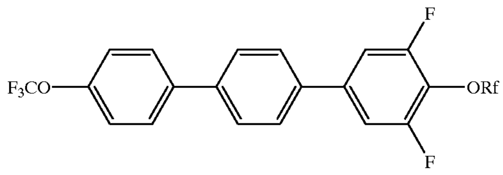

-continued (18)

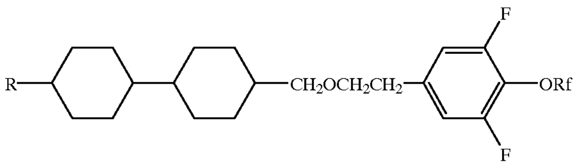

wherein R denotes an alkyl group and Rf denotes a fluoroalkyl group, are now known.

However, compounds shown by the general formulae (10) or (11) which are disclosed in WO 94/26838 or DE 19528085 A1 have no or narrow liquid crystal temperature range, and furthermore their electric anisotropy values can never be said high enough.

As to compounds shown by the general formula (12) which are disclosed in Laid-open Japanese Patent Publication No. Hei 7-165656, their dielectric anisotropy values can also never be said high enough. Furthermore, compounds shown by the general formula (14) are disclosed in DE 4027840 A1, but there is no description about their electric characteristics. Furthermore, compounds shown by the general formulae (13), (15), (16) and (18) are disclosed in DE 4218614 A1, EP 640578 A1, DE 4223501 A1, DE 4222371 A1, WO 9213928 A1, DE 4142519 A1 and DE 4027840 A1 or so. But there is no description about their physical properties, so that it can never be said that the invention is disclosed.

In addition, compounds shown by (17) are disclosed without any information about electric characteristics in DE 4301700 A1, but said compounds are considered to have no sufficient $\Delta\epsilon$ value because dipolar moments thereof are offset by fluoroalkoxy groups at both terminals of the compounds.

We the inventors have studied eagerly to solve the above-mentioned problems and found a novel compound having improved characteristics compared to the known liquid crystalline compounds, and have completed the present invention.

As is clear from the above-mentioned description, an object of the present invention is to provide a liquid crystalline compound of fluoroalkoxybenzene derivatives having ether bond, having in particular large $\Delta\epsilon$ value, being excellent in miscibility with other liquid crystalline compounds, having a low viscosity and being stable chemically and physically, as well as a liquid crystal composition, and a liquid crystal display element comprising the compound.

DISCLOSURE OF THE INVENTION

Inventions to be claimed in the present application are as follows.

(1) A fluoroalkoxybenzene derivative expressed by the general formula (1)

(1)

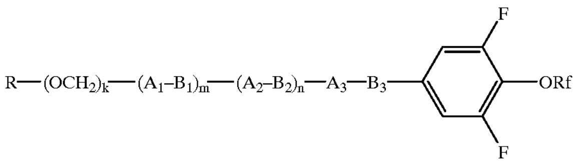

wherein $A_1$, $A_2$ and $A_3$ each independently denote trans-1, 4-cyclohexylene,1,4-phenylene in which one or more hydrogen atoms may optionally be substituted with a fluorine atom(s), 1,3-dioxane-2,5-diyl, pyrimidine-2,5-diyl or 1-sila-1,4-cyclohexylene; $B_1$, $B_2$ and $B_3$ each independently denote a single bond, 1,2-ethylene, 1,2-ethenylene, 1,2-ethynylene, oxymethylene, methyleneoxy, carbonyloxy or 1,4-butylene group; R denotes an alkyl group having 1 to 15 carbon atoms optionally substitutable with a halogen atom (s), wherein one or more non-adjacent ethylene groups may be replaced by 1,2-ethenylene group(s); Rf denotes a fluoroalkyl group having 1 to 3 carbon atoms substitutable with two or more fluorine atoms; k, m, and n each independently denote 0 or 1, with the proviso that when k=0 is a case, then one of $B_1$, $B_2$ and $B_3$ is a methyleneoxy or oxymethylene bond, and that when $m+n\geqq 1$ is a case, then $A_1$ or/and $A_2$ and $A_3$ are not 1,4-phenylene at the same time, and further when $A_1$ or/and $A_2$ and $A_3$ are trans-1, 4-cyclohexylene or 1,4-phenylene and $B_1$ or/and $B_2$ and $B_3$ are all single bonds, then Rf is never $C_2F_5$, $CH_2CF_3$ or $CH_2CF_2CF_3$, and that when m+n=1 is a case, $A_1$ or $A_2$ and $A_3$ are trans-1, 4-cyclohexylene at the same time, $B_1$ or $B_2$ is a single bond and $B_3$ is 1,2-ethylene, then Rf is never $CH_2CF_2CF_3$.

(2) A compound recited in paragraph (1) above wherein k=1.

(3) A compound recited in paragraph (1) above wherein one of $B_1$, $B_2$ or B3 is a methyleneoxy or oxymethylene bond.

(4) A compound recited in paragraph (2) above wherein m=0, n=1, $A_2$ and $A_3$ are 1, 4-cyclohexylene, and $B_2$ and $B_3$ are single bonds.

(5) A compound recited in paragraph (2) above wherein m=0, n=1, $A_2$ is 1, 4-cyclohexylene, $A_3$ is 1, 4-cyclohexylene optionally substitutable with a fluorine atom(s), and $B_2$ and $B_3$ are both single bonds.

(6) A compound recited in paragraph (2) above wherein m+n=1, $A_1$ or $A_2$ and $A_3$ are both trans-1, 4-cyclohexylenes, $B_1$ or $B_2$ is 1, 2-ethylene, and $B_3$ is a single bond.

(7) A compound recited in paragraph (2) above wherein m+n=1, $A_1$ or $A_2$ and $A_3$ are both trans-1, 4-cyclohexylenes, $B_1$ or $B_2$ is a single bond, and $B_3$ is 1,2-ethylene.

(8) A compound recited in paragraph (2) above wherein m=n=1, and $A_1$ and $A_2$ are both trans-1, 4-cyclohexylenes.

(9) A compound recited in paragraph (8) above wherein m=n=1, $A_1$ and $A_2$ are both trans-1, 4-cyclohexylenes, $A_3$ is 1, 4-phenylene one or two hydrogen atoms of which may optionally be substituted with a fluorine atom(s), $B_1$ and $B_3$ are single bonds, and $B_2$ is 1,2-ethylene.

(10) A liquid crystal composition comprising at least one liquid crystalline compound recited in any one of paragraphs (1) to (9).

(11) A liquid crystal composition comprising, as a first component, at least one liquid crystalline compound recited in any one of paragraphs (1) to (9), and as a second component, at least one compound selected from the group of compounds expressed by any one of general formulae (2), (3), and (4)

(2)

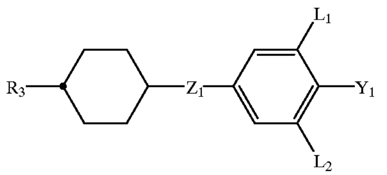

(3)

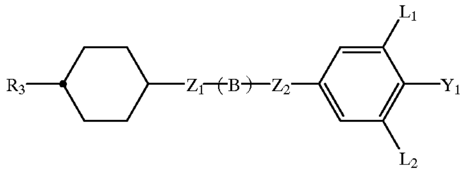

(4)

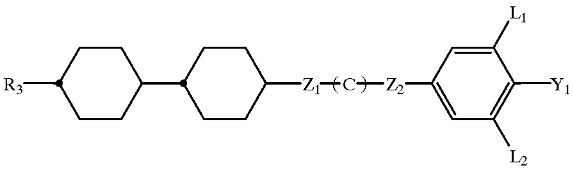

wherein $R_3$ denotes an alkyl group having 1 to 10 carbon atoms in which alkyl group any optional non-adjacent ethylene group may be replaced by an oxygen atom or —CH═CH—, and any optional hydrogen atom may be substituted with a fluorine atom; $Y_1$ denotes a fluorine atom, a chlorine atom, $OCF_3$, $OCF_2$ H, $CF_3$, $CF_2H$, $CFH_2$, $OCF_2CF_2H$ or $OCF_2CFHCF_3$; $L_1$ and $L_2$ each independently denote a hydrogen atom or a fluorine atom; $Z_1$ and $Z_2$ each independently denote 1,2-ethylene group, 1,4-butylene group, —COO—, —$CF_2O$—, —$OCF_2$—, —CH═CH—, or a single bond; ring B denotes trans-1,4-cyclohexylene, 1,3-dioxane-2,5-diyl or 1,4-phenylene any hydrogen atom of which may be substituted with a fluorine atom; and ring C denotes trans-1,4-cyclohexylene or 1,4-phenylene any hydrogen atom of which may be substituted with a fluorine atom.

(12) A liquid crystal composition comprising, as a first component, at least one liquid crystalline compound recited in any one of paragraphs (1) to (9), and as a second component, at least one compound selected from a group of compounds expressed by any one general formulae (5) and (6)

(5)

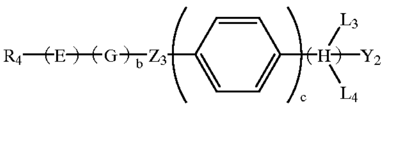

(6)

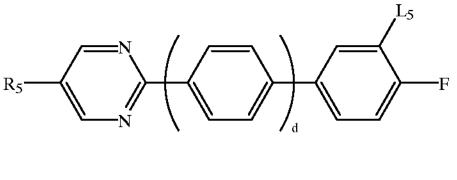

wherein $R_4$ and $R_5$ each independently denote an alkyl group having 1 to 10 carbon atoms in which alkyl group any optional non-adjacent methylene group may be replaced by an oxygen atom or —CH═CH— and any optional hydrogen atom of which may be substituted with a fluorine atom; $Y_2$ denotes —CN group or —C≡C—CN group; ring E denotes trans-1,4-cyclohexylene, 1,4-phenylene, 1,3-dioxane-2,5-diyl or pyrimidine-2,5-diyl; ring G denotes trans-1,4-cyclohexylene, 1,4-phenylene any hydrogen atom of which may be substituted with a fluorine atom or pyrimidine-2, 5-diyl; ring H denotes trans-1, 4-cyclohexylene or 1,4-phenylene; $Z_3$ denotes 1,2-ethylene group, —COO— or a single bond; $L_3$, $L_4$ and $L_5$ each independently denote a hydrogen atom or a fluorine atom, and b, c and d each independently denote 0 or 1.

(13) A liquid crystal composition comprising, as a first component, at least one liquid crystalline compound recited in any one of paragraphs (1) to (9), as a second component, at least one compound selected from the group of compounds expressed by any one of general formulae (2), (3), and (4) described above, and as a third component, at least one compound selected from a group of compounds expressed by any one of the general formulae (7), (8) and (9)

(7)

$R_6-(I)-Z_4-(J)-Z_5-R_7$ (8)

$R_6-(I)-Z_4-(J)-Z_5-(K)-R_7$ (9)

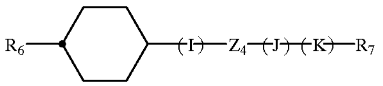

wherein $R_6$ and $R_7$ each independently denote an alkyl group having 1 to 10 carbon atoms in which alkyl group any optional non-adjacent methylene group may be replaced by an oxygen atom or —CH═CH— and any optional hydrogen atom of which may be substituted with a fluorine atom; I, J and K each independently denote trans-1,4-cyclohexylene, pyrimidine-2,5-diyl or 1,4-phenylene any hydrogen atom of which may be substituted with a fluorine atom; and $Z_4$ and $Z_5$ each independently denote —C≡C—, —COO—, —$CH_2CH_2$—, —CH═CH— or a single bond.

(14) A liquid crystal composition comprising, as a first component, at least one liquid crystalline compound recited in any one of paragraphs (1) to (9), as a second component, at least one compound selected from the group of compounds expressed by any one of general formulae (5) and (6) described above, and as a third component, at least one compound selected from a group of compounds expressed by any one of the general formulae (7), (8) and (9) described above.

(15) A liquid crystal composition comprising, as a first component, at least one liquid crystalline compound recited in any one of paragraphs (1) to (9), as a second component, at least one compound selected from the group of compounds expressed by any one of general formulae (2), (3), and (4) described above, as a third component, at least one compound selected from a group of compounds expressed by any one of the general formulae (5) and (6) described above, and as a fourth component, at least one compound selected from a group of compounds expressed by any one of the general formulae (7), (8) and (9) described above.

(16) A liquid crystal composition recited in any one of paragraph (10) to (15) wherein the liquid crystal composition further comprises one or more optically active compounds.

(17) A liquid crystal display element fabricated by using a liquid crystal composition recited in any one of paragraphs (10) to (15)

BEST MODE FOR CARRYING OUT THE INVENTION

Although the liquid crystalline compounds of the present invention are expressed by the general formula (1) as described above, the compounds expressed by the following formulae (1-1) to (1-71) can particularly be mentioned as preferable examples amongst of them.
(1-1)
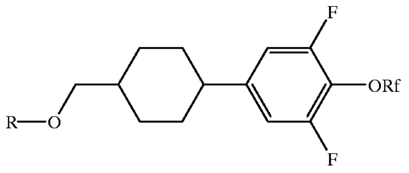
(1-2)
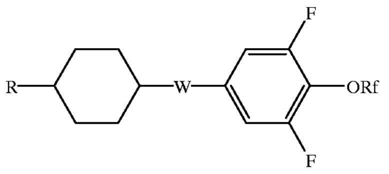
(1-3)
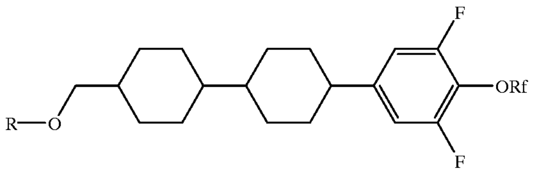
(1-4)
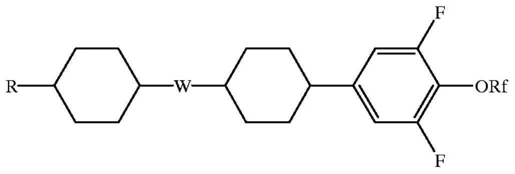
(1-5)
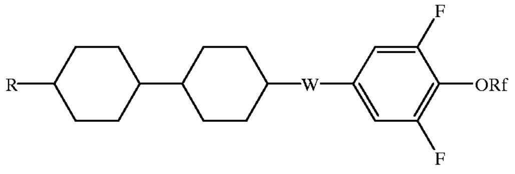
(1-6)
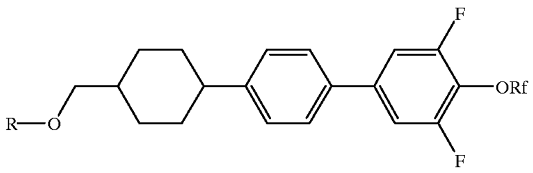
(1-7)
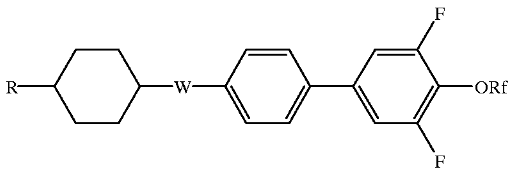
-continued
(1-8)
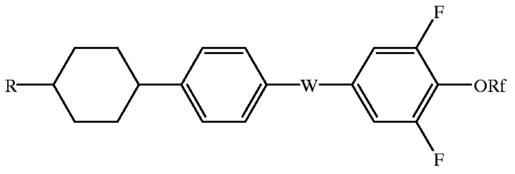
(1-9)
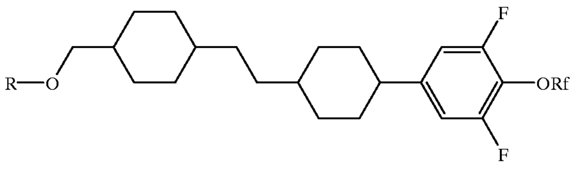
(1-10)
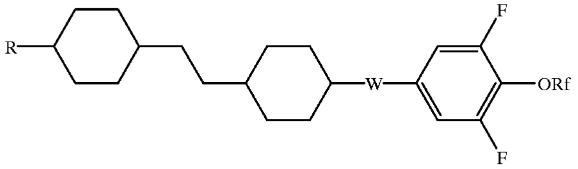
(1-11)
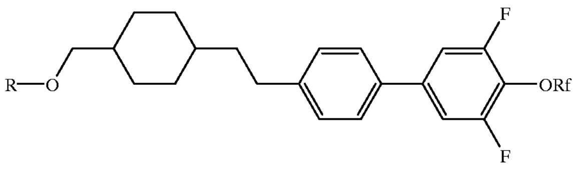
(1-12)
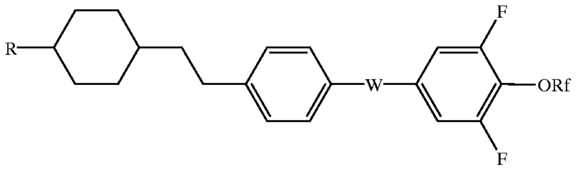
(1-13)
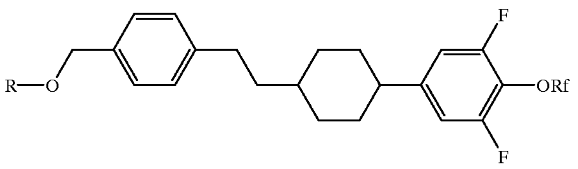
(1-14)
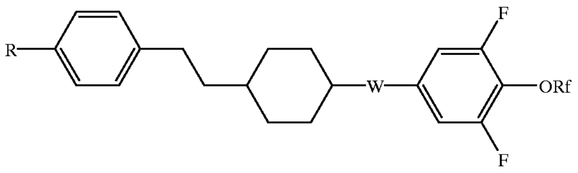

-continued
(1-15)
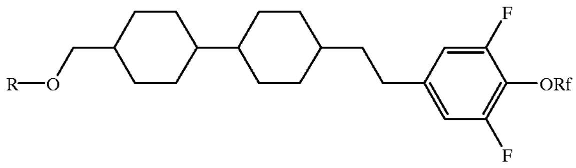
(1-16)
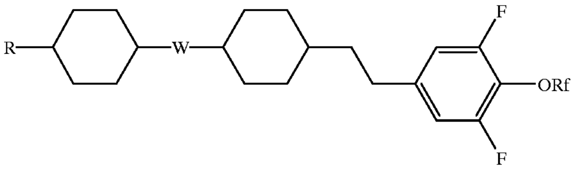
(1-17)
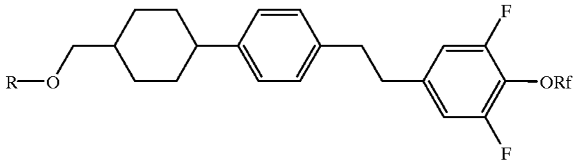
(1-18)
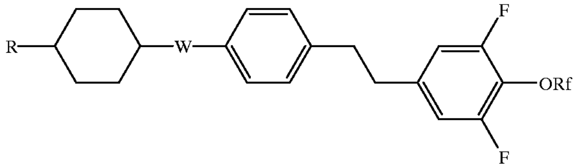
(1-19)
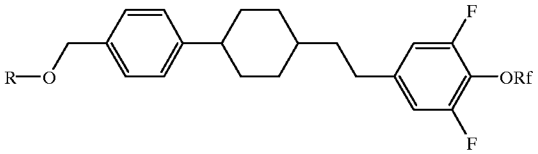
(1-20)
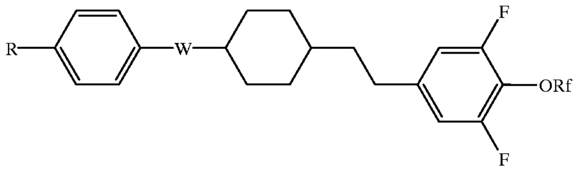
(1-21)
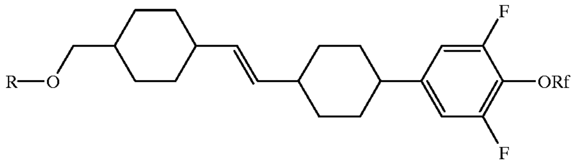
-continued
(1-22)
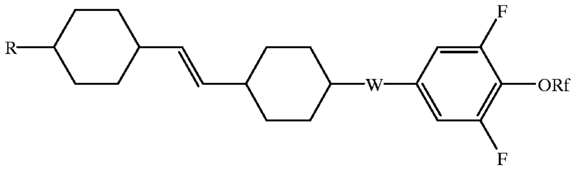
(1-23)
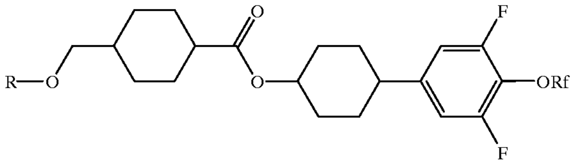
(1-24)
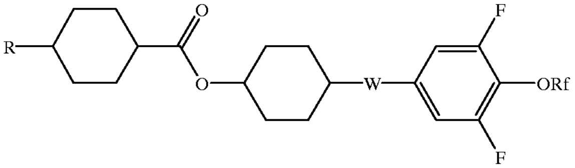
(1-25)
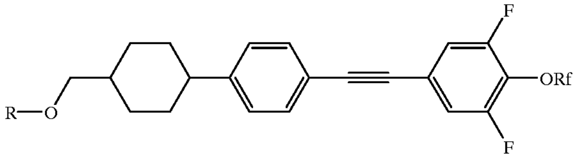
(1-26)
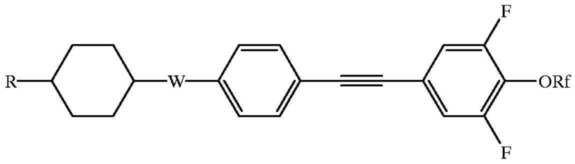
(1-27)
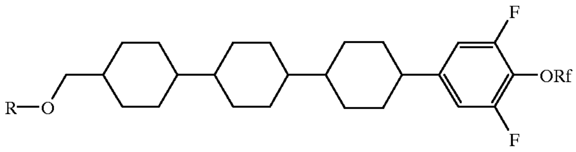
(1-28)
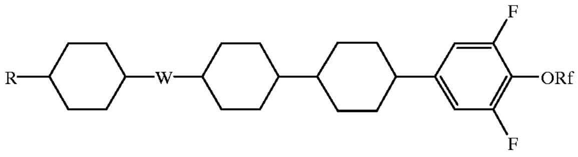
(1-29)
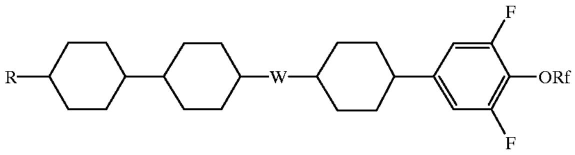

-continued
(1-30)
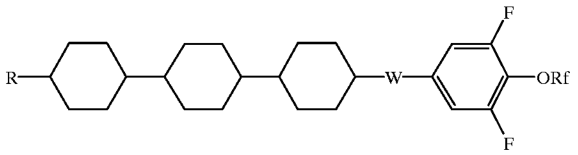
(1-31)
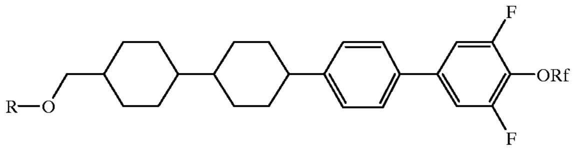
(1-32)
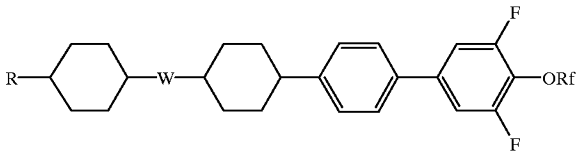
(1-33)
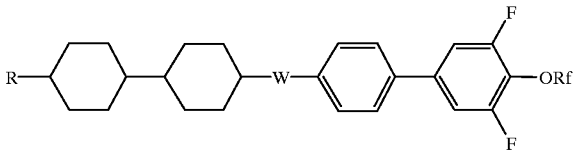
(1-34)
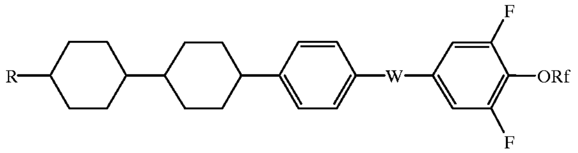
(1-35)
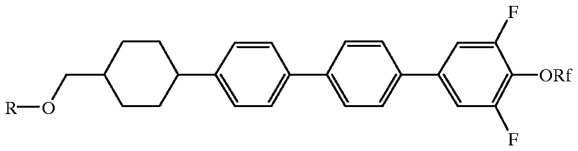
(1-36)
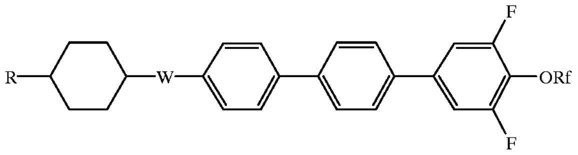
(1-37)
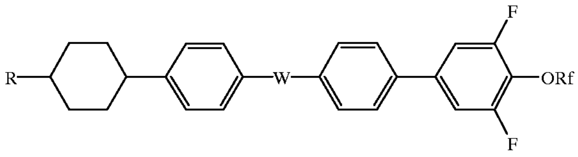
-continued
(1-38)
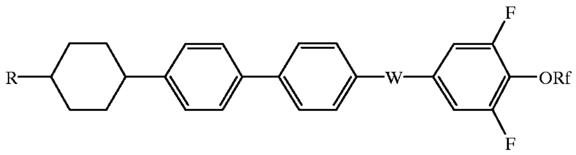
(1-39)
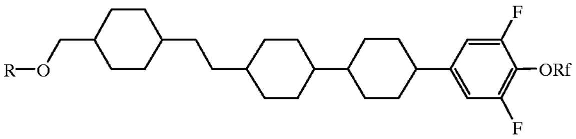
(1-40)
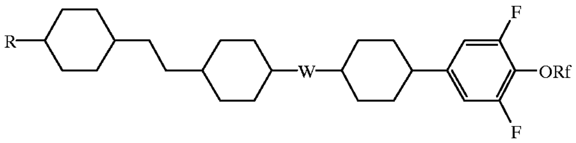
(1-41)
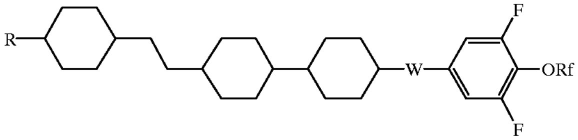
(1-42)
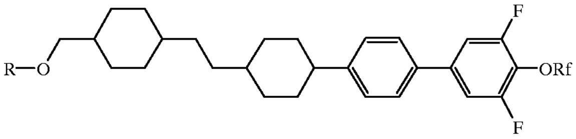
(1-43)
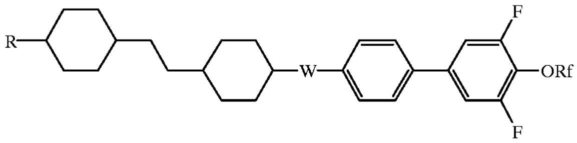
(1-44)
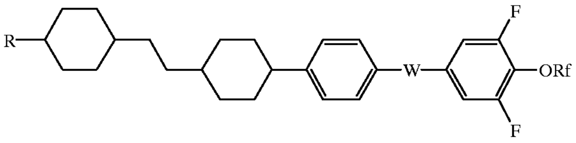
(1-45)
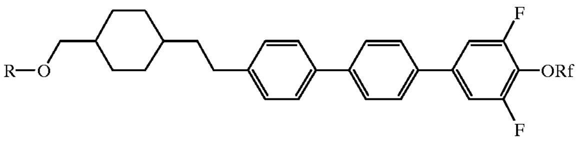

-continued
(1-46)
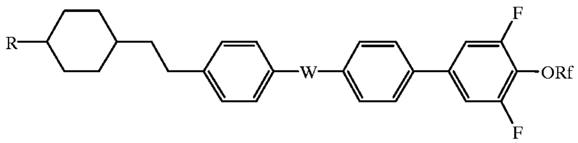
(1-47)
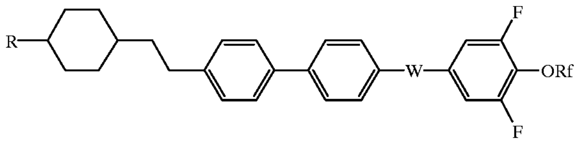
(1-48)
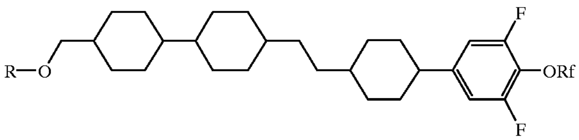
(1-49)
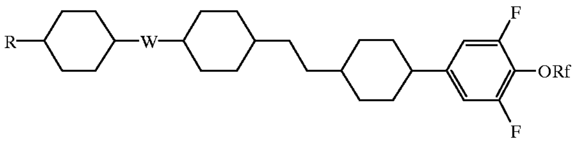
(1-50)
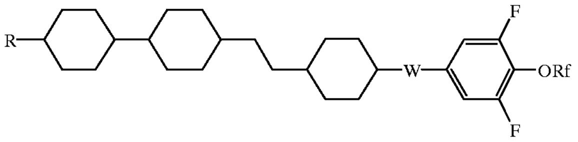
(1-51)
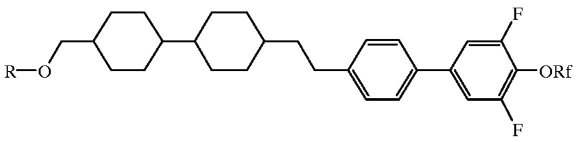
(1-52)
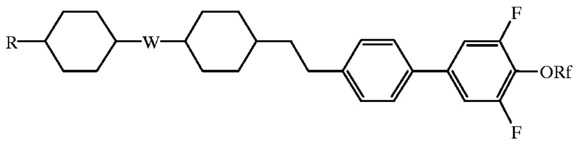
(1-53)
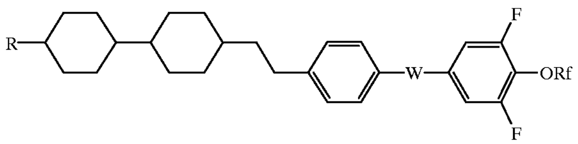
(1-54)
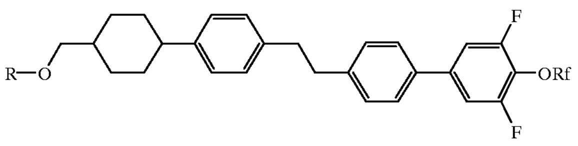
-continued
(1-55)
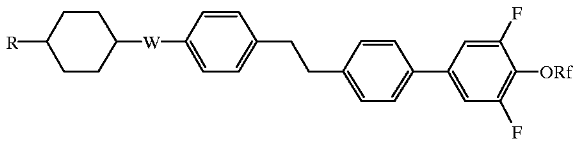
(1-56)
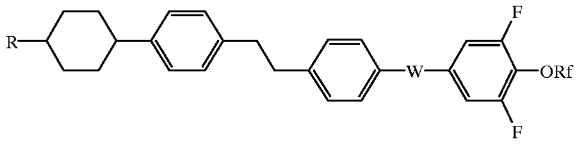
(1-57)
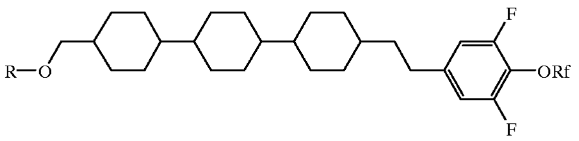
(1-58)
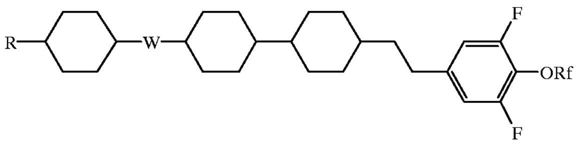
(1-59)
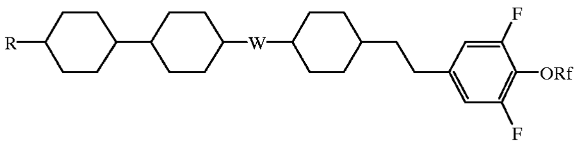
(1-60)
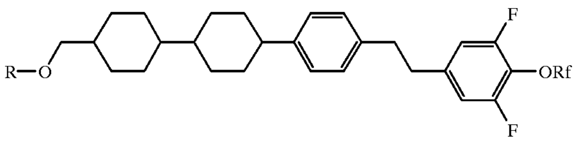
(1-61)
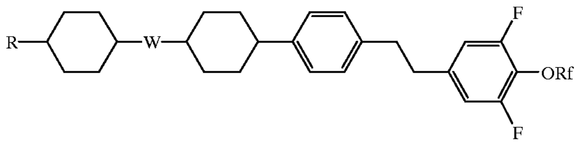
(1-62)
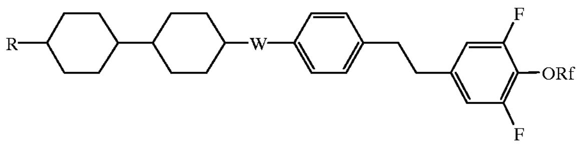
(1-63)
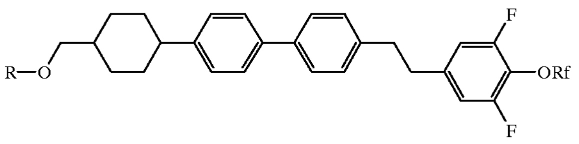

-continued (1-64)

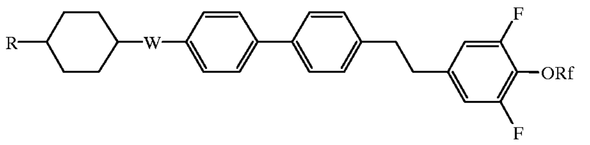

(1-65)

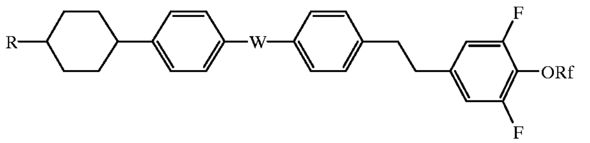

(1-66)

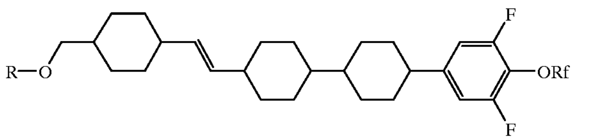

(1-67)

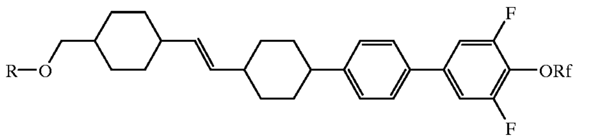

(1-68)

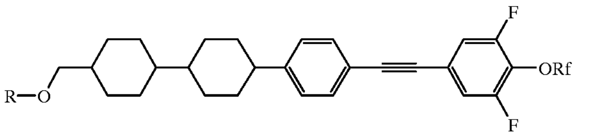

(1-69)

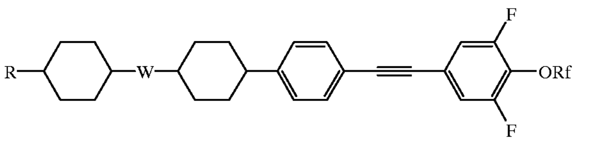

(1-70)

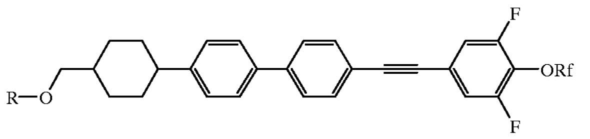

(1-71)

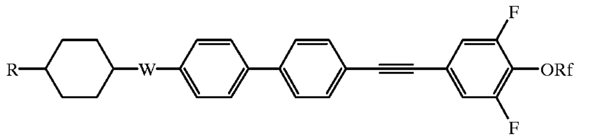

In the above-mentioned formulae, R denotes an alkyl group, W denotes methyleneoxy or oxymethylene group, and Rf denotes a fluoroalkyl group having 1 to 3 carbon atoms in which two or more fluorine atoms are substituted.

Any of these compounds of the present invention have superior characteristics such as exhibiting particularly high dielectric anisotropy, high voltage holding ratio, low viscosity and good miscibility at a low temperature. In particular, two-ring or three-ring system compounds expressed by the formulae (1-1) to (1-26) exhibit high dielectric anisotropy and good miscibility at a low temperature. Therefore, by using liquid crystal compositions comprising these compounds, liquid crystal cells to be driven at a low voltage can be manufactured. Furthermore, four-ring system compounds expressed by the formulae (1-27) to (1-71) exhibit high dielectric anisotropy, and have eminently high clear point while have relatively low viscosity.

Therefore, by using liquid crystal compositions comprising these compounds, liquid crystal cells with wide display temperature range and being driven at low voltage can be manufactured.

Liquid crystalline compounds of the present invention expressed by the general formula (1) do not always exhibit liquid crystal phase. But they are effective when they are mixed with other liquid crystalline compounds, because any of them has a good miscibility with other liquid crystalline compounds and can give compositions without eminently lowered nematic phase temperature or reduced range thereof. Therefore, any of the liquid crystalline compounds expressed by the general formula (1) having such superior optical characteristics as described above can be an useful constitutional component of a liquid crystal composition, even though it does not exhibit a liquid crystal phase by itself.

Liquid crystal compositions of the present invention comprise, as the first component, at least one liquid crystalline compound expressed by the general formula (1).

Its content is preferably 0.1 to 99.9% by weight based on the amount of liquid crystal composition for developing excellent characteristics.

While the liquid crystal composition of the present invention may comprise only the first component described above, the composition in which at least one compound selected from the group consisting of the compound expressed by one of the general formulae (2), (3) and (4) described above (hereinafter referred to as second component A) and/or at least one compound selected from the group consisting of the compound expressed by the general formulae (5) or (6) described above hereinafter referred to as second component B) are mixed as second component in addition to the first component, or the compositions in which at least one compound selected from the group consisting of the compound expressed by one of the general (7), (8), and (9) described above are further mixed as a third component in addition to the first and second components are preferable. Besides, an optically active compound as another component, and a known compound may be mixed for the purpose of adjusting threshold voltage, temperature range of liquid crystal phase, optical anisotropy value ($\Delta n$), $\Delta\epsilon$ and a viscosity.

Among the second component A described above, the compounds expressed by one of the following formulae (2-1) to (2-9) can be mentioned as preferable examples of the ones included in the general formula (2), the compounds of one of the following formulae (3-1) to (3-69) can be mentioned as preferable examples of the ones included in the general formula (3), and the compounds of one of the following formulae (4-1) to (4-24) can be mentioned as preferable examples of the ones included in the general formula as preferable examples of compounds included in the general formula (4), respectively.

(2-1)
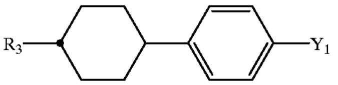
(2-2)
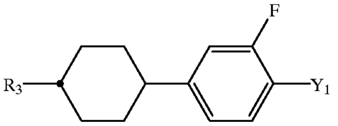
(2-3)
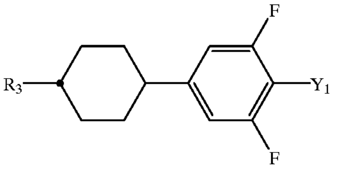
(2-4)
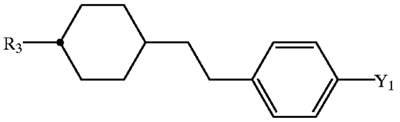
(2-5)
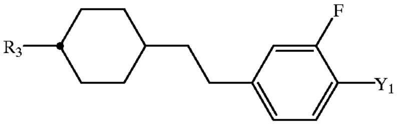
(2-6)
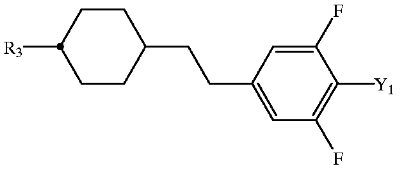
(2-7)
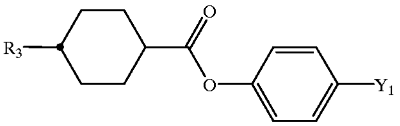
(2-8)
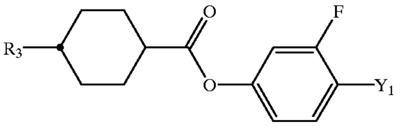
(2-9)
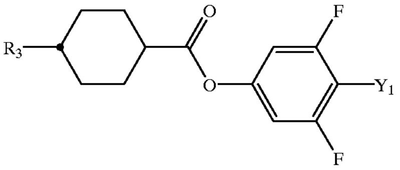
(3-1)
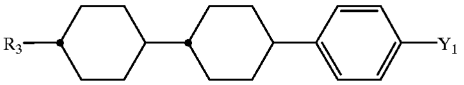
-continued
(3-2)
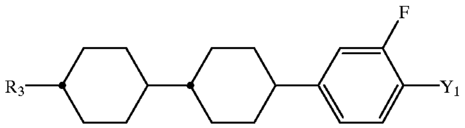
(3-3)
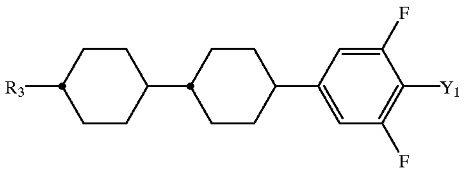
(3-4)
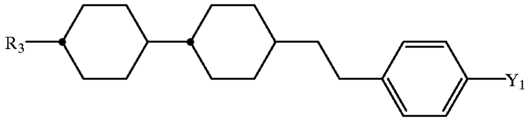
(3-5)
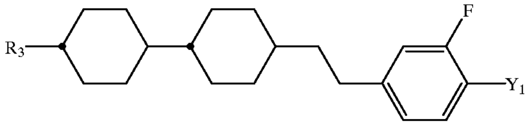
(3-6)
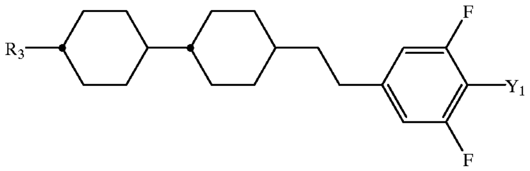
(3-7)
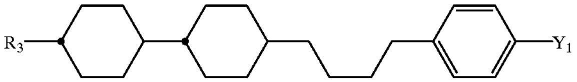
(3-8)
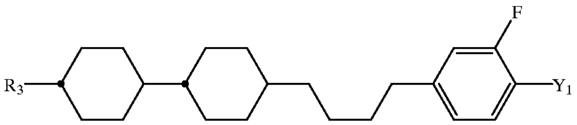
(3-9)
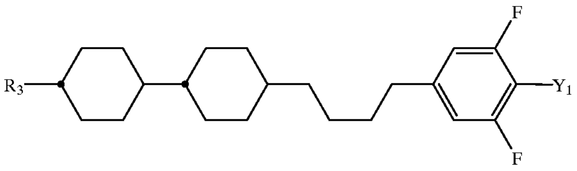
(3-10)
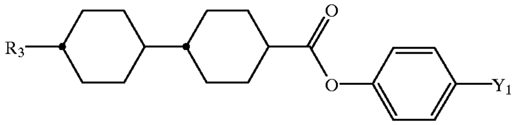

-continued
(3-11)
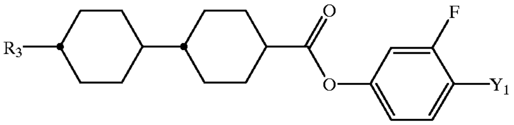
(3-12)
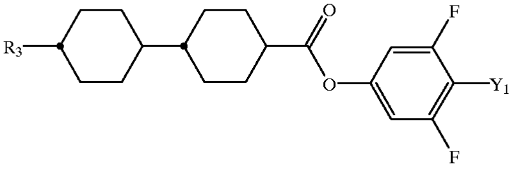
(3-13)
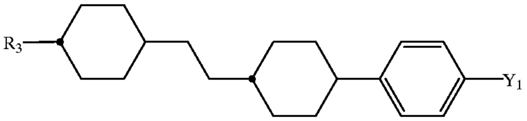
(3-14)
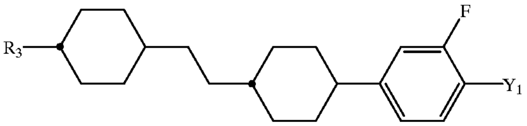
(3-15)
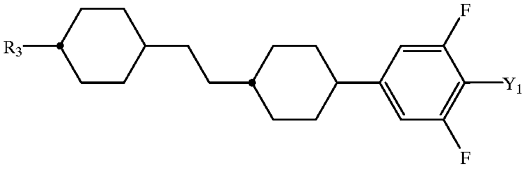
(3-16)
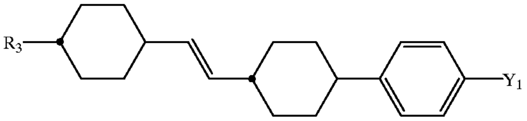
(3-17)
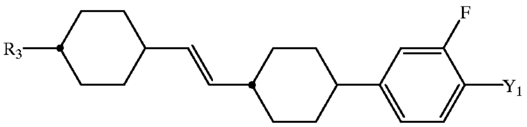
(3-18)
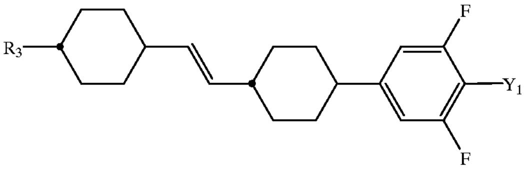
(3-19)
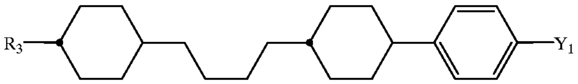
-continued
(3-20)
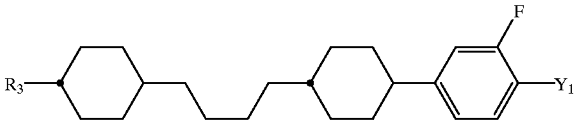
(3-21)
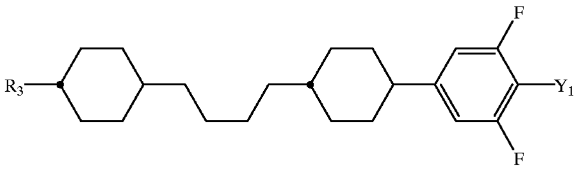
(3-22)
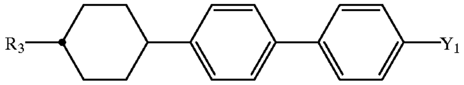
(3-23)
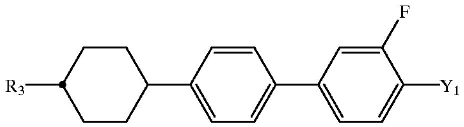
(3-24)
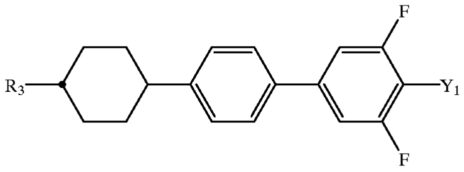
(3-25)
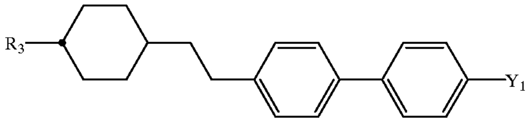
(3-26)
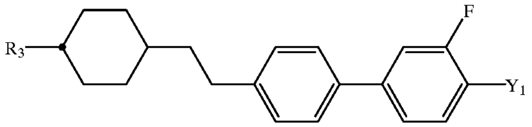
(3-27)
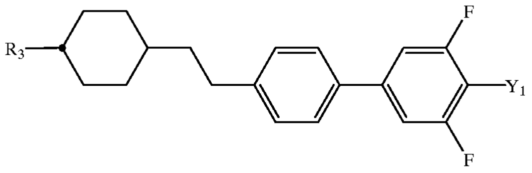
(3-28)
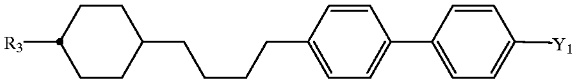

-continued
(3-29)
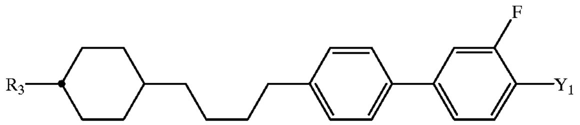
(3-30)
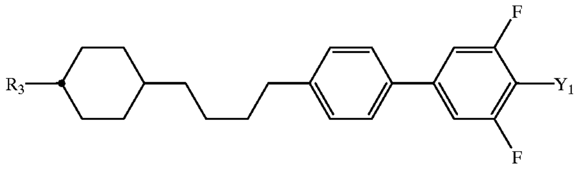
(3-31)
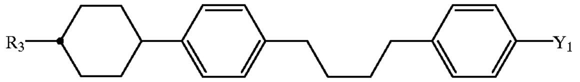
(3-32)
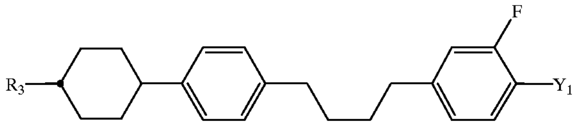
(3-33)
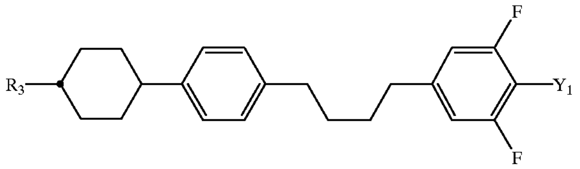
(3-34)
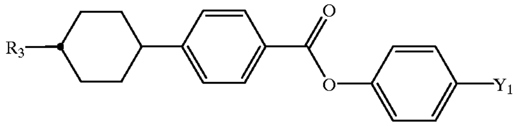
(3-35)
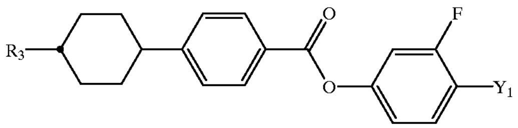
(3-36)
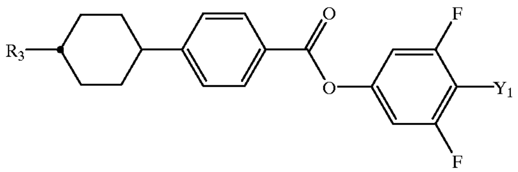
(3-37)
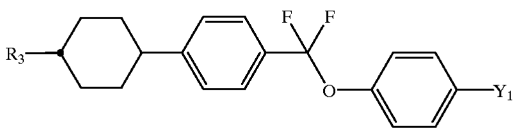
-continued
(3-38)
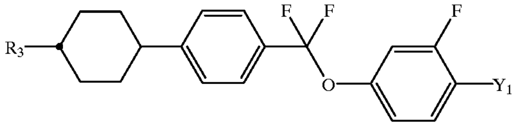
(3-39)
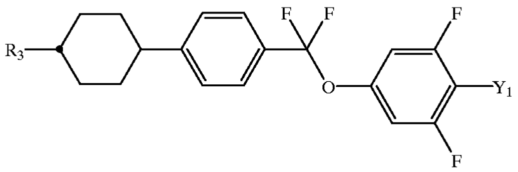
(3-40)
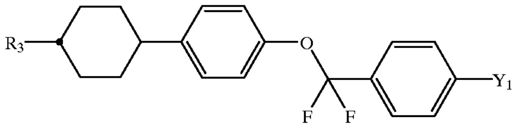
(3-41)
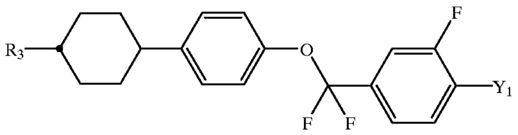
(3-42)
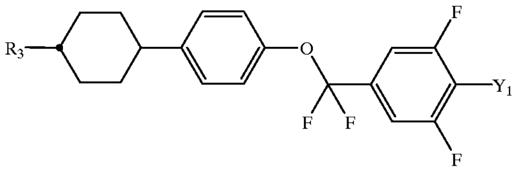
(3-43)
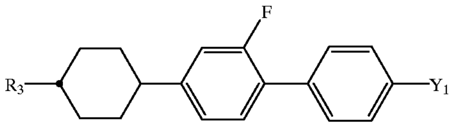
(3-44)
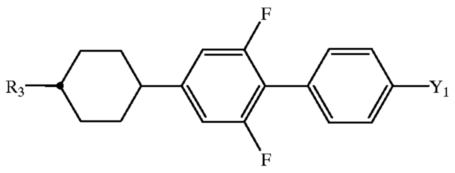
(3-45)
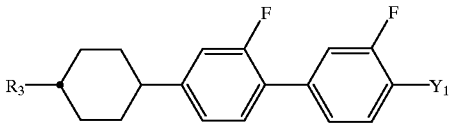
(3-46)
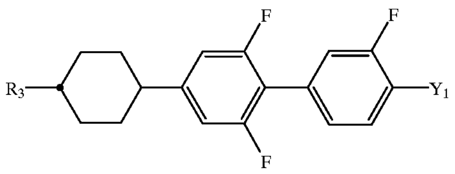

-continued
(3-47)
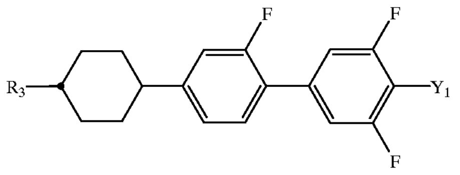
(3-48)
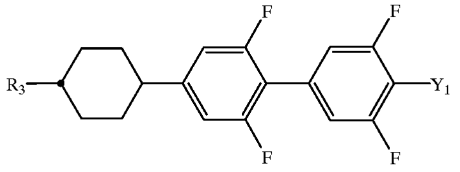
(3-49)
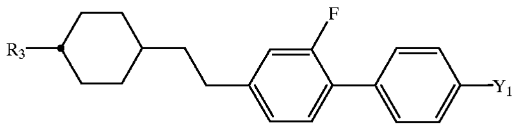
(3-50)
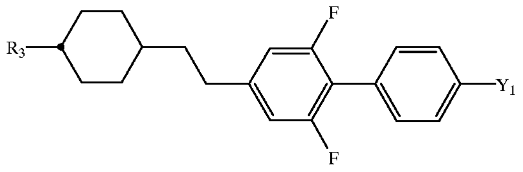
(3-51)
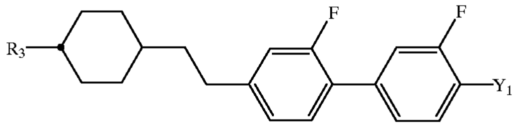
(3-52)
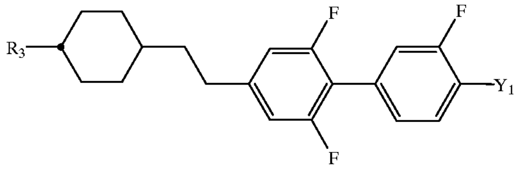
(3-53)
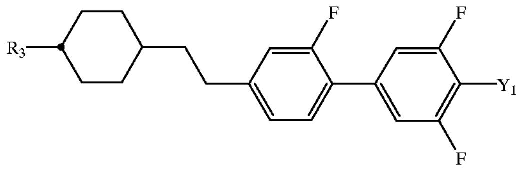
(3-54)
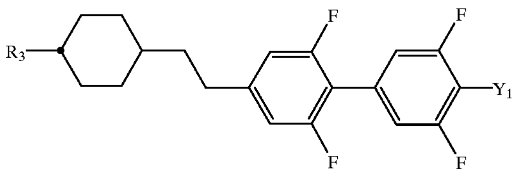
-continued
(3-55)
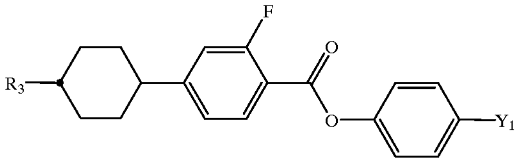
(3-56)
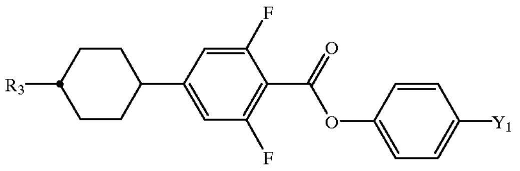
(3-57)
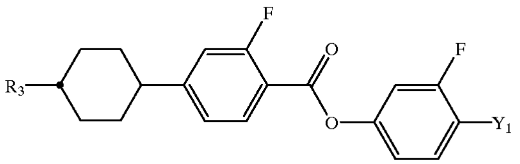
(3-58)
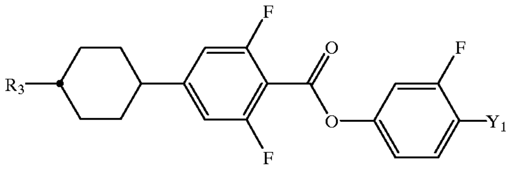
(3-59)
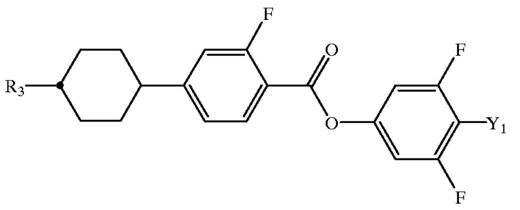
(3-60)
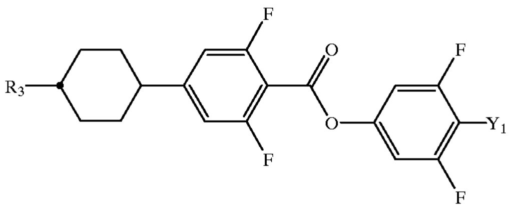
(3-61)
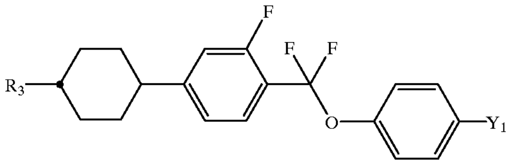

-continued
(3-62)
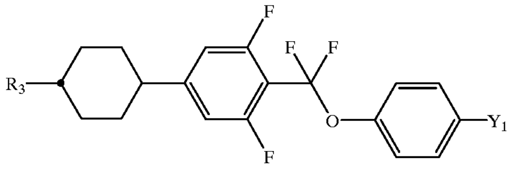
(3-63)
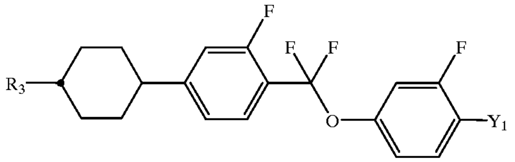
(3-64)
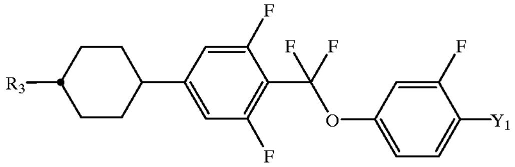
(3-65)
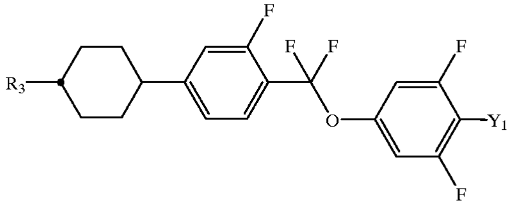
(3-66)
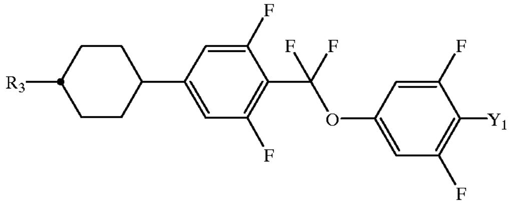
(3-67)
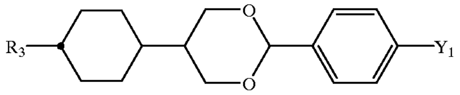
(3-68)
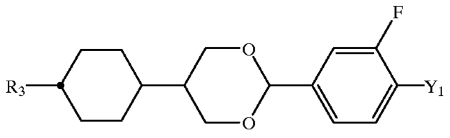
(3-69)
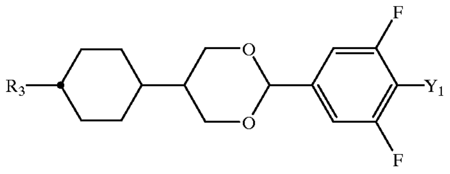
-continued
(4-1)
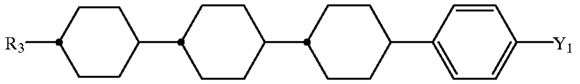
(4-2)
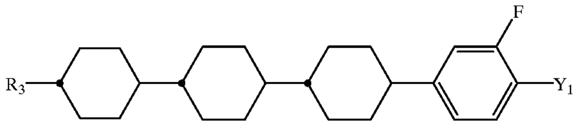
(4-3)
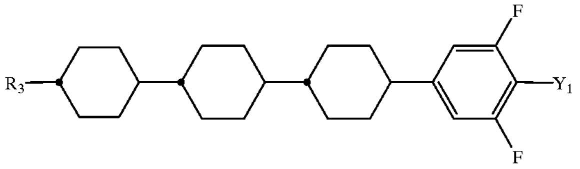
(4-4)
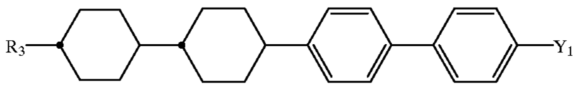
(4-5)
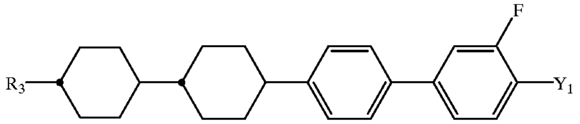
(4-6)
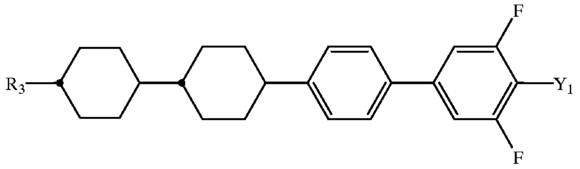
(4-7)
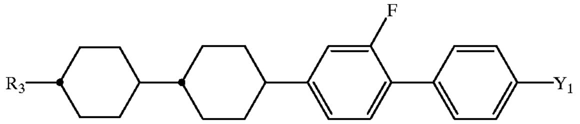
(4-8)
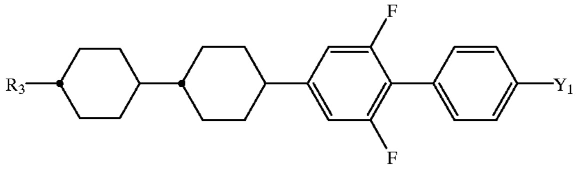
(4-9)
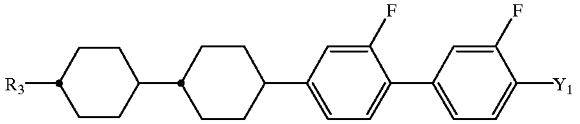

-continued
(4-10)
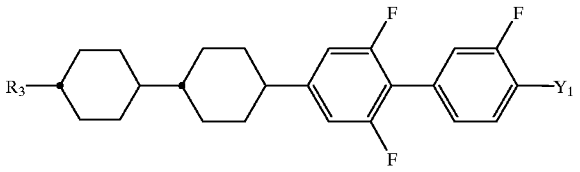
(4-11)
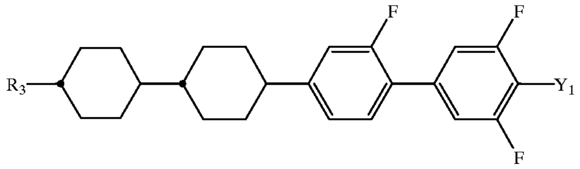
(4-12)
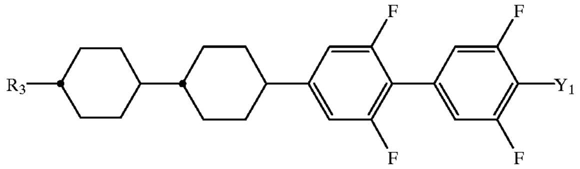
(4-13)
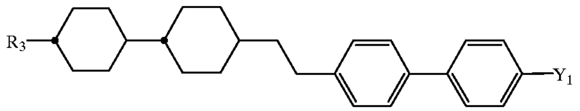
(4-14)
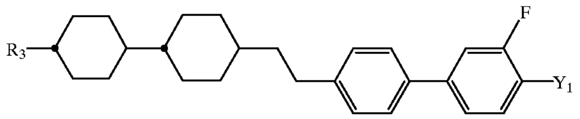
(4-15)
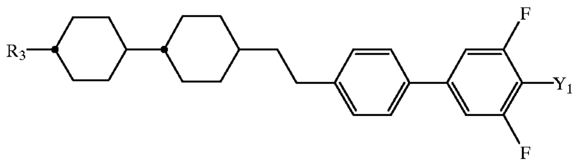
(4-16)
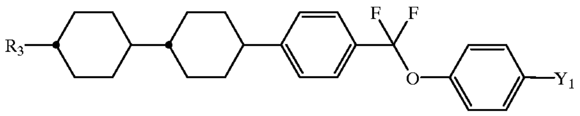
(4-17)
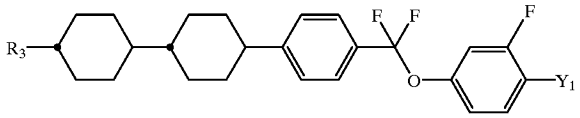
-continued
(4-18)
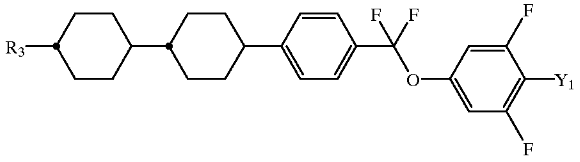
(4-19)
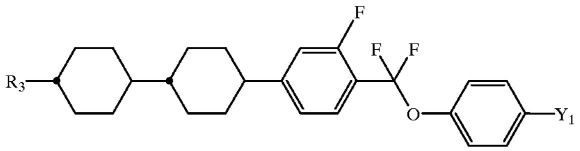
(4-20)
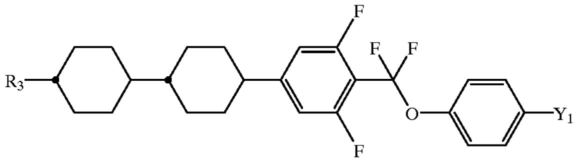
(4-21)
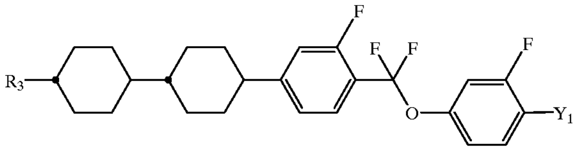
(4-22)
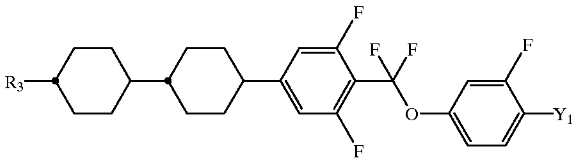
(4-23)
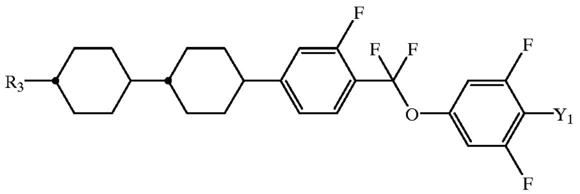
(4-24)
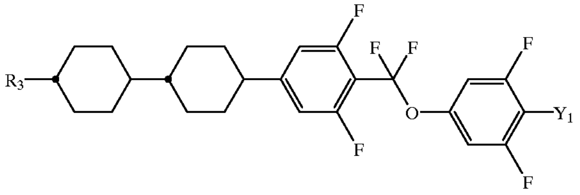
wherein $R_3$ and $Y_1$ have the same meanings as described above.

Any of the compounds expressed by one of the general formulae (2) to (4) exhibit a positive Δε, are excellent in thermal stability and chemical stability, and are indispensable when liquid crystal composition for TFT (AM-LCD) of which a high reliability such as a high voltage holding ratio (large specific resistance) is required are produced.

While the amount of the compound to be used is suitably in the range of 1 to 99.9% by weight based on the total amount of liquid crystal when liquid crystal composition for TFT are produced, it is preferably 10 to 97% by weight and more desirably 40 to 95% by weight. In this case, liquid crystal composition may further comprise a compound expressed by one of the general formulae (7) to (9) for the purpose of adjusting viscosity.

While the compounds expressed by one of the general formulae (2) to (4) described above can be used when liquid crystal compositions for STN display mode or a TN mode are produced, the amount of the compound to be used is preferably less than 50% by weight based on the total amount of liquid crystal composition since this compound is small in its effect of lowering threshold voltage of the liquid crystal composition.

Next, among the second component B, the compounds of one of the formulae (5-1) to (5-40) can be mentioned as preferable examples of the ones included in the general formula (5), and the compounds of one of the formulae (6-1) to (6-3) can be mentioned as preferable examples of the ones included in the general formula (6), respectively.

(5-1)

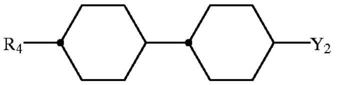

(5-2)

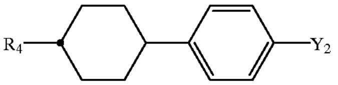

(5-3)

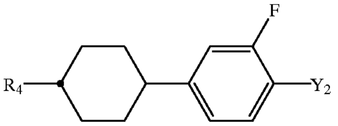

(5-4)

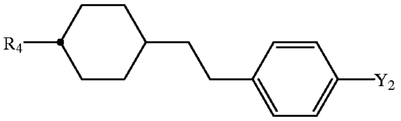

(5-5)

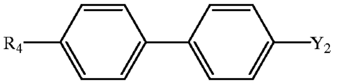

(5-6)

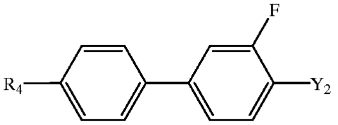

(5-7)

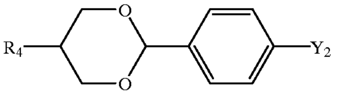

-continued (5-8)

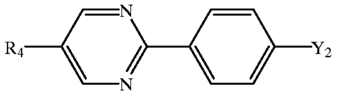

(5-9)

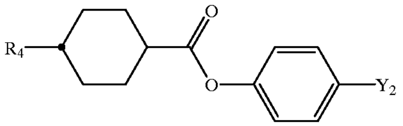

(5-10)

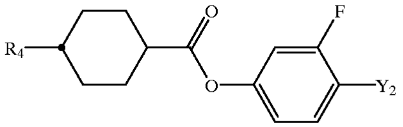

(5-11)

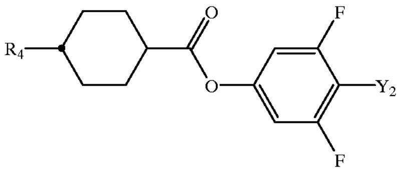

(5-12)

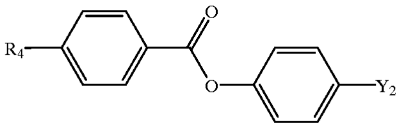

(5-13)

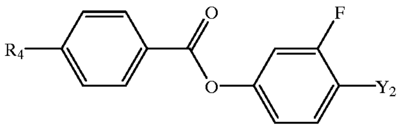

(5-14)

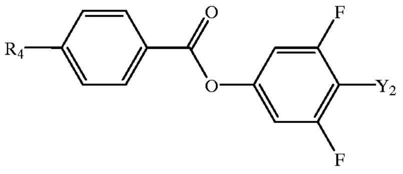

(5-15)

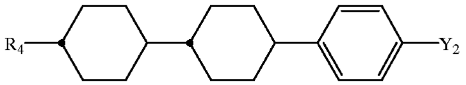

(5-16)

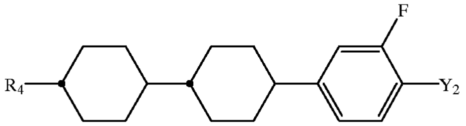

(5-17)

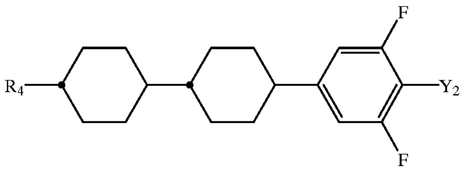

-continued
(5-18)
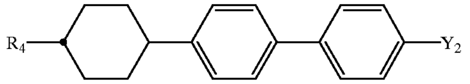
(5-19)
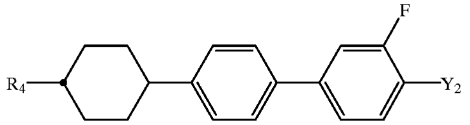
(5-20)
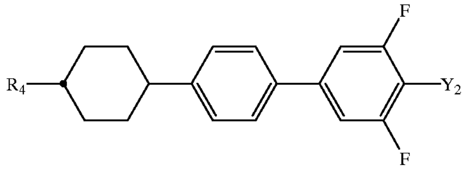
(5-21)
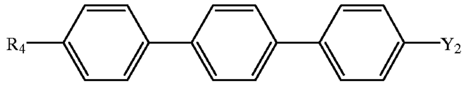
(5-22)
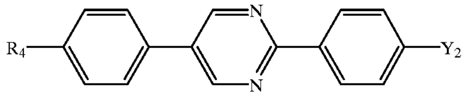
(5-23)
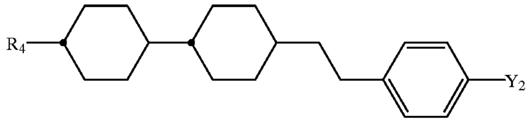
(5-24)
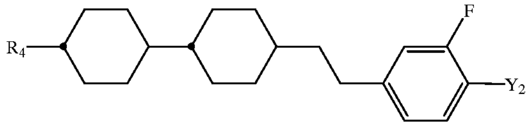
(5-25)
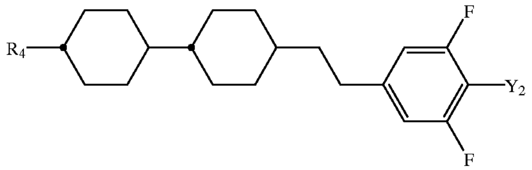
(5-26)
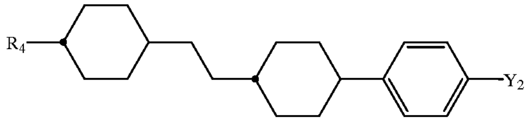
(5-27)
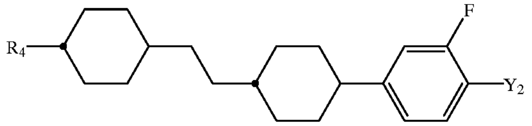
-continued
(5-28)
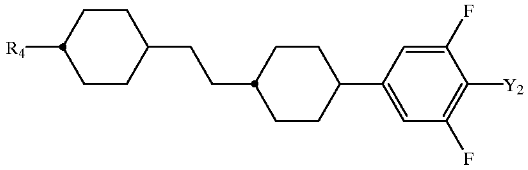
(5-29)
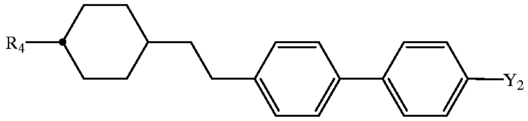
(5-30)
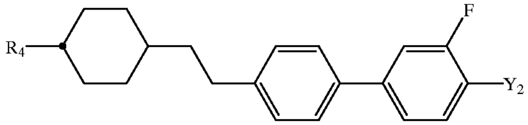
(5-31)
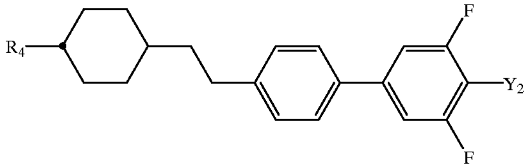
(5-32)
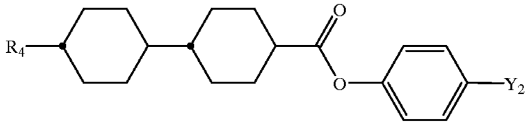
(5-33)
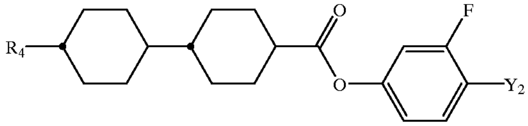
(5-34)
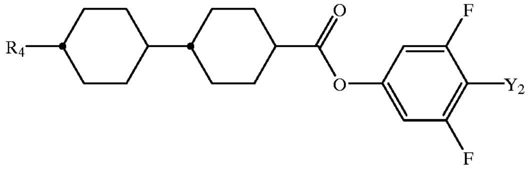
(5-35)
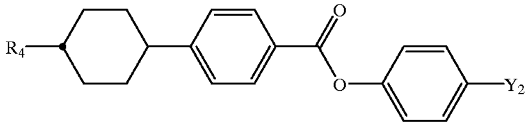

-continued (5-36)

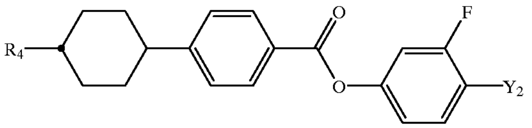

(5-37)

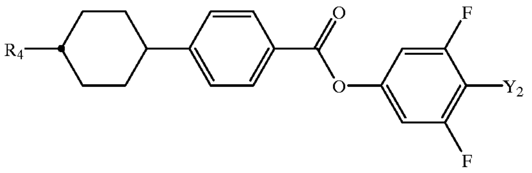

(5-38)

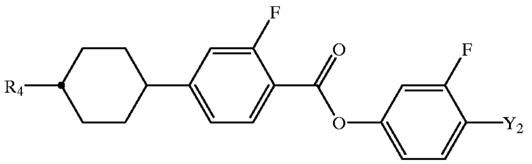

(5-39)

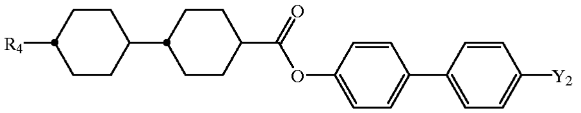

(5-40)

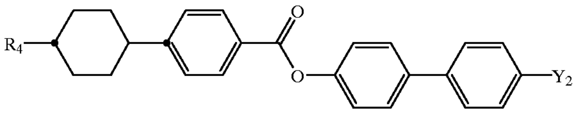

(6-1)

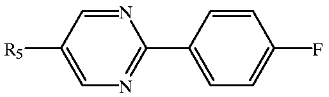

(6-2)

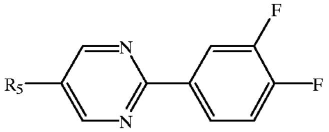

(6-3)

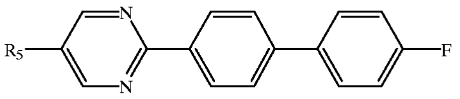

wherein $R_4$, $Y_2$ and $R_5$ have the same meanings as described above.

Any of the compounds expressed by the general formulae (5) or (6) has a positive and large $\Delta\epsilon$ value, and is used particularly for the purpose of lowering threshold voltage of liquid crystal compositions.

Also, the compounds are used for the purposes of improving the steepness of liquid crystal compositions for STN display mode or TN display mode including for the purposes of adjusting $\Delta n$ and raising clearing point of liquid crystal compositions, and thus are indispensable particularly when liquid crystal compositions for STN display mode or TN display mode are produced.

Whereas the compounds can lower threshold voltage of liquid crystal compositions as their amount used is increased, the use of the compounds brings about increase of the viscosity.

Accordingly, it is advantageous to use the compounds in a large amount for driving display element at a lower so far as the viscosity of liquid crystal compositions satisfies required characteristics.

Under such circumstances, the amount of the compounds to be used is suitably in a range of 0.1 to 99.9% by weight, preferably 10 to 97% by weight, and more preferably 40 to 95% by weight, based on the total amount of liquid crystal composition when liquid crystal compositions for STN display mode or TN display mode are produced.

Among the third component described above, the compounds of one of the formulae (7-1) to (7-11) can be mentioned as preferable examples of the ones included in the general formula (7), the compounds of one of the formulae (8-1) to (8-18) can be mentioned as preferable examples of the ones included in the general formula (8), and compounds of one of the formulae (9-1) to (9-6) can be mentioned as preferable examples of compounds included in the general formula (9).

(7-1)

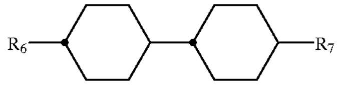

(7-2)

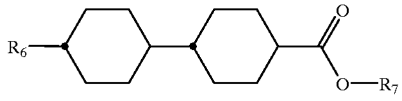

(7-3)

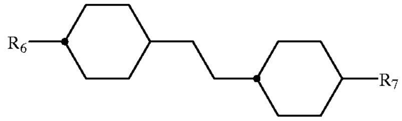

(7-4)

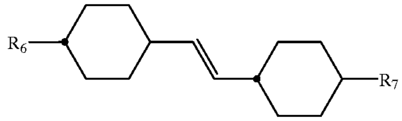

(7-5)

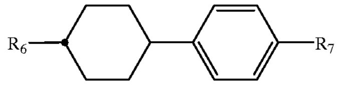

(7-6)

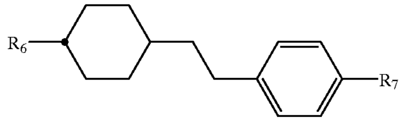

(7-7)

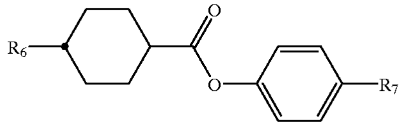

-continued
(7-8)
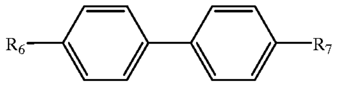
(7-9)
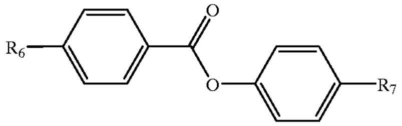
(7-10)
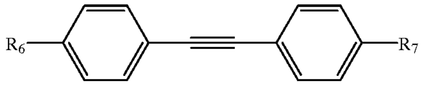
(7-11)
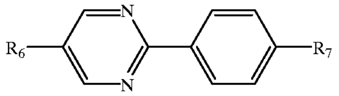
(8-1)
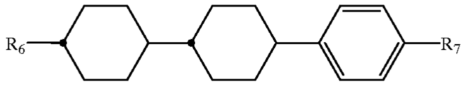
(8-2)
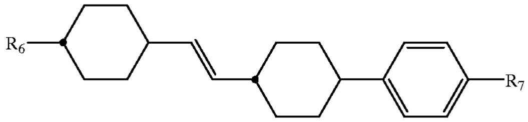
(8-3)
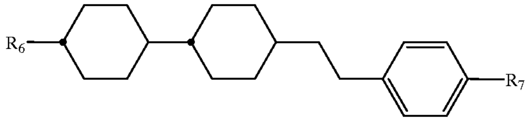
(8-4)
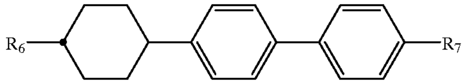
(8-5)
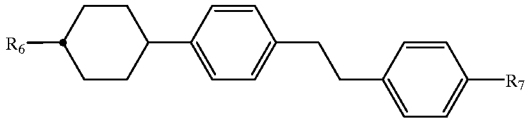
(8-6)
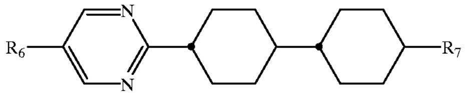
(8-7)
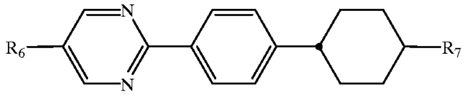
(8-8)
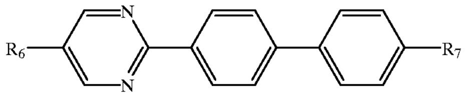
-continued
(8-9)
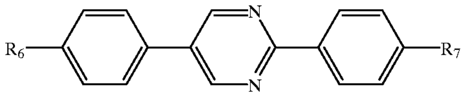
(8-10)
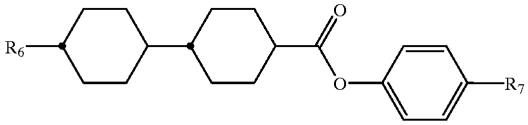
(8-11)
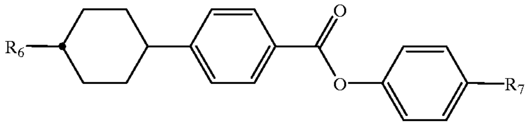
(8-12)
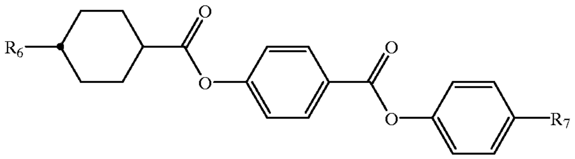
(8-13)
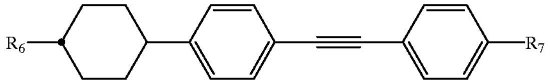
(8-14)
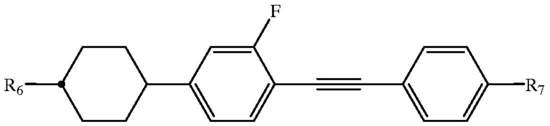
(8-15)
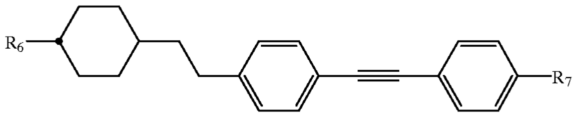
(8-16)
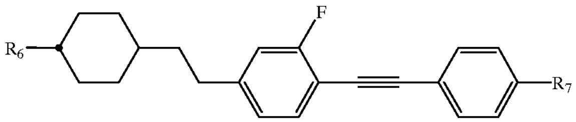
(8-17)
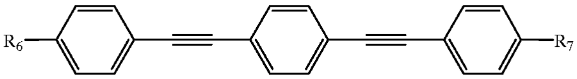
(8-18)
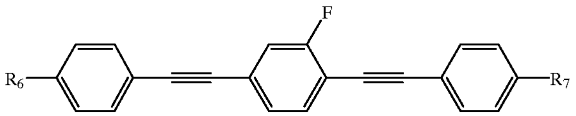

-continued (9-1)

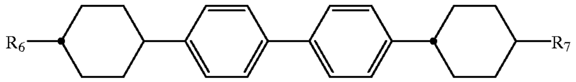

(9-2)

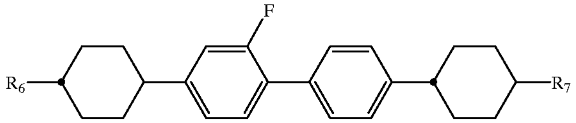

(9-3)

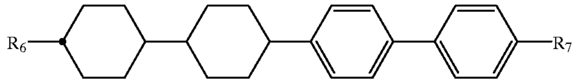

(9-4)

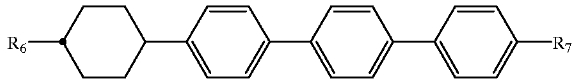

(9-4)

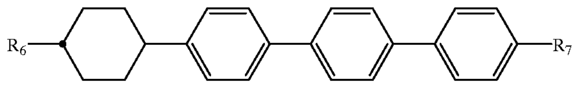

(9-5)

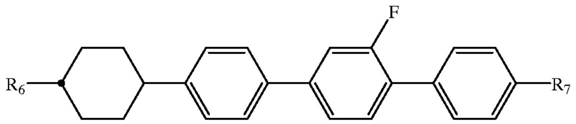

(9-6)

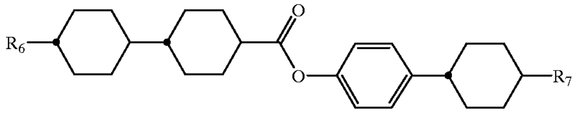

wherein $R_6$ and $R_7$have the same meanings as described above.

Any of the compounds expressed by one of the general formulae (7) to (9) has a small absolute value of $\Delta\epsilon$. Among them, the compounds of the general formula (7) are used for the purpose of adjusting viscosity or adjusting $\Delta n$ of liquid crystal composition, and the compounds of the general formulae (8) and (9) are used for the purposes of widening nematic range by such a way of raising clearing point or adjusting $\Delta n$.

Whereas these compounds raise threshold voltage of the liquid crystal compositions as their amount used is increased, the use of compounds reduces the viscosity. Accordingly, it is desirable to use the compounds in a larger amount so far as the threshold voltage of liquid crystal compositions satisfies required values.

From such circumstances, the used amount of the compounds to be used is suitably less than 40% by weight and preferably less than 35% by weight based on the total amount of liquid crystal composition when liquid crystal composition for a TFT display mode are produced. On the other hand, when liquid crystal compositions for STN display mode or TN display mode are produced, the amount of use described above is suitably less than 70% by weight and preferably less than 60% by weight.

Among other components, an optically active compound is usually added to the liquid crystal compositions of the present invention for the purpose of inducing helical structure of liquid crystal compositions to adjust required twist angle and to prevent reverse twist, with the exception of specific cases, for instance, the case of liquid crystal compositions for OCB (Optically Compensated Birefringence) mode. While the optically active compound is widely selected from known compounds so far as the purposes described above can be achieved, the optically active compounds expressed by one of the following formulae (Op-1) to (Op-8) can preferably be mentioned.

(Op-1)

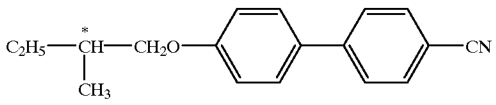

(Op-2)

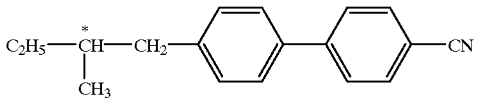

(Op-3)

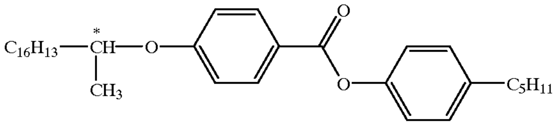

(Op-4)

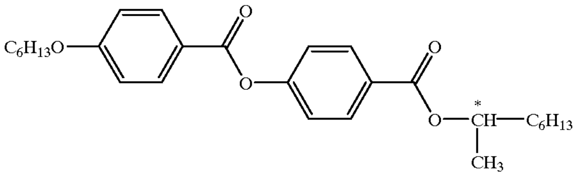

(Op-5)

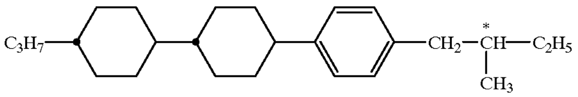

(Op-6)

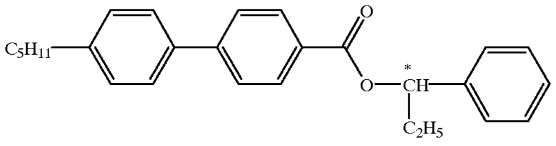

(Op-7)

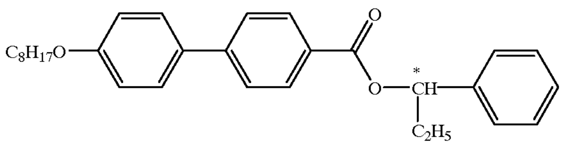

-continued (Op-8)

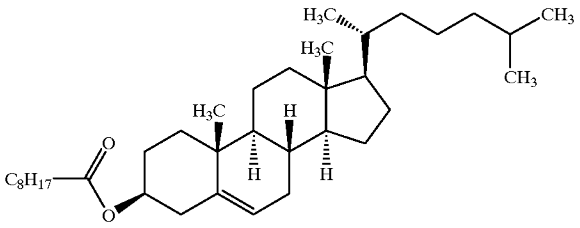

Pitch length of the twist in liquid crystal compositions is adjusted by adding these optically active compounds. The twist pitch length is preferably adjusted in the range of 40 to 200 μm in the case of liquid crystal compositions for TFT or TN mode, preferably adjusted in the range of 60 to 20 μm in the case of the liquid crystal compositions for STN mode, and preferably adjusted in the range of 1.5 to 4 μm in the case of liquid crystal compositions for bistable TN mode, respectively. Further, in such cases, two or more kind of optically active compounds may be added for the purpose of adjusting the dependency of pitch length on temperature.

Liquid crystal compositions of the present invention can be prepared by methods that are conventional by themselves. For instance, the compositions are prepared by a method in which various components are dissolved in one another at a high temperature.

Further, the liquid crystal compositions of the present invention can be used as ones for a guest-host (GH) mode by adding a dichroic dye such as merocyanine type, styryl type, azo type, azomethine type, azoxy type, quinophthalone type, anthraquinone type or tetrazine type. Alternatively, the liquid crystal compositions may be used as NCAP which is prepared by the microencapsulation of a nematic liquid crystal, or as liquid crystal compositions for polymer dispersed liquid crystal display elements (PDLCD) represented by polymer network liquid crystal display elements (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

As of nematic liquid crystal compositions comprising the compounds of and prepared by the present invention as described above are mentioned as Examples below.

In each of the following Composition Examples, compounds are designated by making the groups shown in each of columns of left side terminal group, bonding group, ring structure, and right side terminal group correspond to the symbols shown in the columns of symbol according to the definition shown in Table 1 below.

(60)

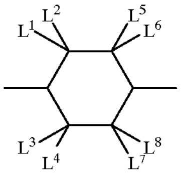

(61)

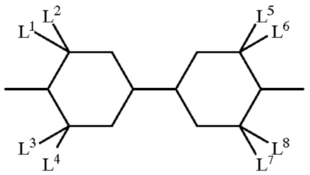

Compound No. appended to the compounds of the present invention in the following Composition Examples means that the compounds are the same as those shown in Examples described below and having the same appended Compound No.; and the content of compounds means % by weight unless otherwise specified. Further, data of characteristics of compositions in Composition Examples are indicated by $T_{NI}$ (phase transition temperature of nematic phase-isotropic liquid, or clearing point), η(viscosity, determined at a temperature of 20.0° C.), Δn (optical anisotropy value, determined at a temperature of 25.0° C.), $V_{th}$ (threshold voltage, determined at a temperature of 25.0° C.) and P (pitch, determined at a temperature of 25.0° C.). Abbreviations shown herein are defined as table 1. [Table 1]

TABLE 1

| Method for designating compounds by using symbols $R-(A_1)-Z_1-\ldots-Z_n-(A_n)-X$ | |
|---|---|
| 1) Left side terminal group R- | Symbol |
| $C_nH_{2n+1}$— | n— |
| $C_nH_{2n+1}O$— | nO— |
| $C_nH_{2n+1}OC_mH_{2m}$— | nOm— |
| $CH_2$═CH— | v— |
| $CH_2$═$CHC_nH_{2n}$— | Vn— |
| $C_nH_{2n+1}CH$═$CHC_mH_{2m}$— | nVm— |
| $CH_2$═$CHC_nH_{2n}CH$═CH— | VnV— |
| 2) Ring structure -(A1)-, -(An)- | Symbol |
| 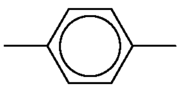 | B |

TABLE 1-continued

| Method for designating compounds by using symbols $R-(A_1)-Z_{1-} \ldots {}_{-Zn}-(A_n)-X$ | |
|---|---|
| 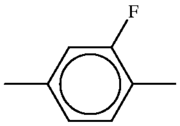 | B(F) |
| 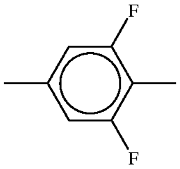 | B(F,F) |
| 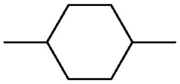 | H |
| 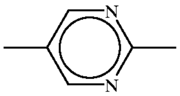 | Py |
| 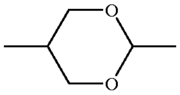 | G |
| 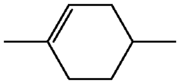 | Ch |
| **3) Bonding group $-Z_1-$, $-Z_n-$** | **Symbol** |
| $—C_2H_4—$ | 2 |
| $—C_4H_8—$ | 4 |
| —COO— | E |
| —C≡C— | T |
| —CH═CH— | V |
| $—CF_2O—$ | CF2O |
| $—OCF_2—$ | OCF2 |
| $—OCH_2—$ | O1 |
| $—CH_2O—$ | 1O |
| **4) Right side terminal group -X** | **Symbol** |
| —F | —F |
| —Cl | —CL |
| —CN | —C |
| $—CF_3$ | —CF3 |
| $—OCF_3$ | —OCF3 |
| $—OCF_2H$ | —OCF2H |
| $—C_nH_{2n+1}$ | —n |
| $—OC_nH_{2n+1}$ | —On |
| $—COOCH_3$ | —EMe |
| $—C_nH_{2n}CH═CH_2$ | —nV |
| $—C_mH_{2m}CH═CHC_nH_{2n+1}$ | —mVn |
| $—CH═CF_2$ | —VFF |
| $—C_nH_{2n}CH═CF_2$ | —nVFF |
| $—CH═CHC_nH_{2n}F$ | —VnF |
| $—CH═CH_2$ | —V |
| —C≡C—CN | —TC |
| **5) Examples of designation** | |

Example 1 3-H2B(F,F)B(F)-F

TABLE 1-continued

Method for designating compounds by using symbols
$R-(A_1)-Z_1-\ldots-Z_n-(A_n)-X$

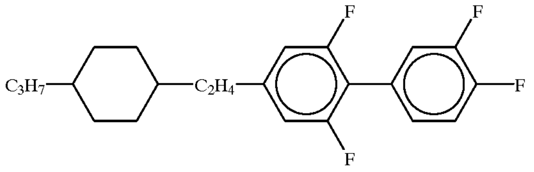

Example 2 3-HB(F)TB-2

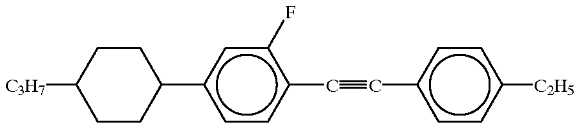

Example 3 1V2-BEB(F,F)-C

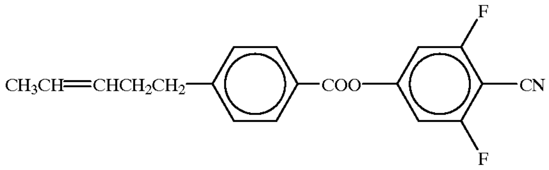

COMPOSITION EXAMPLE 1

| | |
|---|---|
| 101-HHB(F,F)-OCF3 (No. 153) | 5.0% |
| 1V2-BEB(F,F)-C | 5.0% |
| 3-HB-C | 25.0% |
| 1-BTB-3 | 5.0% |
| 2-BTB-1 | 10.0% |
| 3-HH-4 | 11.0% |
| 3-HHB-1 | 11.0% |
| 3-HHB-3 | 4.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

Characteristics of the composition were determined as follows:

TNI=87.5(° C.)

η=16.7(mPa.s)

Δn=0.161

Δε=8.1

Vth=1.92(V)

0.8 parts of an optically active compound expressed by the above-mentioned formula (Op-4) was added to 100 parts of the above-mentioned composition to obtain the secondary composition, which has the following determined pitch: P=1 μm.

COMPOSITION EXAMPLE 2

A liquid crystal composition comprising the following compounds in an amount shown below was prepared:

| | |
|---|---|
| 5-H10BB(F,F)-OCF3 (No. 239) | 5.0% |
| 201-BEB(F)-C | 5.0% |
| 301-BEB(F)-C | 15.0% |
| 401-BEB(F)-C | 13.0% |
| 501-BEB(F)-C | 13.0% |
| 2-HHB(F)-C | 10.0% |
| 3-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-1 | 8.0% |
| 3-HHB-01 | 4.0% |

Characteristics of the composition were determined to be as follows:

TNI=87.8(° C.)

η=87.1(mPa.s)

Δn=0.148

Δε=30.7

Vth=0.88 (V)

COMPOSITION EXAMPLE 3

| | |
|---|---|
| 101-HHB(F,F)-OCF3 (No. 153) | 5.0% |
| 5-H10BB(F,F)-OCF3 (No. 239) | 5.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-05 | 3.0% |

-continued

| | |
|---|---|
| 6-PyB-06 | 3.0% |
| 6-PyB-07 | 3.0% |
| 6-PyB-08 | 3.0% |
| 3-PyBB-F | 6.0% |
| 4-PyBB-F | 6.0% |
| 3-HHB-1 | 6.0% |
| 3-HHB-3 | 8.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

Characteristics of the composition were determined as follows:

TNI=87.6(° C.)

η=39.1(mPa.s)

Δn=0.188

Δε=6.9

Vth=2.18(V)

COMPOSITION EXAMPLE 4

| | |
|---|---|
| 101-HHB(F,F)-OCF3 (No. 153) | 5.0% |
| 101-HB(F,F)B(F,F)-OCF3 (No. 187) | 5.0% |
| 3-GB-C | 10.0% |
| 4-GB-C | 10.0% |
| 2-BEB-C | 12.0% |
| 3-BEB-C | 4.0% |
| 3-PyB(F)-F | 6.0% |
| 3-HEB-04 | 4.0% |
| 4-HEB-02 | 6.0% |
| 5-HEB-01 | 6.0% |
| 3-HEB-02 | 5.0% |
| 5-HEB-5 | 5.0% |
| 5-HEB-5 | 5.0% |
| 10-BEB-5 | 4.0% |
| 3-HHB-1 | 6.0% |
| 3-HHEBB-C | 2.0% |
| 3-HBEBB-C | 2.0% |
| 5-HBEBB-C | 3.0% |

COMPOSITION EXAMPLE 5

| | |
|---|---|
| 5-H10BB(F,F)-OCF3 (No. 239) | 5.0% |
| 3-HB-C | 18.0% |
| 7-HB-C | 3.0% |
| 101-HB-C | 10.0% |
| 3-HB(F)-C | 10.0% |
| 2-PyB-2 | 2.0% |
| 3-PyB-2 | 2.0% |
| 4-PyB-2 | 2.0% |
| 101-HH-3 | 7.0% |
| 2-BTB-01 | 7.0% |
| 3-HHB-1 | 7.0% |
| 3-HHB-F | 4.0% |
| 3-HHB-01 | 4.0% |
| 3-HHB-3 | 6.0% |
| 3-H2BTB-2 | 3.0% |
| 3-H2BTB-3 | 3.0% |
| 2-PyBH-3 | 4.0% |
| 3-PyBB-2 | 3.0% |

Characteristics of the composition were determined as follows:

TNI=74.8(° C.)

η=21.0(mPa.s)

Δn=0.139

Δε=8.4

Vth=1.70(V)

COMPOSITION EXAMPLE 6

| | |
|---|---|
| 101-HHB(F,F)-OCF3 (No. 153) | 3.0% |
| 5-H10BB(F,F)-OCF3 (No. 239) | 3.0% |
| 201-BEB(F)-C | 5.0% |
| 301-BEB(F)-C | 12.0% |
| 501-BEB(F)-C | 4.0% |
| 1V2-BEB(F,F)-C | 10.0% |
| 3-HH-EMe | 10.0% |
| 3-HB-02 | 18.0% |
| 7-HEB-F | 2.0% |
| 3-HHEB-F | 2.0% |
| 5-HHEB-F | 2.0% |
| 3-HBEB-F | 4.0% |
| 201-HBEB(F)-C | 2.0% |
| 3-HB(F)EB(F)-C | 2.0% |
| 3-HBEB(F,F)-C | 2.0% |
| 3-HB-F | 4.0% |
| 3-HHB-0 | 1.0% |
| 3-HHB-3 | 7.0% |
| 2-HEBEB-F | 2.0% |
| 2-HEBEB-1 | 2.0% |

Characteristics of the composition were determined as follows:

TNI=72.2(° C.)

η=38.9(mPa.s)

Δn=0.115

Δε=24.3

Vth=0.98(V)

COMPOSITION EXAMPLE 7

| | |
|---|---|
| 101-HHB(F,F)-OCF3 (No. 153) | 4.0% |
| 5-H10BB(F,F)-OCF3 (No. 239) | 4.0% |
| 201-BEB(F)-C | 5.0% |
| 301-BEB(F)-C | 12.0% |
| 501-BEB(F)-C | 4.0% |
| 1V2-BEB(F,F)-C | 14.0% |
| 3-HB-02 | 10.0% |
| 3-HH-4 | 3.0% |
| 3-HHB-F | 3.0% |
| 3-HHB-1 | 2.0% |
| 3-HHB-01 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |

Characteristics of the composition were determined as follows:

TNI=85.7(° C.)

η=43.6(mPa.s)

Δn=0.141

Δε=27.9

Vth=1.01(V)

COMPOSITION EXAMPLE 8

| | |
|---|---|
| 101-HHB(F,F)-OCF3 (No. 153) | 3.0% |
| 5-H10BB(F,F)-OCF3 (No. 239) | 3.0% |
| 2-BEB-C | 12.0% |
| 3-BEB-C | 4.0% |
| 4-BEB-C | 6.0% |
| 3-HB-C | 28.0% |
| 3-HEB-04 | 12.0% |
| 4-HEB-02 | 8.0% |
| 5-HEB-01 | 5.0% |
| 3-HEB-02 | 6.0% |
| 5-HEB-02 | 5.0% |
| 3-HHB-1 | 4.0% |
| 3-HHB-01 | 4.0% |

Characteristics of the composition were determined as follows:

TNI=60.2(° C.)

η=28.7(mPa.s)

Δn=0.111

Δε=10.7

Vth=1.30(V)

COMPOSITION EXAMPLE 9

| | |
|---|---|
| 101-HHB(F,F)-OCF3 (No. 153) | 5.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 10-BEB-2 | 10.0% |
| 10-BEB-5 | 12.0% |
| 2-HHB-1 | 4.0% |
| 3-HHB-F | 4.0% |
| 3-HHB-1 | 7.0% |
| 3-HHB-01 | 4.0% |
| 3-HHB-3 | 8.0% |

Characteristics of the composition were determined as follows:

TNI=62.9(° C.)

η=22.2(mPa.s)

Δn=0.160

Δε=7.5

Vth=1.69(V)

COMPOSITION EXAMPLE 10

| | |
|---|---|
| 101-HHB(F,F)-OCF3 (No. 153) | 5.0% |
| 5-H10BB(F,F)-OCF3 (No. 239) | 5.0% |
| 101-HB(F,F)B(F,F)-OCF3 (No. 187) | 5.0% |
| 101-HB(F)B(F,F)-OCF3 (No. 199) | 5.0% |
| 2-HB-C | 5.0% |
| 3-HB-C | 12.0% |
| 3-HB-02 | 15.0% |
| 2-BTB-1 | 3.0% |
| 3-HHB-1 | 8.0% |
| 3-HHB-F | 4.0% |
| 3-HHB-01 | 5.0% |
| 3-HHB-3 | 9.0% |
| 3-HHEB-F | 4.0% |
| 2-HHB(F)-F | 3.0% |
| 3-HHB(F)-F | 7.0% |
| 3-HHB(F,F)-F | 5.0% |

-continued

COMPOSITION EXAMPLE 11

| | |
|---|---|
| 5-H10BB(F,F)-OCF3 (No. 239) | 5.0% |
| 3-BEB(D)-C | 8.0% |
| 3-HB-C | 8.0% |
| V-HB-C | 8.0% |
| 1V-HB-C | 8.0% |
| 3-HB-02 | 3.0% |
| 3-HH-2V | 14.0% |
| 3-HH-2V1 | 7.0% |
| V2-HHB-1 | 15.0% |
| 3-HHB-1 | 5.0% |
| 3-HHEB-F | 2.0% |
| 3-H2BTB-2 | 6.0% |
| 3-H2BTB-3 | 6.0% |
| 3-H2BTB-4 | 5.0% |

Characteristics of the composition were determined as follows:

TNI=95.8(° C.)

η=19.3(mPa.s)

Δn=0.135

Δε=8.7

Vth=2.12(V)

COMPOSITION EXAMPLE 12

| | |
|---|---|
| 101-HHB(F,F)-OCF3 (No. 153) | 3.0% |
| 5-H10BB(F,F)-OCF3 (No. 239) | 3.0% |
| V2-HB-C | 12.0% |
| 1V2-HB-C | 12.0% |
| 3-HB-C | 15.0% |
| 3-HB[1D,2D,3D]-C | 9.0% |
| 3-HB(F)-C | 5.0% |
| 2-BTB-1 | 2.0% |
| 3-HH-4 | 8.0% |
| 3-HH-VFF | 6.0% |
| 2-H[1D,2D,3D]HB-C | 3.0% |
| 3-HHB-C | 6.0% |
| 3-HB(F)TB-2 | 2.0% |
| 3-H2BTB-2 | 5.0% |
| 3-H2BTB-3 | 5.0% |
| 3-H2BTB-4 | 4.0% |

Characteristics of the composition were determined as follows:

TNI=82.4(° C.)

η=20.7(mPa.s)

Δn=0.145

Δε=9.3

Vth=1.78(V)

COMPOSITION EXAMPLE 13

| | |
|---|---|
| 101-HHB(F,F)-OCF3 (No. 153) | 5.0% |
| 5-H10BB(F,F)-OCF3 (No. 239) | 5.0% |
| 5-BTB(F)TB-3 | 10.0% |
| V2-HB-TC | 10.0% |
| 3-HB-TC | 10.0% |

-continued

| | |
|---|---|
| 3-HB-C | 10.0% |
| 5-HB-C | 7.0% |
| 5-BB-C | 3.0% |
| 2-BTB-1 | 10.0% |
| 2-BTB-01 | 5.0% |
| 3-HH-4 | 5.0% |
| 3-HHB-1 | 5.0% |
| 3-HHB-3 | 6.0% |
| 3-H2BTB-2 | 3.0% |
| 3-H2BTB-3 | 3.0% |
| 3-HB(F)TB-2 | 3.0% |

Characteristics of the composition were determined as follows:

TNI=100.1(° C.)

η=19.4(mPa.s)

Δn=0.204

Δε=8.1

Vth=1.93(V)

COMPOSITION EXAMPLE 14

| | |
|---|---|
| 101-HHB(F,F)-OCF3 (No. 153) | 5.0% |
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |
| 5-HBB(F)-F | 8.0% |

Characteristics of the composition were determined as follows:

TNI=98.8(° C.)

ηn=27.0(mPa.s)

Δn=0.090

Δε=5.7

Vth=2.11((V)

0.3 parts of an optically active compound expressed by the above-mentioned formula (Op-8) was added to 100 parts of the above-mentioned composition to obtain the secondary composition, which has the following determined pitch: P=79 μm

COMPOSITION EXAMPLE 15

| | |
|---|---|
| 101-HHB(F,F)-OCF3 (No. 153) | 5.0% |
| 5-H10BB(F,F)-OCF3 (No. 239) | 5.0% |
| 101-HB(F,F)B(F,F)-OCF3 (No. 187) | 5.0% |
| 101-HB(F)B(F,F)-OCF3 (No. 199) | 5.0% |
| 7-HB(F,F)-F | 3.0% |
| 3-HB-02 | 7.0% |
| 2-HHB(F)-F | 10.0% |
| 3-HHB(F)-F | 10.0% |
| 2-HBB(F)-F | 9.0% |
| 3-HBB(F)-F | 9.0% |
| 5-HBB(F)-F | 6.0% |
| 2-HBB-F | 4.0% |
| 3-HBB-F | 4.0% |
| 5-HBB-F | 3.0% |

-continued

| | |
|---|---|
| 3-HBB(F,F)-F | 5.0% |
| 5-HBB(F,F)-F | 10.0% |

COMPOSITION EXAMPLE 16

| | |
|---|---|
| 5-H10BB(F,F)-OCF3 (No. 239) | 5.0% |
| 3-HB-CL | 10.0% |
| 5-HB-CL | 4.0% |
| 7-HB-CL | 4.0% |
| 101-HH-5 | 5.0% |
| 2-HBB(F)-F | 8.0% |
| 3-HBB(F)-F | 8.0% |
| 5-HBB(F)-F | 9.0% |
| 4-HHB-CL | 8.0% |
| 5-HHB-CL | 8.0% |
| 3-H2HB(F)-CL | 4.0% |
| 3-HBB(F,F)-F | 10.0% |
| 5-H2BB(F,F)-F | 9.0% |
| 3-HB(F)VB-2 | 4.0% |
| 3-HB(F)VB-3 | 4.0% |

Characteristics of the composition were determined as follows:

TNI=90.2(° C.)

η=24.1(mPa.s)

Δn=0.128

Δε=5.0

Vth=2.29(V)

COMPOSITION EXAMPLE 17

| | |
|---|---|
| 101-HHB(F,F)-OCF3 (No. 153) | 10.0% |
| 5-H10BB(F,F)-OCF3 (No. 239) | 5.0% |
| 3-HHB(F,F)-F | 9.0% |
| 3-H2HB(F,F)-F | 8.0% |
| 4-H2HB(F,F)-F | 8.0% |
| 3-HBB(F,F)-F | 21.0% |
| 5-HBB(F,F)-F | 13.0% |
| 3-H2BB(F,F)-F | 10.0% |
| 5-HHBB(F,F)-F | 3.0% |
| 5-HHEBB-F | 2.0% |
| 3-HH2BB(F,F)-F | 3.0% |
| 101-HBBH-4 | 4.0% |
| 101-HBBH-5 | 4.0% |

Characteristics of the composition were determined as follows:

TNI=98.1(° C.)

η=40.4(mPa.s)

Δn=0.116

Δε=9.9

Vth=1.62(V)

COMPOSITION EXAMPLE 18

| | |
|---|---|
| 101-HHB(F,F)-OCF3 (No. 153) | 5.0% |
| 5-H10BB(F,F)-OCF3 (No. 239) | 5.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |

-continued

| | |
|---|---|
| 4-HHB-OCF3 | 7.0% |
| 3-HH2B-OCF3 | 4.0% |
| 5-HH2B-OCF3 | 4.0% |
| 3-HHB(F,F)-OCF3 | 5.0% |
| 3-HBB(F)-F | 10.0% |
| 5-HBB(F)-F | 5.0% |
| 3-HH2B(F)-F | 3.0% |
| 3-HB(F)BH-3 | 3.0% |
| 5-HBBH-3 | 3.0% |
| 3-HHB(F,F)-OCF2H | 4.0% |

Characteristics of the composition were determined as follows:

COMPOSITION EXAMPLE 19

| | |
|---|---|
| 101-HHB(F,F)-OCF3 (No. 153) | 5.0% |
| 101-HB(F,F)B(F,F)-OCF3 (No. 187) | 5.0% |
| 2-HHB(F)-F | 2.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)-F | 5.0% |
| 2-H2BB(F)-F | 9.0% |
| 3-H2BB(F)-F | 4.0% |
| 3-HBB(F,F)-F | 25.0% |
| 5-HBB(F,F)-F | 19.0% |
| 101-HBBH-4 | 5.0% |
| 101-HBBH-5 | 5.0% |

COMPOSITION EXAMPLE 20

| | |
|---|---|
| 101-HHB(F,F)-OCF3 (No. 153) | 8.0% |
| 5-H10BB(F,F)-OCF3 (No. 239) | 8.0% |
| 7-HB(F)-F | 5.0% |
| 5-H2B(F)-F | 5.0% |
| 3-HB-02 | 10.0% |
| 3-HH-4 | 2.0% |
| 3-HB[5D,6D,7D]-4 | 3.0% |
| 3-HHB(F)-F | 10.0% |
| 5-HH[5D,6D,7D]B(F)-F | 10.0% |
| 3-H2HB(F)-F | 5.0% |
| 2-HBB(F)-F | 3.0% |
| 3-HBB(F)-F | 3.0% |
| 5-HBB(F)-F | 6.0% |
| 2-H2BB(F)-F | 5.0% |
| 3-HHB-1 | 8.0% |
| 3-HHB-01 | 5.0% |
| 3-HHB-3 | 4.0% |

Characteristics of the composition were determined as follows:

TNI=87.2(° C.)

η=26.3(mPa.s)

Δn=0.094

Δε=4.4

Vth=2.50(V)

COMPOSITION EXAMPLE 21

| | |
|---|---|
| 101-HHB(F,F)-OCF3 (No. 153) | 10.0% |
| 5-H10BB(F,F)-OCF3 | 10.0% |

-continued

| | |
|---|---|
| 7-HB(F,F)-F | 3.0% |
| 3-H2HB(F,F)-F | 12.0% |
| 4-H2HB(F,F)-F | 10.0% |
| 3-HHB(F,F)-F | 5.0% |
| 4-HHB(F,F)-F | 5.0% |
| 3-HH2B(F,F)-F | 15.0% |
| 3-HBB(F,F)-F | 12.0% |
| 5-HBB(F,F)-F | 12.0% |
| 3-HBCF20B(F,F)-F | 6.0% |

Characteristics of the composition were determined as follows:

TNI=70.8(° C.)

η=35.8(mPa.s)

Δn=0.092

Δε=9.9

Vth=1.43(V)

COMPOSITION EXAMPLE 22

| | |
|---|---|
| 101-HHB(F,F)-OCF3 (No. 153) | 10.0% |
| 5-H10BB(F,F)-OCF3 (No. 239) | 5.0% |
| 7-HB(F,F)-F | 5.0% |
| 3-H2HB(F,F)-F | 12.0% |
| 4-H2HB(F,F)-F | 10.0% |
| 3-HHB(F,F)-F | 10.0% |
| 4-HHB(F,F)-F | 5.0% |
| 3-HBB(F,F)-F | 10.0% |
| 4-HHEB(F,F)-F | 3.0% |
| 5-HHEB(F,F)-F | 3.0% |
| 2-HBEB(F,F)-F | 3.0% |
| 3-HBEB(F,F)-F | 5.0% |
| 5-HBEB(F,F)-F | 3.0% |
| 3-HGB(F,F)-F | 10.0% |
| 3-HHBB(F,F)-F | 6.0% |

Characteristics of the composition were determined as follows:

TNI=74.8(° C.)

η=39.5(mPa.s)

Δn=0.088

Δε=13.8

Vth=1.32(V)

COMPOSITION EXAMPLE 23

| | |
|---|---|
| 101-HHB(F,F)-OCF3 (No. 153) | 5.0% |
| 5-H10BB(F,F)-OCF3 (No. 239) | 5.0% |
| 5-H4HB(F,F)-F | 7.0% |
| 5-H4HB-OCF3 | 15.0% |
| 3-H4HB(F,F)-CF3 | 8.0% |
| 5-H4HB(F,F)-CF3 | 5.0% |
| 3-HB-CL | 6.0% |
| 5-HB-CL | 4.0% |
| 2-H2BB(F)-F | 5.0% |
| 3-H2BB(F)-F | 5.0% |
| 5-HVHB(F,F)-F | 5.0% |
| 3-HHB-OCF3 | 5.0% |
| 3-H2HB-OCF3 | 5.0% |
| V-HHB(F)-F | 5.0% |
| 3-HHB(F)-F | 5.0% |
| 5-HHEB-OCF3 | 2.0% |
| 3-HBEB(F,F)-F | 5.0% |
| 5-HH-V2F | 3.0% |

Characteristics of the composition were determined as follows:

TNI=69.3(° C.)

η=28.9(mPa.s)

Δn=0.093

Δε=8.8

Vth=1.67(V)

COMPOSITION EXAMPLE 24

| | |
|---|---|
| 5-H10BB(F,F)-OCF3 (No. 239) | 5.0% |
| 101-HHB(F,F)-OCF3 (No. 153) | 5.0% |
| 5-H01BB(F,F)-OCF3 (No. 241) | 5.0% |
| 3-HH10BB(F,F)-OCF3 (No. 692) | 3.0% |
| 5-BEB(F)-C | 5.0% |
| V-HB-C | 11.0% |
| 5-PyB-C | 6.0% |
| 4-BB-3 | 6.0% |
| 3-HH-2V | 2.0% |
| 5-HH-V | 11.0% |
| V-HHB-1 | 7.0% |
| V2-HHB-1 | 10.0% |
| 3-HHB-1 | 9.0% |
| 1V2-HBB-2 | 10.0% |
| 3-HHEBH-3 | 5.0% |

COMPOSITION EXAMPLE 25

| | |
|---|---|
| 3-B10B(F,F)-OCF3 (No. 122) | 3.0% |
| 3-H10B(F,F)-OCF3 (No. 118) | 3.0% |
| 3-HH10B(F,F)-OCF3 (No. 235) | 5.0% |
| 101-HVHB(F,F)-OCF3 (No. 165) | 5.0% |
| 1V2-BEB(F,F)-C | 8.0% |
| 3-HB-C | 10.0% |
| V2V-HB-C | 14.0% |
| V2V-HH-3 | 13.0% |
| 3-HB-02 | 4.0% |
| 3-HHB-1 | 10.0% |
| 3-HHB-3 | 9.0% |
| 3-HB(F)TB-2 | 4.0% |
| 3-HB(F)TB-3 | 4.0% |
| 3-H2BTB-3 | 4.0% |
| 3-H2BTB-4 | 4.0% |

COMPOSITION EXAMPLE 26

| | |
|---|---|
| 101-HGB(F,F)-OCF3 (No. 212) | 3.0% |
| 301-HB(F)B(F,F)-OCF3 (No. 202) | 3.0% |
| 101-H2HB(F,F)-OCF3 (No. 160) | 3.0% |
| 101-H2B(F,F)B(F,F)-OCF3 (No. 192) | 3.0% |
| 1V2-BEB(F,F)-C | 4.0% |
| 3-HB-C | 18.0% |
| 2-BTB-1 | 10.0% |
| 5-HH-VFF | 30.0% |
| 1-BHH-VFF | 6.0% |
| 1-BHH-2VFF | 11.0% |
| 3-H2BTB-2 | 5.0% |
| 3-HHB-1 | 4.0% |

COMPOSITION EXAMPLE 27

| | |
|---|---|
| 101-HHB(F,F)-OCF3 (No. 153) | 4.0% |
| 5-H10BB(F,F)-OCF3 (No. 239) | 4.0% |
| 101-HGB(F,F)-OCF3 (No. 212) | 4.0% |
| 5-H01BB(F,F)-OCF3 (No. 241) | 4.0% |

-continued

| | |
|---|---|
| 3-HH10B(F,F)-OCF3 (No. 235) | 4.0% |
| 101-HVHB(F,F)-OCF3 (No. 165) | 4.0% |
| 3-H2HB(F,F)-F | 7.0% |
| 3-HHB(F,F)-F | 10.0% |
| 4-HHB(F,F)-F | 5.0% |
| 3-HH2B(F,F)-F | 9.0% |
| 3-HBB(F,F)-F | 15.0% |
| 5-HBB(F,F)-F | 15.0% |
| 3-HBEB(F,F)-F | 2.0% |
| 4-HBEB(F,F)-F | 2.0% |
| 5-HBEB(F,F)-F | 2.0% |
| 3-HHEB(F,F)-F | 3.0% |
| 4-HHEB(F,F)-F | 3.0% |
| 5-HHEB(F,F)-F | 3.0% |

COMPOSITION EXAMPLE 28

| | |
|---|---|
| 101-HB(F,F)-OCF3 (No. 1) | 4.0% |
| 3-B10B(F,F)-OCF3 (No. 122) | 4.0% |
| 3-HH10BB(F,F)-OCF3 (No. 692) | 4.0% |
| 301-HB(F)B(F,F)-OCF3 (No. 200) | 4.0% |
| 101-H2B(F,F)B(F,F)-OCF3 (No. 192) | 4.0% |
| 5-HB-CL | 12.0% |
| 3-HH-4 | 7.0% |
| 3-HB-02 | 15.0% |
| 3-H2HB(F,F)-F | 8.0% |
| 3-HHB(F,F)-F | 3.0% |
| 3-HBB(F,F)-F | 6.0% |
| 3-HHB(F)-F | 5.0% |
| 2-H2HB(F)-F | 2.0% |
| 3-H2HB(F)-F | 1.0% |
| 5-H2HB(F)-F | 2.0% |
| 3-HHBB(F,F)-F | 4.0% |
| 3-HBCF20B-OCF3 | 4.0% |
| 5-HBCF20B(F,F)-CF3 | 4.0% |
| 3-HHB-1 | 3.0% |
| 3-HHB-01 | 4.0% |

COMPOSITION EXAMPLE 29

| | |
|---|---|
| 101-HHB(F,F)-OCF3 (No. 153) | 5.0% |
| 3-HH10B(F,F)-OCF3 (No. 235) | 5.0% |
| 301-HB(F)B(F,F)-OCF3 (No. 200) | 10.0% |
| 101-H2HB(F,F)-OCF3 (No. 160) | 10.0% |
| 101-H2B(F,F)B(F,F)-OCF3 (No. 192) | 10.0% |
| 2-HHB(F)-F | 17.0% |
| 3-HHB(F)-F | 17.0% |
| 5-HHB(F)-F | 12.0% |
| 3-H2HB(F)-F | 5.0% |
| 3-HBB(F)-F | 6.0% |
| 5-HBB(F)-F | 3.0% |

COMPOSITION EXAMPLE 30

| | |
|---|---|
| 101-HHB(F,F)-OCF3 (No. 153) | 5.0% |
| 5-H10BB(F,F)-OCF3 (No. 239) | 5.0% |
| 5-H01BB(F,F)-OCF3 (No. 241) | 5.0% |
| 3-HH10B(F,F)-OCF3 (No. 235) | 5.0% |
| 3-HH10BB(F,F)-OCF3 (No. 692) | 5.0% |
| 301-HB(F)B(F,F)-OCF3 (No. 200) | 10.0% |
| 101-H2HB(F,F)-OCF3 (No. 160) | 5.0% |
| 101-H2B(F,F)B(F,F)-OCF3 (No. 192) | 10.0% |
| 7-HB(F,F)-F | 5.0% |
| 3-HHB(F,F)-F | 10.0% |
| 3-HBB(F,F)-F | 10.0% |

-continued

| | |
|---|---|
| 3-HHEB(F,F)-F | 8.0% |
| 4-HHEB(F,F)-F | 3.0% |
| 5-HHEB(F,F)-F | 3.0% |
| 2-HBEB(F,F)-F | 3.0% |
| 3-HBEB(F,F)-F | 5.0% |
| 5-HBEB(F,F)-F | 3.0% |

Compounds of the present invention expressed by the general formula (1) can be produced by known methods of ordinary organic synthesis as illustrated below.

(A) Production of compounds expressed by the general formula (1) in which $B_3$ a single bond and $A_3$ is 1,4-cyclohexylene group:

An alcohol expressed by (24-1) or (25-1) can easily be synthesized by reacting ketone (19) with compounds (22) or (23) which are prepared from 4-bromo-2,6-difluorotrifluoromethoxybenzene (20) or 4-bromo-2,6-difluorobenzene (21) according to the method described in Jikken Kagaku Koza, Vol.20, p96, Maruzen. Herein, the compound (19) can easily be synthesized according to the similar methods described in Organic Functional Group Preparations, Vol.1, p206, Academic Press or The Fourth Edition of Jikken Kagaku Koza, Vol.21, p149, Maruzen.

Then, cyclohexene derivative expressed by (24-2) or (25-2) can easily be synthesized by dehydrating thus obtained alcohol in the presence of an acid catalyst such as toluene sulfonic acid according to the conventional method.

The derivative compound can then be reduced in the presence of such a catalyst as Raney nickel according to the conventional method, to synthesize easily a compound which has trifluoromethyl group as Rf in the general formula (1) or a compound shown by (25-3).

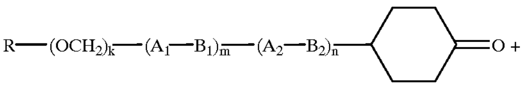

(19)

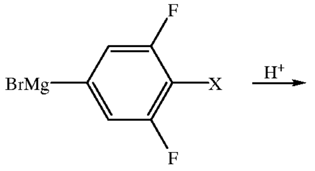

(22); X = $OCF_3$
(23); = H

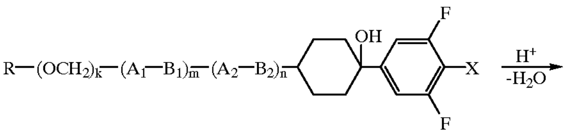

(24-1); X = $OCF_3$
(25-1): X = H

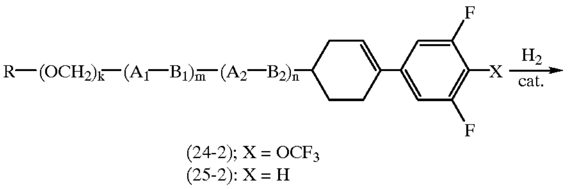

(24-2); X = $OCF_3$
(25-2): X = H

-continued

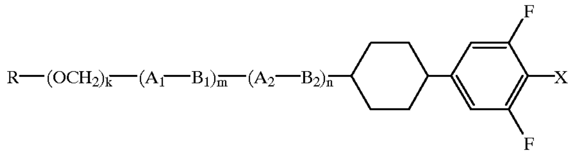

(1); X = $OCF_3$
(25-3): X = H wherein R, $A_1$, $A_2$, $B_1$, $B_2$, k, m and n have the same meanings as above.

The compound (25-3) is further converted into a compound expressed by the general formula (1) by carrying out the following reactions. That is, the compound (25-3) is reacted with n-BuLi, followed by reaction with triisopropyl borate, and then treated with an acid according to the method described in The Chemistry of Boron, Academic Press, New York, (1961), which shares similar method described as above to be converted into compound (25-4). The said compound is reacted with hydrogen peroxide according to the method described in Tetrahedron Lett., 21, 3435 (1980) or so to be converted into a phenol derivative expressed by (25-5), and this derivative is easily converted into a compound expressed by the general formula (1) according to known methods.

That is, compounds expressed by the general formula (1) wherein Rf is $CF_2H$, $C_2F_5$, $CHFCF_3$, $CF_2CF_2H$, $CH_2CF_3$, $CHFCF_2H$, $CH_2CF_2H$, $CF_2CH_3$, $CF_2CFHCF_3$, $CH_2CF_2CF_2H$, $CF_2CH_2CF_3$, $CF_2CH_2CH_3$ or $CH_2CH_2CF_3$ can easily be synthesized according to the known methods described in DE 4027840 A1, WO 9426338 A1, DE 4445224 A1, DE 19528085 A1, DE 4142519 A1, DE 4222371 A1, DE 19531165 A1, WO 9221734 A1, WO 9212928 A1, WO Laid-open Japanese Patent Publication No. Hei 8-510220, Laid-open Japanese Patent Publication No. Hei 7-18184 or Laid-open Japanese Patent Publication No. Hei 6-40988.

(25-3)

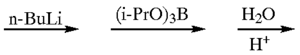

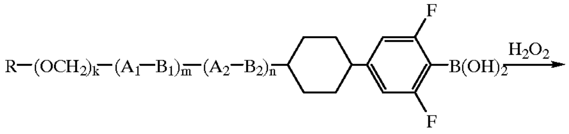

(25-4)

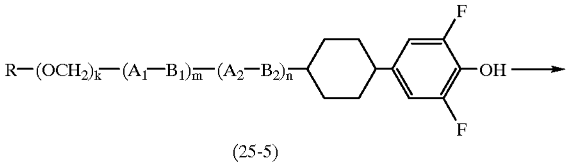

(25-5)

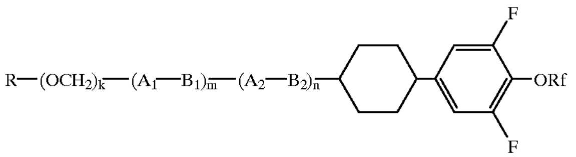

(1)

wherein R, $A_1$, $A_2$, $B_1$, $B_2$, k, m, n and Rf have the same meanings as above.

Further, compounds in which Rf is $CF_2CF_2CH_3$ or $CFHCF_2CF_3$ can easily be synthesized by the following methods. That is, in the case of $CF_2CF_2CH_3$, the compound (25-5) is converted into a compound (25-6) according to the method described in J. Chem. Soc. Perkin Trans. 1, 439 (1994) etc., and then the compound (25-6) is converted into the objective compound by fluorination of carbonyl oxygen thereof with $SF_4/HF$ or so according to the similar method described in WO 9426838 A1 etc.

In the case of $CFHCF_2CF_3$, the compound (25-5) is converted into a compound (25-7) according to the similar method described in DE 4445224 A1 etc., and then the compound (25-7) is converted into the objective compound by fluorination of hydroxide group thereof with diethyl aminosulfate trifluoride (DAST) or so.

(25-5)

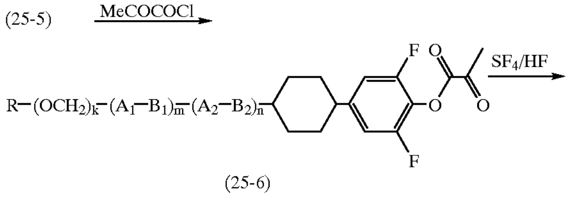

(25-6)

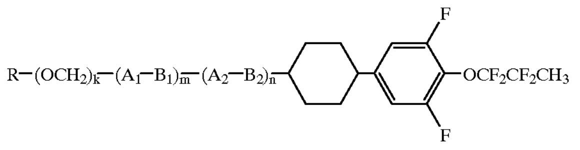

(25-5)

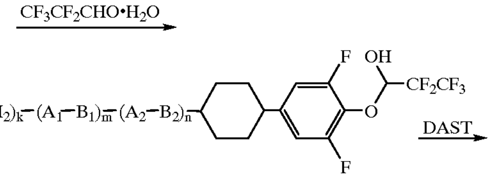

(25-7)

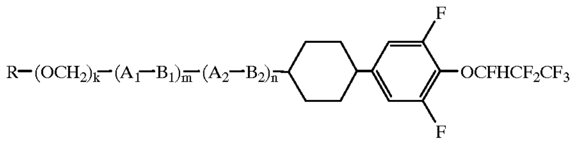

wherein R, $A_1$, $A_2$, $B_1$, $B_2$, k, m and n have the same meanings as above.

(B) Production of compounds expressed by the general formula (1) in which $B_3$is a single bond and $A_3$ is 1,4-phenylene or pyrimidine-2, 5-diyl group in each of which any hydrogen atom on the rings may optionally be substituted with a fluorine atom:

A compound (1) or (29) can easily be synthesized by reacting a halide (26) with a boric acid derivative (27) or (28) in the presence of a palladium catalyst or so according to the method described in Comprehensive Organometallic Chemistry, Vol.12, p 192, Pergamon etc.

Herein, the compound (26) can easily be synthesized according to the similar method described in Organic Functional Group Preparations, Vol.1, p148, Academic Press and Shin Jikken Kagaku Koza, Vol.14, p307, Maruzen etc., and the compound (27) or (28) can easily be synthesized according to the similar method described in The Fourth Edition of Jikken Kagaku Koza 24, Organic Synthesis VI, p80, Maruzen.

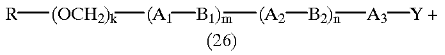

(26)

-continued

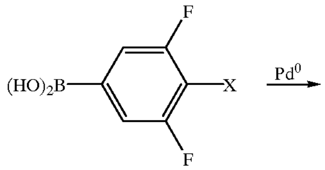

(27); X = $OCF_3$
(28); = H

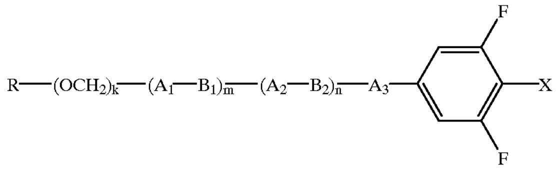

(1); X = $OCF_3$
(29); = H wherein R, $A_1$, $A_2$, $A_3$, $B_1$, $B_2$, k, m and n have the same meanings as above, and Y denotes halogen or trifluoromethanesulfonate group.

Furthermore, the compound (29) is easily converted into the compound expressed by the general formula (1) by carrying out the similar reactions to the above-mentioned (25-3).

The said compound can easily be synthesized by the following method. That is, the compound (1) or (29) can easily be synthesized by reacting a zinc complex (30) with compound (20) or (21) in the presence of a palladium catalyst or a platinum catalyst or so.

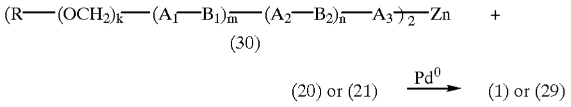

(30)

(20) or (21) (1) or (29)

wherein R, $A_1$, $A_2$, $A_3$, $B_1$, $B_2$, k, m, and n have the same meanings as above.

(C) Production of compounds expressed by the general formula (1) in which $B_3$ is a single bond and $A_3$ is dioxane-2, 5-diyl group:

A compound (1) or (34) can easily be synthesized by dehydrating and condensing diol (31) with aldehyde (32) or (33) in the presence of an acid catalyst such as toluenesulfonic acid according to the method described in J. Chem. Soc., Perkin Trans. I, 158, (1979) etc. Herein, the compound (31) can easily be synthesized according to the similar method described in Org. Chem., 32, 113 (1967) etc., and the compound (32) can easily be synthesized from (20) according to the similar method described in Comprehensive Organic Functional Group Transformations, Vol.3, p1, Pergamon etc.

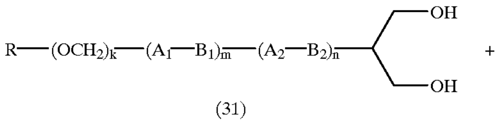

(31)

-continued

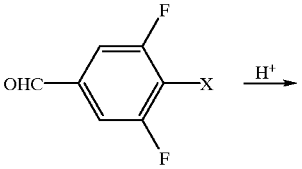

(32); X = $OCF_3$
(33); = H

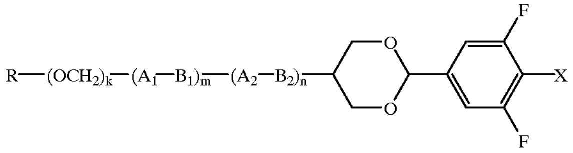

(1); X = $OCF_3$
(34); = H wherein R, $A_1$, $A_2$, $B_1$, $B_2$, k, m and n have the same meanings as above.

The compound (34) can easily be converted into the compound expressed by the general formula (1) by carrying out the similar reactions to the above-mentioned (25-3).

(D) Production of compounds expressed by the general formula (1) in which $B_3$ is 1,2-ethylene, (E)-1,2-ethenylene or 1,4-butylene group:

A compound expressed by the general formulae (1), (36-2) or (37-2) can easily be synthesized by the similar method to (A) above-mentioned. Herein, the compound (35) can easily be synthesized according to the similar method described in Comprehensive Organic Functional Group Transformations, Vol.3, p 1, Pergamon and Shin Jikken Kagaku Koza, Vol. 14, p633, Maruzen etc.

$R-(OCH_2)_k-(A_1-B_1)_m-(A_2-B_2)_n-A_3-(CH_2)_r-CHO$ +
(35)

(22) (23)

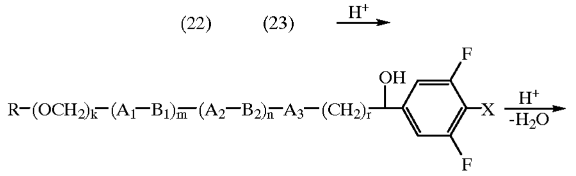

(36-1); X = $OCF_3$
(37-1); = H

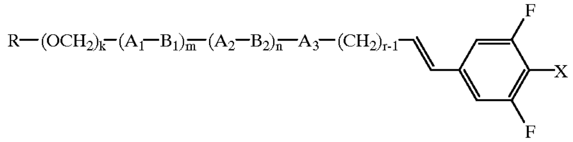

(1) or (36-2); X = $OCF_3$
(37-2); = H wherein R, $A_1$, $A_2$, $A_3$, $B_1$, $B_2$, k, m and n have the same meanings as above.

The compound (37-2) can easily be converted into the compound expressed by the general formula (1) in which $B_3$ is (E)-1,2-ethenylene group by carrying out the similar reactions to the above-mentioned (25-3).

The compound (36-2) or (37-2) is easily converted into the compound expressed by the general formula (1) or (37-3) in which $B_3$ is 1,2-ethylene or 1,4-butylene group by hydrogenation.

(36-2) or (37-2)

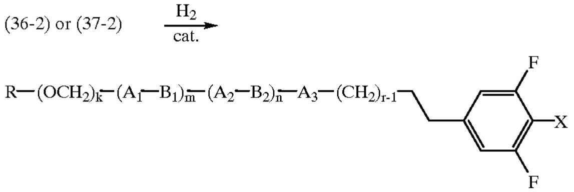

(1); X = $OCF_3$
(37-3); = H wherein R, $A_1$, $A_2$, $A_3$, $B_1$, $B_2$, k, m and n have the same meanings as above and r denotes 1 or 3.

The compound (37-3) can easily be converted into the compound expressed by the general formula (1) in which $B_3$ is 1,2-ethylene or 1,4-butylene group by carrying out the similar reactions to the above-mentioned.

(E) Production of compounds expressed by the general formula (1) in which $B_3$ is 1,2-ethynylene group:

By converting the above-mentioned compound (36-2) or (37-2) into (36-4) or (37-4) according to the method described in J. Am. Chem. Soc., 89, 6149 (1967) etc. and then treating them with a base, the compound (1) or (37-5) in which $B_3$ is 1,2-ethynylene group can easily be obtained.

(36-2) or (37-2)

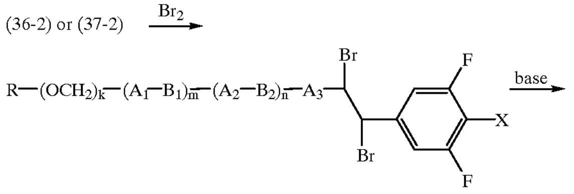

(36-4); X = $OCF_3$
(37-4); = H (1); X = $OCF_3$
(37-5); = H wherein R, $A_1$, $A_2$, $A_3$, $B_1$, $B_2$, k, m and n have the same meanings as above.

The compound (37-5) can easily be converted into the compound expressed by the general formula (1) by carrying out the similar reactions to the above.

(F) Production of compounds expressed by the general formula (1) in which $B_3$ is oxymethylene group:

A compound (1) or (41) can easily be synthesized by reacting alcohol (38) with halide (39) or (40) according to the method described in Comprehensive Organic Functional Group Transformations, Vol. 2, p88, Pergamon etc. Herein, the compound (38) can easily be synthesized according to the similar method described in Comprehensive Organic Functional Group Transformations, Vol.2, p37, Pergamon etc., and the compound (39) or (40) can easily be synthesized from the compound (20) or (21) above-mentioned and according to the similar method described in J. Am. Chem. Soc., 89, 6149 (1967) and Shin Jikken Kagaku Koza, Vol.14, p307, Maruzen etc.

$R-(OCH_2)_k-(A_1-B_1)_m-(A_2-B_2)_n-A_3-OH$ +
(38)

-continued

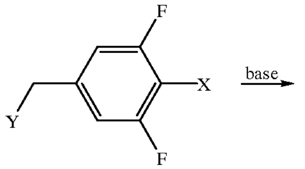

(39); X = OCF3
(40); = H

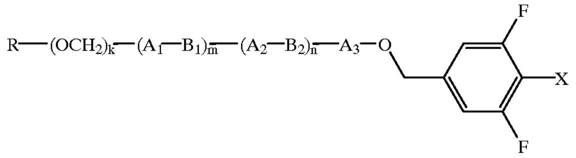

(1); X = OCF3
(41); = H wherein R, $A_1$, $A_2$, $A_3$, $B_1$, $B_2$, k, m, n and Y have the same meanings as above.

The compound (41) can easily be converted into the compound expressed by the general formula (1) by carrying out the similar reactions as above.

(G) Production of compounds expressed by the general formula (1) in which $B_3$ is methyleneoxy group:

A compound (1) or (45) can easily be synthesized according to the similar method as above-mentioned (F). Herein, the compound (43) can easily be synthesized according to the similar method described in J. Am. Chem. Soc., 79, 5659 (1957).

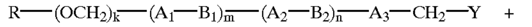

(42)

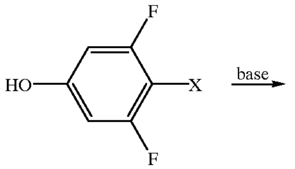

(43); X = OCF3
(44); = H

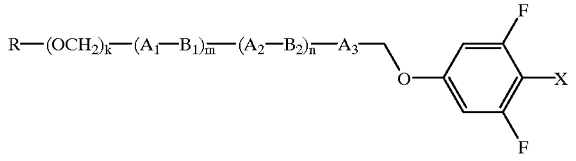

(1); X = OCF3
(45); = H wherein R, $A_1$, $A_2$, $A_3$, $B_1$, $B_2$, k, m, n and Y have the same meanings as above.

The compound (45) can easily be converted into the compound expressed by the general formula (1) by carrying out the similar reactions as above-mentioned (25-3).

(H) Production of compounds expressed by the general formula (1) in which $B_3$ is carbonyloxy group:

The compound expressed by the general formula (1) in which Rf is trifluoromethyl group can easily be synthesized by condensing carboxylic acid (46) and the compound (43) above-mentioned in the presence of dicyclohexylcarbdiimide or so according to the method described in Jikken Kagaku Koza, Vol.22, p43, Maruzen. Herein, the compound (46) can easily be synthesized according to the similar method described in Organic Functional Group Preparations, Vol.1, p236, Academic Press etc.

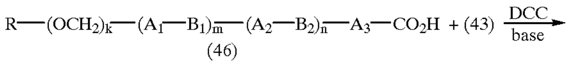

(46)

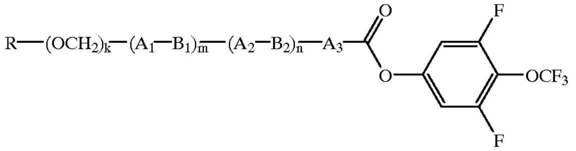

wherein R, $A_1$, $A_2$, $A_3$, $B_1$, $B_2$, k, m and n have the same meanings as above.

The compounds in which Rf is other than trifluoromethyl group can be synthesized by the following method.

That is, the compound (47) derived from 3,5-difluorophenol is let to a similar reaction as that of (25-3) above-mentioned to synthesize a compound (48), and then the benzyl group of the compound (48) is deprotected by hydrogenation to synthesize easily the phenol expressed by (49).

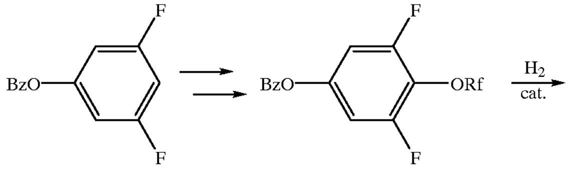

(47) (48)

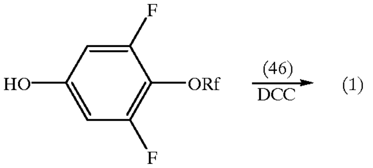

(49)

wherein Rf has the same meaning as above.

Also, those in which ring A is a silacyclohexane ring can be synthesized by using the starting compounds of the general formulae (19), (26), (30), (31), (35), (38), (42) and (46) prepared according to the method described in Laid-open Japanese Patent Publication No.Hei 7-70148 and Laid-open Japanese Patent Publication No.Hei 8-239388 etc.

After the reaction, the above-mentioned compound (1) is let to a conventional after-treatment and then to operations such as distillation, recrystallization, column chromatography or so, to be purified and isolated.

EXAMPLE

The following examples illustrate the present invention in more detail without limiting it to those examples. In every examples, C denotes crystals, N denotes a nematic phase, S denotes a smectic phase, I denotes isotropic liquid, and the phase transition temperatures are all given by unit of ° C.

Example 1

Synthesis of 2,6-difluoro-4-(trans-4-(trans-4-methoxymethyl cyclohexyl) cyclohexyl) trifluoromethoxybenzene (compound expressed by the general formula (1) wherein R is methyl group, k=1, m=0, n=1, $A_2$ and $A_3$ are both 1,4-cyclohexylene groups, $B_2$ and $B_3$ are both single bonds, and Rf is triiluoromethyl group (Compound No. 153))

No. 153

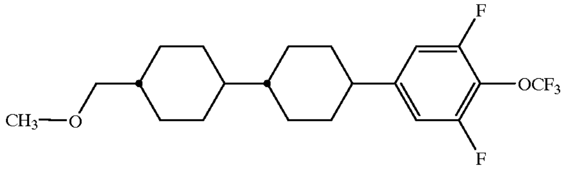

1.2 g (49 mmol) of magnesium was added in tetralydrofuran (hereinafter abbreviated to THF, 50 ml), and 13 g (47 mmol) of 4-bromo-2,6-difluorotrifluoromethoxybenzene dissolved in THF (80 ml) was dropwise added thereto, followed by stirring at a room temperature for 1.5 hours. To the reaction solution was dropwise added 10 g (45mmol) of 4-(4-methoxymethylcyclohexyl) cyclohexanone dissolved in THF (80 ml) and reaction was carried out at a room temperature for one night. This reaction solution was added with a saturated aqueous ammonium chloride solution (180 ml) and then extracted twice with toluene (100 ml). The organic layer thus obtained was washed with brine (200 ml), dried over anhydrous magnesium sulphate and filtered, and the solvent therein was distilled off under a reduced pressure. The compound thus obtained was used for subsequent reaction without any purification. 18 g (yield 96%).

18 g (43 mmol) of the alcohol derivative obtained above and 3.0 g (22 mmol) of potassium hydrogen sulfate were refluxed in toluene for 3 hours with removing produced water. After cooling, the reaction solution was filtered and the solvent therein was distilled off under a reduced pressure.

The residue thus obtained was purified by column chromatography (silica gel/toluene) and recrystallization (heptane) to obtain colorless crystals of 2,6-difluoro-4-(4-(trans-4-methoxymethylcyclohexyl)-1-cyclohexenyl) trifluoromethoxybenzene.

6.9 g (yield 40%).

6.8 g (17 mmol) of this compound was dissolved in a mixed solvent of toluene-alcohol (1/1 v/v, 200 ml) and hydrogenated in the presence of a Raney nickel catalyst for one night (under hydrogen pressure of 800 kPa). The reaction mixture was filtered and the solvent therein was distilled off under a reduced pressure. The residue thus obtained was purified by column chromatography (silica gel/toluene) and recrystallization heptane) to obtain objective colorless crystals of 2,6-difluoro-4-(trans-4-(trans-4-methoxymethylcyclohexyl) cyclohexyl)trifluoromethoxy benzene.

4.2 g (yield 61%).

Various spectral data of this compound and intermediate compounds in respective step well support the constitutions thereof.

Phase transition temperature C·76.0·N99.9·I

MS m/e =406 (M+). 1H NMR: δ (ppm) 6.84 (dd, 2H, J=11.0, 2.0 Hz), 3.33 (s, 3H), 3.18 (d, 2H, J=6.1 Hz), 2.7–0.5 (m, 20H).

19F NMR; δ (ppm) −60.3 (3F) −126.1 (2F).

Example 2

Synthesis of 2,6-difluoro-4-(4-(trans-4-methoxymethylcyclohexyl)-2,6-difluorophenyl) trifluoromethoxy benzene (compound expressed by the general formula (1) wherein R is methyl group, k=1, m=0, n=1, $A_2$ is 1,4-cyclohexylene group, $A_3$ is 3,5-difluoro-1,4-phenylene group, $B_2$ and $B_3$ are single bonds, and Rf is trifluoromethyl group (Compound No. 187))

No. 187

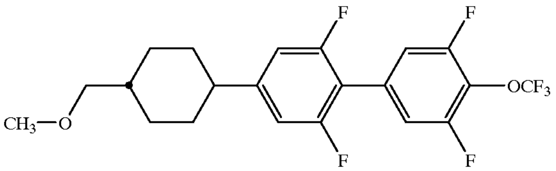

9.2 g (39 mmol) of 3,5-difluoro-1-(4-methoxymethyl) cyclohexyl benzene was dissolved in THF (80 ml). This solution was added with 28 ml of n-BuLi containing hexane solution (1.65M) (46.2 mmol) at a temperature of −60° C. or lower and was stirred for 20 minutes. To the reaction mixture, 93 ml of zinc chloride containing THF solution (0.5M) (96.5 mmol) was added at a temperature of −45° C. or lower and the solution was stirred until the time when the mixture was warmed up to a room temperature.

To the reaction mixture, 13 g (47 mmol) of 4-bromo-2,6-difluorotrifluoromethoxybenzene and 1.0 g (0.86 mmol) of tetrakistriphenylphosphine palladium (0) both dissolved in THF (50 ml) were added and the reaction mixture was refluxed for 5 hours. After cooling, 3N HCl (100 ml) was added thereto to separate an organic layer, while an aqueous layer was further extracted with toluene (200 ml). The organic layer was washed with a saturated sodium hydrogen carbonate solution (150 ml), then dried over anhydrous magnesium sulfate and filtered, and the solvent therein was distilled off under a reduced pressure.

The residue thus obtained was purified by column chromatography (silica gel/toluene: ethyl acetate=20:1) and to obtain colorless crystals of 2,6-difluoro-4-(4-(trans-4-methoxymethylcyclohexyl)-2,6-difluorophenyl) trifluoromethoxybenzene.

2.1 g (yield 12%).

Various spectral data of this compound and intermediate compounds in respective step well support the constitutions thereof.

Phase transition temperature C·75.4·I MS m/e=436 (M+). 1H NMR: δ (ppm) 6.8–7.0, 7.0–7.3 (m, 4H), 3.36 (s, 3H), 3.25(d, 2H, 5.7 Hz), 2.8–0.8 (m, 10H). 19F NMR; δ (ppm) −60.1 (3F), −115.3 (2F), −125.6 (2F).

Example 3

Synthesis of 2,6-difluoro-4-(4-(trans-4-pentylcyclohexyl) methoxyphenyl) trifluoromethoxybenzene (compound expressed by the general formula (1) wherein R is pentyl group, k=0, m=0, n=1, $A_2$ is 1,4-cyclohexylene group, $A_3$ is 1,4-phenylene group, $B_3$ is methyleneoxy group, $B_3$ is a single bond, and Rf is trifluoromethyl group (Compound No. 239)

No. 239

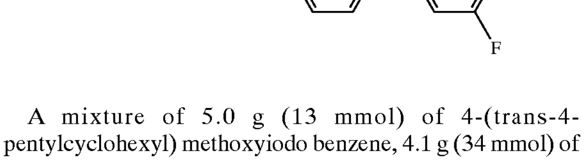

A mixture of 5.0 g (13 mmol) of 4-(trans-4-pentylcyclohexyl) methoxyiodo benzene, 4.1 g (34 mmol) of dihydroxy (3,5-difluoro-4-trifluoromethoxyphenyl) borane, 3.0 g of 5% palladium on activated charcoal and 7.2 g (136 mmol) of sodium carbonate was refluxed in toluene/alcohol/water (1/1/1 v/v, 75 ml) under a nitrogen atmosphere for 3 days. After cooling, the reaction solution was added with water (100 ml) and extracted twice with toluene (100 ml). An organic layer was dried over anhydrous magnesium sulfate, filtered and the solvent therein was distilled off under a reduced pressure. The residue thus obtained was purified by column chromatography (silica gel/heptane:toluene=5:1) and recrystallization (heptane-ethanol) to obtain colorless crystals of 2,6-difluoro-4-(4-(trans-4-pentylcyclohexyl) methoxyphenyl) trifluoromethoxybenzene.

3.7 g (yield 62%).

Various spectral data of this compound and intermediate compounds in respective step well support the constitutions thereof.

Phase transition points C·67.4·N·83.9·I MS m/e=456 (M+). 1H NMR: δ (ppm) 7.6–7.4, 7.3–6.8 (m, 6H), 3.79 (d, 2H, J=5.7 Hz), 2.2–0.6 (m, 21H). 19F NMR; δ (ppm) −60.3 (3F), −125.2 (2F).

Example 4

Synthesis of 2,6-difluoro-4-(trans-4-(trans-4-methoxymethyl cyclohexyl) cyclohexyl) difluoromethoxybenzene (compound expressed by the general formula (1) wherein R is methyl group, k=1, m=0, n=1, $A_2$ and $A_3$ are both 1,4-cyclohexylene groups, $B_2$ and $B_3$ are both single bonds, and Rf is difluoromethyl group (Compound No. 269))

1.5 g (62 mmol) of magnesium was added to THF (50 ml), and the resultant solution was dropwise added with 11 g (57 mmol) of 3,5-difluorobromobenzene dissolved in THF (50 ml) and was stirred at a room temperature for one hour.

The reaction solution was dropwise added with 12 g (55 mmol) of 4-(4-methoxymethyl cyclohexyl) cyclohexanone dissolved in THF (100 ml), reacted at a room temperature overnight and then let to a similar after-treatments as described in Example 1 to obtain the objective compound. This compound was used for the subsequent reaction without any purification. 18 g (yield 97%).

18 g (54 mmol) of the alcohol derivative obtained above and 2.0 g (11 mmol) of p-toluenesulfonic acid were refluxed in toluene for 2 hours with removing produced water. After cooling, the reaction solution was filtered and the solvent therein was distilled off under a reduced pressure. The residue thus obtained was purified by column chromatography (silica gel/toluene) to obtain colorless crystals of 3,5-difluoro-1-(4-(trans-4-methoxymethylcyclohexyl)-1-cyclohexenyl) benzene.

12 g (yield 67%).

12 g (36 mmol) of this compound was dissolved in a mixed solvent of toluene-alcohol (1/1 v/v, 200 ml) and hydrogenated in the presence of a Raney nickel catalyst for two days (under hydrogen pressure of 800 kPa). The reaction mixture was filtered and the solvent therein was distilled off under a reduced pressure. The residue thus obtained was purified by recrystallization (heptane-ethanol) to obtain colorless crystals of 3,5-difluoro-1-(trans-4-(trans-4-methoxymethylcyclohexyl) cyclohexyl) benzene.

6.3 g (yield 54%).

5.0 g (16 mmol) of this compound was dissolved in THF (50 ml). This solution was added with 11 ml of n-BuLi containing hexane solution (1.65M) (19 mmol) at a temperature of −60° C. or lower and was stirred at the same temperature for 20 minutes. To the reaction mixture, 4.3 ml (19 mmol) of triisopropyl borate dissolved in THF (30 ml) was dropwise added at a temperature of −50° C. or lower. After the addition, a dry ice bath was removed and the mixture was let to stand until time when it was cooled down to a room temperature. The reaction mixture was added with water (40 ml) at a temperature of −30° C. or lower and stirred at a room temperature for 1 hour, and added further with aqueous 3N HCl solution (40 ml) and reacted at a room temperature for 2 hours. After separation of an organic layer, an aqueous layer was further extracted with ether (100 ml). The organic layer was washed with saturated brine (100 ml), dried over anhydrous magnesium sulfate and filtered, and the solvent therein was distilled off under a reduced pressure. This obtained compound was-used for subsequent reaction without any purification.

5.1 g (yield 90%).

5.1 g (14 mmol) of this boronic acid derivative was dissolved in THF (50 ml) and 36% aqueous hydrogen peroxide solution (3.2 ml) was added thereto at 0° C., followed by stirring for 36 hours. The reaction mixture was added with a saturated aqueous sodium thiosulfate solution (40 ml) and reacted at a room temperature for 15 minutes, added with 3N HCl aqueous solution (40 ml) and then extracted with ethyl acetate (50 ml) three times. The organic layer was washed with saturated brine (50 ml), dried over anhydrous magnesium sulfate and filtered, and the solvent therein was distilled off under a reduced pressure.

The residue thus obtained was recrystallized with toluene to obtain colorless crystals of 2,6-difluoro-4-(trans-4-(trans-4-methoxymethylcyclohexyl) cyclohexyl) phenol.

3.1 g (yield 66%).

3.0 g (8.9 mmol) of this compound, 2.2 g (55 mmol) of NaOH and 110 mg (0.63 mmol) of $Na_2S_2O_4$ were dissolved in a mixed solvent of dioxaneisopropanol-water (1/1/1 v/v/v 30 ml), and the solution was stirred at 60° C. for 9 hours after the vessel containing the contents was purged with $CHF_2Cl$ gas.

2.2 g (55 mmol) of NaOH and 110 mg (0.63 mmol) of $Na_2S_2O_4$ were added to the reaction mixture, and the mixture was further stirred at 60° C. for overnight after the vessel was purged with $CHF_2Cl$ gas. After cooled, the reaction mixture was added with 3N HCl aqueous solution (150 ml) and extracted with toluene (150 ml). The organic layer was washed with an aqueous sodium hydrogen carbonate solution (150 ml), dried over anhydrous magnesium sulfate and filtered. The solvent therein was distilled off under a reduced pressure and the residue thus obtained was purified by column chromatography (silica gel/toluene) and recrystallization (heptane-ethanol) to obtain colorless crystals of 2,6-difluoro-4-(trans-4-(trans-4-methoxymethylcyclohexyl) cyclohexyl) difluoromethoxybenzene.

1.8 g (yield 53%).

Various spectral data of this compound and intermediate compounds in respective step well support the constitutions thereof.

No. 269

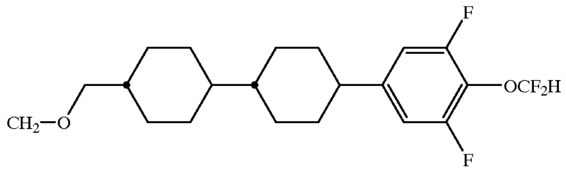

Phase transition temperature C·57.9·N·101.7·I MS m/e=388 (M+). 1H NMR: δ (ppm) 7.0–6.7 (m, 4H), 6.53 (t, 1H, J=74.1 Hz), 3.33 (s, 3H), 3.18 (d, 2H, J=5.9 Hz), 2.7–0.5 (m, 20H). 19F NMR; δ (ppm) −82.8 (2F), −126.9 (2F).

Example 5

Synthesis of 4-(2-(4-(4-ethoxymethylcyclohexyl) cyclohexyl) ethyl) phenyl)-2,6-difluorotrifluoromethoxybenzene (compound expressed by the general formula (1) wherein R is ethyl group, k=1, m=n=1, $A_1$ and $A_2$ are 1, 4-cyclohexylene groups, $A_3$ is 1,4-phenylene group, $B_1$ and $B_3$ are single bonds, $B_2$ is 1,2-ethylene group and Rf is trifluoromethyl group (Compound No. 615)

6.3 g (13 mmol) of 4-(2-(4-(4-ethoxymethylcyclohexyl) cyclohexyl) ethyl) trifluoromethylsulfonyloxybenzene, 4.2 g (17 mmol) of dihydroxy (3,5-difluoro-4-trifluoromethoxyphenyl) borane, 5% palladium on activated charcoal (1.0 g) and 5.7 g (54 mmol) of sodium carbonate were refluxed in toluene/alcohol/water (1/1/1 v/v, 80 ml) under a nitrogen atmosphere for 3 days. After cooling, the reaction solution was added with water (150 ml) and extracted twice with toluene (150 ml). An organic layer was dried over anhydrous magnesium sulfate, filtered and the solvent therein was distilled off under a reduced pressure. The residue thus obtained was purified by column chromatography (silica gel/heptane:toluene=5:1) and recrystallization (heptane-ethanol) to obtain colorless crystals of 4-(4-(2-(4-(4-ethoxymethylcyclohexyl)cyclohexyl)ethyl) phenyl)- 2,6-difluorotrifluoromethoxybenzene.

2.4 g (yield 35%).

Various spectral data of this compound and compounds in respective step well support the constitutions thereof.

No. 615

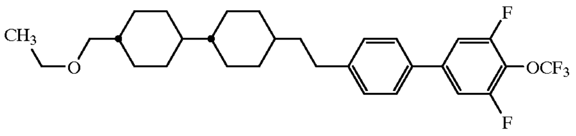

The following compounds 1 to 1252 can be prepared in accordance with the methods of Examples 1 to 5 abovementioned.

k = 1, m = n = 0, $R_1$ = $CF_3$
| No. | R | $A_3$ | $B_3$ |
|---|---|---|---|
| 1 | CH3 | 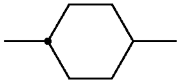 | — |
| 2 | n-$C_3H_7$ | 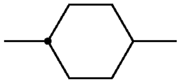 | — |
| 3 | n-$C_5H_{11}$ | 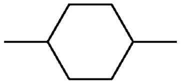 | — |
| 4 | $CH_3$ | 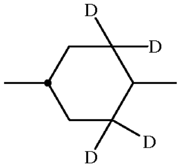 | — |
| 5 | $CH_3$ | 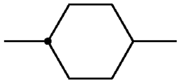 | 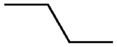 |
| 6 | n-$C_3H_7$ | 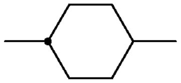 | 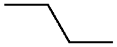 |
| 8 | $CH_3$ | 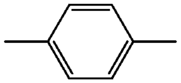 | — |
| 9 | n-$C_3H_7$ | 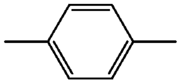 | — |

-continued
| | | | |
|---|---|---|---|
| 10 | $CH_3$ | 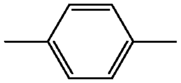 | 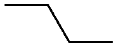 |
| 11 | n-$C_3H_7$ | 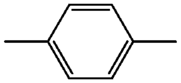 | 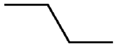 |
| 12 | $CH_3$ | 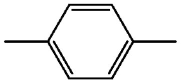 | 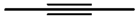 |
| 13 | $CH_3$ | 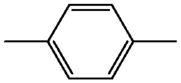 | 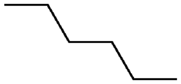 |
| 14 | $CH_3$ | 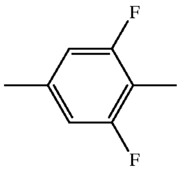 | — |
| 15 | n-$C_3H_7$ | 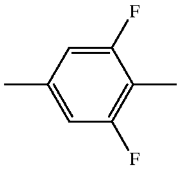 | — |
| 16 | $CH_3$ | 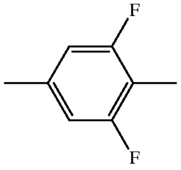 | 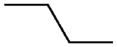 |

-continued
| | | | |
|---|---|---|---|
| 17 | n-$C_3H_7$ | 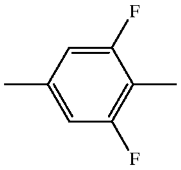 | 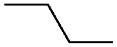 |
| 19 | n-$C_3H_7$ | 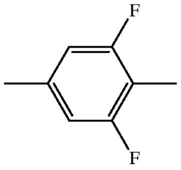 | 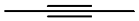 |
| 20 | $CH_3$ | 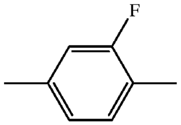 | — |
| 21 | n-$C_3H_7$ | 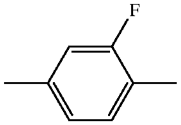 | 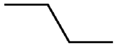 |
| 23 | $CH_3$ | 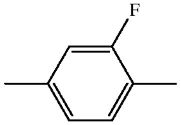 | 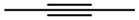 |
| 24 | $CH_3$ | 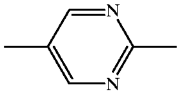 | — |
| 25 | $CH_3$ | 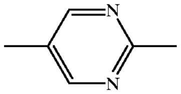 | 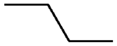 |

-continued
| | | | |
|---|---|---|---|
| 26 | $CH_3$ | 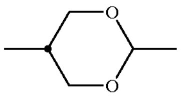 | — |
| 27 | n-$C_3H_7$ | 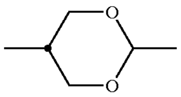 | — |
| 28 | $CH_3$ | 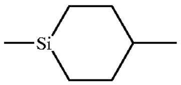 | 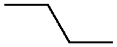 |
| 29 | CH3 | 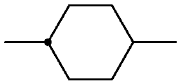 | — |
| 30 | n-$C_3H_7$ | 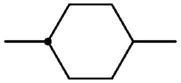 | — |
| 31 | n-$C_5H_{11}$ | 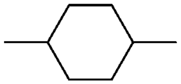 | — |
| 32 | $CH_3$ | 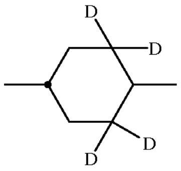 | — |
| 33 | $CH_3$ | 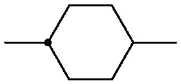 | 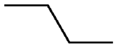 |

-continued
| | | | |
|---|---|---|---|
| 34 | n-$C_3H_7$ | 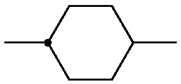 | 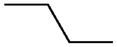 |
| 36 | $CH_3$ | 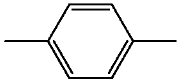 | — |
| 37 | n-$C_3H_7$ | 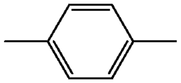 | — |
| 38 | $CH_3$ | 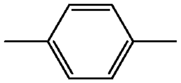 | 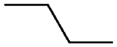 |
| 39 | n-$C_3H_7$ | 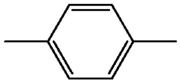 | 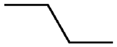 |
| 40 | $CH_3$ | 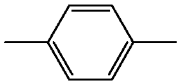 | 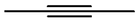 |
| 41 | $CH_3$ | 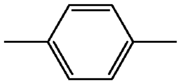 | 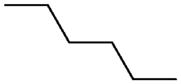 |
| 42 | $CH_3$ | 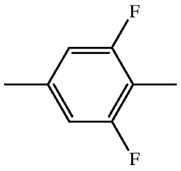 | — |

-continued
| | | | |
|---|---|---|---|
| 43 | n-$C_3H_7$ | 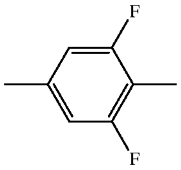 | — |
| 44 | $CH_3$ | 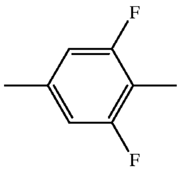 | 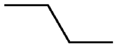 |
| 45 | n-$C_3H_7$ | 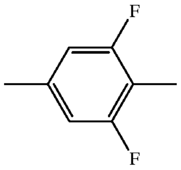 | 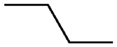 |
| 47 | n-$C_3H_7$ | 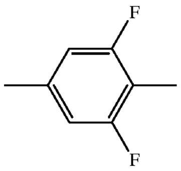 | 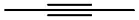 |
| 48 | $CH_3$ | 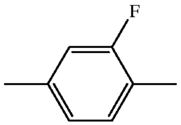 | — |
| 49 | n-$C_3H_7$ | 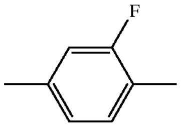 | 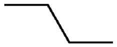 |

-continued
| | | | |
|---|---|---|---|
| 51 | $CH_3$ | 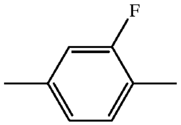 | 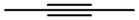 |
| 52 | $CH_3$ | 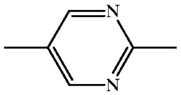 | — |
| 53 | $CH_3$ | 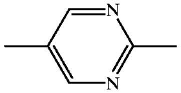 | 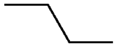 |
| 54 | $CH_3$ | 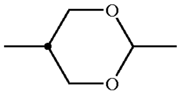 | — |
| 55 | n-$C_3H_7$ | 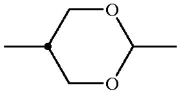 | — |
| 56 | $CH_3$ | 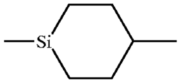 | 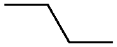 |
| k = 1, m = n = 0, $R_f$ = $CH_2CF_3$ | | | |
| 57 | CH3 | 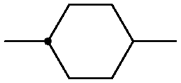 | — |
| 58 | n-$C_3H_7$ | 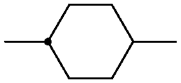 | — |

-continued
| | | | |
|---|---|---|---|
| 59 | n-$C_5H_{11}$ | 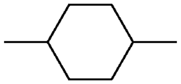 | — |
| 60 | $CH_3$ | 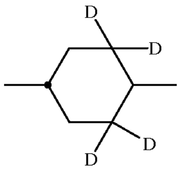 | — |
| 61 | $CH_3$ | 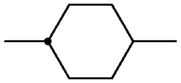 | 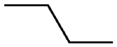 |
| 62 | n-$C_3H_7$ | 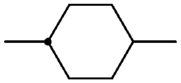 | 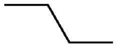 |
| 63 | $CH_3$ | 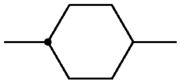 | $—CO_2—$ |
| 64 | $CH_3$ | 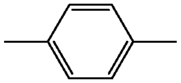 | — |
| 65 | n-$C_3H_7$ | 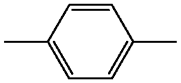 | — |
| 66 | $CH_3$ | 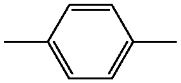 | 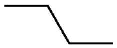 |
| 67 | n-$C_3H_7$ | 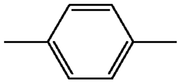 | 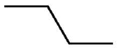 |

-continued
| | | | |
|---|---|---|---|
| 68 | $CH_3$ | 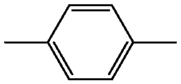 | 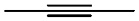 |
| 69 | $CH_3$ | 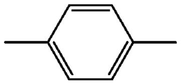 | 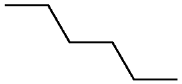 |
| 70 | $CH_3$ | 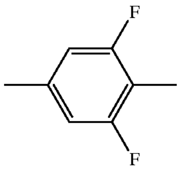 | — |
| 71 | $n-C_3H_7$ | 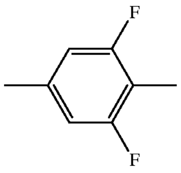 | — |
| 72 | $CH_3$ | 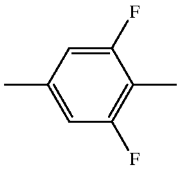 | 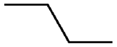 |
| 73 | $n-C_3H_7$ | 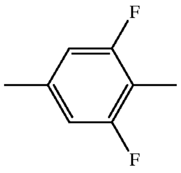 | 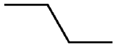 |

-continued
| | | | |
|---|---|---|---|
| 74 | $CH_3$ | 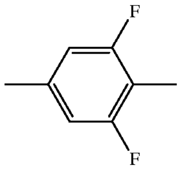 | $—CO_2—$ |
| 75 | n-$C_3H_7$ | 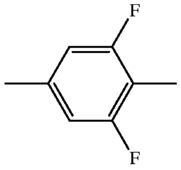 | 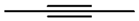 |
| 76 | $CH_3$ | 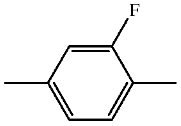 | — |
| 77 | $CH_3$ | 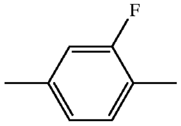 | — |
| 78 | n-$C_3H_7$ | 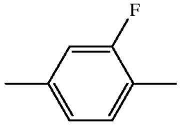 | 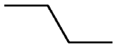 |
| 79 | $CH_3$ | 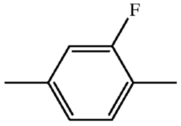 | 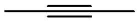 |
| 80 | $CH_3$ | 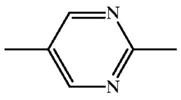 | — |

-continued
| | | | |
|---|---|---|---|
| 81 | $CH_3$ | 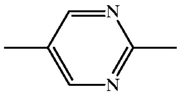 | 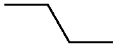 |
| 82 | $CH_3$ | 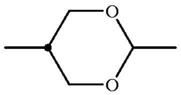 | — |
| 83 | $n\text{-}C_3H_7$ | 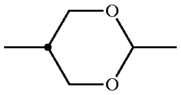 | — |
| 84 | $CH_3$ | 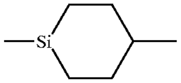 | 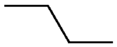 |
| k = 1, m = n = 0, $R_f = CF_2CFHCF_3$ | | | |
| 85 | CH3 | 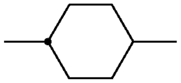 | — |
| 86 | $n\text{-}C_3H_7$ | 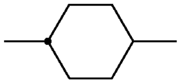 | — |
| 87 | $n\text{-}C_5H_{11}$ | 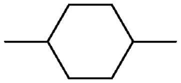 | — |
| 88 | $CH_3$ | 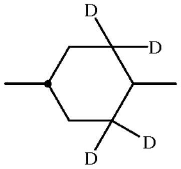 | — |

-continued
| | | | |
|---|---|---|---|
| 89 | $CH_3$ | 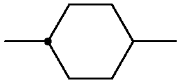 | 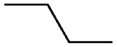 |
| 90 | n-$C_3H_7$ | 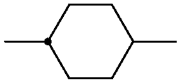 | 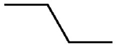 |
| 91 | $CH_3$ | 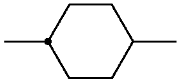 | —$CO_2$— |
| 92 | $CH_3$ | 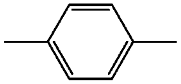 | — |
| 93 | n-$C_3H_7$ | 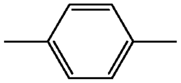 | — |
| 94 | $CH_3$ | 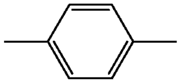 | 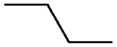 |
| 95 | n-$C_3H_7$ | 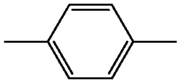 | 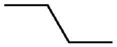 |
| 96 | $CH_3$ | 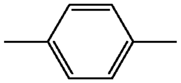 | 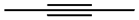 |
| 97 | $CH_3$ | 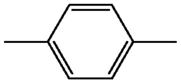 | 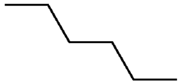 |

-continued
| | | | |
|---|---|---|---|
| 98 | $CH_3$ | 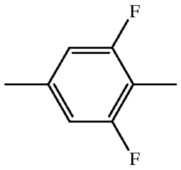 | — |
| 99 | n-$C_3H_7$ | 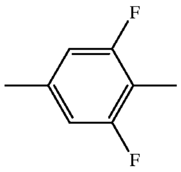 | — |
| 100 | $CH_3$ | 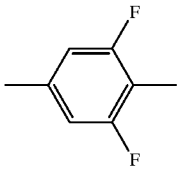 | 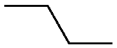 |
| 101 | n-$C_3H_7$ | 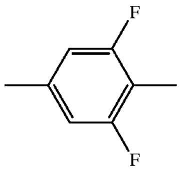 | 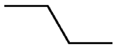 |
| 102 | $CH_3$ | 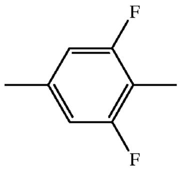 | —$CO_2$— |

-continued
| | | | |
|---|---|---|---|
| 103 | n-$C_3H_7$ | 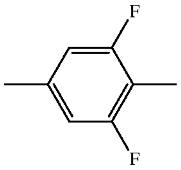 | 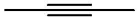 |
| 104 | $CH_3$ | 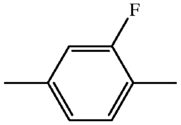 | — |
| 105 | n-$C_3H_7$ | 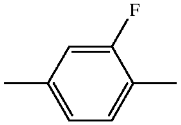 | 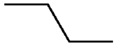 |
| 106 | $CH_3$ | 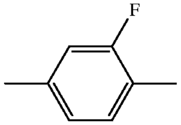 | 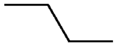 |
| 107 | $CH_3$ | 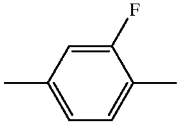 | 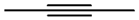 |
| 108 | $CH_3$ | 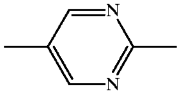 | — |
| 109 | $CH_3$ | 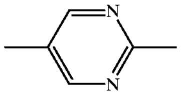 | 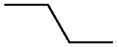 |

-continued
| | | | |
|---|---|---|---|
| 110 | $CH_3$ | 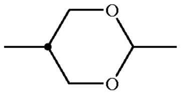 | — |
| 111 | n-$C_3H_7$ | 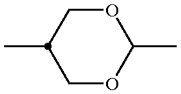 | — |
| 112 | $CH_3$ | 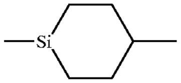 | 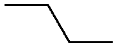 |
| k = 0, m = = n = 0. $R_f$ = $CF_3$ | | | |
| 113 | $CH_3$ | 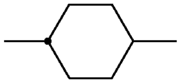 | 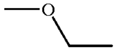 |
| 114 | n-$C_3H_7$ | 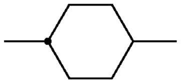 | 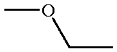 |
| 115 | n-$C_5H_{11}$ | 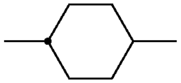 | 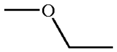 |
| 116 | $CH_3$ | 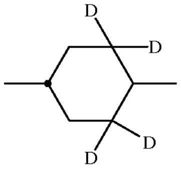 | 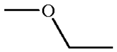 |
| 117 | $CH_3$ | 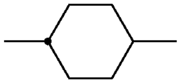 | 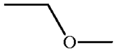 |

-continued
| | | | |
|---|---|---|---|
| 118 | n-$C_3H_7$ | 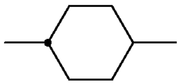 | 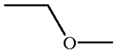 |
| 119 | $CH_3$ | 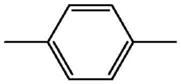 | 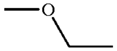 |
| 120 | n-$C_3H_7$ | 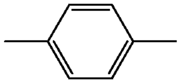 | 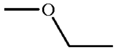 |
| 121 | $CH_3$ | 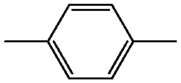 | 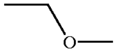 |
| 122 | n-$C_3H_7$ | 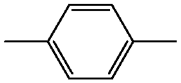 | 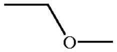 |
| 123 | $CH_3$ | 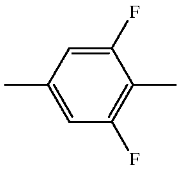 | 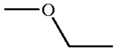 |
| 124 | n-$C_3H_7$ | 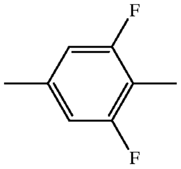 | 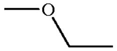 |

-continued
| | | | |
|---|---|---|---|
| 125 | $CH_3$ | 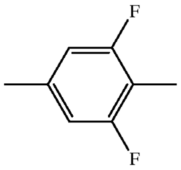 | 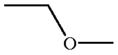 |
| 126 | n-$C_3H_7$ | 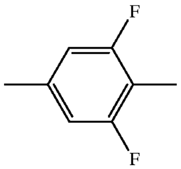 | 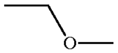 |
| 127 | $CH_3$ | 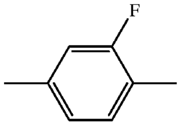 | 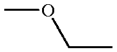 |
| 128 | n-$C_3H_7$ | 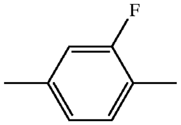 | 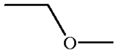 |
| 129 | $CH_3$ | 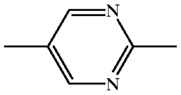 | 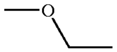 |
| 130 | $CH_3$ | 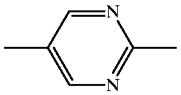 | 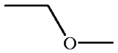 |
| 131 | $CH_3$ | 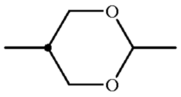 | 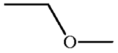 |

-continued
| | | | |
|---|---|---|---|
| 132 | $CH_3$ | 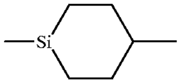 | 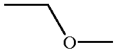 |
| k = 0, m = n = 0, $R_f = CF_2H$ | | | |
| 133 | $CH_3$ | 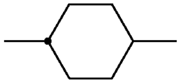 | 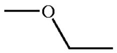 |
| 134 | n-$C_3H_7$ | 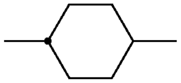 | 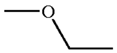 |
| 135 | n-$C_5H_{11}$ | 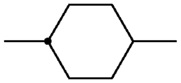 | 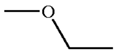 |
| 136 | $CH_3$ | 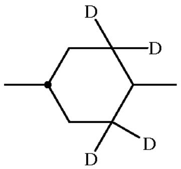 | 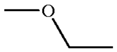 |
| 137 | $CH_3$ | 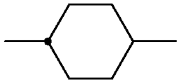 | 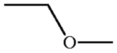 |
| 138 | n-$C_3H_7$ | 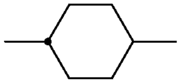 | 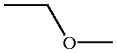 |
| 139 | $CH_3$ | 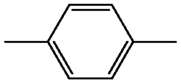 | 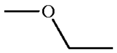 |

-continued
| | | | |
|---|---|---|---|
| 140 | n-$C_3H_7$ | 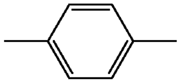 | 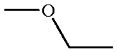 |
| 141 | $CH_3$ | 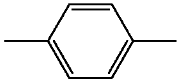 | 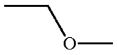 |
| 142 | n-$C_3H_7$ | 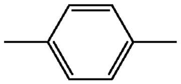 | 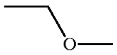 |
| 143 | $CH_3$ | 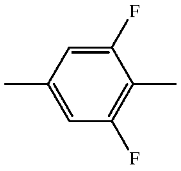 | 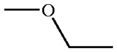 |
| 144 | n-$C_3H_7$ | 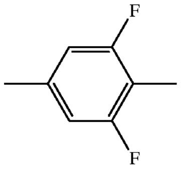 | 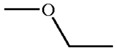 |
| 145 | $CH_3$ | 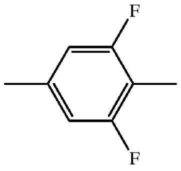 | 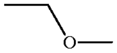 |
| 146 | n-$C_3H_7$ | 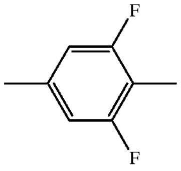 | 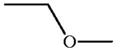 |

-continued
| | | | |
|---|---|---|---|
| 147 | $CH_3$ | 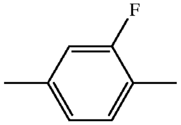 | 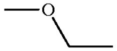 |
| 148 | n-$C_3H_7$ | 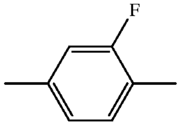 | 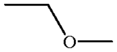 |
| 149 | $CH_3$ | 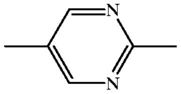 | 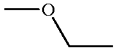 |
| 150 | $CH_3$ | 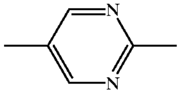 | 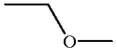 |
| 151 | $CH_3$ | 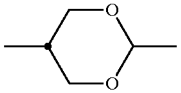 | 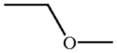 |
| 152 | $CH_3$ | 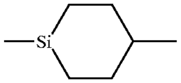 | 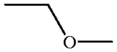 |
$K = 1,\ m = 0,\ n = 1,\ R_1 = CF_3$
| | R | $A_2$ | $B_2$ | $A_3$ | $B_3$ |
|---|---|---|---|---|---|
| 153 | CH | 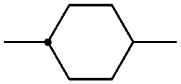 | — | 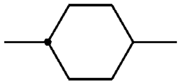 | — |
| 154 | $C_2H_5$ | 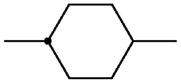 | — | 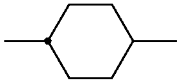 | — |

-continued
| | | | | | | |
|---|---|---|---|---|---|---|
| 155 | n-$C_3H_7$ | 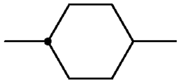 | — | 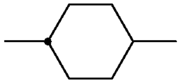 | — | |
| 156 | n-$C_5H_{11}$ | 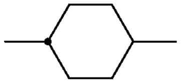 | — | 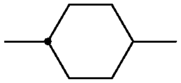 | — | |
| 157 | $CH_3$ | 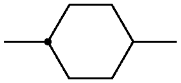 | — | 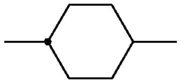 | 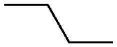 | |
| 158 | $C_2H_5$ | 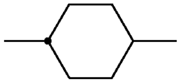 | — | 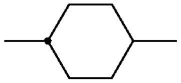 | 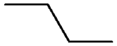 | |
| 159 | n-$C_3H_7$ | 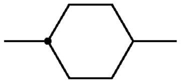 | — | 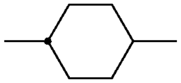 | 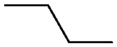 | |
| 160 | $CH_3$ | 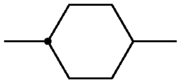 | 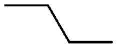 | 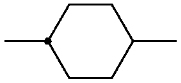 | — | |
| 161 | $C_2H_5$ | 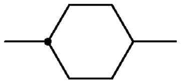 | 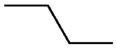 | 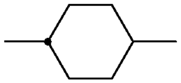 | — | |
| 162 | n-$C_3H_7$ | 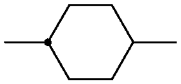 | 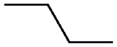 | 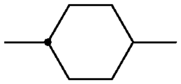 | — | |
| 163 | $CH_3$ | 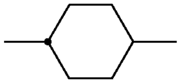 | — | | 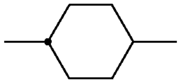 | 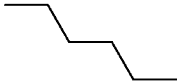 |

-continued
| | | | | | |
|---|---|---|---|---|---|
| 164 | $CH_3$ | 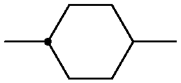 | 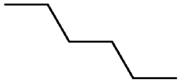 | 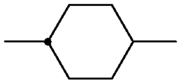 | — |
| 165 | $CH_3$ | 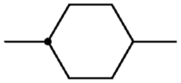 | 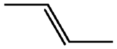 | 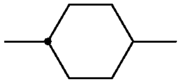 | — |
| 166 | n-$C_3H_7$ | 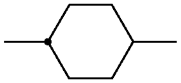 | 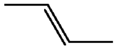 | 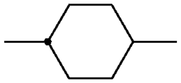 | — |
| 171 | $CH_3$ | 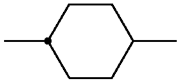 | — | 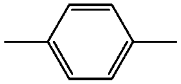 | — |
| 172 | $C_2H_5$ | 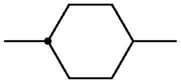 | — | 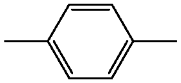 | — |
| 173 | n-$C_3H_7$ | 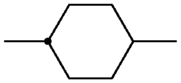 | — | 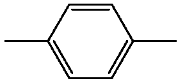 | — |
| 174 | n-$C_5H_{11}$ | 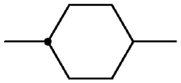 | — | 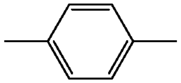 | — |
| 175 | $CH_3$ | 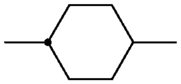 | — | 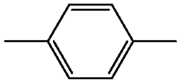 | 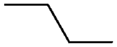 |
| 176 | n-$C_3H_7$ | 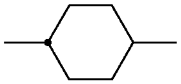 | — | 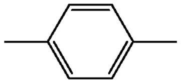 | 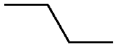 |

-continued
| | | | | | | |
|---|---|---|---|---|---|---|
| 177 | n-$C_5H_{11}$ | 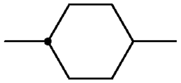 | — | 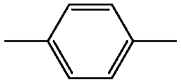 | 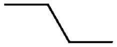 | |
| 178 | $CH_3$ | 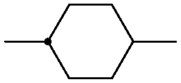 | 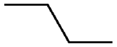 | 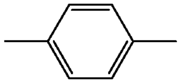 | — | — |
| 179 | $C_2H_5$ | 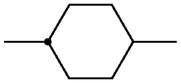 | 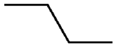 | 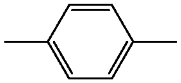 | — | — |
| 180 | n-$C_3H_7$ | 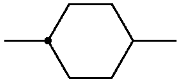 | 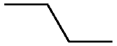 | 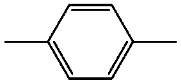 | — | |
| 181 | $CH_3$ | 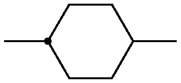 | — | 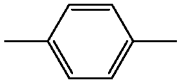 | 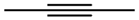 | |
| 182 | n-$C_3H_7$ | 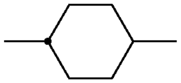 | — | 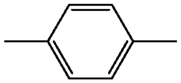 | 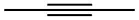 | |
| 187 | $CH_3$ | 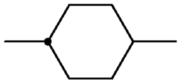 | — | 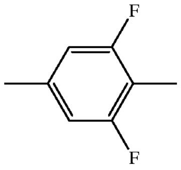 | — | |
| 188 | $C_2H_5$ | 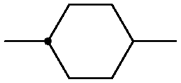 | — | 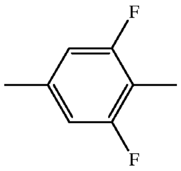 | — | |

-continued
| | | | | | |
|---|---|---|---|---|---|
| 189 | n-$C_3H_7$ | 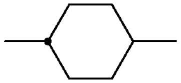 | — | 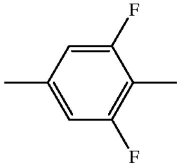 | — |
| 190 | $CH_3$ | 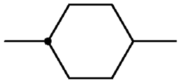 | — | 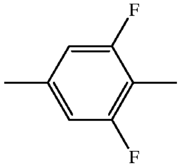 | 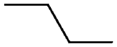 |
| 191 | n$C_3H_7$ | 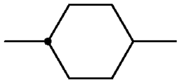 | — | 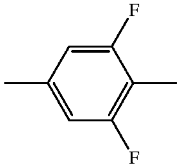 | 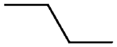 |
| 192 | $CH_3$ | 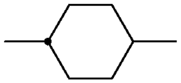 | 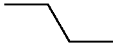 | 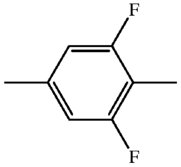 | — |
| 193 | n-$C_3H_7$ | 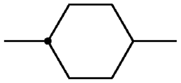 | 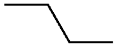 | 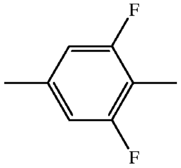 | — |
| | R | $A_3$ | $B_3$ | $A_4$ | $B_3$ |

-continued
| | | | | | |
|---|---|---|---|---|---|
| 194 | $CH_3$ | 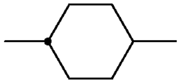 | — | 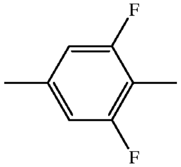 | 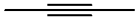 |
| 195 | $n-C_3H_7$ | 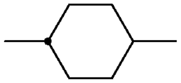 | — | 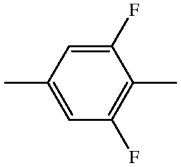 | 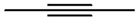 |
| 199 | $CH_3$ | 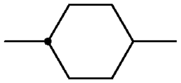 | — | 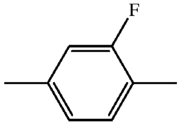 | — |
| 200 | $n-C_3H_7$ | 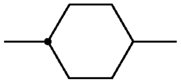 | 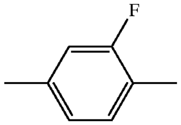 | — | |
| 201 | $CH_3$ | 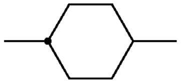 | — | 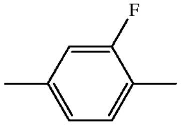 | 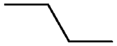 |
| 202 | $n-C_3H_7$ | 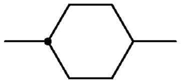 | — | 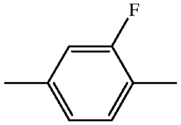 | 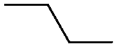 |

-continued
| | | | | | |
|---|---|---|---|---|---|
| 203 | $CH_3$ | 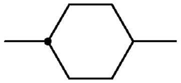 | 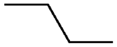 | 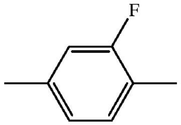 | — |
| 204 | n-$C_3H_7$ | 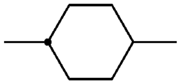 | 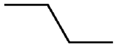 | 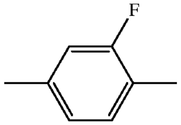 | — |
| 205 | n-$C_3H_7$ | 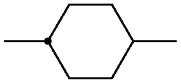 | — | 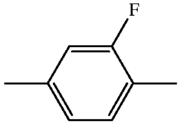 | 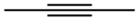 |
| 207 | $CH_3$ | 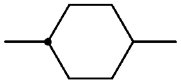 | — | 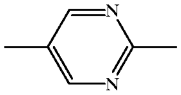 | — |
| 208 | n-$C_3H_7$ | 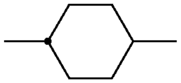 | 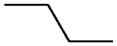 | 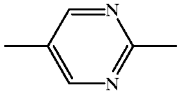 | |
| | R | $A_2$ | $B_2$ | $A_3$ | $B_3$ |
| 209 | $CH_3$ | 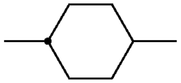 | — | 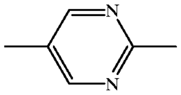 | 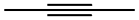 |
| 212 | $CH_3$ | 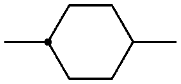 | — | 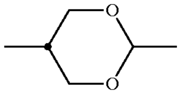 | — |
| 213 | n-$C_3H_7$ | 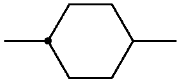 | — | 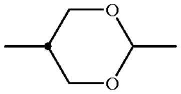 | — |

-continued
| | | | | | |
|---|---|---|---|---|---|
| 214 | $CH_3$ | 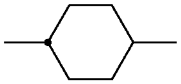 | — | 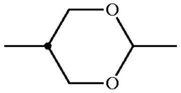 | 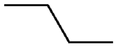 |
| 215 | n-$C_3H_7$ | 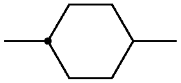 | — | 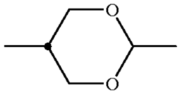 | 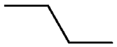 |
| 216 | $CH_3$ | 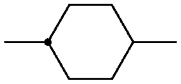 | 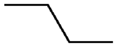 | 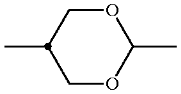 | — |
| 217 | n-$C_3H_7$ | 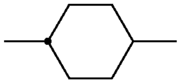 | 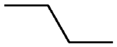 | 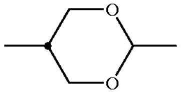 | — |
| 220 | $CH_3$ | 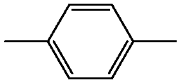 | — | 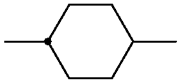 | — |
| 221 | $CH_3$ | 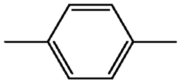 | — | 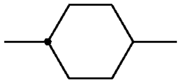 | 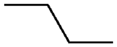 |
| 222 | $CH_3$ | 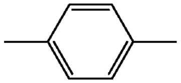 | 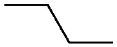 | 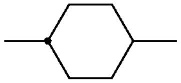 | — |
| 225 | $CH_3$ | 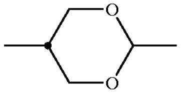 | — | 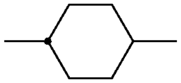 | — |
| 226 | n-$C_3H_7$ | 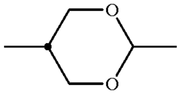 | — | | |

-continued
| | | | | | |
|---|---|---|---|---|---|
| 227 | $CH_3$ | 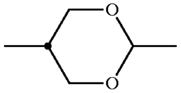 | — | 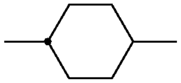 | 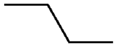 |
| 228 | $CH_3$ | 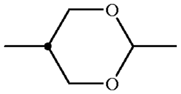 | 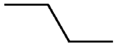 | 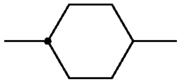 | — |
| 229 | $CH_3$ | 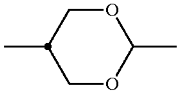 | — | 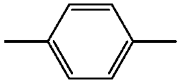 | — |
| 230 | $CH_3$ | 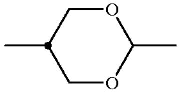 | — | 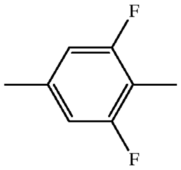 | — |
| 231 | $n\text{-}C_3H_7$ | 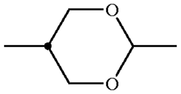 | — | 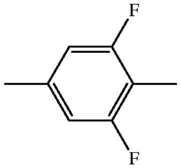 | — |
| 232 | $CH_3$ | 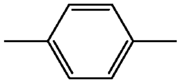 | — | 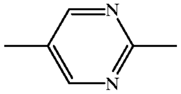 | — |
| 233 | $CH_3$ | 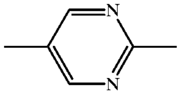 | — | 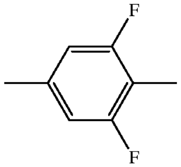 | — |

-continued
| | | | | | |
|---|---|---|---|---|---|
| 234 | $CH_3$ | 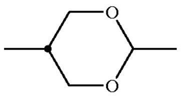 | — | 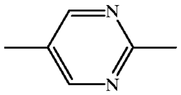 | — |
| 235 | n-$C_3H_7$ | 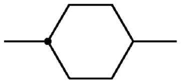 | — | 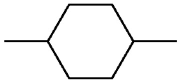 | 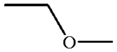 |
| 236 | n-$C_5H_{11}$ | 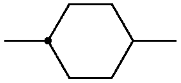 | — | 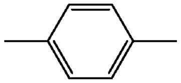 | 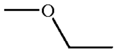 |
| 237 | 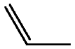 | 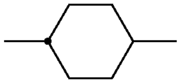 | — | 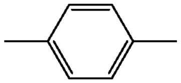 | 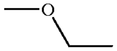 |
| 238 | $CH_3$ | 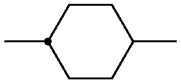 | 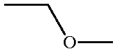 | 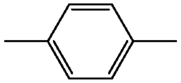 | — |
| 239 | n-$C_5H_{11}$ | 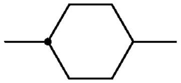 | 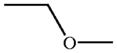 | 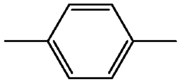 | — |
| 240 | n-$C_3H_7$ | 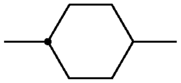 | 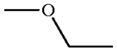 | 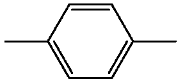 | — |
| 241 | n-$C_5H_{11}$ | 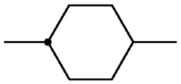 | 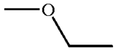 | 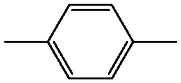 | — |

-continued
| | | | | | |
|---|---|---|---|---|---|
| 242 | $CH_3$ | 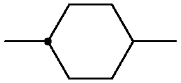 | — | 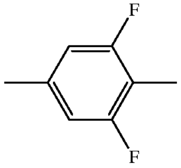 | 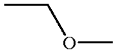 |
| 243 | $n-C_3H_7$ | 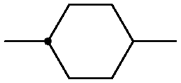 | — | 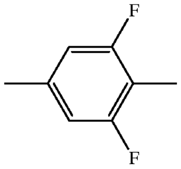 | 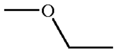 |
| 244 | $n-C_3H_7$ | 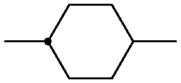 | 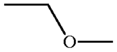 | 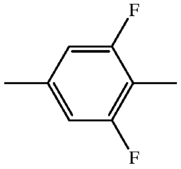 | — |
| 245 | $n-C_5H_{11}$ | 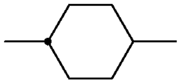 | 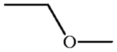 | 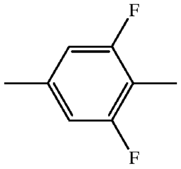 | — |
| 246 | $n-C_3H_7$ | 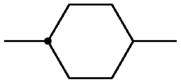 | 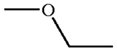 | 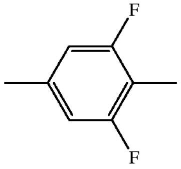 | — |

-continued
| | | | | | |
|---|---|---|---|---|---|
| 247 | n-$C_5H_{11}$ | 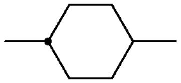 | 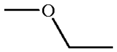 | 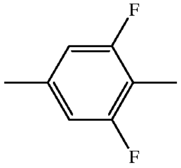 | — |
| 248 | n-$C_3H_7$ | 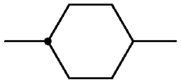 | — | 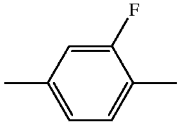 | 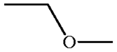 |
| 249 | n-$C_3H_7$ | 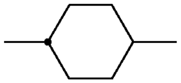 | — | 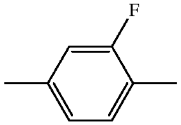 | 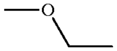 |
| 250 | n-$C_5H_{11}$ | 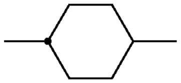 | 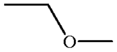 | 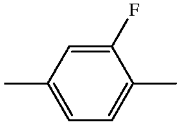 | — |
| 251 | n-$C_3H_7$ | 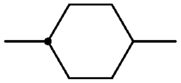 | 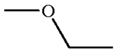 | 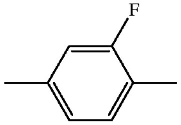 | — |
| 252 | n--$C_3H_7$ | 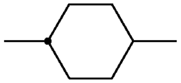 | — | 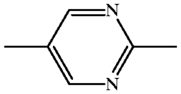 | 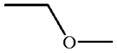 |
| 253 | n-$C_5H_{11}$ | 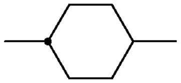 | — | 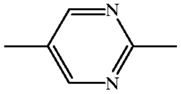 | 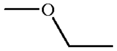 |

-continued
| | | | | | |
|---|---|---|---|---|---|
| 254 | n-$C_3H_7$ | 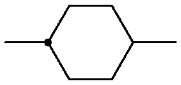 | 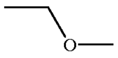 | 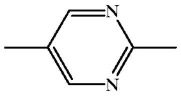 | — |
| 255 | n$C_3H_7$ | 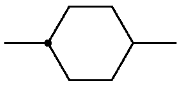 | 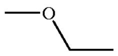 | 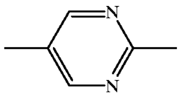 | — |
| 256 | n-$C_3H_7$ | 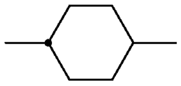 | — | 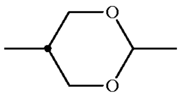 | 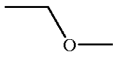 |
| 257 | n-$C_5H_{11}$ | 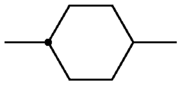 | 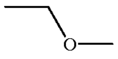 | 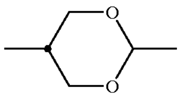 | — |
| 258 | n-$C_3H_7$ | 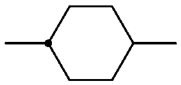 | 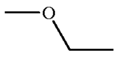 | 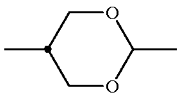 | — |
| 259 | $CH_3$ | 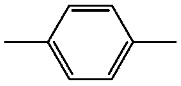 | — | 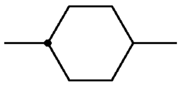 | 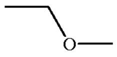 |
| 260 | n-$C_3H_7$ | 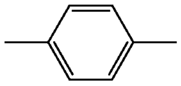 | — | 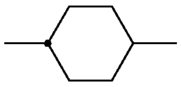 | 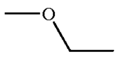 |
| 261 | n-$C_5H_{11}$ | 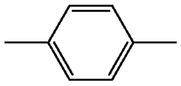 | 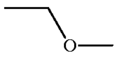 | 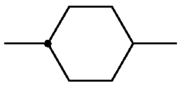 | — |
| 262 | $CH_3$ | 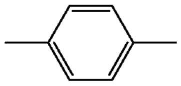 | 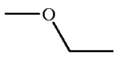 | 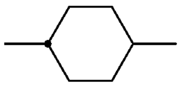 | — |

-continued
| | | | | | |
|---|---|---|---|---|---|
| 263 | $CH_3$ | 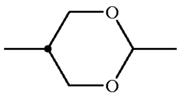 | — | 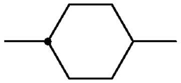 | 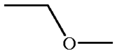 |
| 264 | n-$C_3H_7$ | 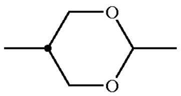 | — | 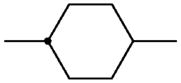 | 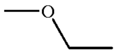 |
| 265 | n-$C_5H_{11}$ | 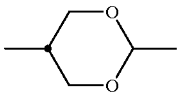 | 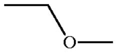 | 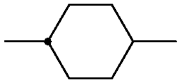 | — |
| 266 | n-$C_3H_7$ | 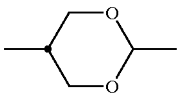 | — | 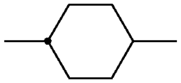 | 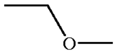 |
| 267 | n-$C_3H_7$ | 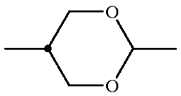 | — | 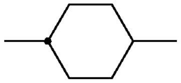 | 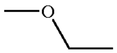 |
| 268 | n-$C_5H_{11}$ | 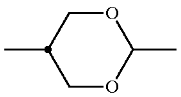 | 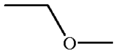 | 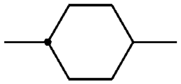 | — |
| k = 1, m = 0, n = 1, $R_f$ = $CF_2H$ | | | | | |
| 269 | $CH_3$ | 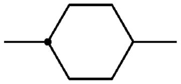 | — | 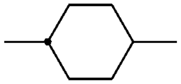 | — |
| 270 | $C_2H_5$ | 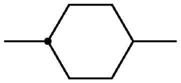 | — | 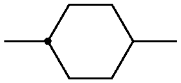 | — |

-continued
| | | | | | |
|---|---|---|---|---|---|
| 271 | n-$C_3H_7$ | 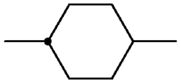 | — | 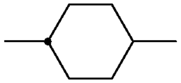 | — |
| 272 | n-$C_5H_{11}$ | 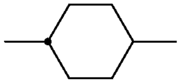 | — | 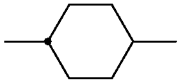 | — |
| 273 | $CH_3$ | 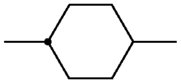 | — | 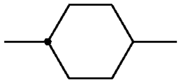 | 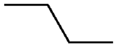 |
| 274 | $C_2H_5$ | 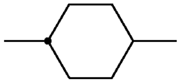 | — | 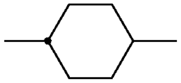 | 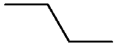 |
| 275 | n-$C_3H_7$ | 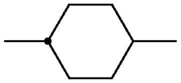 | — | 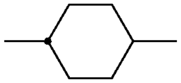 | 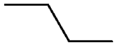 |
| 276 | $CH_3$ | 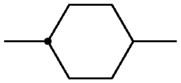 | 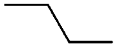 | 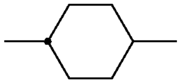 | — |
| 277 | $C_2H_5$ | 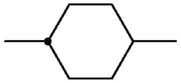 | 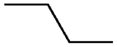 | 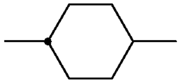 | — |
| 278 | n-$C_3H_7$ | 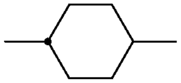 | 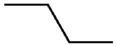 | 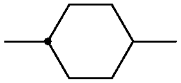 | — |
| 279 | $CH_3$ | 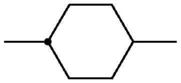 | — | 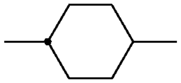 | 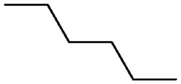 |

-continued
| | | | | | | |
|---|---|---|---|---|---|---|
| 280 | $CH_3$ | 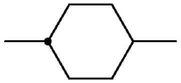 | 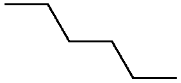 | | 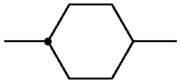 | — |
| 281 | $CH_3$ | 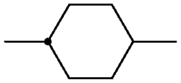 | 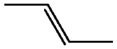 | 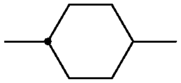 | — | |
| 282 | n-$C_3H_7$ | 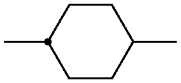 | 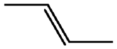 | 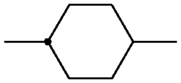 | — | |
| 287 | $CH_3$ | 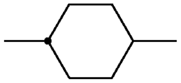 | — | 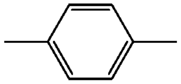 | — | |
| 288 | $C_2H_5$ | 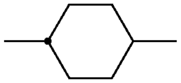 | — | 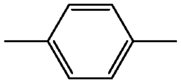 | — | |
| 289 | n-$C_3H_7$ | 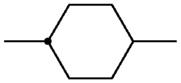 | — | 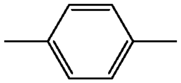 | — | |
| 290 | n-$C_5H_{11}$ | 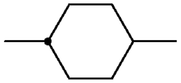 | — | 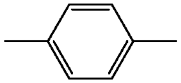 | — | |
| 291 | $CH_3$ | 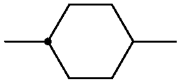 | — | 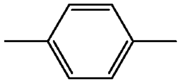 | 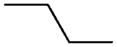 | |
| 292 | n-$C_3H_7$ | 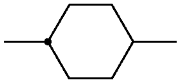 | — | 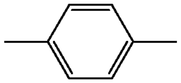 | 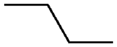 | |

-continued
| | | |
|---|---|---|
| 293 | n-$C_5H_{11}$ | 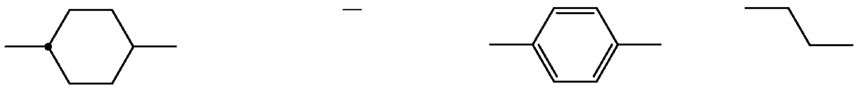 |
| 294 | $CH_3$ | 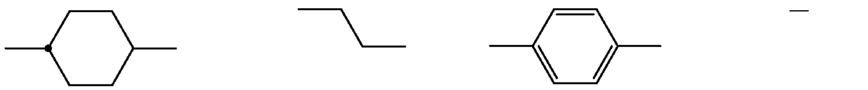 |
| 295 | $C_2H_5$ | 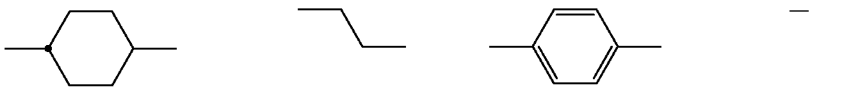 |
| 296 | n-$C_3H_7$ | 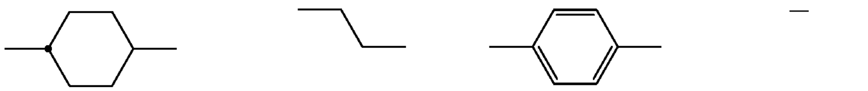 |
| 297 | $CH_3$ | 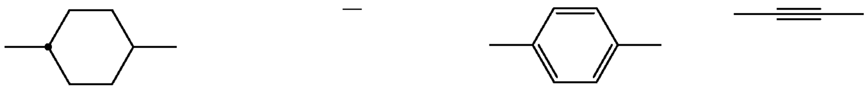 |
| 298 | n-$C_3H_7$ | 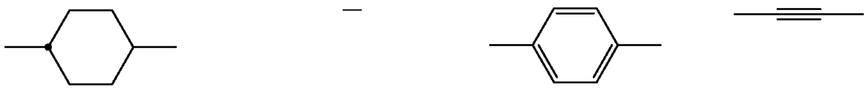 |
| 303 | $CH_3$ | 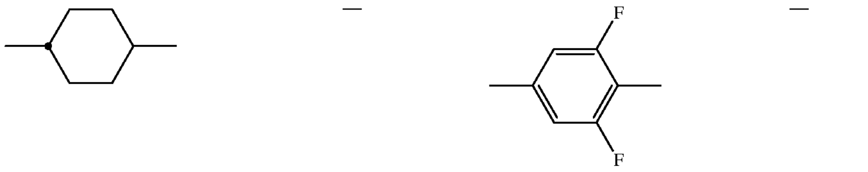 |
| 304 | $C_2H_5$ | 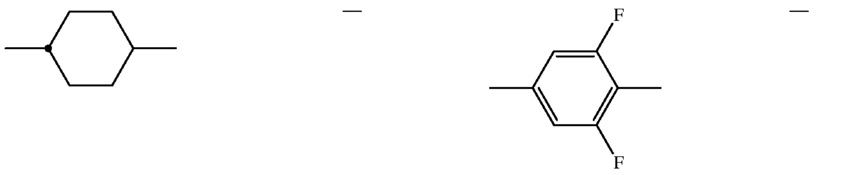 |

-continued
| | R | $A_3$ | $B_3$ | $A_4$ | $B_3$ |
|---|---|---|---|---|---|
| 305 | n-$C_3H_7$ | 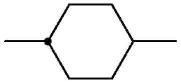 | — | 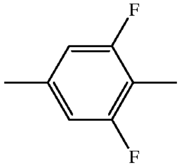 | — |
| 306 | $CH_3$ | 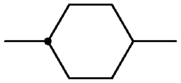 | — | 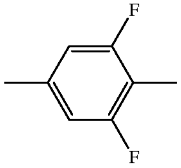 | 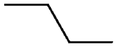 |
| 307 | n-$C_3H_7$ | 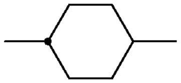 | — | 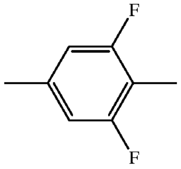 | 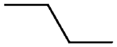 |
| 308 | $CH_3$ | 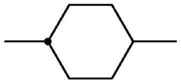 | 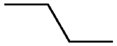 | 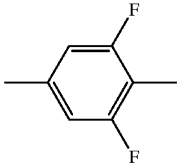 | — |
| 309 | n-$C_3H_7$ | 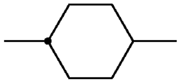 | 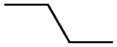 | 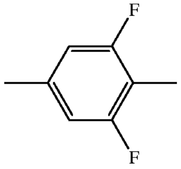 | — |

-continued
| | | | | | |
|---|---|---|---|---|---|
| 310 | $CH_3$ | 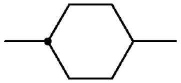 | — | 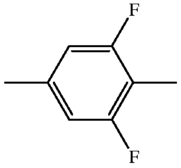 | 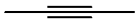 |
| 311 | n-$C_3H_7$ | 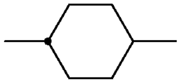 | — | 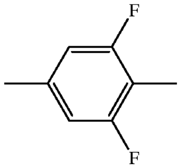 | 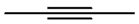 |
| 315 | $CH_3$ | 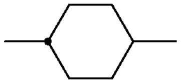 | — | 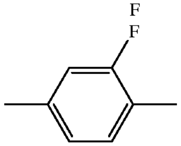 | — |
| 316 | n-$C_3H_7$ | 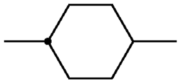 | — | 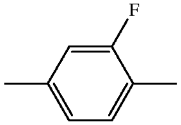 | — |
| 317 | $CH_3$ | 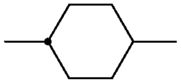 | — | 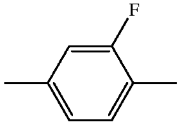 | 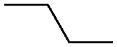 |
| 318 | n-$C_3H_7$ | 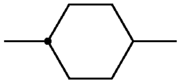 | — | 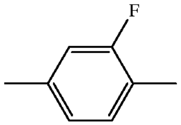 | 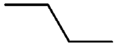 |

-continued
| No. | R | $A_2$ | $B_2$ | $A_3$ | $B_3$ |
|---|---|---|---|---|---|
| 319 | $CH_3$ | 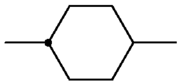 | 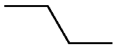 | 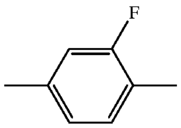 | — |
| 320 | n-$C_3H_7$ | 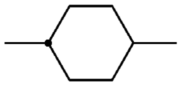 | 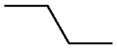 | 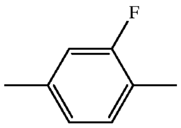 | — |
| 321 | n-$C_3H_7$ | 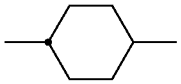 | — | 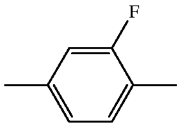 | 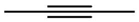 |
| 323 | $CH_3$ | 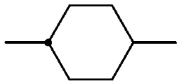 | — | 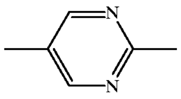 | — |
| 324 | n-$C_3H_7$ | 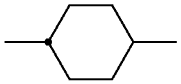 | — | 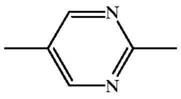 | — |
| 325 | $CH_3$ | 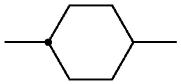 | — | 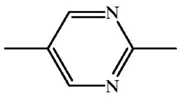 | 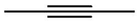 |
| 326 | $CH_3$ | 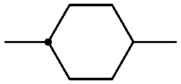 | — | 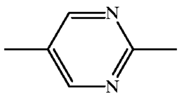 | —$CO_2$— |
| 327 | $CH_3$ | 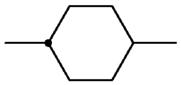 | —$CO_2$— | 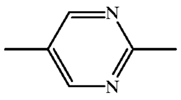 | — |

-continued
| | | | | | |
|---|---|---|---|---|---|
| 328 | $CH_3$ | 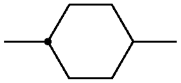 | — | 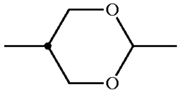 | — |
| 329 | n-$C_3H_7$ | 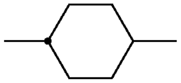 | — | 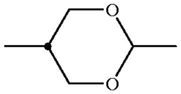 | — |
| 330 | $CH_3$ | 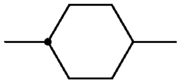 | — | 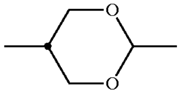 | 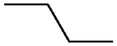 |
| 331 | n-$C_3H_7$ | 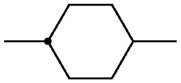 | — | 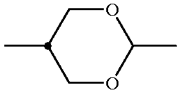 | 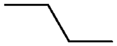 |
| 332 | $CH_3$ | 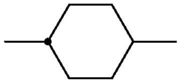 | 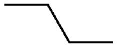 | 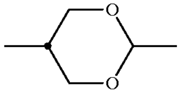 | — |
| 333 | n-$C_3H_7$ | 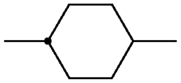 | 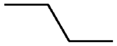 | 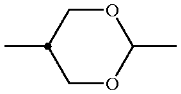 | — |
| 336 | $CH_3$ | 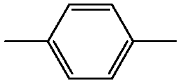 | — | 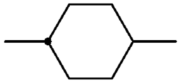 | — |
| 337 | $CH_3$ | 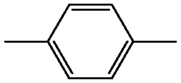 | — | 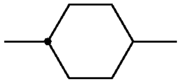 | 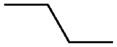 |
| 338 | $CH_3$ | 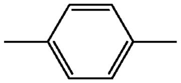 | 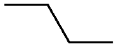 | 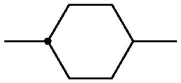 | — |

-continued
| | | | | | |
|---|---|---|---|---|---|
| 341 | $CH_3$ | 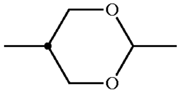 | — | 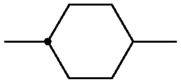 | — |
| 342 | n-$C_3H_7$ | 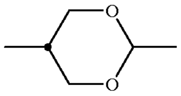 | — | 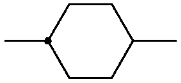 | — |
| 343 | $CH_3$ | 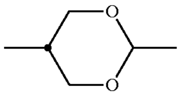 | — | 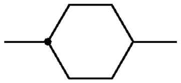 | 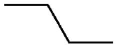 |
| 344 | $CH_3$ | 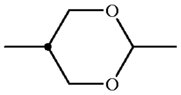 | 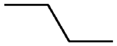 | 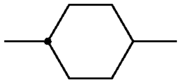 | — |
| 345 | $CH_3$ | 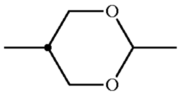 | — | 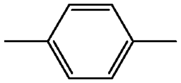 | — |
| 346 | $CH_3$ | 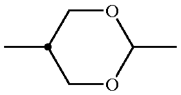 | — | 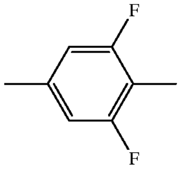 | — |
| 347 | n-$C_3H_7$ | 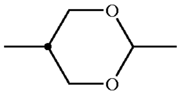 | — | 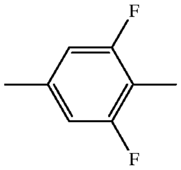 | — |

-continued
| | | | | | |
|---|---|---|---|---|---|
| 348 | $CH_3$ | 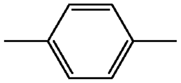 | — | 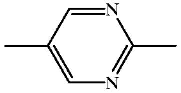 | — |
| 349 | $CH_3$ | 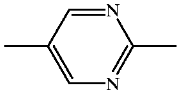 | — | 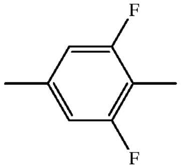 | — |
| 350 | $CH_3$ | 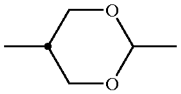 | — | 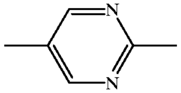 | — |
| 351 | n-$C_3H_7$ | 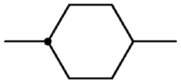 | — | 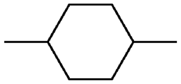 | 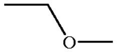 |
| 352 | n-$C_5H_{11}$ | 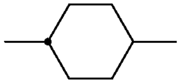 | — | 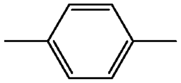 | 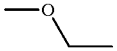 |
| 353 | 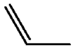 | 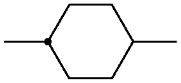 | — | 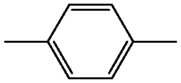 | 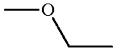 |
| 354 | $CH_3$ | 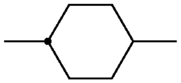 | 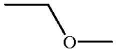 | 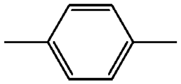 | — |
| 355 | n-$C_5H_{11}$ | 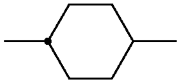 | 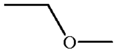 | 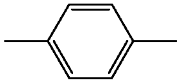 | — |

-continued
| | | | | | |
|---|---|---|---|---|---|
| 356 | n-$C_3H_7$ | 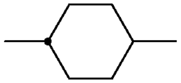 | 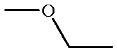 | 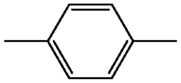 | — |
| 357 | n-$C_5H_{11}$ | 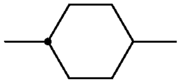 | 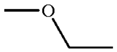 | 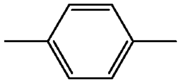 | — |
| 358 | $CH_3$ | 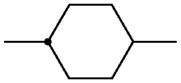 | — | 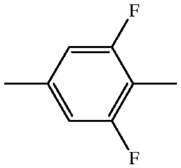 | 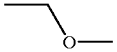 |
| 359 | n-$C_3H_7$ | 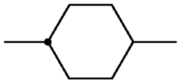 | — | 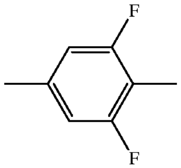 | 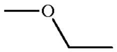 |
| 360 | n-$C_3H_7$ | 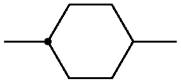 | 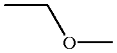 | 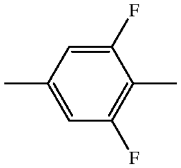 | — |
| 361 | n-$C_5H_{11}$ | 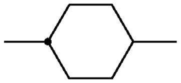 | 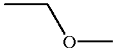 | 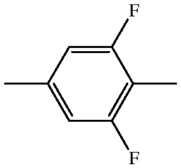 | — |

-continued
| | | |
|---|---|---|
| 362 | n-$C_3H_7$ | 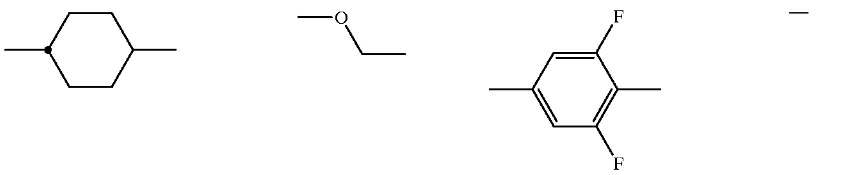 |
| 363 | n-$C_5H_{11}$ | 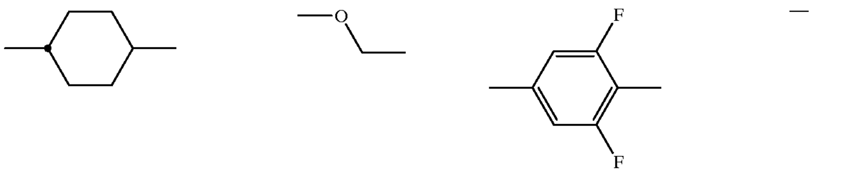 |
| 364 | n-$C_3H_7$ | 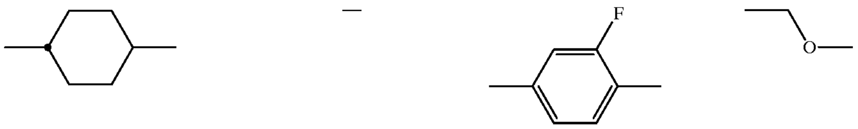 |
| 365 | n-$C_3H_7$ | 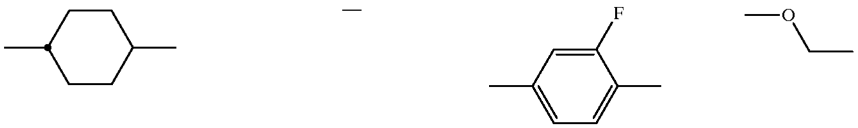 |
| 366 | n-$C_5H_{11}$ | 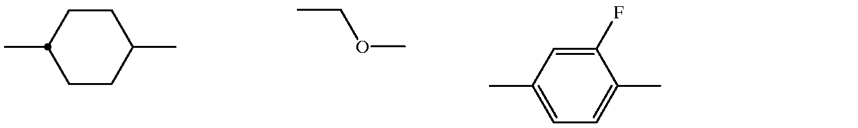 |
| 367 | n-$C_3H_7$ | 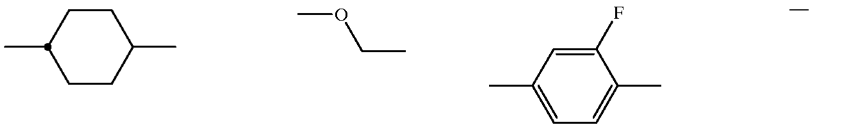 |
| 368 | n-$C_3H_7$ | 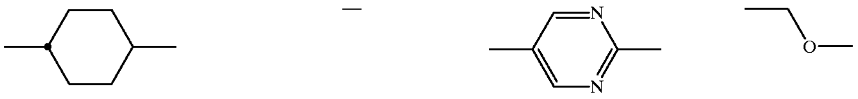 |

-continued
| | | | | | |
|---|---|---|---|---|---|
| 369 | $n\text{-}C_5H_{11}$ | 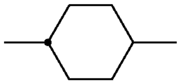 | — | 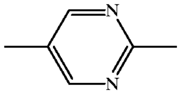 | 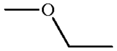 |
| 370 | $n\text{-}C_5H_7$ | 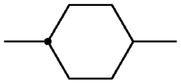 | 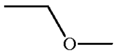 | 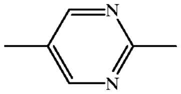 | — |
| 371 | $n\text{-}C_3H_7$ | 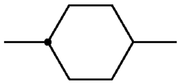 | 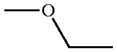 | 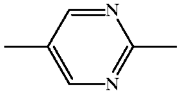 | — |
| 372 | $n\text{-}C_3H_7$ | 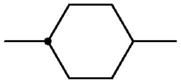 | — | 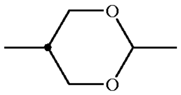 | 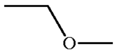 |
| 373 | $n\text{-}C_5H_{11}$ | 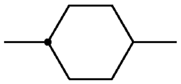 | 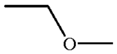 | 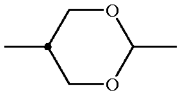 | — |
| 374 | $n\text{-}C_3H_7$ | 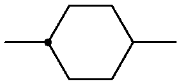 | 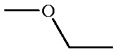 | 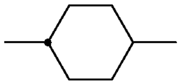 | — |
| 375 | $CH_3$ | 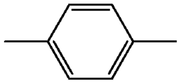 | — | 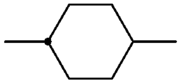 | 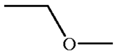 |
| 376 | $n\text{-}C_3H_7$ | 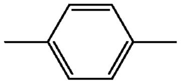 | — | 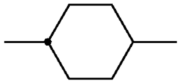 | 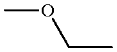 |
| 377 | $n\text{-}C_5H_{11}$ | 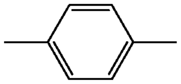 | 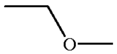 | 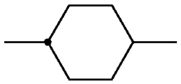 | — |

-continued
| | | | | | |
|---|---|---|---|---|---|
| 378 | $CH_3$ | 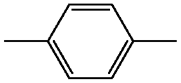 | 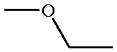 | 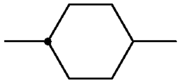 | — |
| 379 | $CH_3$ | 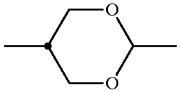 | — | 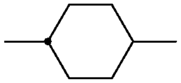 | 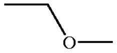 |
| 380 | $n-C_3H_7$ | 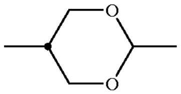 | — | 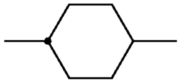 | 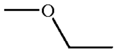 |
| 381 | $n-C_5H_{11}$ | 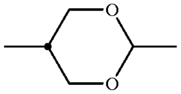 | 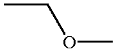 | 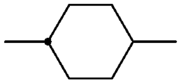 | — |
| 382 | $n-C_3H_7$ | 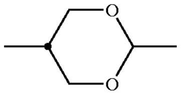 | — | 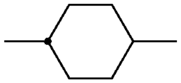 | 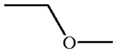 |
| 383 | $n-C_3H_7$ | 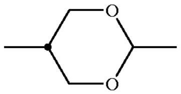 | — | 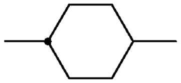 | 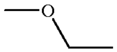 |
| 384 | $n-C_5H_{11}$ | 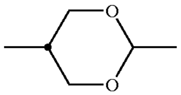 | 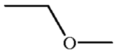 | 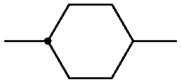 | — |
| $k = 0, m = 0, n = 1, R_f = CF_2H$ | | | | | |
| 385 | $CH_3$ | 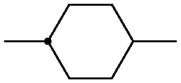 | — | 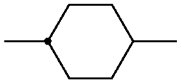 | 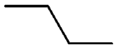 |

-continued
| | | | | | |
|---|---|---|---|---|---|
| 386 | n-$C_3H_7$ | 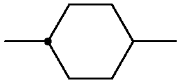 | 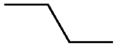 | 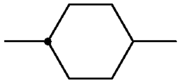 | — |
| 387 | $CH_3$ | 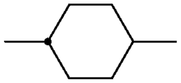 | — | 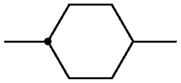 | 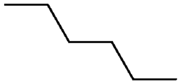 |
| 388 | $CH_3$ | 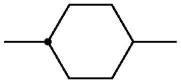 | 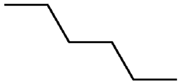 | 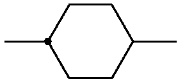 | — |
| 389 | $CH_3$ | 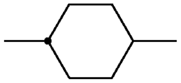 | 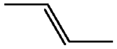 | 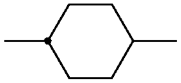 | — |
| 390 | n-$C_3H_7$ | 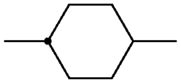 | — | 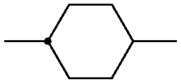 | —$CO_2$— |
| 391 | $CH_3$ | 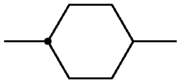 | —$CO_2$— | 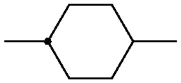 | — |
| 392 | $CH_3$ | 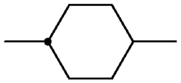 | — | 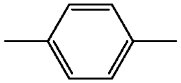 | 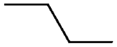 |
| 393 | $CH_3$ | 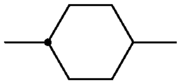 | 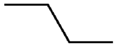 | 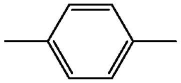 | — |
| 394 | $CH_3$ | 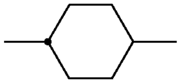 | — | 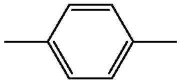 | 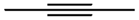 |

-continued
| | | | | | |
|---|---|---|---|---|---|
| 395 | $CH_3$ | 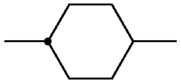 | — | 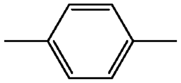 | —$CO_2$— |
| 396 | $CH_3$ | 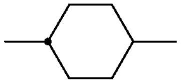 | —$CO_2$— | 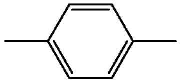 | — |
| 397 | $CH_3$ | 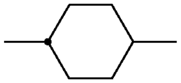 | — | 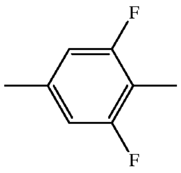 | 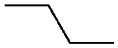 |
| 398 | $CH_3$ | 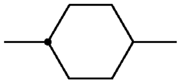 | 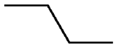 | 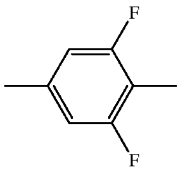 | — |
| 399 | $CH_3$ | 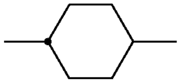 | — | 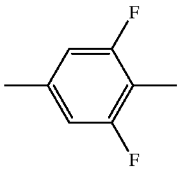 | 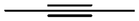 |
| 400 | n-$C_3H_7$ | 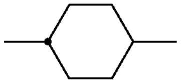 | — | 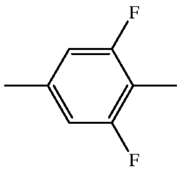 | —$CO_2$— |

-continued
| | R | $A_3$ | $B_3$ | $A_4$ | $B_3$ |
|---|---|---|---|---|---|
| 401 | $CH_3$ | 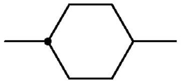 | $—CO_2—$ | 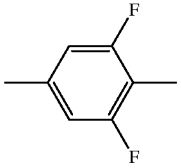 | — |
| 402 | $CH_3$ | 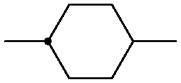 | — | 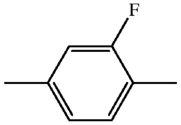 | 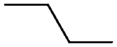 |
| 403 | $CH_3$ | 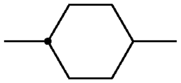 | 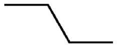 | 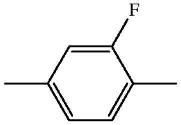 | — |
| 404 | n-$C_3H_7$ | 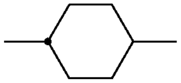 | — | 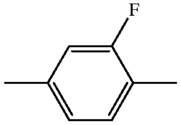 | 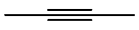 |
| 405 | $CH_3$ | 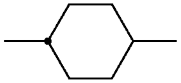 | — | 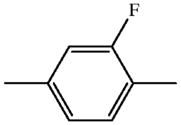 | $—CO_2—$ |
| 406 | $CH_3$ | 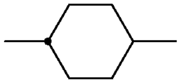 | — | 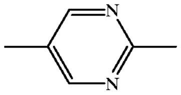 | — |
| 407 | $CH_3$ | 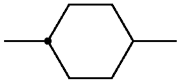 | — | 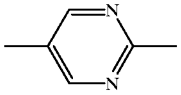 | 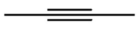 |

-continued
| | | | | | |
|---|---|---|---|---|---|
| 408 | $CH_3$ | 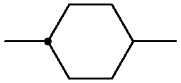 | — | 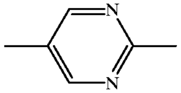 | $—CO_2—$ |
| 409 | $CH_3$ | 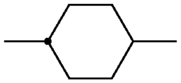 | $—CO_2—$ | 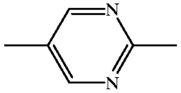 | — |
| 410 | $CH_3$ | 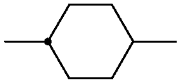 | — | 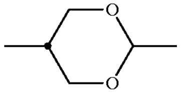 | 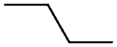 |
| 411 | $CH_3$ | 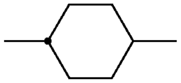 | 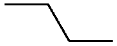 | 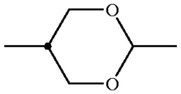 | — |
| 412 | $CH_3$ | 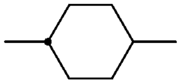 | — | 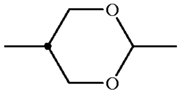 | $—CO_2—$ |
| 413 | $n-C_3H_7$ | 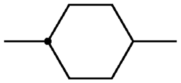 | $—CO_2—$ | 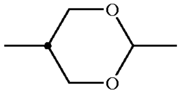 | — |
| 414 | $CH_3$ | 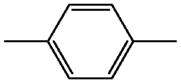 | — | 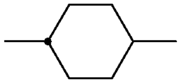 | 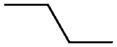 |
| 415 | $CH_3$ | 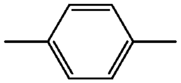 | 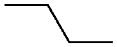 | 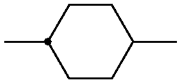 | — |
| 416 | $CH_3$ | 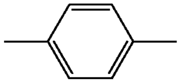 | — | 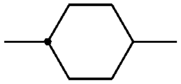 | $—CO_2—$ |

-continued
| | | | | | |
|---|---|---|---|---|---|
| 417 | n-$C_3H_7$ | 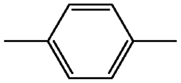 | —$CO_2$— | 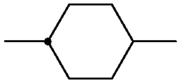 | — |
| 418 | $CH_3$ | 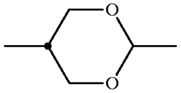 | — | 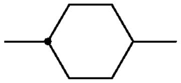 | — |
| 419 | $CH_3$ | 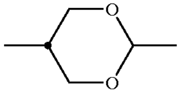 | — | 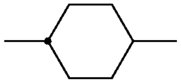 | 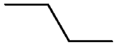 |
| 420 | $CH_3$ | 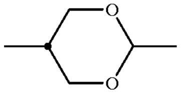 | 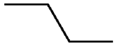 | 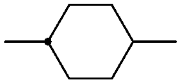 | — |
| 421 | $CH_3$ | 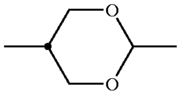 | — | 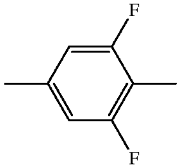 | — |
| 422 | $CH_3$ | 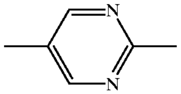 | — | 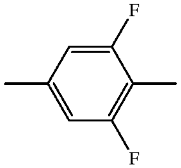 | — |
| | R | $A_2$ | $B_2$ | $A_3$ | $B_3$ |
| 423 | n-$C_3H_7$ | 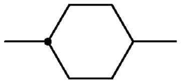 | — | 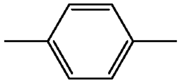 | 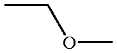 |

-continued
| | | | | | |
|---|---|---|---|---|---|
| 424 | n-$C_5H_{11}$ | 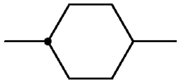 | — | 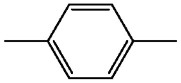 | 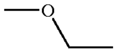 |
| 425 | 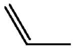 | 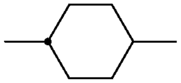 | — | 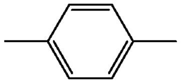 | 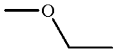 |
| 426 | $CH_3$ | 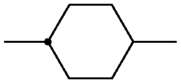 | 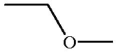 | 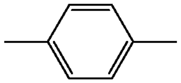 | — |
| 427 | n-$C_5H_{11}$ | 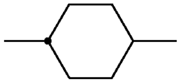 | 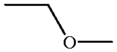 | 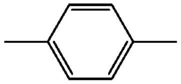 | — |
| 428 | n-$C_3H_7$ | 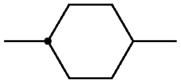 | 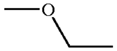 | 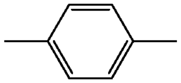 | — |
| 429 | n-$C_5H_{11}$ | 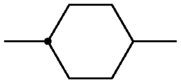 | 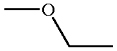 | 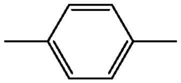 | — |
| 430 | $CH_3$ | 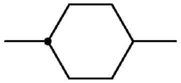 | — | 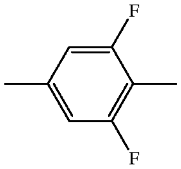 | 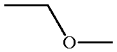 |
| 431 | n-$C_3H_7$ | 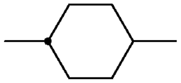 | — | 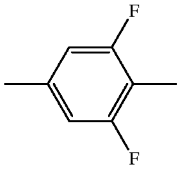 | 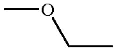 |

-continued
| | | | | | |
|---|---|---|---|---|---|
| 432 | n-$C_3H_7$ | 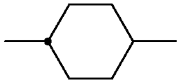 | 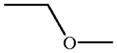 | 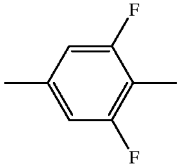 | — |
| 433 | n-$C_5H_{11}$ | 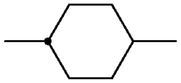 | 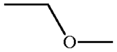 | 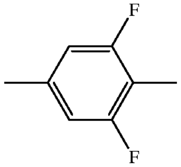 | — |
| 434 | n-$C_3H_7$ | 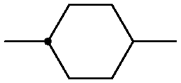 | 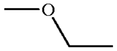 | 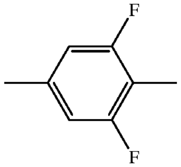 | — |
| 435 | n-$C_5H_{11}$ | 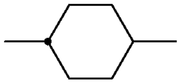 | 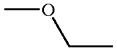 | 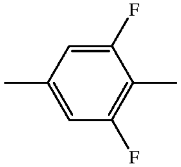 | — |
| 436 | n-$C_3H_7$ | 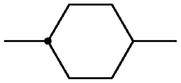 | — | 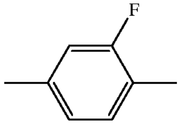 | 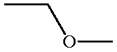 |
| 437 | n-$C_3H_7$ | 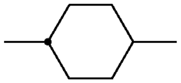 | — | 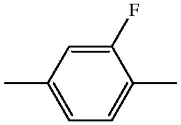 | 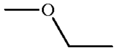 |

-continued
| | | |
|---|---|---|
| 438 | n-$C_5H_{11}$ | 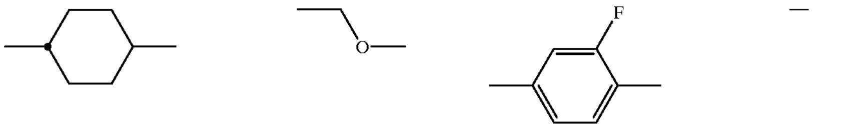 |
| 439 | n-$C_3H_7$ | 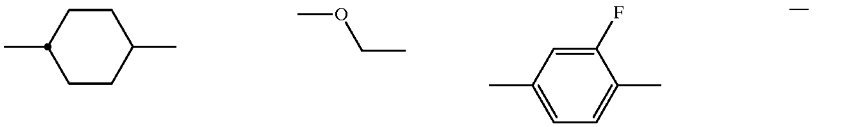 |
| 440 | n$C_3H_7$ | 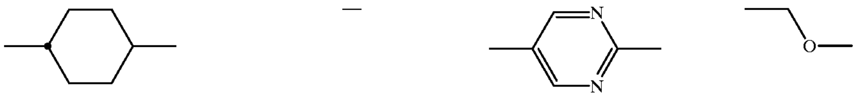 |
| 441 | n-$C_5H_{11}$ | 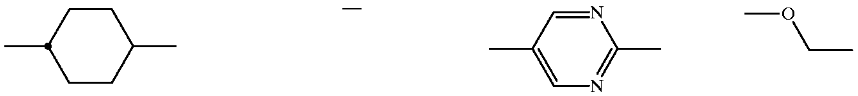 |
| 442 | n-$C_3H_7$ | 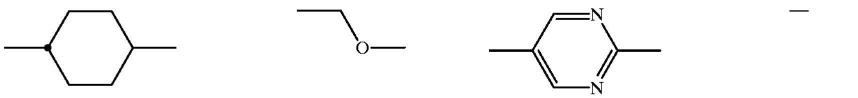 |
| 443 | n-$C_3H_7$ | 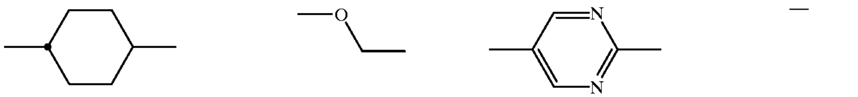 |
| 444 | n-$C_3H_7$ | 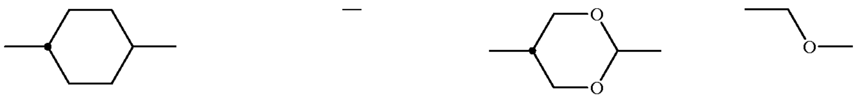 |
| 445 | n-$C_5H_{11}$ | 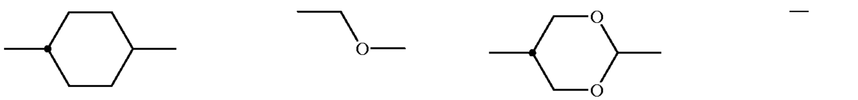 |

-continued
| | | | | | |
|---|---|---|---|---|---|
| 446 | n-$C_3H_7$ | 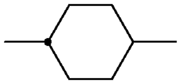 | 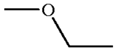 | 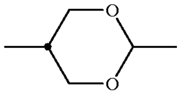 | — |
| 447 | $CH_3$ | 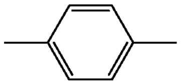 | — | 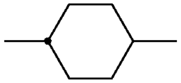 | 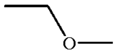 |
| 448 | n-$C_3H_7$ | 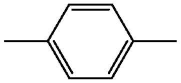 | — | 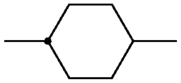 | 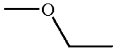 |
| 449 | n-$C_5H_{11}$ | 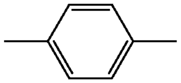 | 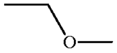 | 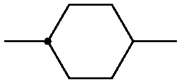 | — |
| 450 | $CH_3$ | 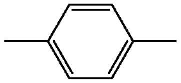 | 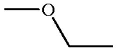 | 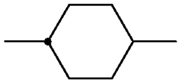 | — |
| 451 | $CH_3$ | 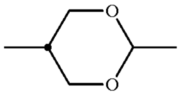 | — | 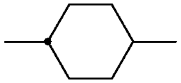 | 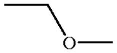 |
| 452 | n-$C_3H_7$ | 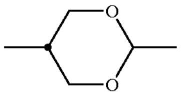 | — | 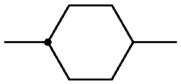 | 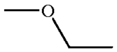 |
| 453 | n-$C_5H_{11}$ | 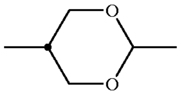 | 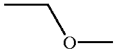 | 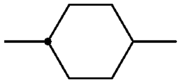 | — |
| 454 | n-$C_3H_7$ | 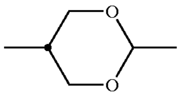 | — | 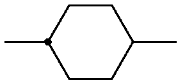 | 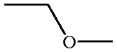 |

-continued
| | | | | | |
|---|---|---|---|---|---|
| 455 | n-$C_3H_7$ | 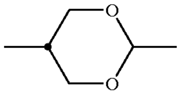 | — | 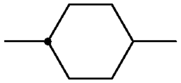 | 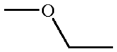 |
| 456 | n-$C_5H_{11}$ | 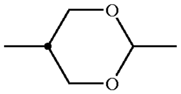 | 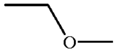 | 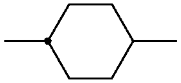 | — |
k = 1, m = 0, n = 1, $R_f$ = $CF_2CFHCF_3$
| | R | $A_2$ | $B_2$ | $A_3$ | $B_3$ |
|---|---|---|---|---|---|
| 457 | $CH_3$ | 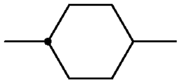 | — | 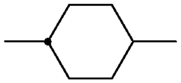 | 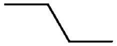 |
| 458 | n-$C_3H_7$ | 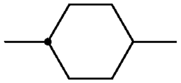 | 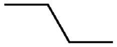 | 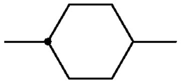 | — |
| 459 | $CH_3$ | 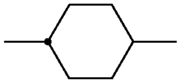 | — | 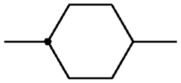 | 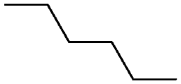 |
| 460 | $CH_3$ | 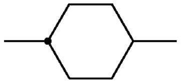 | 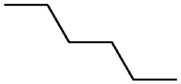 | 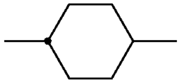 | — |
| 461 | $CH_3$ | 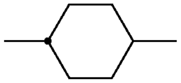 | 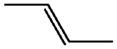 | 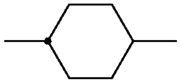 | — |
| 462 | n-$C_3H_7$ | 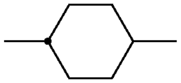 | — | 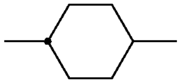 | —$CO_2$— |

-continued
| | | | | | |
|---|---|---|---|---|---|
| 463 | $CH_3$ | 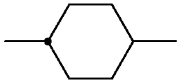 | $—CO_2—$ | 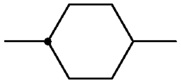 | — |
| 464 | $CH_3$ | 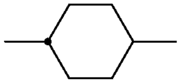 | — | 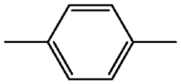 | 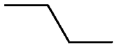 |
| 465 | $CH_3$ | 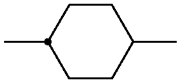 | 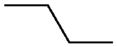 | 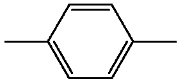 | — |
| 466 | $CH_3$ | 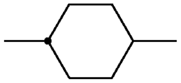 | — | 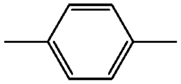 | 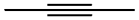 |
| 467 | $CH_3$ | 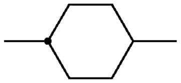 | — | 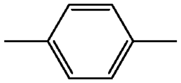 | $—CO_2—$ |
| 468 | $CH_3$ | 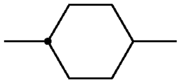 | $—CO_2—$ | 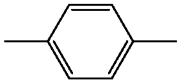 | — |
| 469 | $CH_3$ | 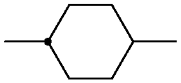 | — | 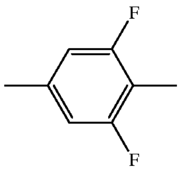 | 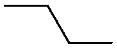 |
| 470 | $CH_3$ | 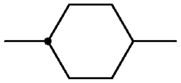 | 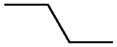 | 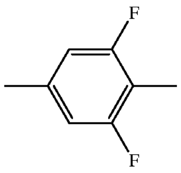 | — |

-continued
| | | | | | |
|---|---|---|---|---|---|
| 471 | $CH_3$ | 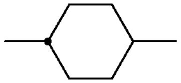 | — | 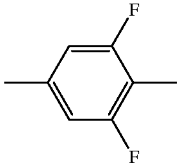 | 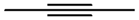 |
| 472 | n-$C_3H_7$ | 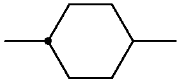 | — | 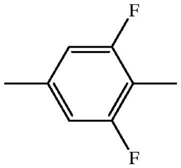 | —$CO_2$— |
| 473 | $CH_3$ | 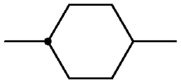 | —$CO_2$— | 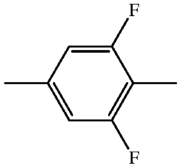 | — |
| 474 | $CH_3$ | 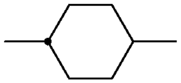 | — | 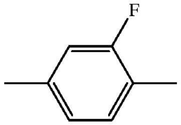 | 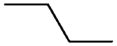 |
| | R | $A_3$ | $B_3$ | $A_4$ | $B_3$ |
| 475 | $CH_3$ | 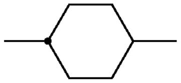 | 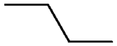 | 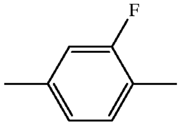 | — |
| 476 | n-$C_3H_7$ | 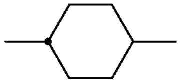 | — | 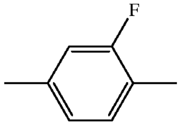 | 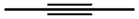 |

-continued
| | | | | | |
|---|---|---|---|---|---|
| 477 | $CH_3$ | 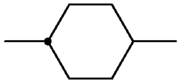 | — | 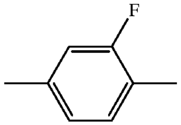 | —$CO_2$— |
| 478 | $CH_3$ | 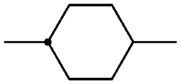 | — | 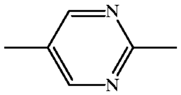 | — |
| 479 | $CH_3$ | 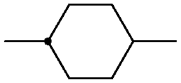 | — | 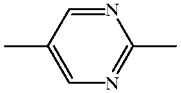 | 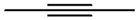 |
| 480 | $CH_3$ | 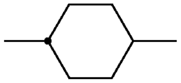 | — | 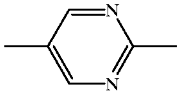 | —$CO_2$— |
| 481 | $CH_3$ | 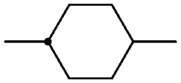 | —$CO_2$— | 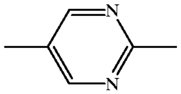 | — |
| 482 | $CH_3$ | 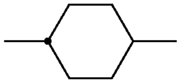 | — | 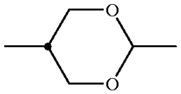 | 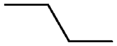 |
| 483 | $CH_3$ | 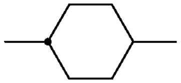 | 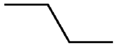 | 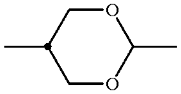 | — |
| 484 | $CH_3$ | 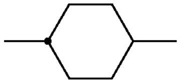 | — | 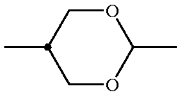 | —$CO_2$— |

-continued
| | | | | | |
|---|---|---|---|---|---|
| 485 | n-$C_3H_7$ | 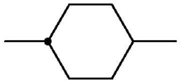 | —$CO_2$— | 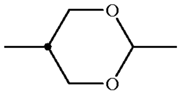 | — |
| 486 | $CH_3$ | 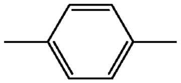 | — | 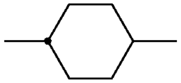 | 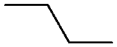 |
| 487 | $CH_3$ | 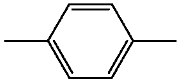 | 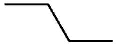 | 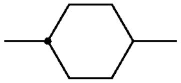 | — |
| 488 | $CH_3$ | 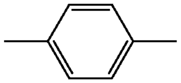 | — | 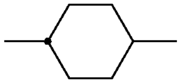 | —$CO_2$— |
| 489 | n-$C_3H_7$ | 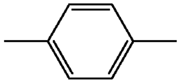 | —$CO_2$— | 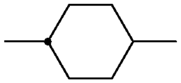 | — |
| 490 | $CH_3$ | 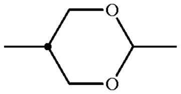 | — | 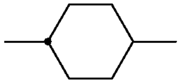 | — |
| 491 | $CH_3$ | 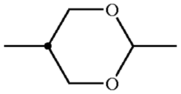 | — | 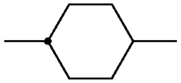 | 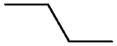 |
| 492 | $CH_3$ | 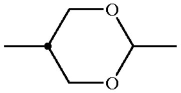 | 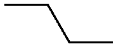 | 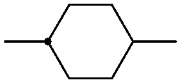 | — |

-continued
| | | | | | |
|---|---|---|---|---|---|
| 493 | $CH_3$ | 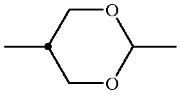 | — | 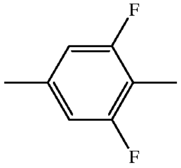 | — |
| 494 | $CH_3$ | 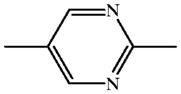 | — | 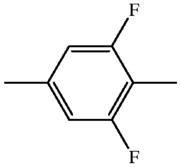 | — |
| | R | $A_2$ | $B_2$ | $A_3$ | $B_3$ |
| 495 | n-$C_3H_7$ | 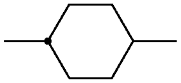 | — | 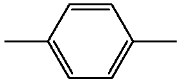 | 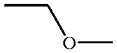 |
| 496 | n-$C_5H_{11}$ | 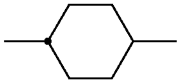 | — | 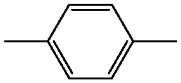 | 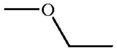 |
| 497 | 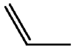 | 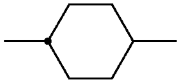 | — | 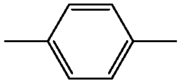 | 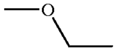 |
| 498 | $CH_3$ | 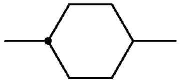 | 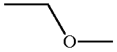 | 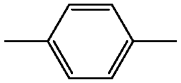 | — |
| 499 | n-$C_5H_{11}$ | 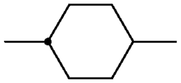 | 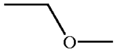 | 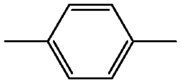 | — |

-continued
| | | | | | |
|---|---|---|---|---|---|
| 500 | n-$C_3H_7$ | 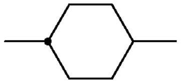 | 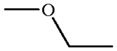 | 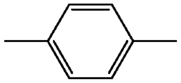 | — |
| 501 | n-$C_5H_{11}$ | 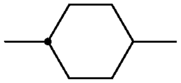 | 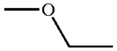 | 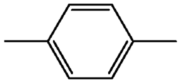 | — |
| 502 | $CH_3$ | 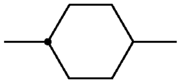 | — | 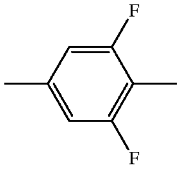 | 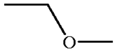 |
| 503 | n-$C_3H_7$ | 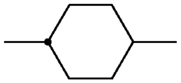 | — | 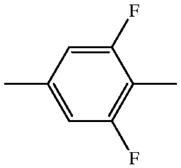 | 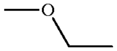 |
| 504 | n-$C_3H_7$ | 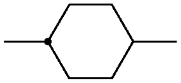 | 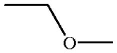 | 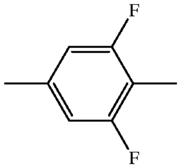 | — |
| 505 | n-$C_5H_{11}$ | 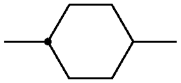 | 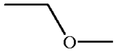 | 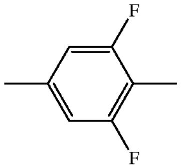 | — |

-continued
| | | | | | |
|---|---|---|---|---|---|
| 506 | n-$C_3H_7$ | 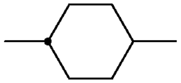 | 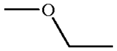 | 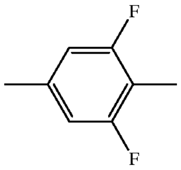 | — |
| 507 | n-$C_5H_{11}$ | 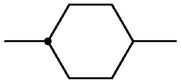 | 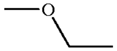 | 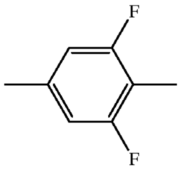 | — |
| 508 | n-$C_3H_7$ | 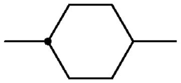 | — | 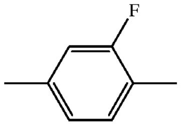 | 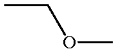 |
| 509 | n-$C_3H_7$ | 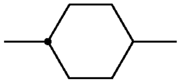 | — | 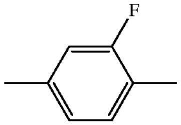 | 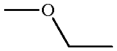 |
| 510 | n-$C_5H_{11}$ | 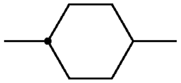 | 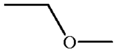 | 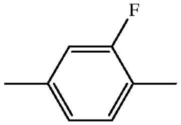 | — |
| 511 | n-$C_3H_7$ | 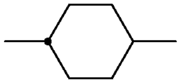 | 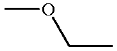 | 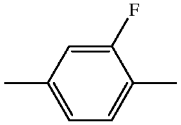 | — |
| 512 | n-$C_3H_7$ | 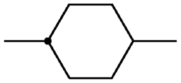 | — | 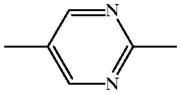 | 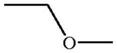 |

-continued
| | | | | | |
|---|---|---|---|---|---|
| 513 | n-$C_5H_{11}$ | 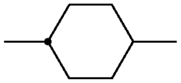 | — | 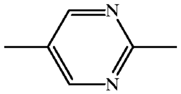 | 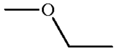 |
| 514 | n-$C_3H_7$ | 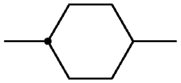 | 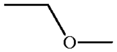 | 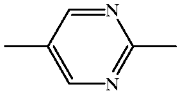 | — |
| 515 | n-$C_3H_7$ | 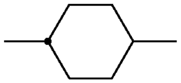 | 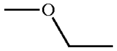 | 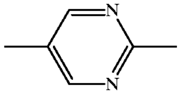 | — |
| 516 | n-$C_3H_7$ | 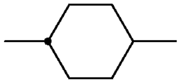 | — | 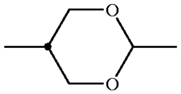 | 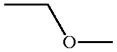 |
| 517 | n-$C_5H_{11}$ | 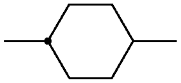 | 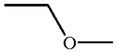 | 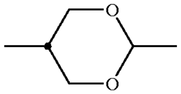 | — |
| 518 | n-$C_3H_7$ | 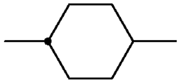 | 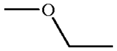 | 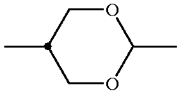 | — |
| 519 | $CH_3$ | 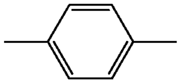 | — | 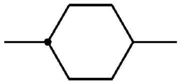 | 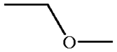 |
| 520 | n-$C_3H_7$ | 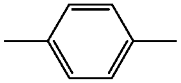 | — | 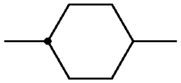 | 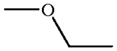 |
| 521 | n-$C_5H_{11}$ | 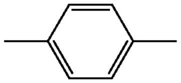 | 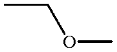 | 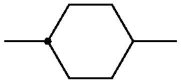 | — |

-continued
| | | | | | |
|---|---|---|---|---|---|
| 522 | $CH_3$ | 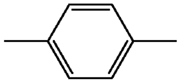 | 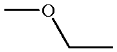 | 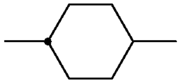 | — |
| 523 | $CH_3$ | 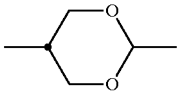 | — | 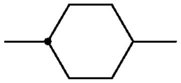 | 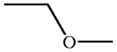 |
| 524 | $n\text{-}C_3H_7$ | 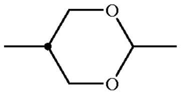 | — | 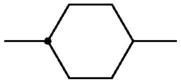 | 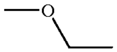 |
| 525 | $n\text{-}C_5H_{11}$ | 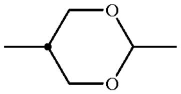 | 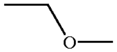 | 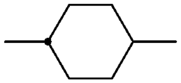 | — |
| 526 | $n\text{-}C_3H_7$ | 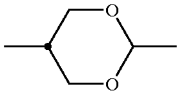 | — | 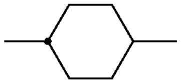 | 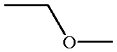 |
| 527 | $n\text{-}C_3H_7$ | 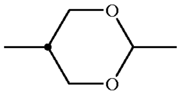 | — | 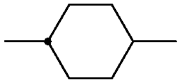 | 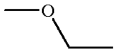 |
| 528 | $n\text{-}C_3H_7$ | 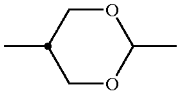 | 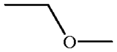 | 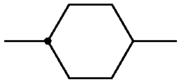 | — |
| 529 | $CH_3$ | 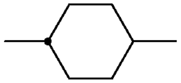 | — | 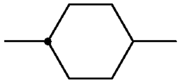 | 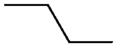 |
| 530 | $n\text{-}C_3H_7$ | 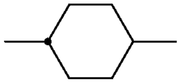 | 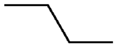 | 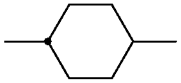 | — |

-continued
| | | | | | |
|---|---|---|---|---|---|
| 531 | $CH_3$ | 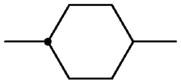 | — | 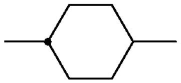 | 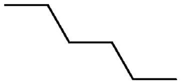 |
| 532 | $CH_3$ | 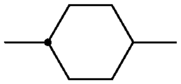 | 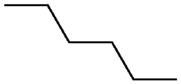 | 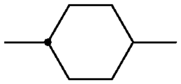 | — |
| 533 | $CH_3$ | 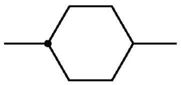 | 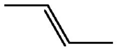 | 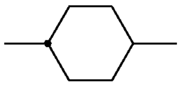 | — |
| 534 | n-$C_3H_7$ | 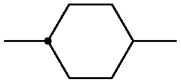 | — | 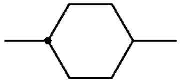 | —$CO_2$— |
| 535 | $CH_3$ | 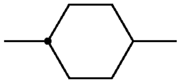 | —$CO_2$— | 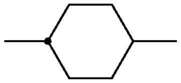 | — |
| 536 | $CH_3$ | 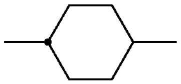 | 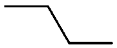 | 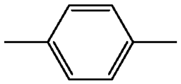 | — |
| 537 | $CH_3$ | 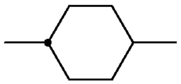 | — | 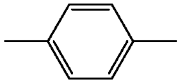 | 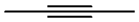 |
| 538 | $CH_3$ | 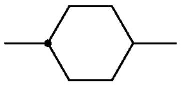 | — | 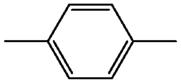 | —$CO_2$— |
| 539 | $CH_3$ | 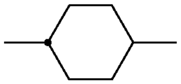 | —$CO_2$— | 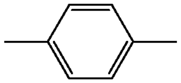 | — |

-continued
| | | | | | |
|---|---|---|---|---|---|
| 540 | $CH_3$ | 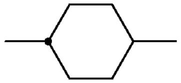 | — | 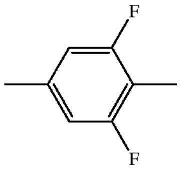 | 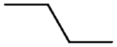 |
| 541 | $CH_3$ | 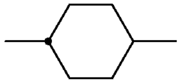 | 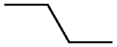 | 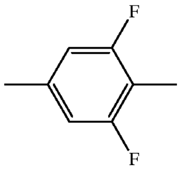 | — |
| 542 | $CH_3$ | 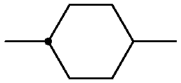 | — | 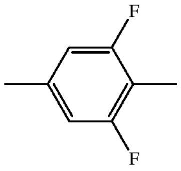 | 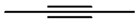 |
| 543 | $n\text{-}C_3H_7$ | 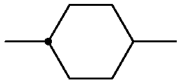 | — | 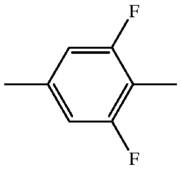 | $—CO_2—$ |
| 544 | $CH_3$ | 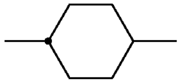 | $—CO_2—$ | 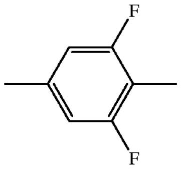 | — |

-continued
| | | | | | | |
|---|---|---|---|---|---|---|
| 545 | $CH_3$ | 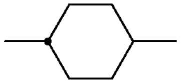 | — | 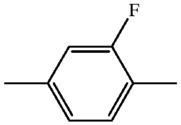 | 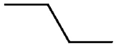 | |
| | R | $A_3$ | $B_3$ | $B_3$ | $A_4$ | $B_3$ |
| 546 | $CH_3$ | 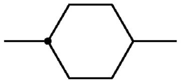 | 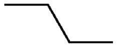 | 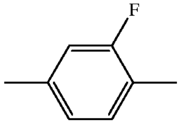 | — | |
| 547 | n-$C_3H_7$ | 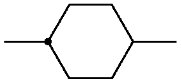 | — | 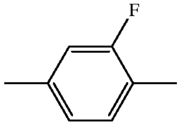 | 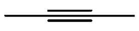 | |
| 548 | $CH_3$ | 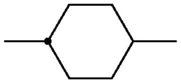 | — | 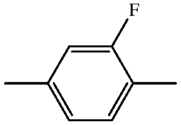 | —$CO_2$— | |
| 549 | $CH_3$ | 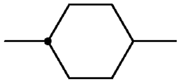 | — | 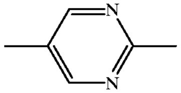 | — | |
| 550 | $CH_3$ | 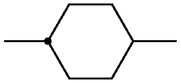 | — | 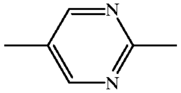 | 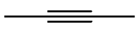 | |
| 551 | $CH_3$ | 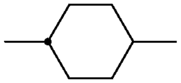 | — | 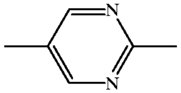 | —$CO_2$— | |

-continued
| | | | | | |
|---|---|---|---|---|---|
| 552 | $CH_3$ | 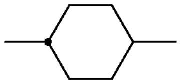 | $—CO_2—$ | 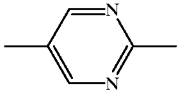 | — |
| 553 | $CH_3$ | 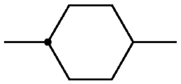 | — | 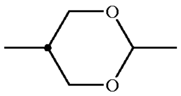 | 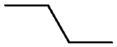 |
| 554 | $CH_3$ | 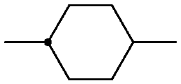 | 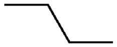 | 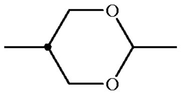 | — |
| 555 | $CH_3$ | 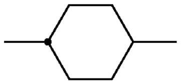 | — | 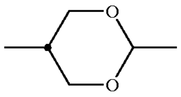 | $—CO_2—$ |
| 556 | $n-C_3H_7$ | 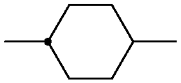 | $—CO_2—$ | 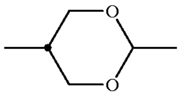 | — |
| 557 | $CH_3$ | 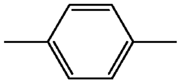 | — | 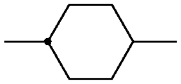 | 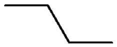 |
| 558 | $CH_3$ | 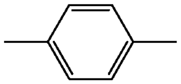 | 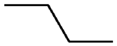 | 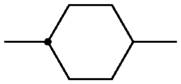 | — |
| 559 | $CH_3$ | 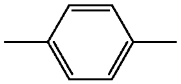 | — | 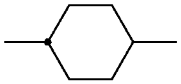 | $—CO_2—$ |
| 560 | $n-C_3H_7$ | 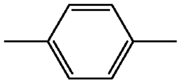 | $—CO_2—$ | 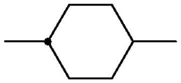 | — |

-continued
| | | | | | |
|---|---|---|---|---|---|
| 561 | $CH_3$ | 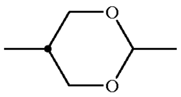 | — | 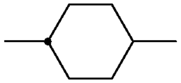 | — |
| 562 | $CH_3$ | 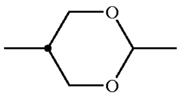 | — | 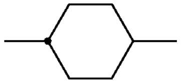 | 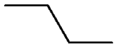 |
| 563 | $CH_3$ | 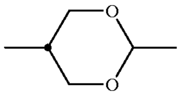 | 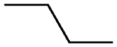 | 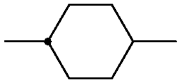 | — |
| 564 | $CH_3$ | 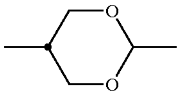 | — | 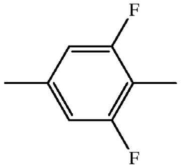 | — |
| 565 | $CH_3$ | 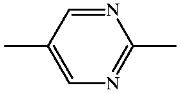 | — | 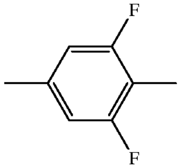 | — |
| | R | $A_2$ | $B_2$ | $A_3$ | $B_3$ |
| 566 | n-$C_3H_7$ | 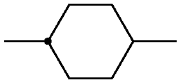 | — | 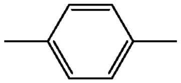 | 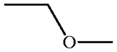 |
| 567 | n-$C_5H_{11}$ | 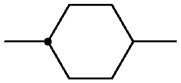 | — | 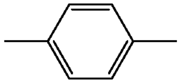 | 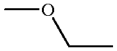 |

-continued
| | | | | | |
|---|---|---|---|---|---|
| 568 | 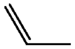 | 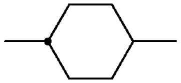 | — | 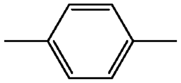 | 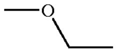 |
| 569 | $CH_3$ | 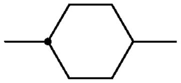 | 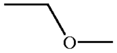 | 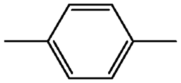 | — |
| 570 | n-$C_5H_{11}$ | 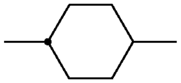 | 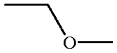 | 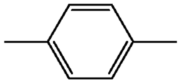 | — |
| 571 | n-$C_3H_7$ | 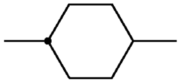 | 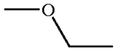 | 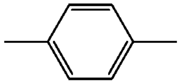 | — |
| 572 | n-$C_5H_{11}$ | 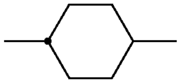 | 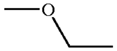 | 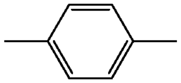 | — |
| 573 | $CH_3$ | 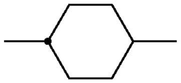 | — | 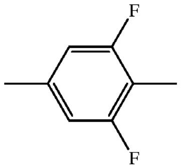 | 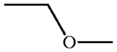 |
| 574 | n-$C_3H_7$ | 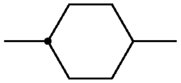 | — | 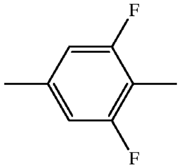 | 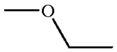 |

-continued
| | | | | | |
|---|---|---|---|---|---|
| 575 | n-$C_3H_7$ | 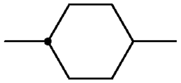 | 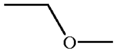 | 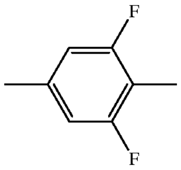 | — |
| 576 | n-$C_5H_{11}$ | 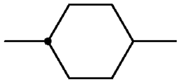 | 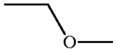 | 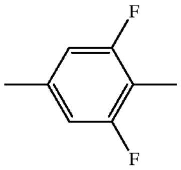 | — |
| 577 | n-$C_3H_7$ | 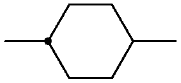 | 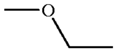 | 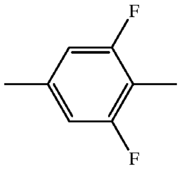 | — |
| 578 | n-$C_5H_{11}$ | 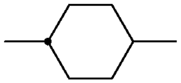 | 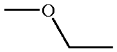 | 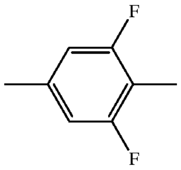 | — |
| 579 | n-$C_3H_7$ | 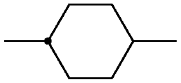 | — | 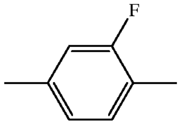 | 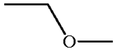 |
| 580 | n-$C_3H_7$ | 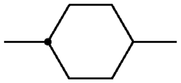 | — | 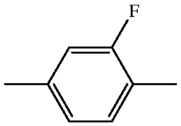 | 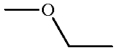 |

-continued
| | | |
|---|---|---|
| 581 | n-$C_5H_{11}$ | 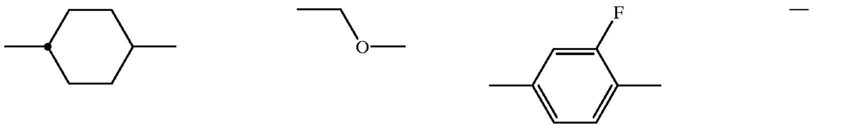 |
| 582 | n-$C_3H_7$ | 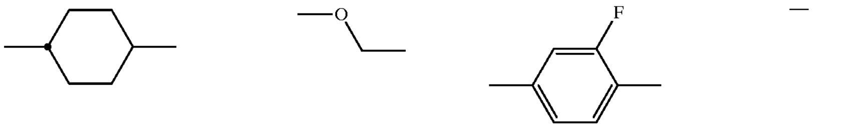 |
| 583 | n-$C_3H_7$ | 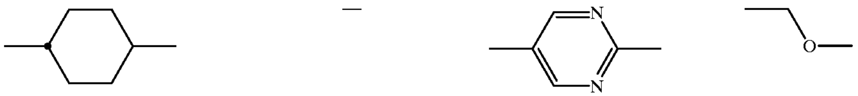 |
| 584 | n-$C_5H_{11}$ | 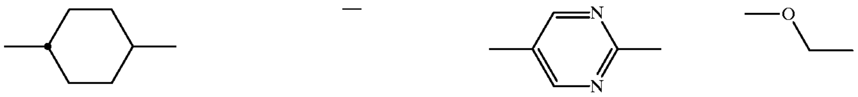 |
| 585 | n-$C_3H_7$ | 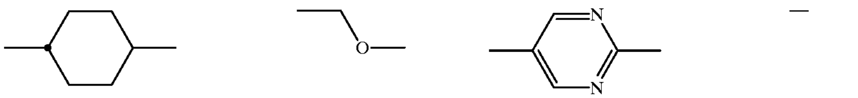 |
| 586 | n-$C_3H_7$ | 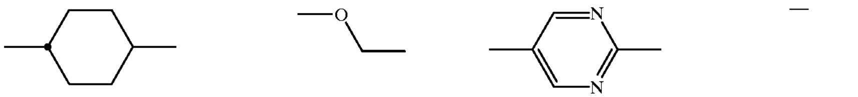 |
| 587 | n-$C_3H_7$ | 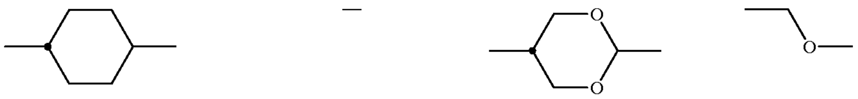 |
| 588 | n-$C_5H_{11}$ | 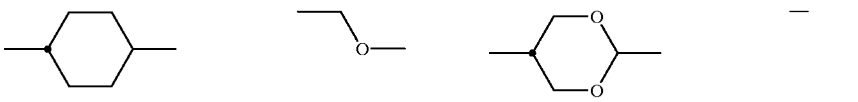 |

-continued
| | | |
|---|---|---|
| 589 | n-$C_3H_7$ | 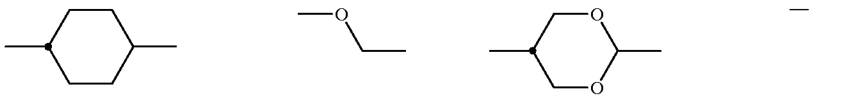 |
| 590 | $CH_3$ | 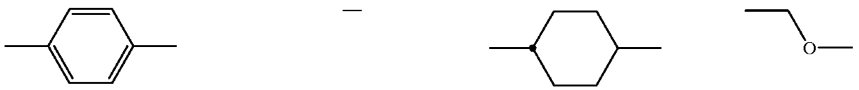 |
| 591 | n-$C_3H_7$ | 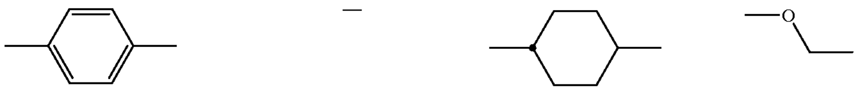 |
| 592 | n-$C_5H_{11}$ | 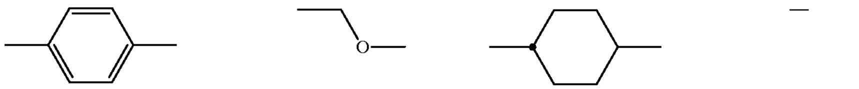 |
| 593 | $CH_3$ | 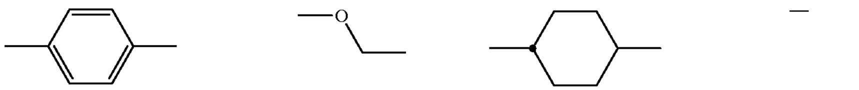 |
| 594 | $CH_3$ | 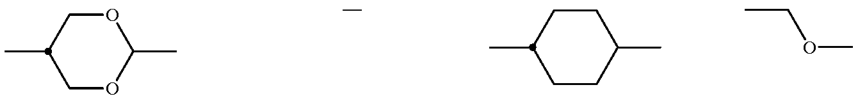 |
| 595 | n-$C_3H_7$ | 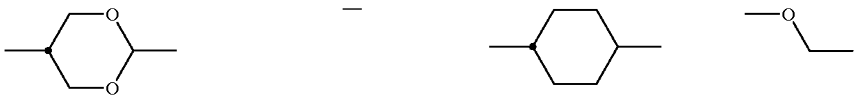 |
| 596 | n-$C_5H_{11}$ | 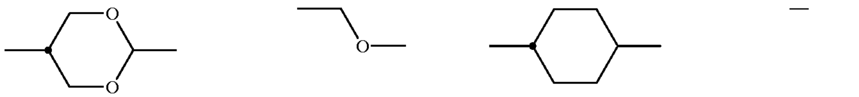 |
| 597 | n-$C_3H_7$ | 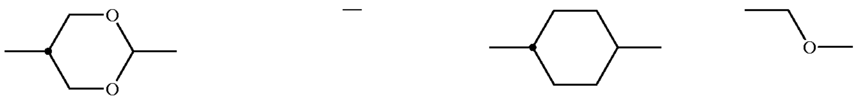 |

-continued
| | | | | | |
|---|---|---|---|---|---|
| 598 | n-$C_3H_7$ | 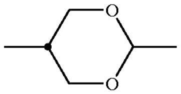 | — | 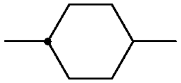 | 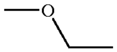 |
| 599 | n-$C_5H_{11}$ | 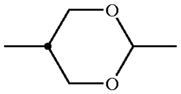 | 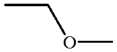 | 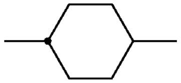 | — |
k = m = n = 1, $R_f$ = $CF_3$
| | R | $A_1$ | $B_1$ | $A_2$ | $B_2$ | $A_3$ | $B_3$ |
|---|---|---|---|---|---|---|---|
| 600 | $CH_3$ | 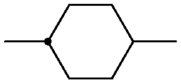 | — | 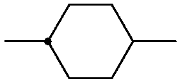 | — | 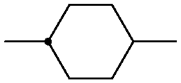 | — |
| 601 | n-$C_3H_7$ | 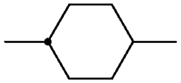 | — | 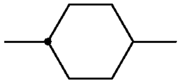 | — | 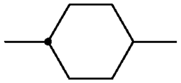 | — |
| 602 | $CH_3$ | 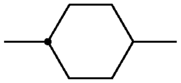 | — | 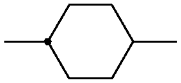 | — | 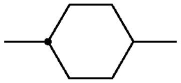 | 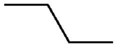 |
| 603 | n-$C_3H_7$ | 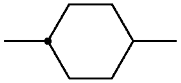 | — | 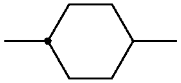 | — | 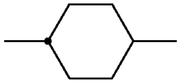 | 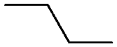 |
| 604 | $CH_3$ | 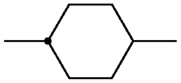 | — | 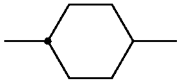 | 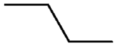 | 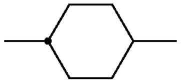 | — |
| 605 | n-$C_3H_7$ | 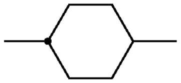 | — | 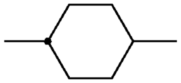 | 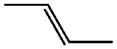 | 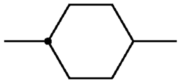 | — |

-continued
| | | |
|---|---|---|
| 606 | $CH_3$ | 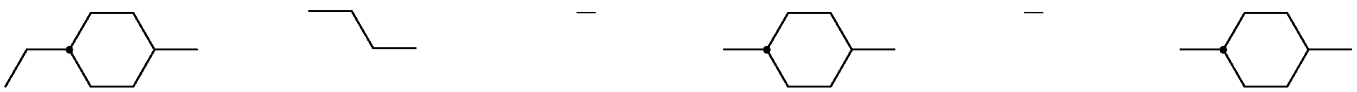 |
| 607 | $n-C_3H_7$ | 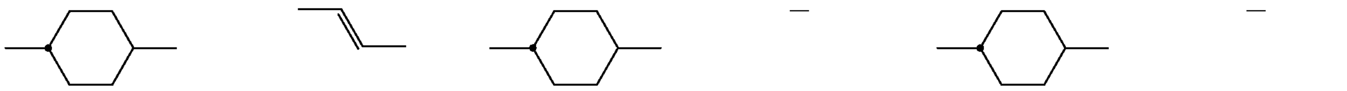 |
| 611 | $CH_3$ | 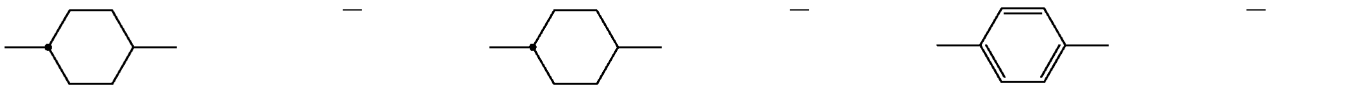 |
| 612 | $n-C_3H_7$ | 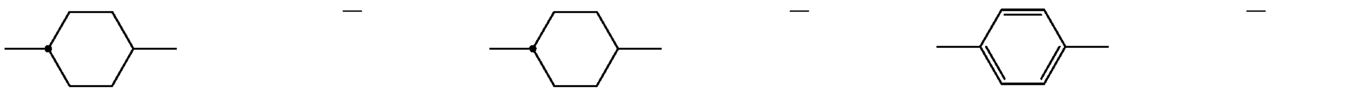 |
| 613 | $CH_3$ | 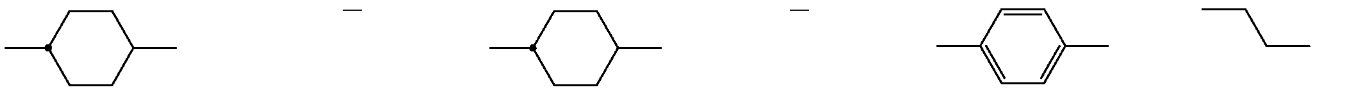 |
| 614 | $C_2H_5$ | 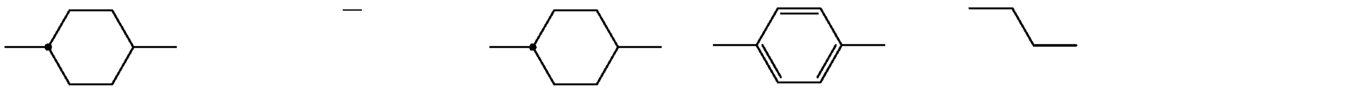 |
| 615 | $C_2H_5$ | 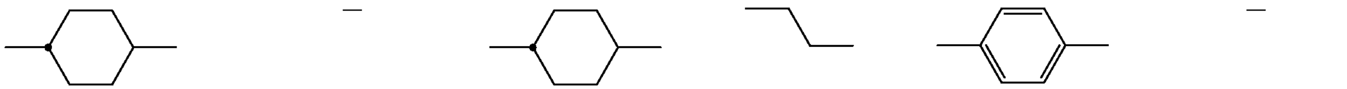 |
| 616 | $n-C_3H_7$ | 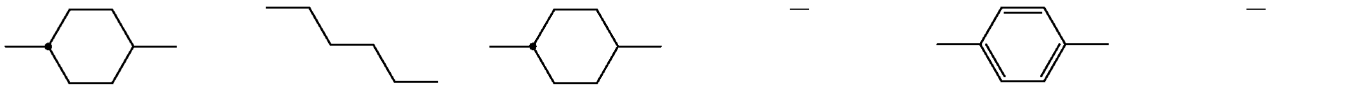 |
| 617 | $CH_3$ | 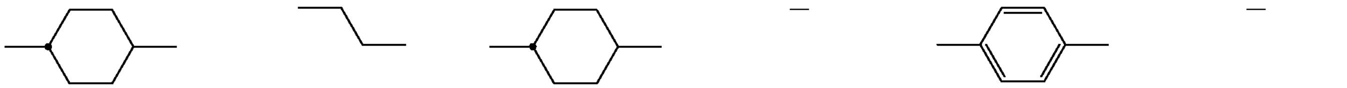 |

-continued
| | | | | | | | |
|---|---|---|---|---|---|---|---|
| 618 | n-$C_3H_7$ | 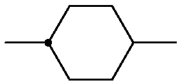 | 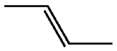 | 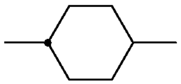 | — | 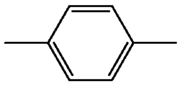 | — |
| 622 | $CH_3$ | 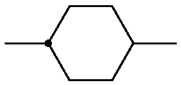 | — | 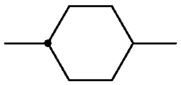 | — | 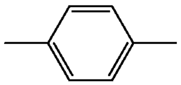 | 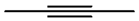 |
| 623 | $CH_3$ | 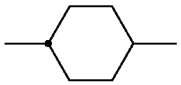 | — | 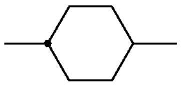 | — | 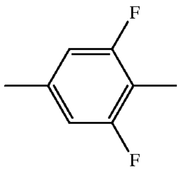 | — |
| 624 | n-$C_3H_7$ | 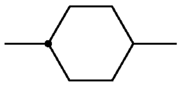 | — | 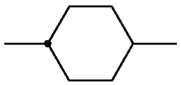 | — | 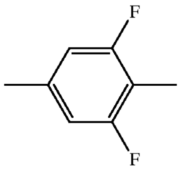 | — |
| 628 | $CH_3$ | 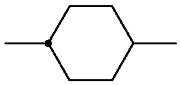 | — | 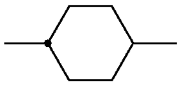 | — | 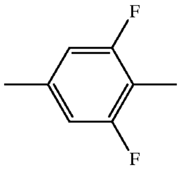 | 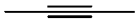 |
| 629 | $CH_3$ | 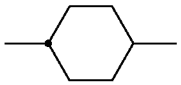 | — | 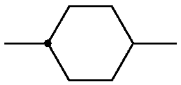 | — | 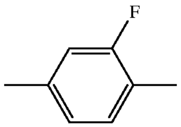 | — |
| 630 | n-$C_3H_7$ | 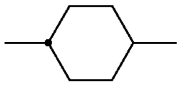 | — | 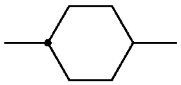 | — | 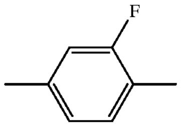 | — |

-continued
| | | |
|---|---|---|
| 631 | $CH_3$ | 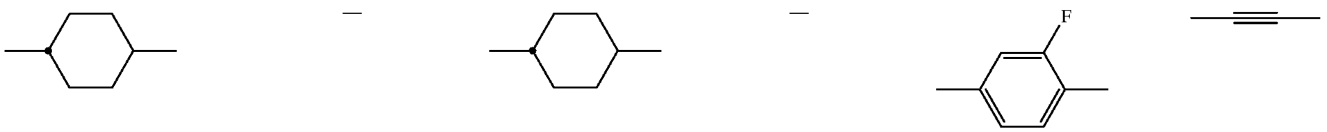 |
| 635 | $CH_3$ | 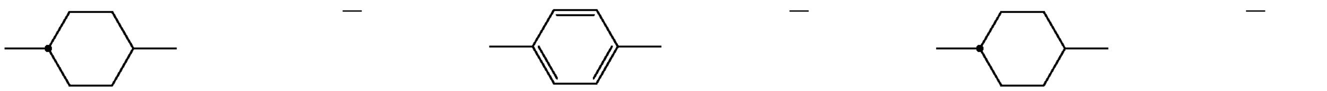 |
| 636 | $CH_3$ | 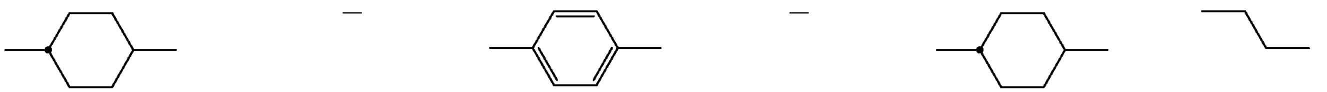 |
| 637 | $CH_3$ | 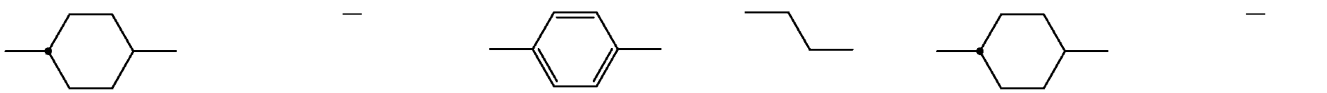 |
| 638 | $CH_3$ | 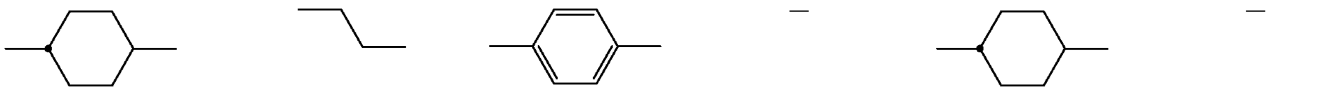 |
| 642 | $CH_3$ | 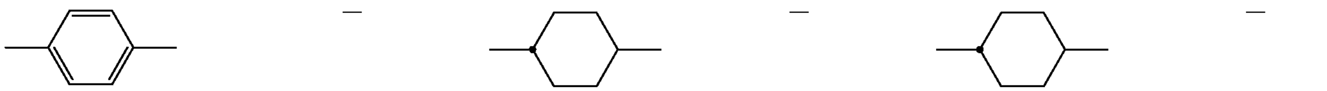 |
| 643 | $n-C_3H_7$ | 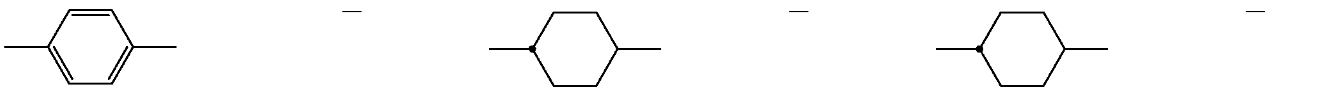 |
| 644 | $CH_3$ | 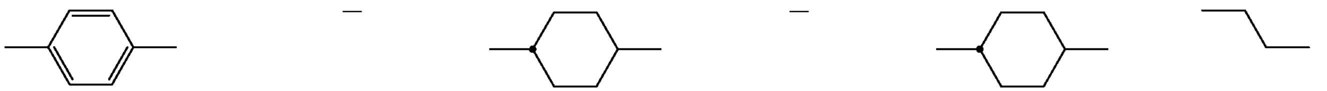 |
| 645 | $CH_3$ | 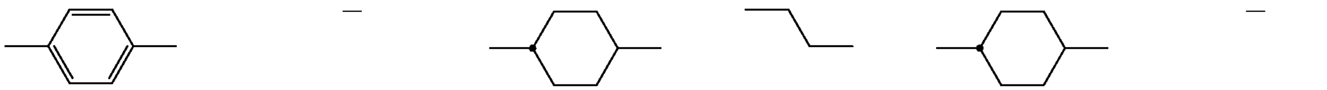 |

-continued
| | | | | | | | |
|---|---|---|---|---|---|---|---|
| 646 | n-$C_3H_7$ | 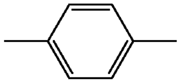 | — | 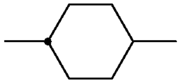 | 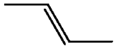 | 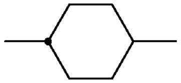 | — |
| 647 | n-$C_3H_7$ | 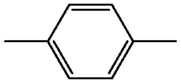 | 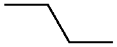 | 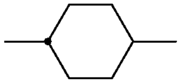 | — | 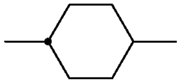 | — |
| 648 | n-$CH_3$ | 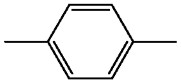 | 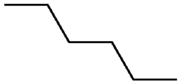 | 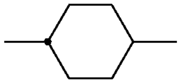 | — | 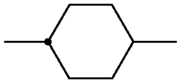 | — |
| 652 | $CH_3$ | 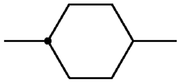 | — | 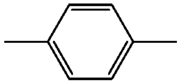 | — | 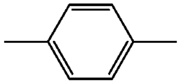 | — |
| 653 | n-$C_3H_7$ | 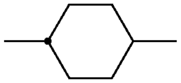 | — | 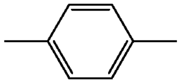 | — | 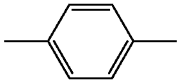 | — |
| 654 | n-$C_3H_7$ | 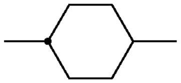 | — | 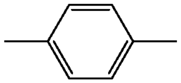 | — | 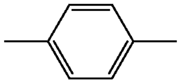 | 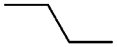 |
| 655 | $CH_3$ | 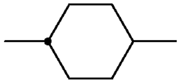 | — | 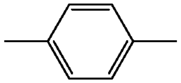 | 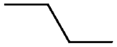 | 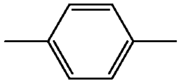 | — |
| 656 | $CH_3$ | 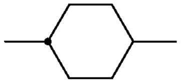 | 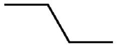 | 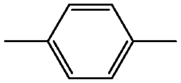 | — | 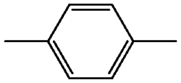 | — |
| 660 | $CH_3$ | 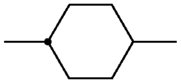 | — | 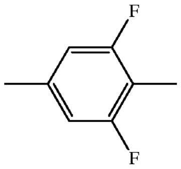 | — | 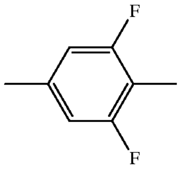 | — |

-continued
| | | | | | | | |
|---|---|---|---|---|---|---|---|
| 661 | n-$C_3H_7$ | 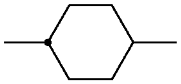 | — | 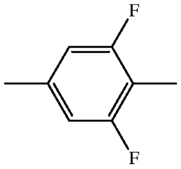 | — | 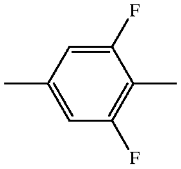 | — |
| 665 | $CH_3$ | 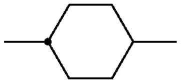 | — | 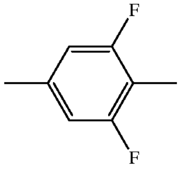 | — | 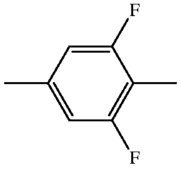 | 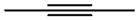 |
| 666 | $CH_3$ | 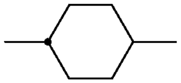 | — | 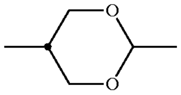 | — | 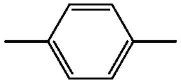 | — |
| 667 | $CH_3$ | 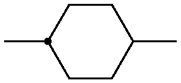 | — | 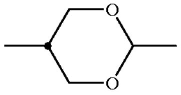 | — | 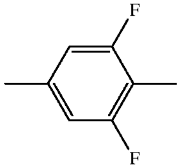 | — |
| 668 | $CH_3$ | 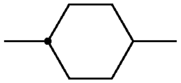 | — | 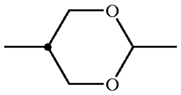 | — | 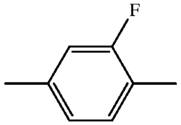 | — |
| 669 | $CH_3$ | 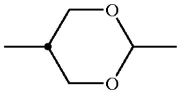 | — | 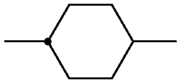 | — | 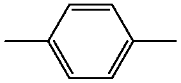 | — |

-continued
| | | | | | | | |
|---|---|---|---|---|---|---|---|
| 670 | $CH_3$ | 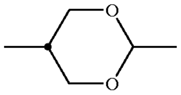 | — | 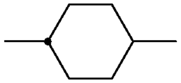 | — | 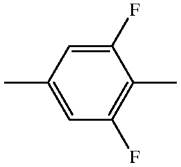 | — |
| 671 | n-$C_3H_7$ | 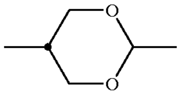 | — | 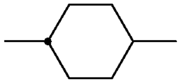 | — | 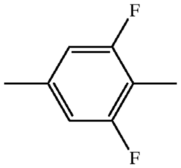 | — |
| 672 | $CH_3$ | 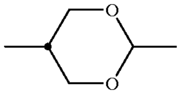 | — | 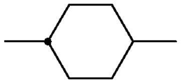 | — | 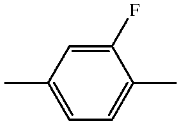 | — |
| 673 | $CH_3$ | 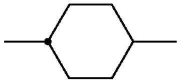 | — | 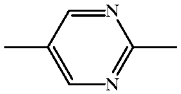 | — | 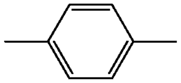 | — |
| 674 | $CH_3$ | 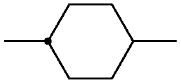 | — | 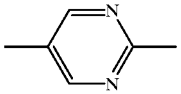 | — | 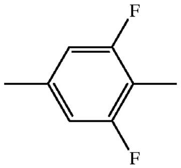 | — |
| 675 | $CH_3$ | 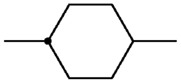 | — | 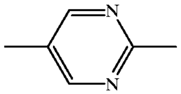 | — | 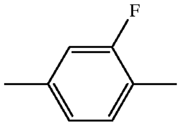 | — |

-continued
| | | | | | | | |
|---|---|---|---|---|---|---|---|
| 676 | $CH_3$ | 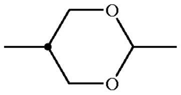 | — | 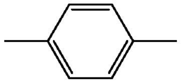 | — | 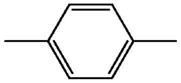 | — |
| 677 | n-$C_3H_7$ | 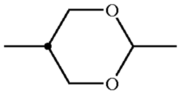 | — | 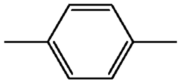 | — | 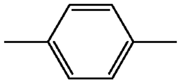 | — |
| 678 | $CH_3$ | 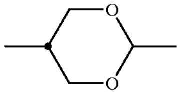 | — | 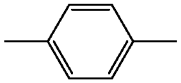 | — | 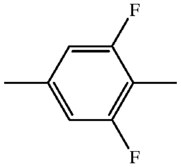 | — |
| 679 | n-$C_3H_7$ | 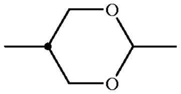 | — | 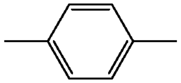 | — | 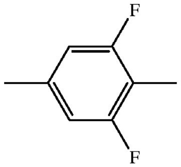 | — |
| 680 | $CH_3$ | 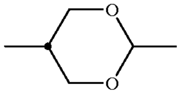 | 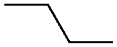 | 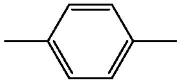 | — | 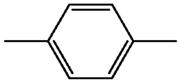 | — |
| 681 | n-$C_3H_7$ | 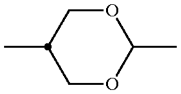 | 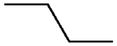 | 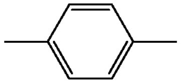 | — | 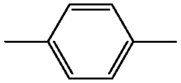 | — |
| 682 | $CH_3$ | 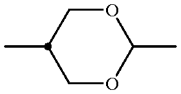 | 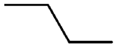 | 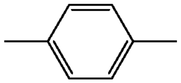 | — | 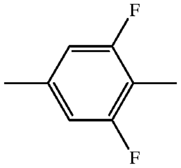 | — |

-continued
| | | | | | | | |
|---|---|---|---|---|---|---|---|
| 683 | $CH_3$ | 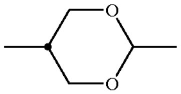 | — | 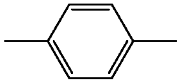 | — | 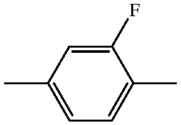 | — |
| k = 0, m = n = 1, $R_f = CF_3$ | | | | | | | |
| 684 | n-$C_3H_7$ | 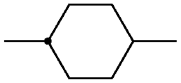 | — | 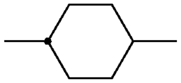 | — | 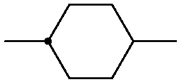 | 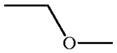 |
| 685 | n-$C_5H_{11}$ | 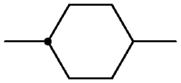 | — | 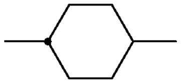 | — | 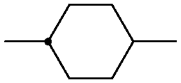 | 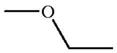 |
| 686 | $CH_3$ | 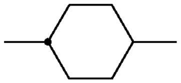 | — | 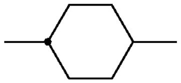 | 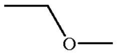 | 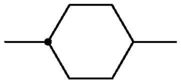 | — |
| 687 | n-$C_5H_{11}$ | 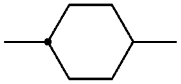 | — | 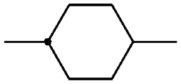 | 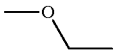 | 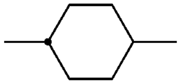 | — |
| 688 | n-$C_5H_{11}$ | 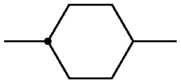 | 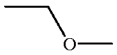 | 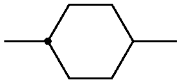 | — | 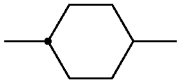 | — |
| 689 | n-$C_3H_7$ | 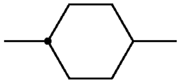 | 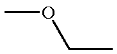 | 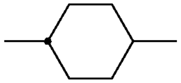 | — | 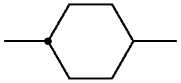 | — |
| 690 | n-$C_3H_7$ | 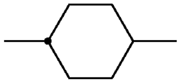 | — | 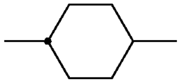 | — | 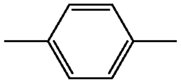 | 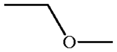 |
| 691 | $CH_3$ | 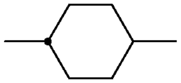 | — | 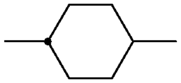 | — | 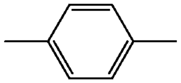 | 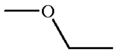 |

-continued
| | | | | | | | |
|---|---|---|---|---|---|---|---|
| 692 | n-$C_3H_7$ | 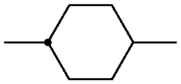 | — | 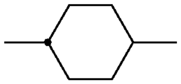 | 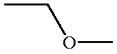 | 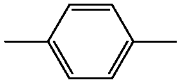 | — |
| 693 | n-$C_5H_{11}$ | 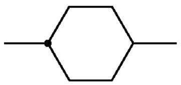 | — | 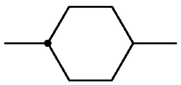 | 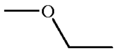 | 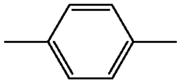 | — |
| 694 | n-$C_5H_{11}$ | 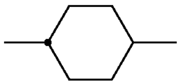 | 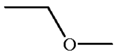 | 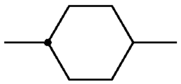 | — | 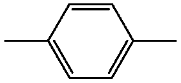 | — |
| 695 | n-$C_3H_7$ | 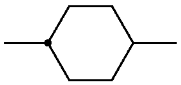 | 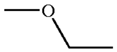 | 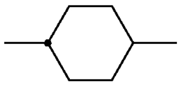 | — | 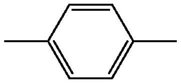 | — |
| 696 | n-$C_3H_7$ | 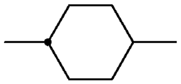 | — | 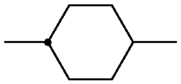 | — | 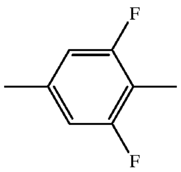 | 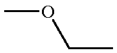 |
| 697 | n-$C_5H_{11}$ | 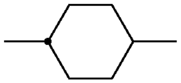 | — | 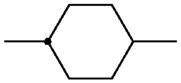 | — | 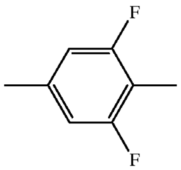 | 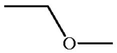 |
| 698 | n-$C_3H_7$ | 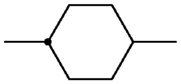 | — | 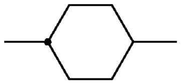 | 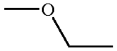 | 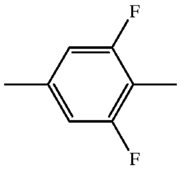 | — |

-continued
| | | | | | | | |
|---|---|---|---|---|---|---|---|
| 699 | n-$C_3H_7$ | 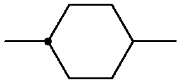 | — | 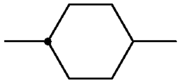 | 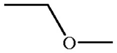 | 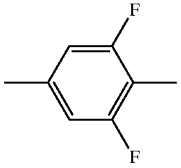 | — |
| 700 | n-$C_3H_7$ | 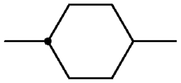 | 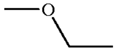 | 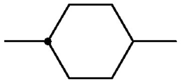 | — | 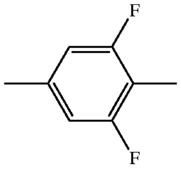 | — |
| 701 | n-$C_5H_{11}$ | 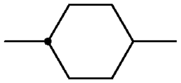 | 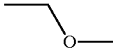 | 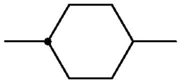 | — | 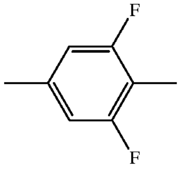 | — |
| 702 | n-$C_3H_7$ | 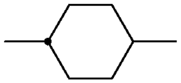 | — | 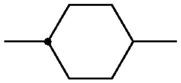 | — | 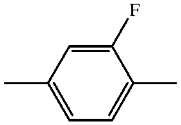 | 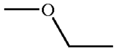 |
| 703 | n-$C_3H_{11}$ | 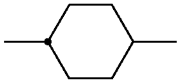 | — | 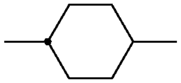 | — | 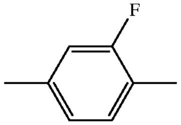 | 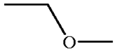 |
| 704 | n-$C_3H_7$ | 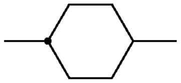 | — | 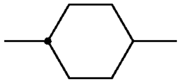 | 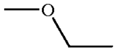 | 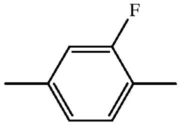 | — |

-continued
| | | | | | | | |
|---|---|---|---|---|---|---|---|
| 705 | n-$C_3H_7$ | 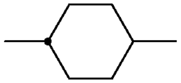 | — | 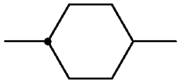 | 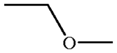 | 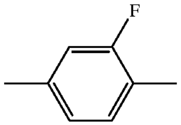 | — |
| 706 | $CH_3$ | 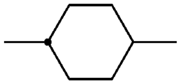 | 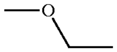 | 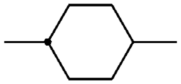 | — | 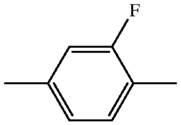 | — |
| 707 | n-$C_5H_{11}$ | 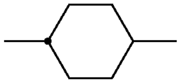 | 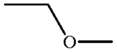 | 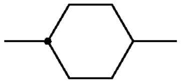 | — | 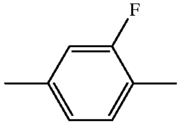 | — |
| 708 | n-$C_3H_7$ | 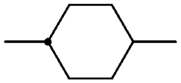 | — | 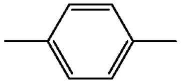 | — | 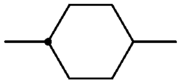 | 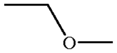 |
| 709 | $CH_3$ | 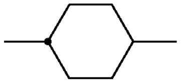 | — | 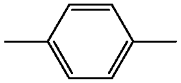 | — | 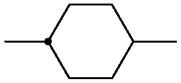 | 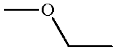 |
| 710 | n-$C_3H_7$ | 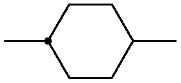 | — | 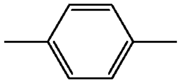 | 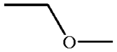 | 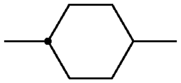 | — |
| 711 | n-$C_5H_{11}$ | 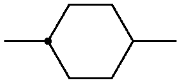 | — | 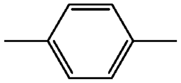 | 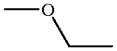 | 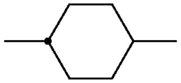 | — |
| 712 | n-$C_3H_7$ | 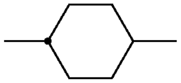 | 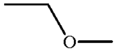 | 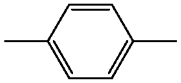 | — | 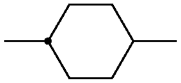 | — |

-continued
| | | |
|---|---|---|
| 713 | n-$C_3H_7$ | 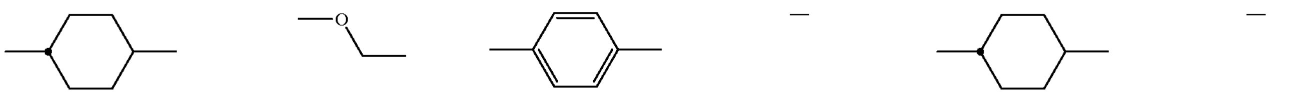 |
| 714 | $CH_3$ | 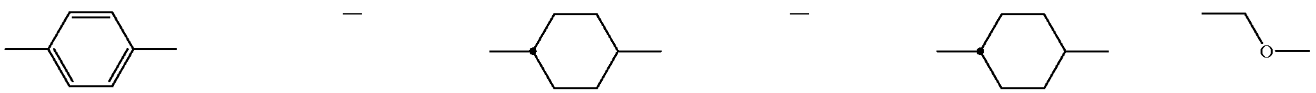 |
| 715 | n-$C_3H_7$ | 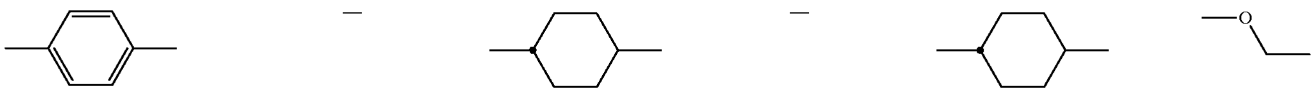 |
| 716 | n-$C_3H_7$ | 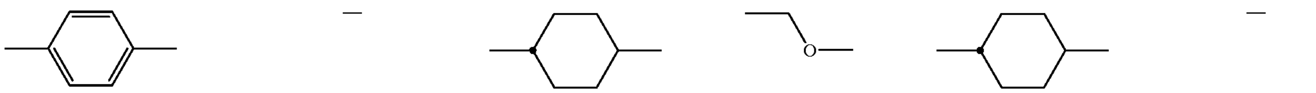 |
| 717 | n-$C_5H_{11}$ | 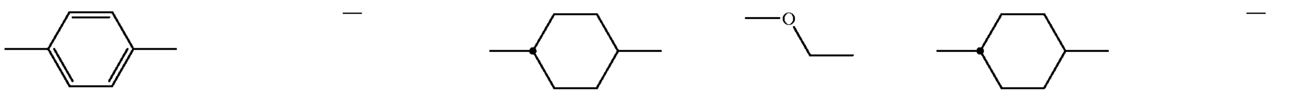 |
| 718 | n-$C_5H_{11}$ | 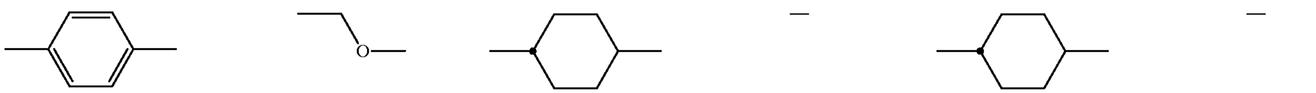 |
| 719 | $CH_3$ | 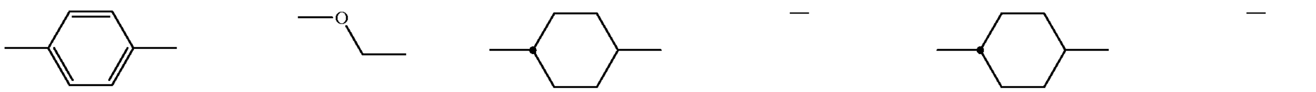 |
| 720 | n-$C_3H_7$ | 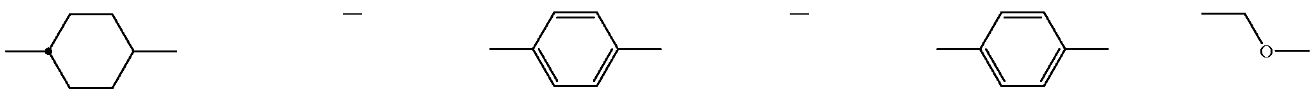 |
| 721 | n-$C_5H_{11}$ | 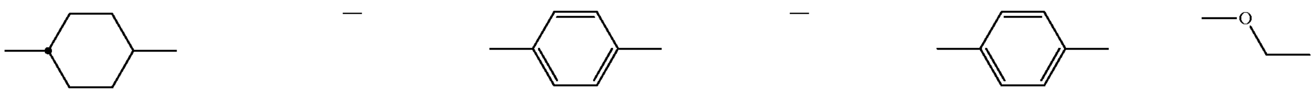 |

-continued
| | | |
|---|---|---|
| 722 | n-$C_3H_7$ | 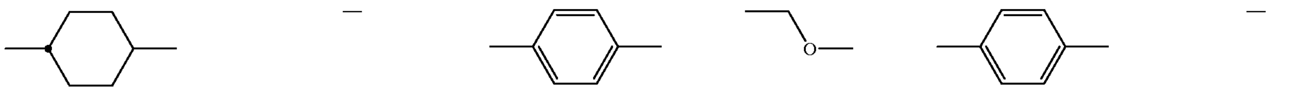 |
| 723 | n-$C_5H_{11}$ | 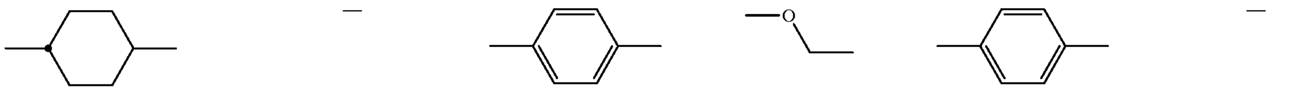 |
| 724 | n-$C_5H_{11}$ | 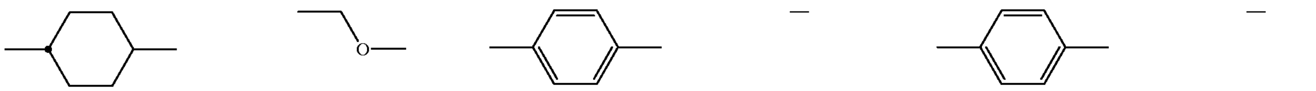 |
| 725 | $CH_3$ | 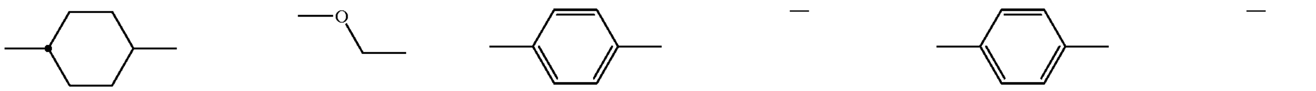 |
| 726 | n-$C_3H_7$ | 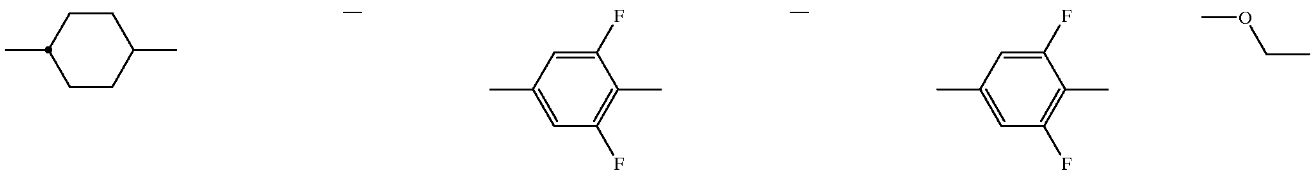 |
| 727 | n-$C_5H_{11}$ | 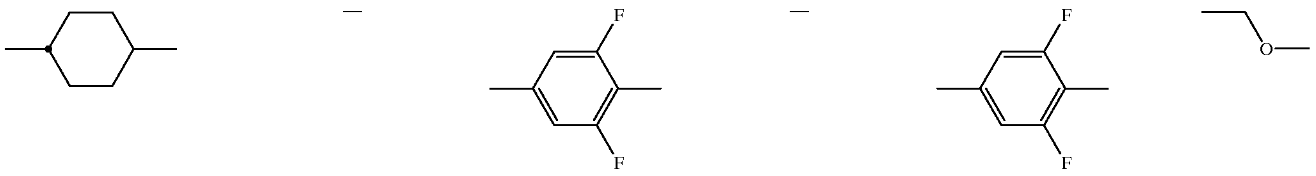 |
| 728 | $CH_3$ | 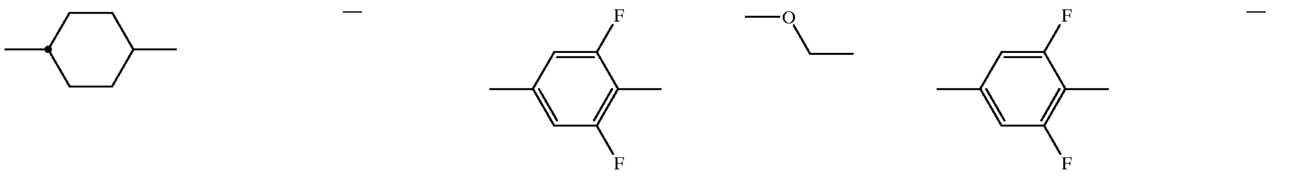 |

-continued
| | | |
|---|---|---|
| 729 | n-$C_3H_7$ | 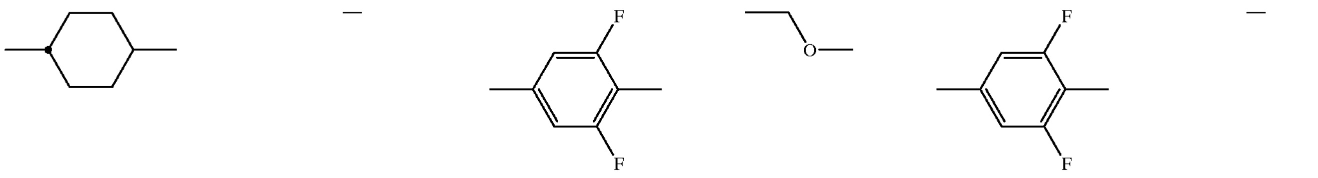 |
| 730 | n-$C_3H_7$ | 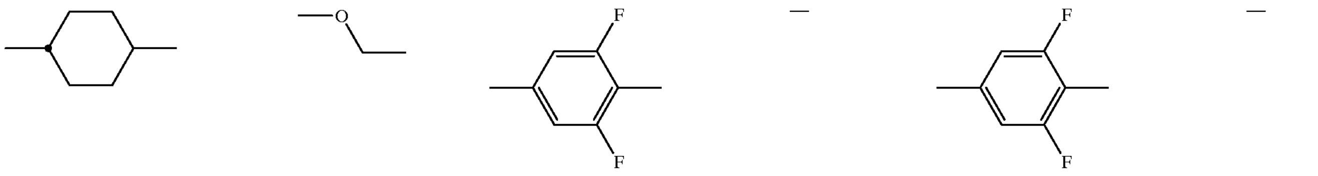 |
| 731 | $CH_3$ | 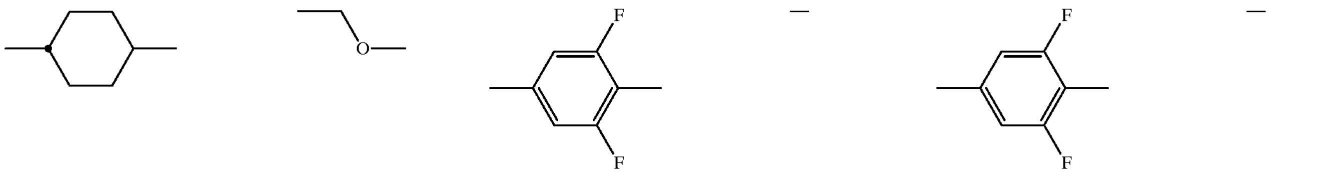 |
| 732 | n-$C_3H_7$ | 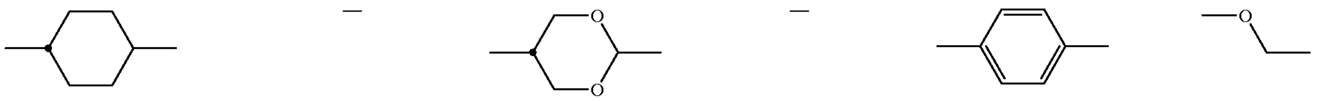 |
| 733 | n-$C_5H_{11}$ | 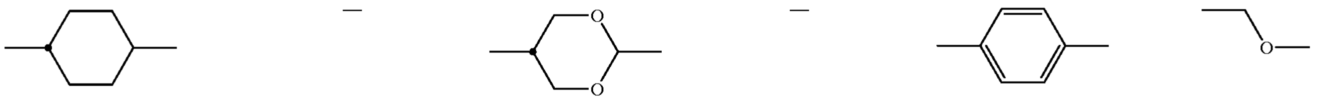 |
| 734 | n-$C_3H_7$ | 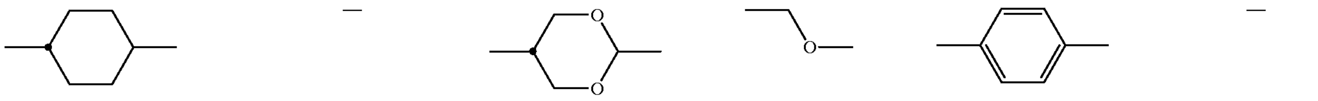 |
| 735 | n-$C_3H_7$ | 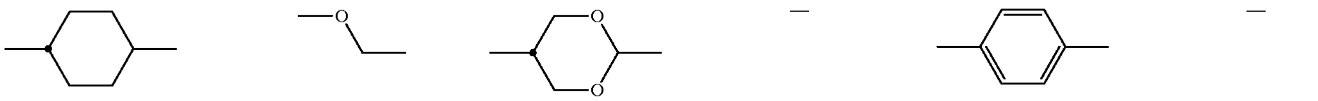 |

-continued
| | | |
|---|---|---|
| 736 | $CH_3$ | 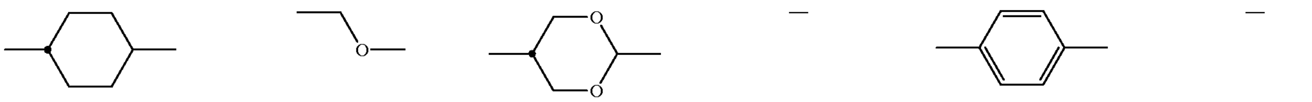 |
| 737 | n-$C_3H_7$ | 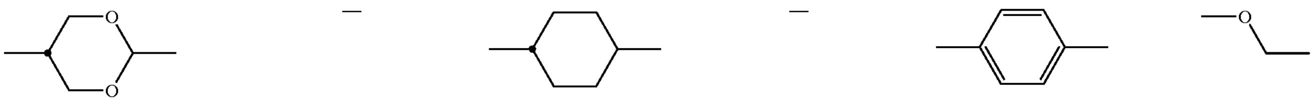 |
| 738 | n-$C_5H_{11}$ | 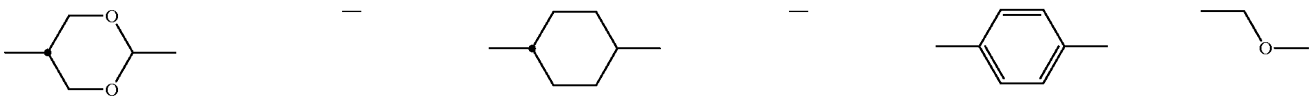 |
| 739 | n-$C_3H_7$ | 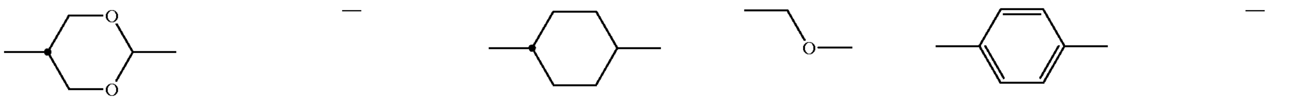 |
| k = m = n = 1, $R_f$ = $CF_2H$ | | |
| 740 | $CH_3$ | 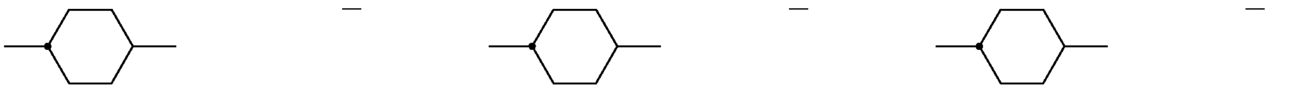 |
| 741 | n-$C_3H_7$ | 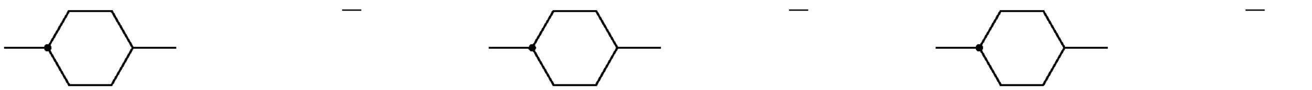 |
| 742 | $CH_3$ | 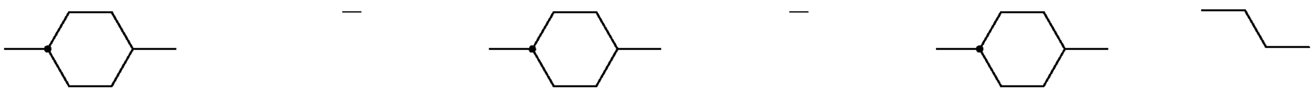 |
| 743 | n-$C_3H_7$ | 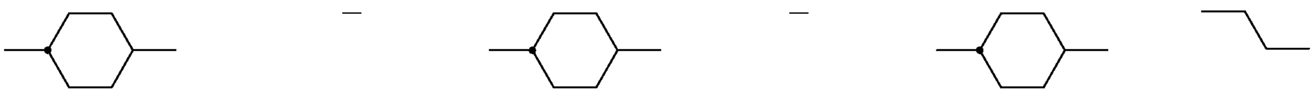 |
| 744 | $CH_3$ | 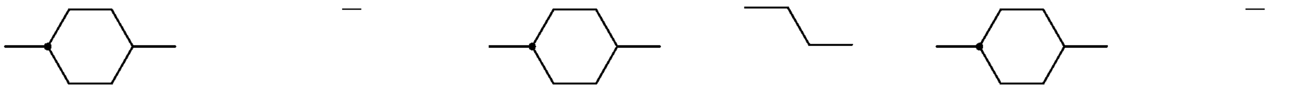 |

-continued
| | | |
|---|---|---|
| 745 | n-$C_3H_7$ | 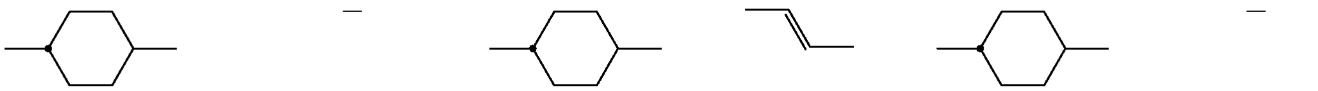 |
| 746 | $CH_3$ | 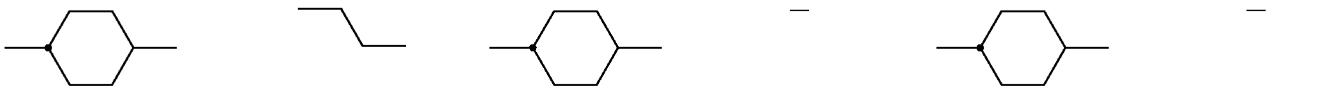 |
| 747 | n-$C_3H_7$ | 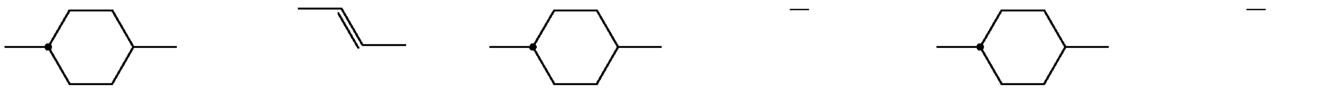 |
| 751 | $CH_3$ | 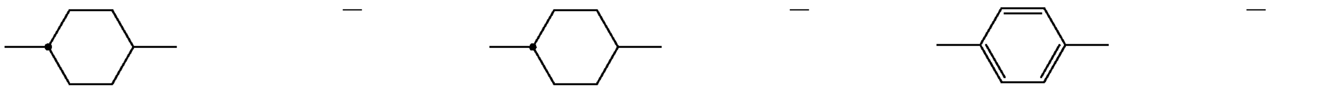 |
| 752 | n-$C_3H_7$ | 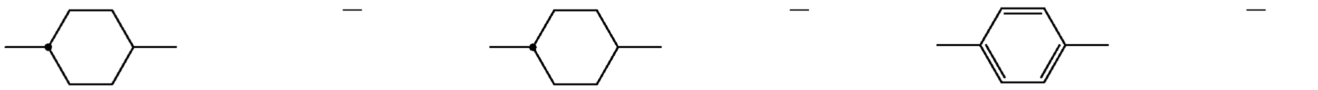 |
| 753 | $CH_3$ | 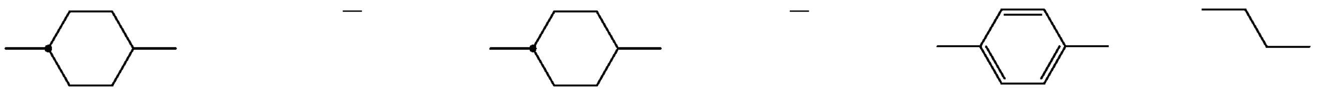 |
| 754 | n-$C_3H_7$ | 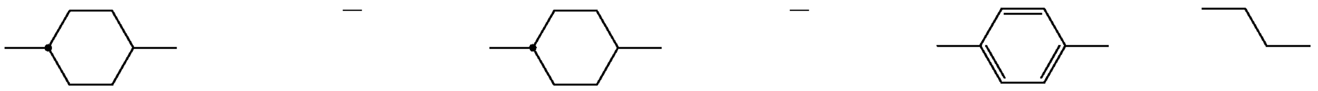 |
| 755 | $CH_3$ | 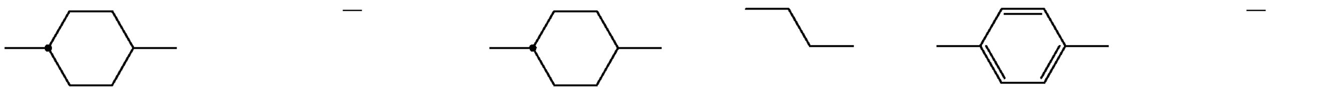 |
| 756 | n-$C_3H_7$ | 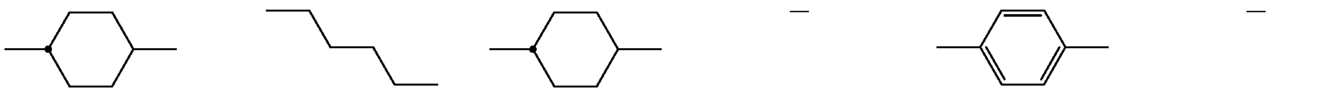 |

-continued
| | | | | | | | |
|---|---|---|---|---|---|---|---|
| 757 | $CH_3$ | 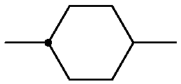 | 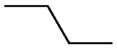 | 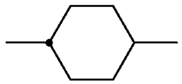 | — | 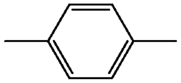 | — |
| 758 | n-$C_3H_7$ | 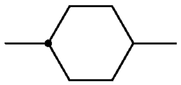 | 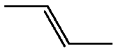 | 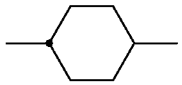 | — | 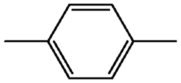 | — |
| 762 | $CH_3$ | 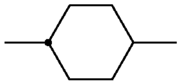 | — | 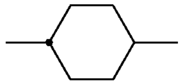 | — | 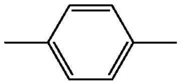 | 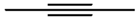 |
| 763 | $CH_3$ | 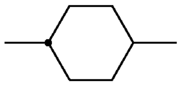 | — | 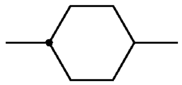 | — | 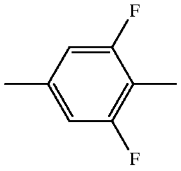 | — |
| 764 | n-$C_3H_7$ | 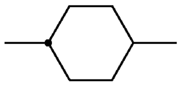 | — | 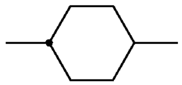 | — | 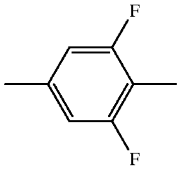 | — |
| 768 | $CH_3$ | 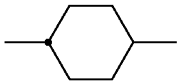 | — | 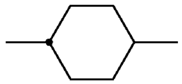 | — | 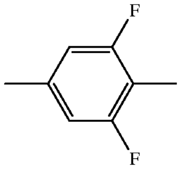 | 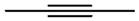 |
| 769 | $CH_3$ | 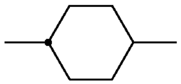 | — | 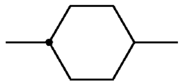 | — | 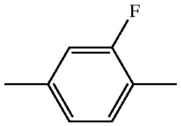 | — |

-continued
| | | |
|---|---|---|
| 770 | n-$C_3H_7$ | 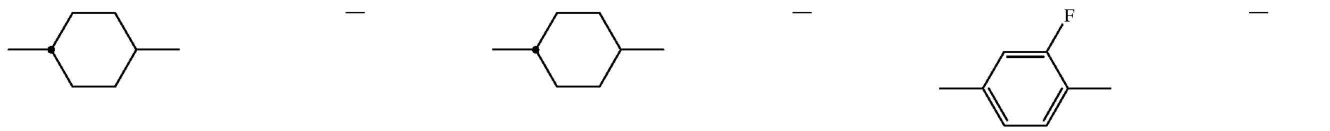 |
| 771 | $CH_3$ | 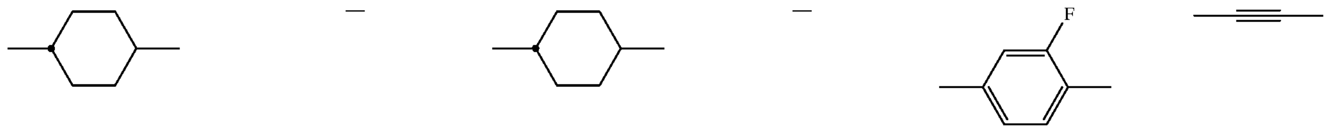 |
| 775 | $CH_3$ | 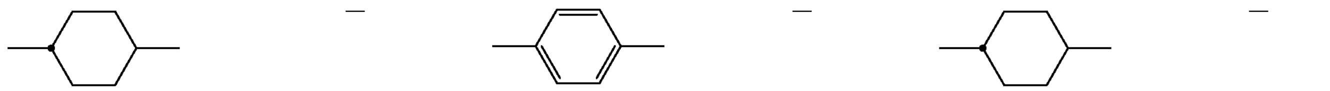 |
| 776 | $CH_3$ | 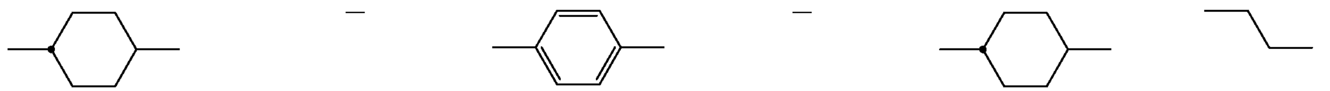 |
| 777 | $CH_3$ | 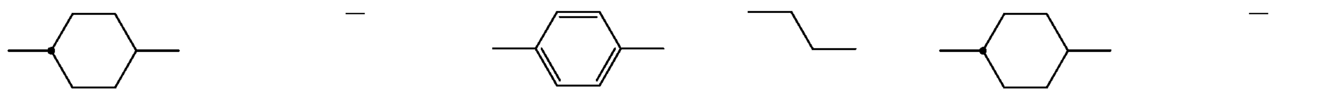 |
| 778 | $CH_3$ | 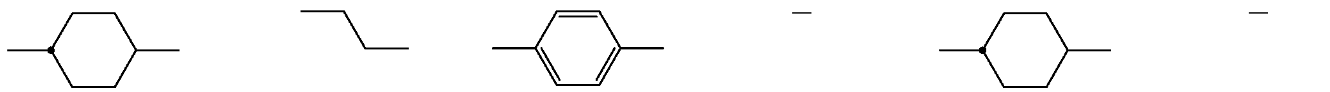 |
| 782 | $CH_3$ | 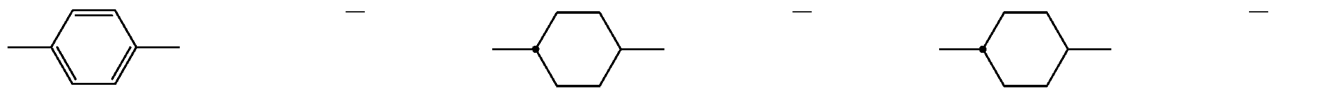 |
| 783 | n-$C_3H_7$ | 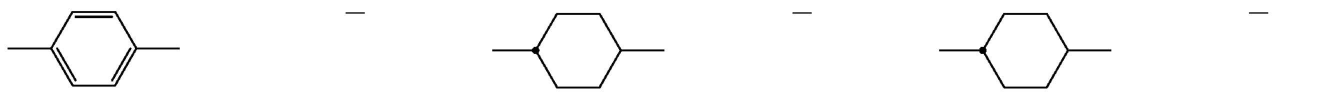 |
| 784 | $CH_3$ | 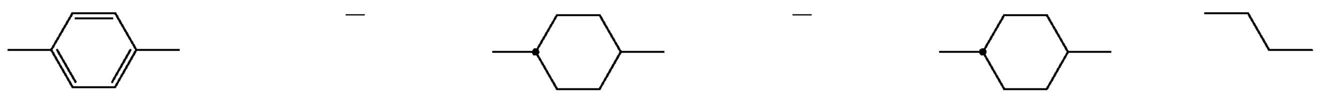 |

-continued
| | | |
|---|---|---|
| 785 | $CH_3$ | 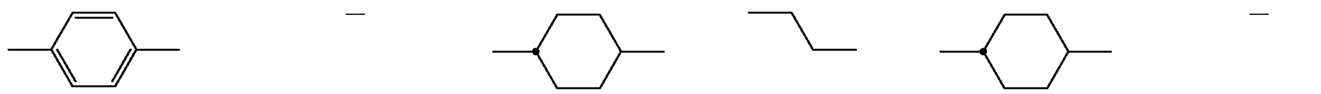 |
| 786 | n $C_3H_7$ | 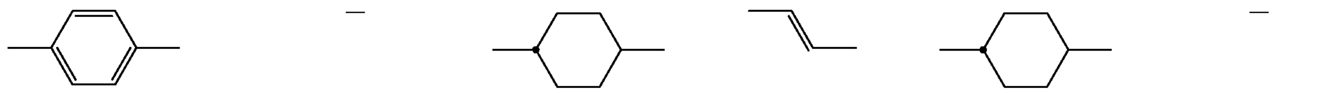 |
| 787 | n-$C_3H_7$ | 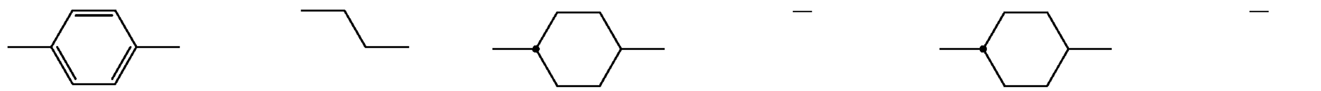 |
| 789 | n-$CH_3$ | 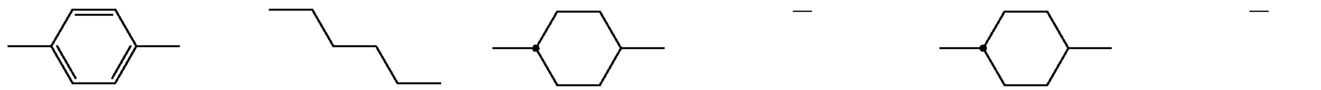 |
| 793 | $CH_3$ | 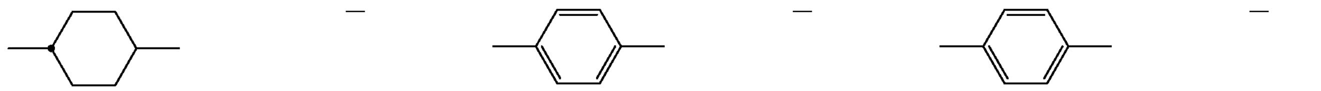 |
| 794 | n-$C_3H_7$ | 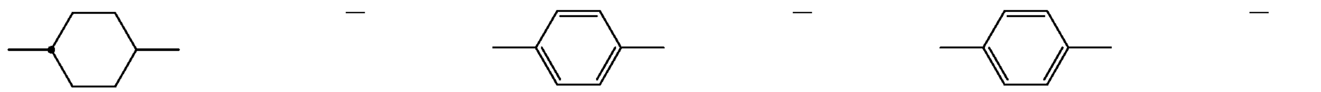 |
| 795 | n-$C_3H_7$ | 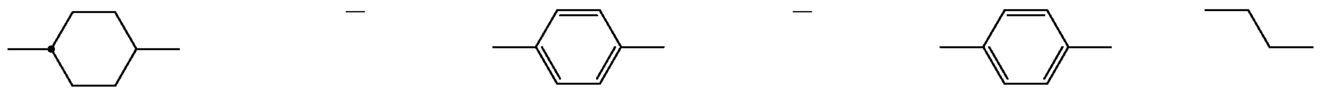 |
| 796 | $CH_3$ | 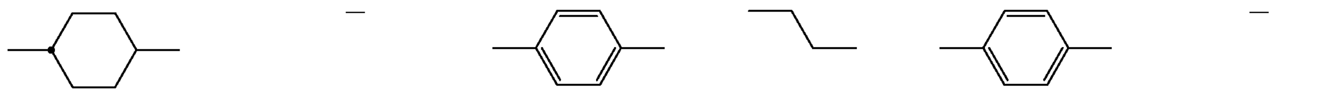 |
| 797 | $CH_3$ | 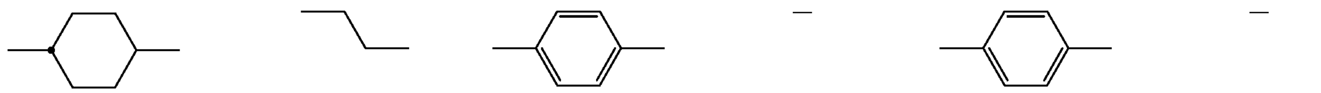 |

-continued
| | | | | | | | |
|---|---|---|---|---|---|---|---|
| 801 | $CH_3$ | 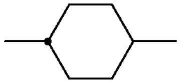 | — | 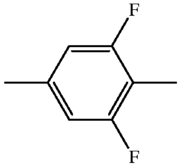 | — | 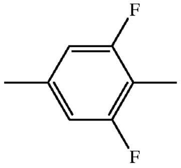 | — |
| 802 | n-$C_3H_7$ | 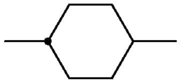 | — | 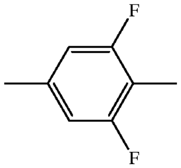 | — | 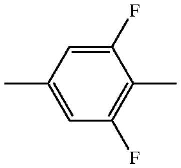 | — |
| 806 | $CH_3$ | 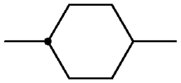 | — | 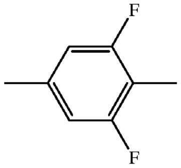 | — | 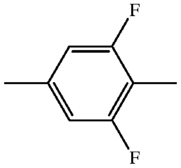 | 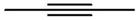 |
| 807 | $CH_3$ | 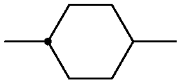 | — | 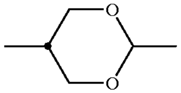 | — | 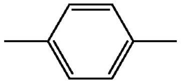 | — |
| 808 | $CH_3$ | 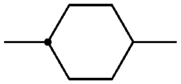 | — | 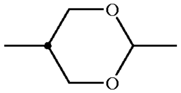 | — | 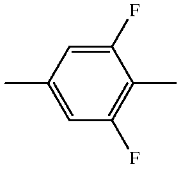 | — |
| 809 | $CH_3$ | 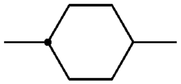 | — | 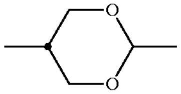 | — | 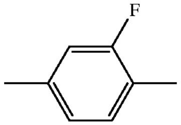 | — |

-continued
| | | | | | | | |
|---|---|---|---|---|---|---|---|
| 810 | $CH_3$ | 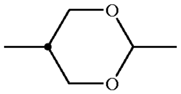 | — | 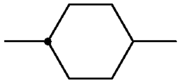 | — | 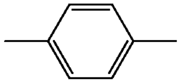 | — |
| 811 | $CH_3$ | 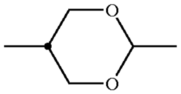 | — | 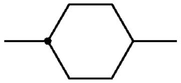 | — | 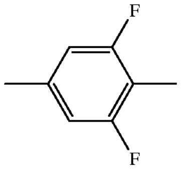 | — |
| 812 | $n-C_3H_7$ | 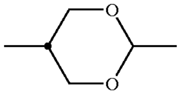 | — | 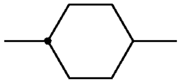 | — | 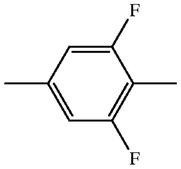 | — |
| 813 | $CH_3$ | 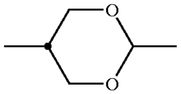 | — | 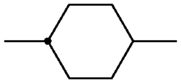 | — | 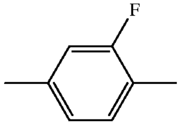 | — |
| 814 | $CH_3$ | 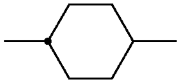 | — | 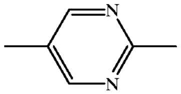 | — | 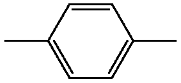 | — |
| 815 | $CH_3$ | 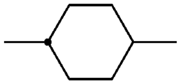 | — | 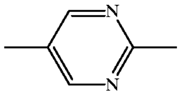 | — | 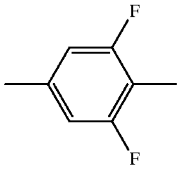 | — |

-continued
| | | | | | | | |
|---|---|---|---|---|---|---|---|
| 816 | $CH_3$ | 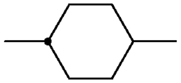 | — | 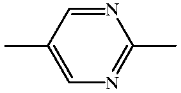 | — | 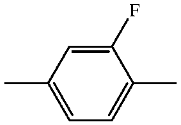 | — |
| 817 | $CH_3$ | 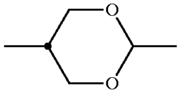 | — | 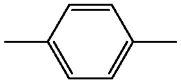 | — | 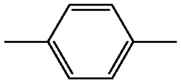 | — |
| 818 | $n\text{-}C_3H_7$ | 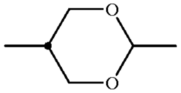 | — | 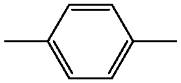 | — | 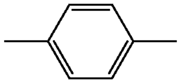 | — |
| 819 | $CH_3$ | 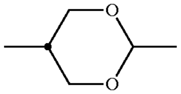 | — | 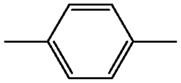 | — | 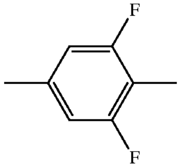 | — |
| 820 | $n\text{-}C_3H_7$ | 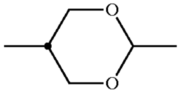 | — | 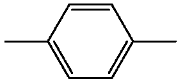 | — | 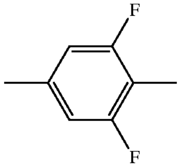 | — |
| 821 | $CH_3$ | 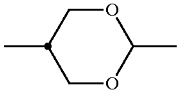 | 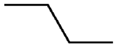 | 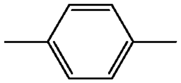 | 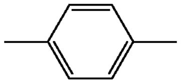 | — | |
| 822 | $n\text{-}C_3H_7$ | 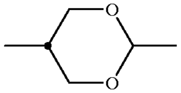 | 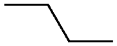 | 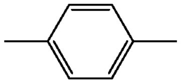 | 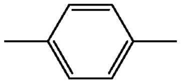 | — | |

-continued
| | | | | | | | |
|---|---|---|---|---|---|---|---|
| 823 | $CH_3$ | 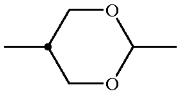 | 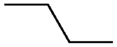 | 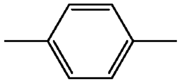 | 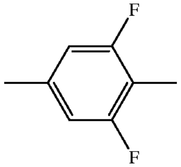 | — | |
| 824 | $CH_3$ | 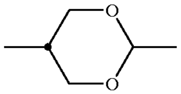 | — | 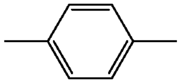 | — | 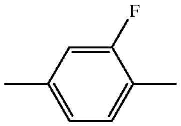 | — |
| k = 0, m = n = 1, $R_f = CF_2H$ | | | | | | | |
| 825 | $n-C_3H_7$ | 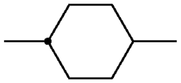 | — | 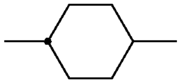 | — | 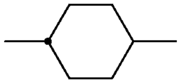 | 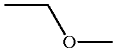 |
| 826 | $n-C_5H_{11}$ | 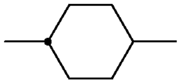 | — | 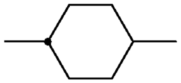 | — | 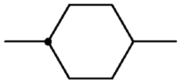 | 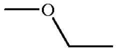 |
| 827 | $CH_3$ | 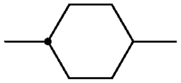 | — | 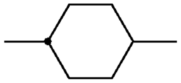 | 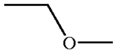 | 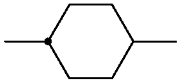 | — |
| 828 | $n-C_5H_{11}$ | 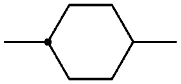 | — | 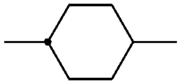 | 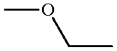 | 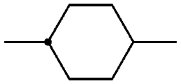 | — |
| 829 | $n-C_5H_{11}$ | 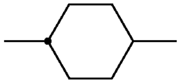 | 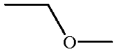 | 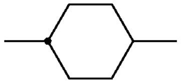 | — | 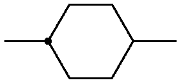 | — |
| 830 | $n-C_3H_7$ | 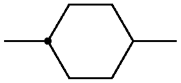 | 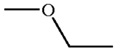 | 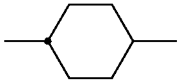 | — | 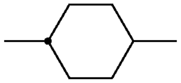 | — |

-continued
| | | |
|---|---|---|
| 831 | n-$C_3H_7$ | 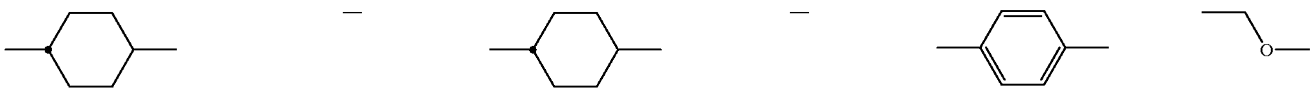 |
| 832 | $CH_3$ | 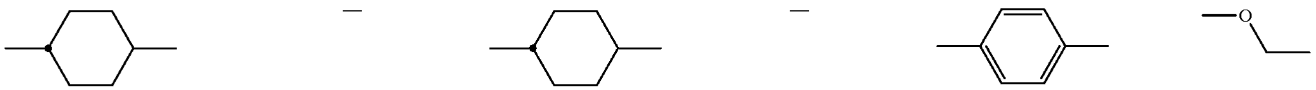 |
| 833 | n-$C_3H_7$ | 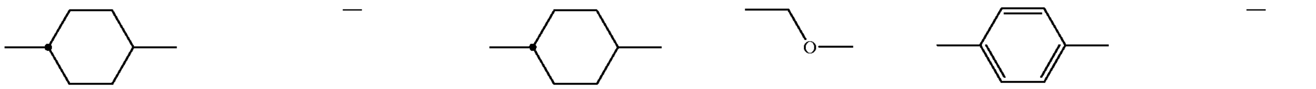 |
| 834 | n-$C_5H_{11}$ | 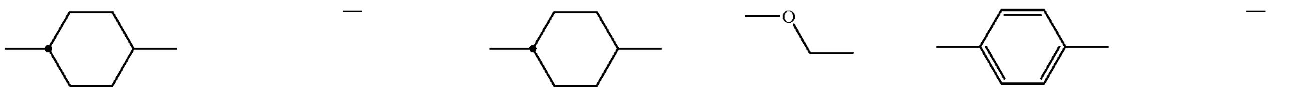 |
| 835 | n-$C_5H_{11}$ | 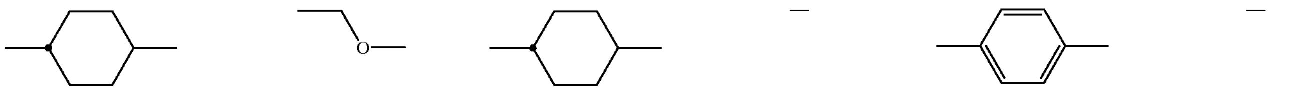 |
| 836 | n-$C_3H_7$ | 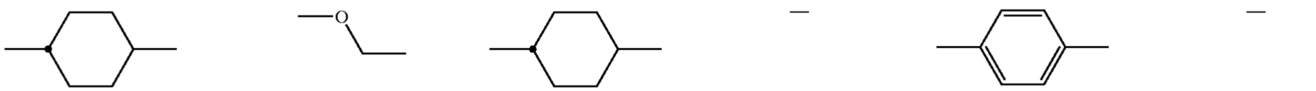 |
| 837 | n-$C_3H_7$ | 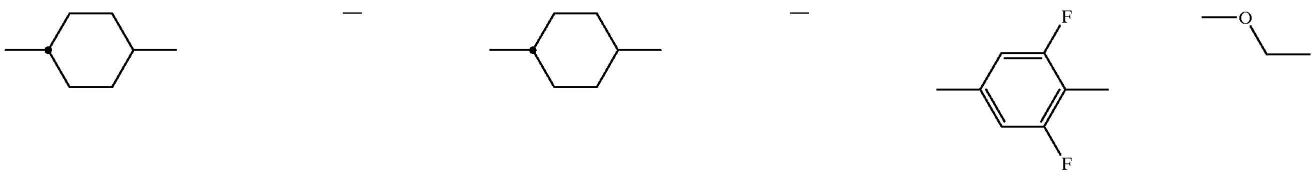 |
| 838 | n-$C_5H_{11}$ | 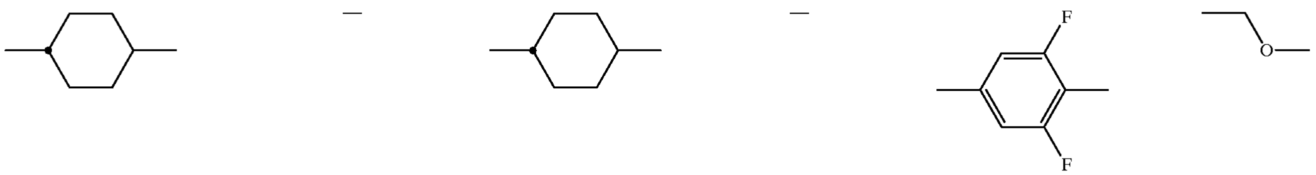 |

-continued
| | | |
|---|---|---|
| 839 | n-$C_3H_7$ | 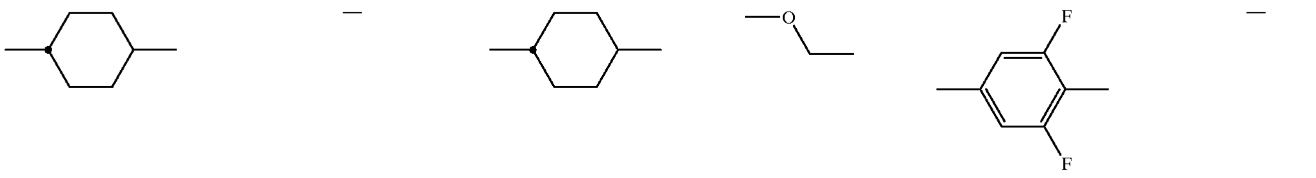 |
| 840 | n-$C_3H_7$ | 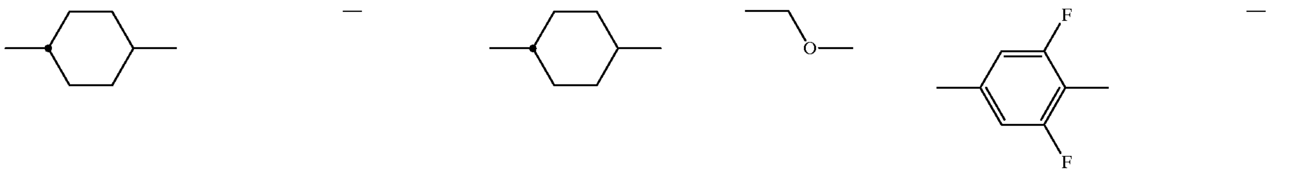 |
| 841 | n-$C_3H_7$ | 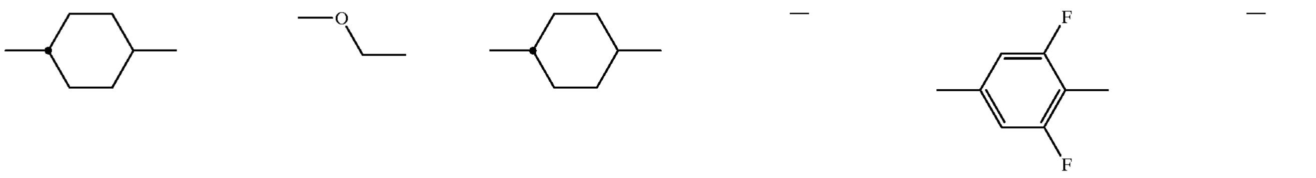 |
| 842 | n-$C_5H_{11}$ | 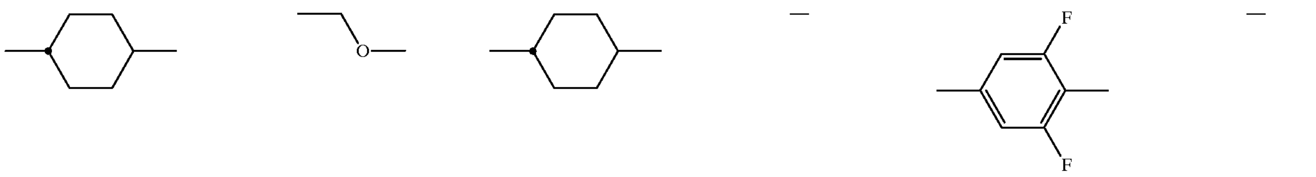 |
| 843 | n-$C_3H_7$ | 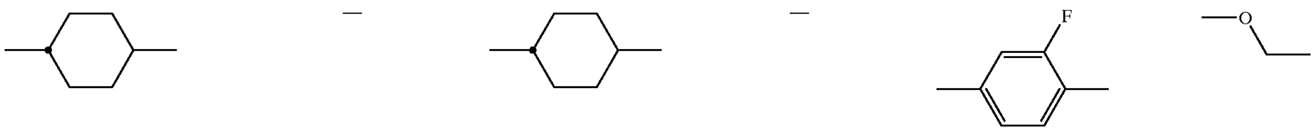 |
| 844 | n-$C_5H_{11}$ | 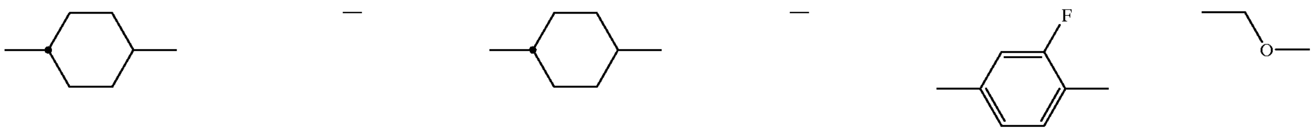 |

-continued
| | | |
|---|---|---|
| 845 | n-$C_3H_7$ | 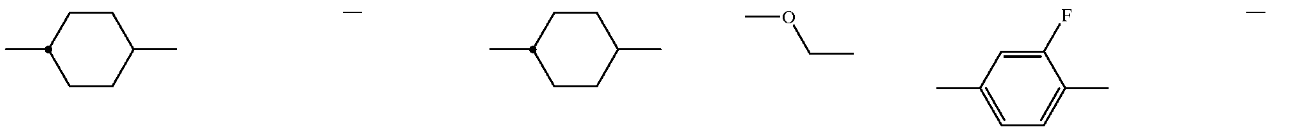 |
| 846 | n-$C_3H_7$ | 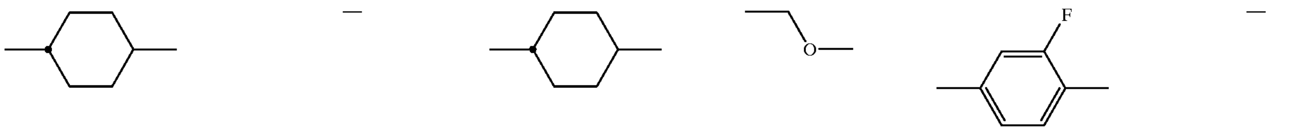 |
| 847 | $CH_3$ | 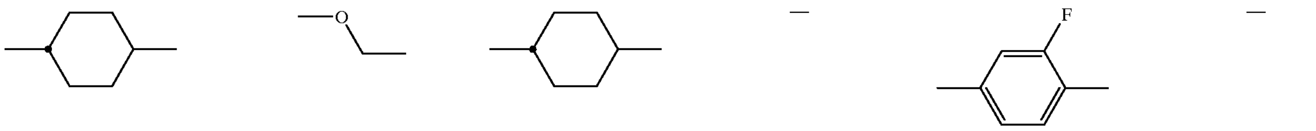 |
| 848 | n-$C_5H_{11}$ | 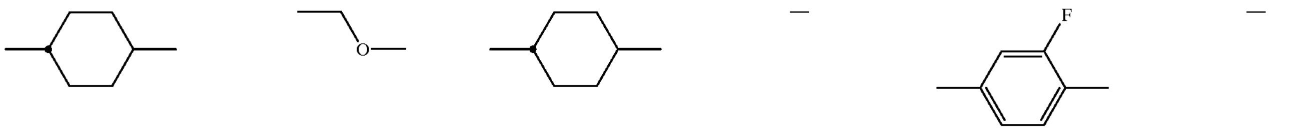 |
| 849 | n-$C_3H_7$ | 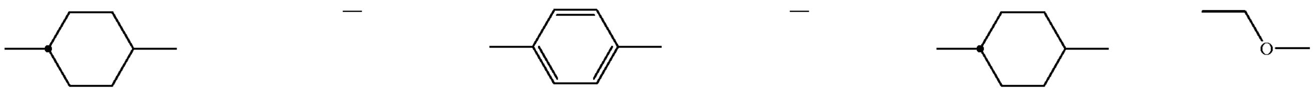 |
| 850 | $CH_3$ | 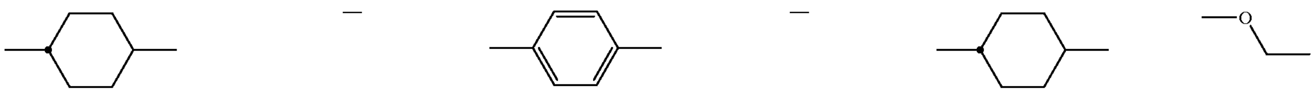 |
| 851 | n-$C_3H_7$ | 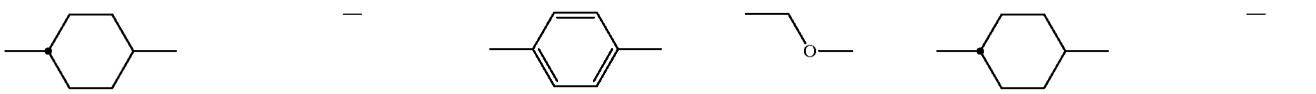 |
| 852 | n-$C_5H_{11}$ | 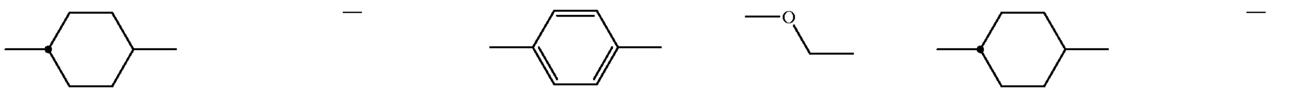 |

-continued
| | | |
|---|---|---|
| 853 | n-$C_3H_7$ | 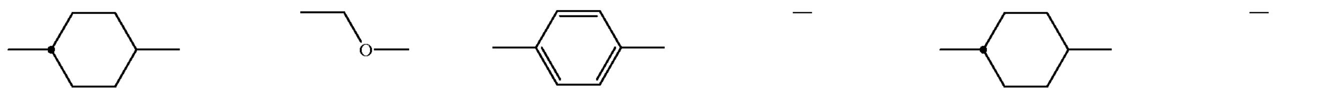 |
| 854 | n-$C_3H_7$ | 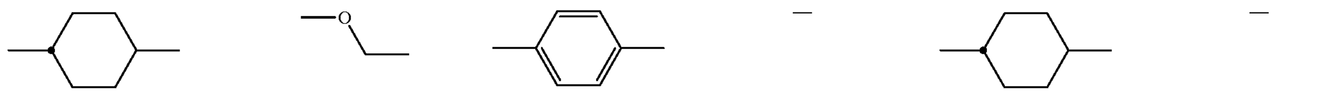 |
| 855 | $CH_3$ | 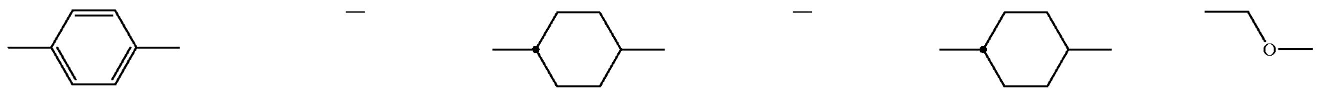 |
| 856 | n-$C_3H_7$ | 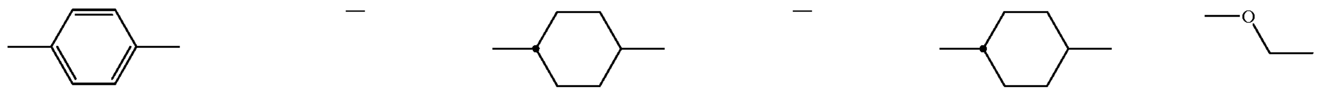 |
| 857 | n-$C_3H_7$ | 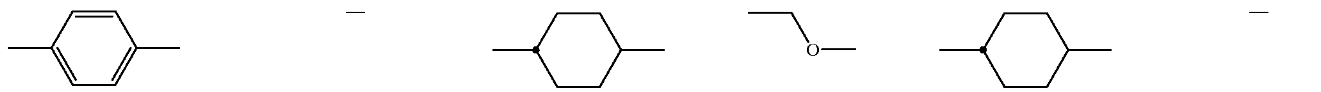 |
| 858 | n-$C_5H_{11}$ | 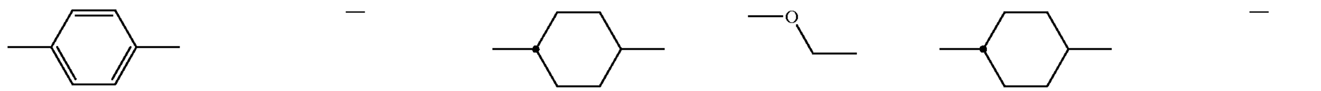 |
| 859 | n-$C_5H_{11}$ | 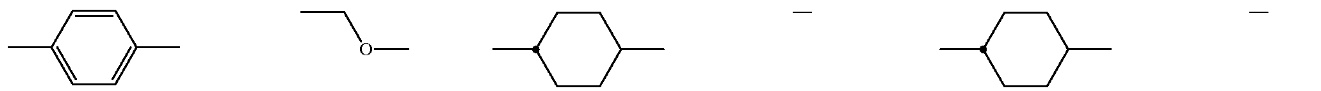 |
| 860 | $CH_3$ | 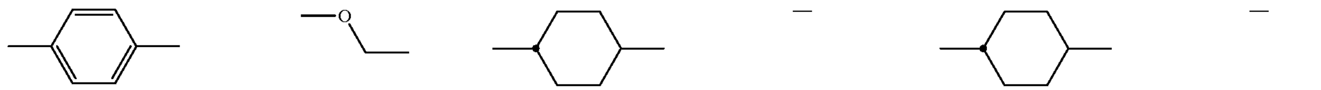 |
| 861 | n-$C_3H_7$ | 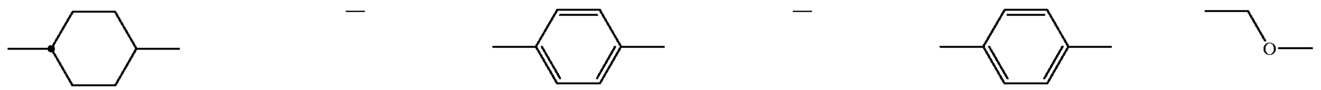 |

-continued
| | | |
|---|---|---|
| 862 | n-$C_5H_{11}$ | 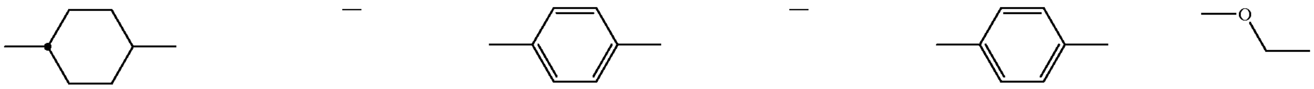 |
| 863 | n-$C_3H_7$ | 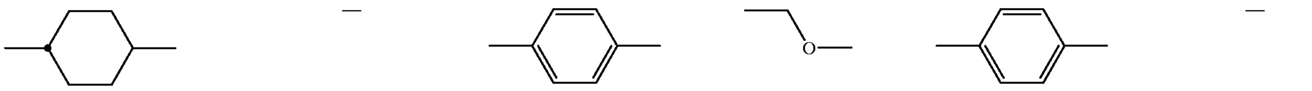 |
| 864 | n-$C_5H_{11}$ | 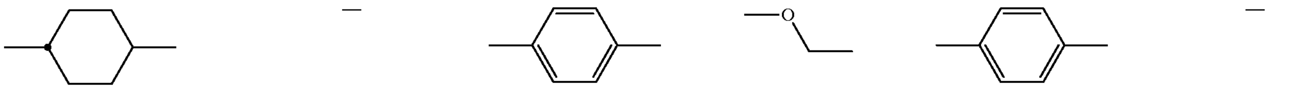 |
| 865 | n-$C_5H_{11}$ | 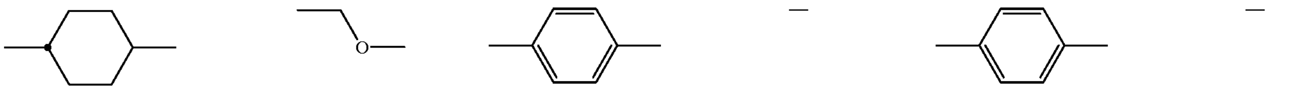 |
| 866 | $CH_3$ | 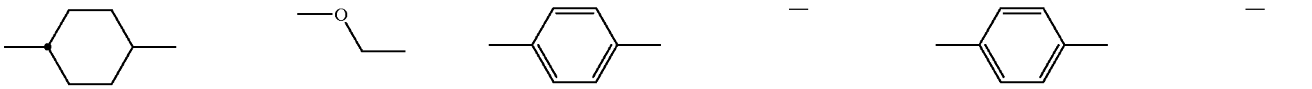 |
| 867 | n-$C_3H_7$ | 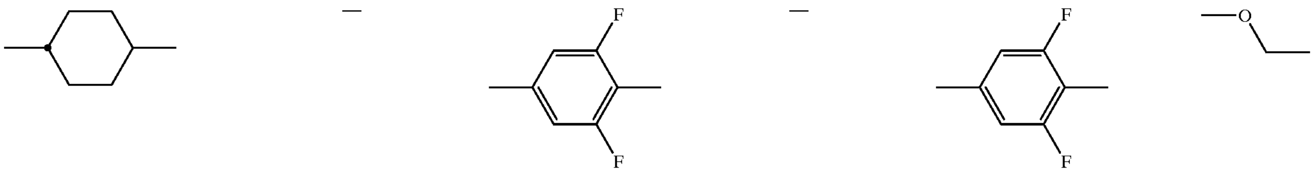 |
| 868 | n-$C_5H_{11}$ | 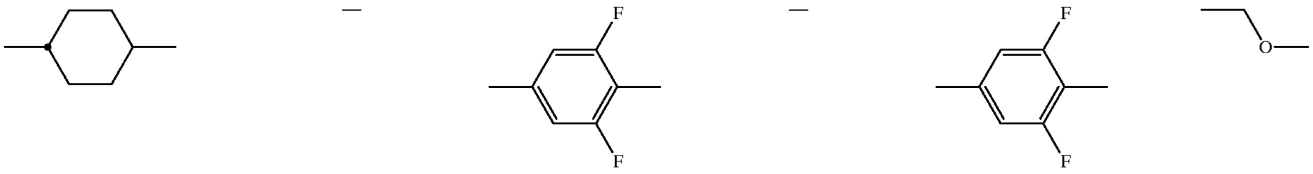 |

-continued
| | | | | | | | |
|---|---|---|---|---|---|---|---|
| 869 | $CH_3$ | 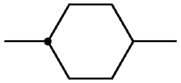 | — | 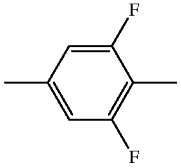 | 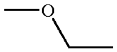 | 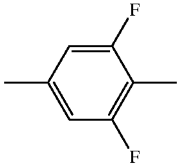 | — |
| 870 | n-$C_3H_7$ | 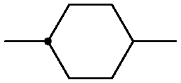 | — | 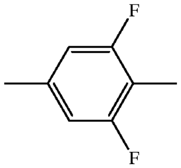 | 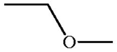 | 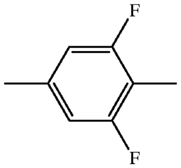 | — |
| 871 | n-$C_3H_7$ | 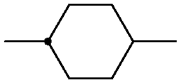 | 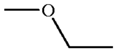 | 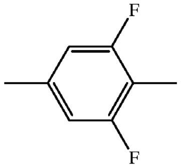 | — | 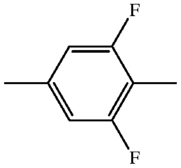 | — |
| 872 | $CH_3$ | 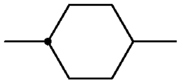 | 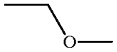 | 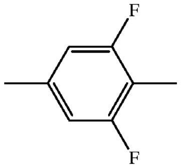 | — | 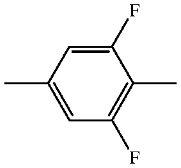 | — |
| 873 | n-$C_3H_7$ | 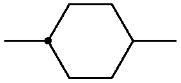 | — | 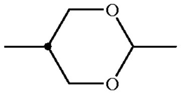 | — | 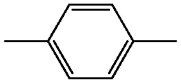 | 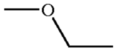 |
| 874 | n-$C_5H_{11}$ | 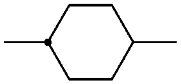 | — | 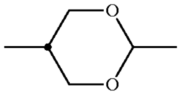 | — | 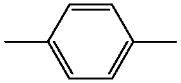 | 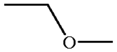 |

-continued
| | | | | | | | |
|---|---|---|---|---|---|---|---|
| 875 | n-$C_3H_7$ | 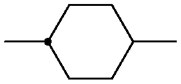 | — | 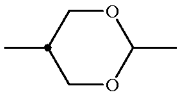 | 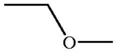 | 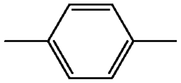 | — |
| 876 | n-$C_3H_7$ | 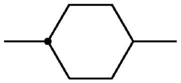 | 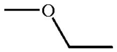 | 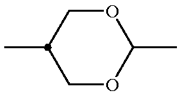 | — | 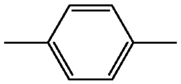 | — |
| 877 | $CH_3$ | 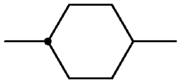 | 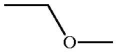 | 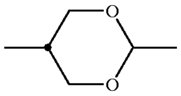 | — | 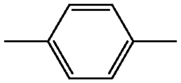 | — |
| 878 | n-$C_3H_7$ | 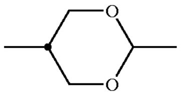 | — | 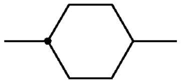 | — | 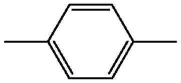 | 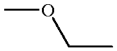 |
| 879 | n-$C_5H_{11}$ | 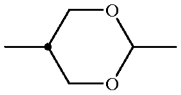 | — | 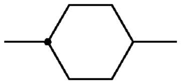 | — | 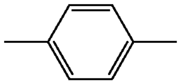 | 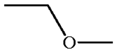 |
| 880 | n-$C_3H_7$ | 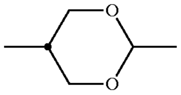 | — | 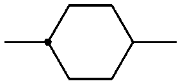 | 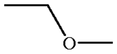 | 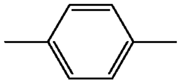 | — |
| k = m = n = 1, $R_f$ $CH_2CF_3$ | | | | | | | |
| 881 | $CH_3$ | 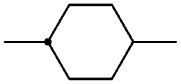 | — | 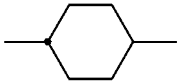 | — | 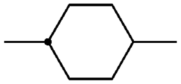 | 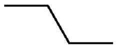 |
| 882 | $CH_3$ | 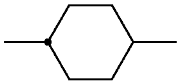 | — | 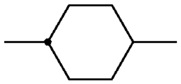 | — | 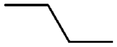 | 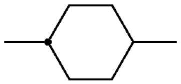 |

-continued
| | | |
|---|---|---|
| 883 | n-$C_3H_7$ | 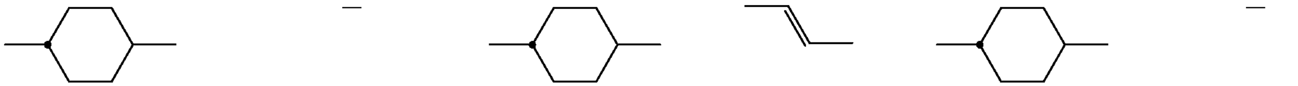 |
| 884 | $CH_3$ | 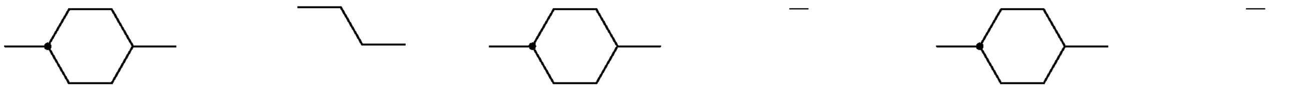 |
| 885 | n-$C_3H_7$ | 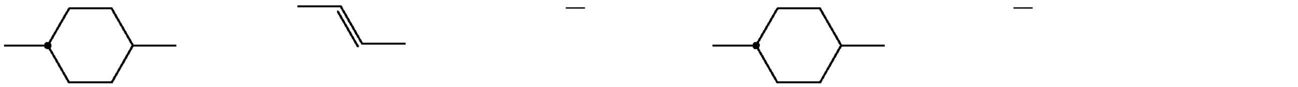 |
| 886 | $CH_3$ | 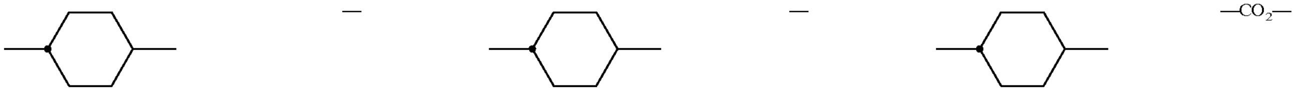 |
| 887 | n-$C_3H_7$ | 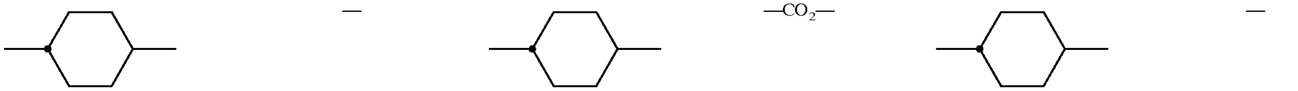 |
| 888 | $CH_3$ | 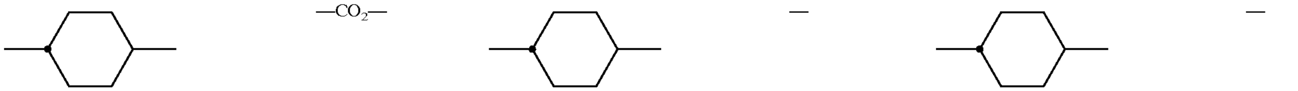 |
| 889 | $CH_3$ | 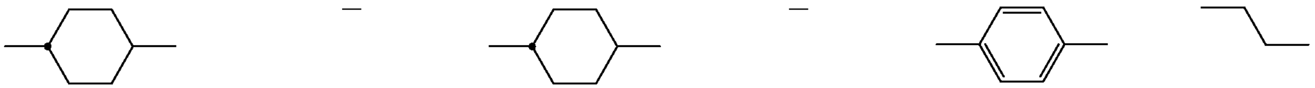 |
| 890 | $CH_3$ | 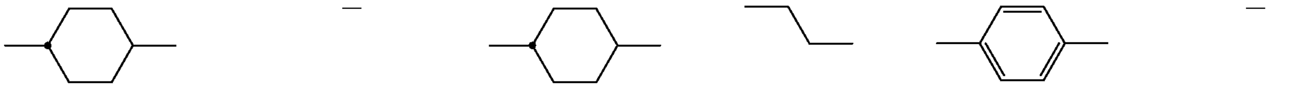 |
| 891 | n-$C_3H_7$ | 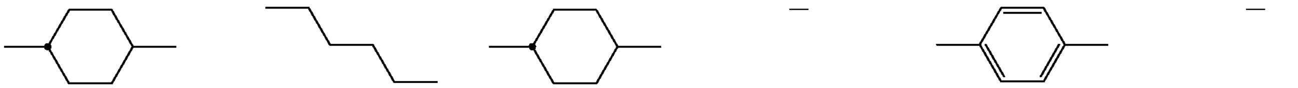 |

-continued
| | | | | | | | |
|---|---|---|---|---|---|---|---|
| 892 | $CH_3$ | 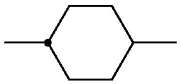 | 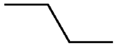 | 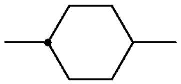 | — | 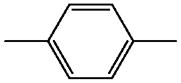 | — |
| 893 | n-$C_3H_7$ | 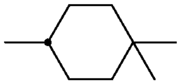 | 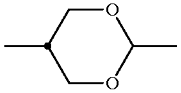 | 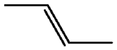 | — | 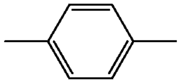 | — |
| 894 | $CH_3$ | 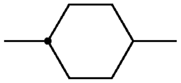 | — | 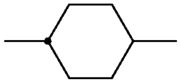 | — | 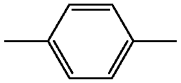 | —$CO_2$— |
| 895 | n-$C_3H_7$ | 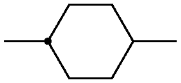 | — | 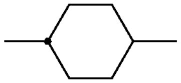 | —$CO_2$— | 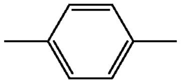 | — |
| 896 | $CH_3$ | 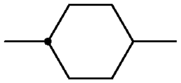 | —$CO_2$— | 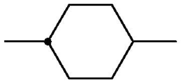 | — | 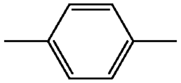 | — |
| 897 | $CH_3$ | 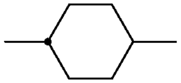 | — | 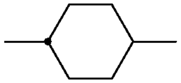 | — | 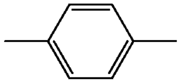 | 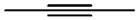 |
| 898 | $CH_3$ | 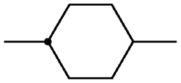 | — | 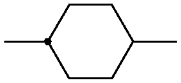 | — | 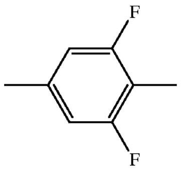 | —$CO_2$— |
| 899 | $CH_3$ | 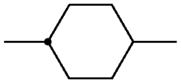 | — | 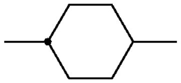 | —$CO_2$— | 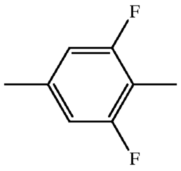 | — |

-continued
| | | | | | | | |
|---|---|---|---|---|---|---|---|
| 900 | $CH_3$ | 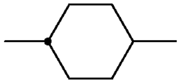 | —$CO_2$— | 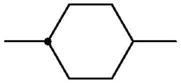 | —$CO_2$— | 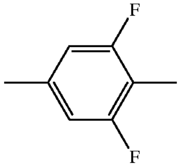 | — |
| 901 | $CH_3$ | 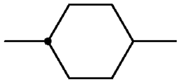 | — | 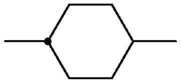 | — | 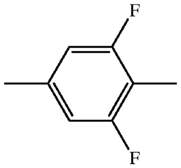 | 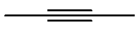 |
| 902 | $CH_3$ | 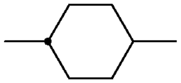 | — | 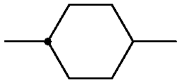 | — | 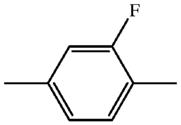 | 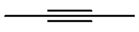 |
| 903 | $CH_3$ | 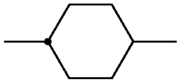 | — | 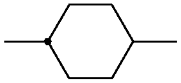 | — | 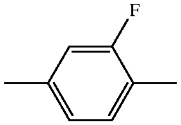 | —$CO_2$— |
| 904 | $CH_3$ | 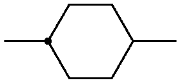 | — | 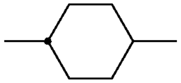 | —$CO_2$— | 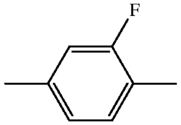 | — |
| 905 | $CH_3$ | — | 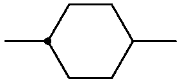 | —$CO_2$— | 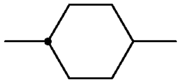 | — | 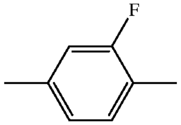 |
| 906 | $CH_3$ | 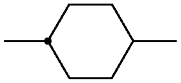 | — | 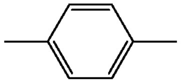 | — | 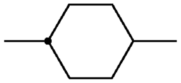 | — |

-continued
| | | | | | | | |
|---|---|---|---|---|---|---|---|
| 907 | $CH_3$ | 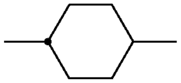 | — | 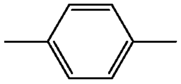 | — | 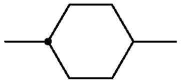 | 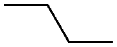 |
| 908 | $CH_3$ | 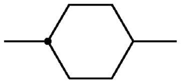 | — | 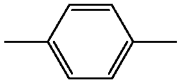 | 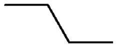 | 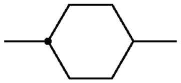 | — |
| 909 | $CH_3$ | 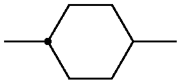 | 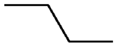 | 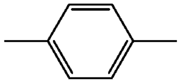 | — | 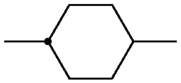 | — |
| 910 | $CH_3$ | 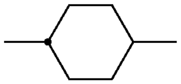 | — | 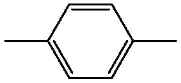 | — | 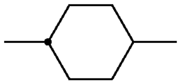 | $—CO_2—$ |
| 911 | n-$C_3H_7$ | 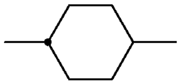 | — | 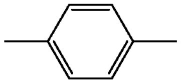 | $—CO_2—$ | 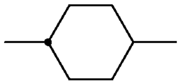 | — |
| 912 | $CH_3$ | 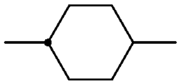 | $—CO_2—$ | 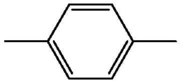 | — | 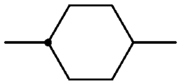 | — |
| 913 | $CH_3$ | 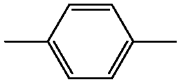 | — | 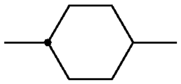 | — | 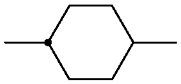 | 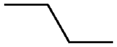 |
| 914 | $CH_3$ | 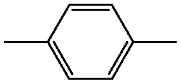 | — | 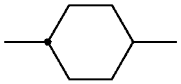 | 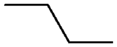 | 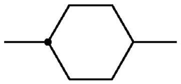 | — |
| 915 | n-$C_3H_7$ | 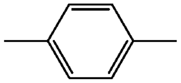 | — | 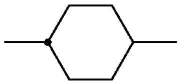 | 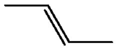 | 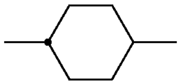 | — |

-continued
| | | | | | | | |
|---|---|---|---|---|---|---|---|
| 916 | n-$C_3H_7$ | 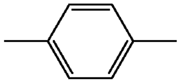 | 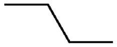 | 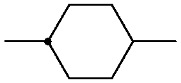 | — | 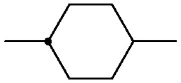 | — |
| 917 | n-$CH_3$ | 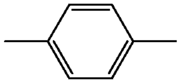 | 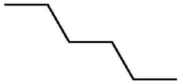 | 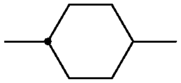 | — | 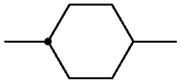 | — |
| 918 | $CH_3$ | 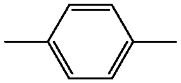 | — | 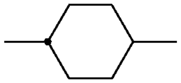 | — | 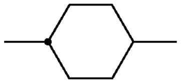 | —$CO_2$— |
| 919 | n-$C_3H_7$ | 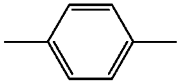 | — | 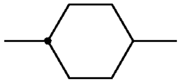 | —$CO_2$— | — | |
| 920 | $CH_3$ | 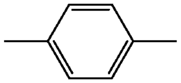 | —$CO_2$— | 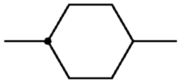 | — | 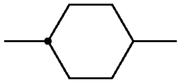 | — |
| 921 | n-$C_3H_7$ | 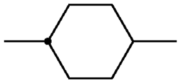 | — | 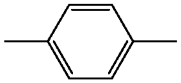 | — | 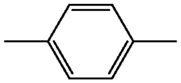 | 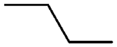 |
| 922 | $CH_3$ | 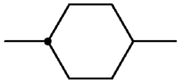 | — | 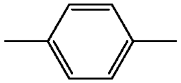 | 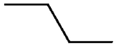 | 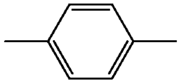 | — |
| 923 | $CH_3$ | 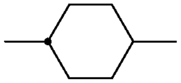 | 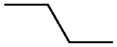 | 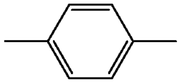 | — | 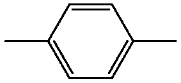 | — |
| 924 | $CH_3$ | 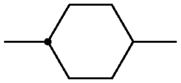 | — | 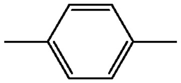 | — | 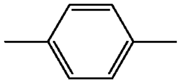 | —$CO_2$— |

-continued
| | | | | | | | |
|---|---|---|---|---|---|---|---|
| 925 | $CH_3$ | 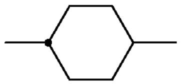 | — | 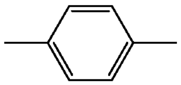 | —$CO_2$— | 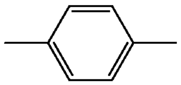 | — |
| 926 | $CH_3$ | 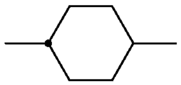 | —$CO_2$— | 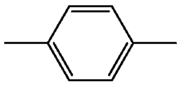 | — | 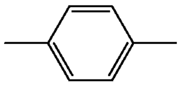 | — |
| 927 | $CH_3$ | 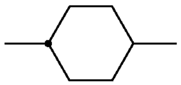 | | 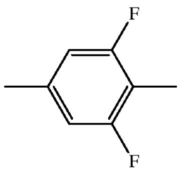 | — | 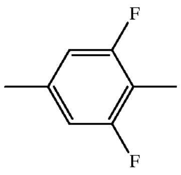 | —$CO_2$— |
| 928 | $CH_3$ | 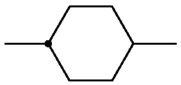 | — | 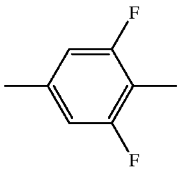 | —$CO_2$— | 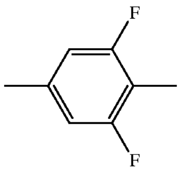 | — |
| 929 | $CH_3$ | 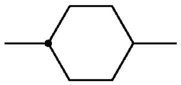 | —$CO_2$— | 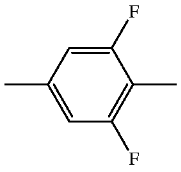 | —$CO_2$— | 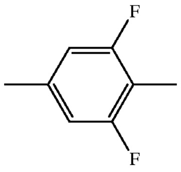 | — |
| 930 | $CH_3$ | 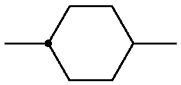 | — | 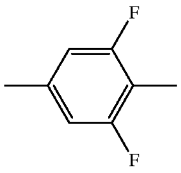 | — | 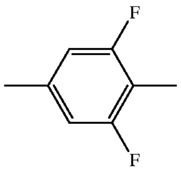 | 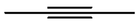 |

-continued
| | | | | | | | |
|---|---|---|---|---|---|---|---|
| 931 | $CH_3$ | 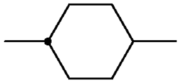 | — | 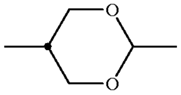 | — | 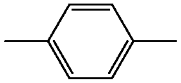 | — |
| 932 | $CH_3$ | 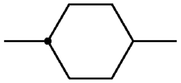 | — | 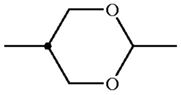 | — | 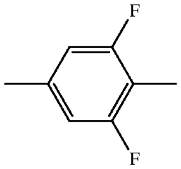 | — |
| 933 | $CH_3$ | 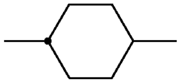 | — | 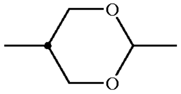 | — | 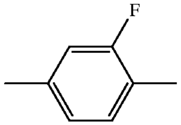 | — |
| 934 | $CH_3$ | 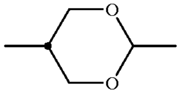 | — | 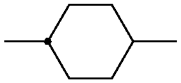 | — | 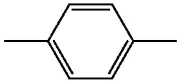 | — |
| 935 | $CH_3$ | 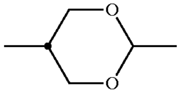 | — | 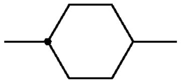 | — | 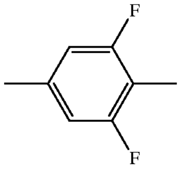 | — |
| 936 | n-$C_3H_7$ | 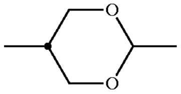 | — | 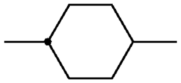 | — | 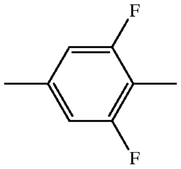 | — |

-continued
| | | | | | | | |
|---|---|---|---|---|---|---|---|
| 937 | $CH_3$ | 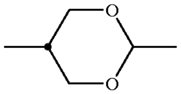 | — | 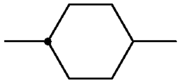 | — | 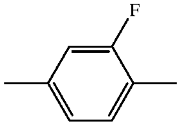 | — |
| 938 | $CH_3$ | 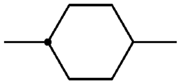 | — | 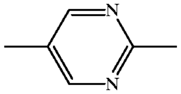 | — | 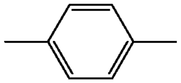 | — |
| 939 | $CH_3$ | 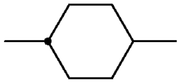 | — | 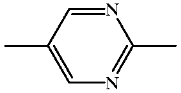 | — | 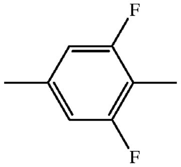 | — |
| 940 | $CH_3$ | 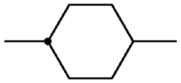 | — | 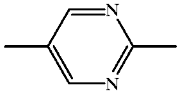 | — | 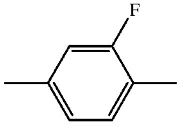 | — |
| 941 | $CH_3$ | 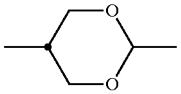 | — | 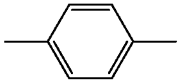 | — | 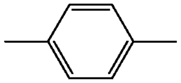 | — |
| 942 | n-$C_3H_7$ | 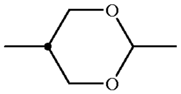 | — | 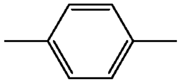 | — | 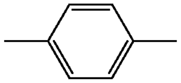 | — |
| 943 | $CH_3$ | 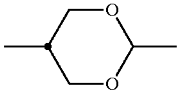 | — | 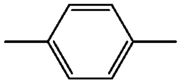 | — | 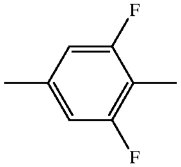 | — |

-continued
| | | | | | | | |
|---|---|---|---|---|---|---|---|
| 944 | n-$C_3H_7$ | 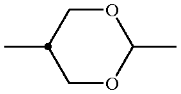 | — | 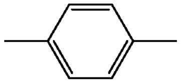 | — | 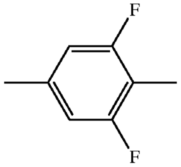 | — |
| 945 | $CH_3$ | 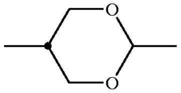 | 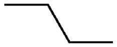 | 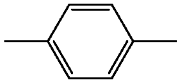 | — | 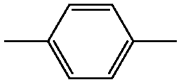 | — |
| 946 | n-$C_3H_7$ | 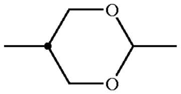 | 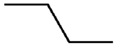 | 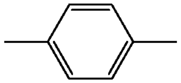 | — | 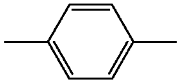 | — |
| 947 | $CH_3$ | 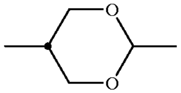 | 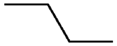 | 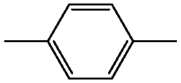 | — | 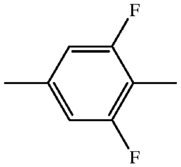 | — |
| 948 | $CH_3$ | 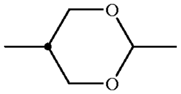 | — | 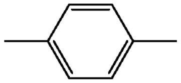 | — | 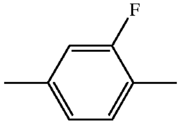 | — |
| 949 | n-$C_3H_7$ | 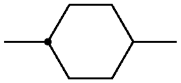 | — | 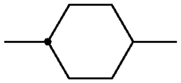 | — | 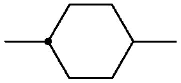 | 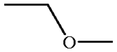 |
| 950 | n-$C_3H_7$ | 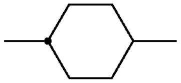 | — | 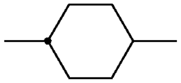 | — | 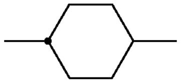 | 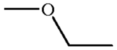 |

-continued
| | | | | | | | |
|---|---|---|---|---|---|---|---|
| 951 | $CH_3$ | 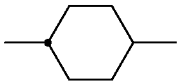 | — | 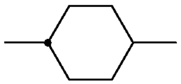 | 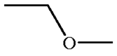 | 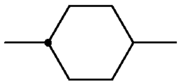 | — |
| 952 | n-$C_5H_{11}$ | 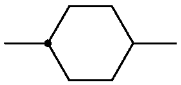 | — | 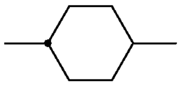 | 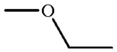 | 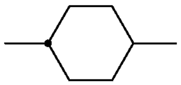 | — |
| 953 | n-$C_5H_{11}$ | 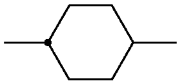 | 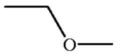 | 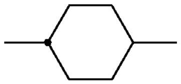 | — | 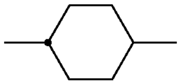 | — |
| 954 | n-$C_3H_7$ | 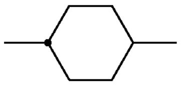 | 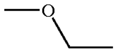 | 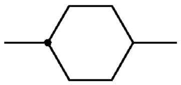 | — | 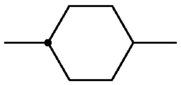 | — |
| 955 | n-$C_3H_7$ | 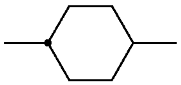 | — | 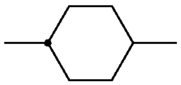 | — | 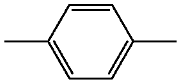 | 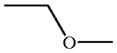 |
| 956 | $CH_3$ | 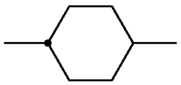 | — | 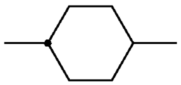 | — | 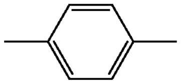 | 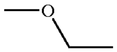 |
| 957 | n-$C_3H_7$ | 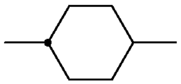 | — | 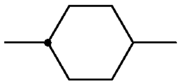 | 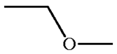 | 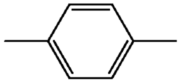 | — |
| 958 | n-$C_5H_{11}$ | 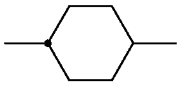 | — | 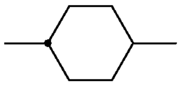 | 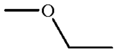 | 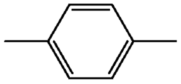 | — |
| 959 | n-$C_5H_{11}$ | 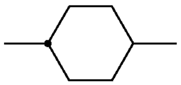 | 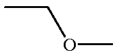 | 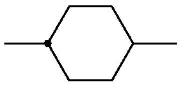 | — | 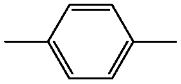 | — |

-continued
| | | |
|---|---|---|
| 960 | n-$C_3H_7$ | 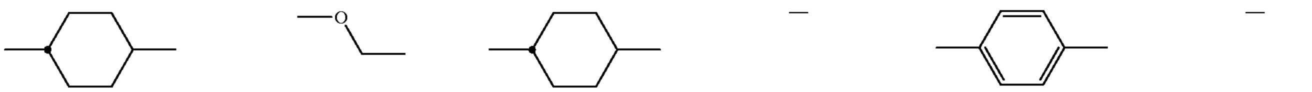 |
| 961 | n-$C_3H_7$ | 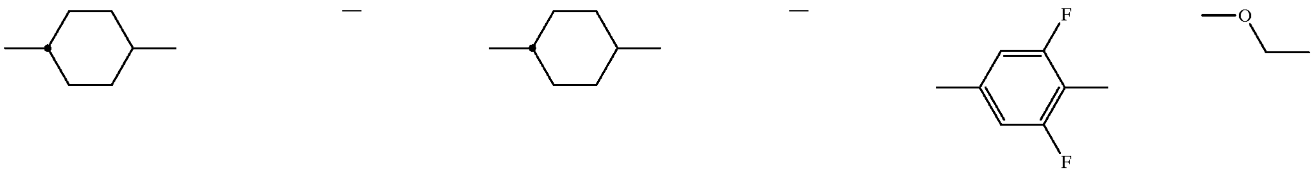 |
| 962 | n-$C_5H_{11}$ | 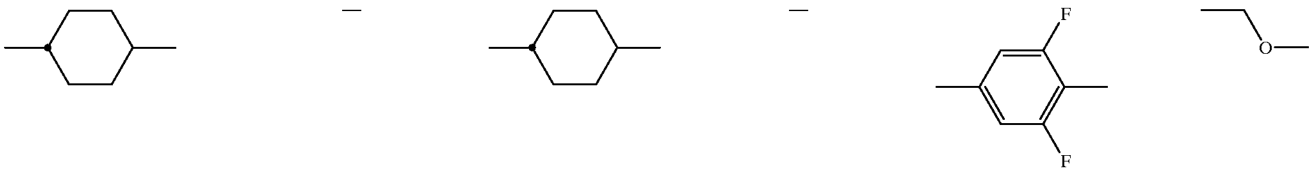 |
| 963 | n-$C_3H_7$ | 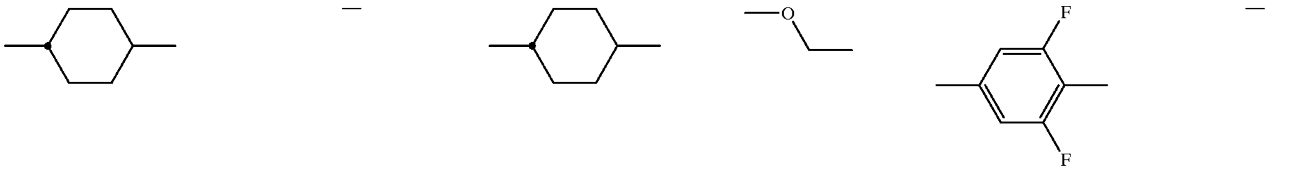 |
| 964 | n-$C_3H_7$ | 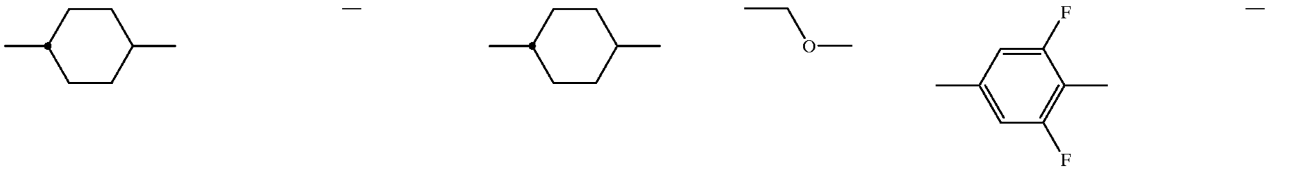 |
| 965 | n-$C_3H_7$ | 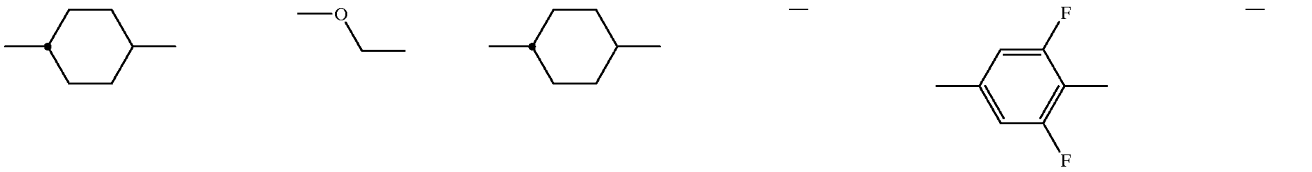 |

-continued
| | | | | | | | |
|---|---|---|---|---|---|---|---|
| 966 | n-$C_5H_{11}$ | 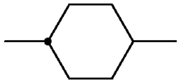 | 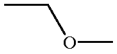 | 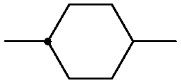 | — | 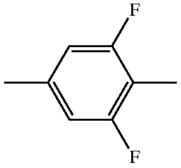 | — |
| 967 | n-$C_3H_7$ | 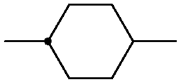 | — | 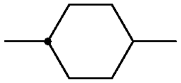 | — | 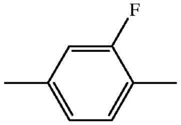 | 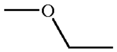 |
| 968 | n-$C_5H_{11}$ | 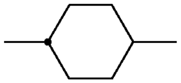 | — | 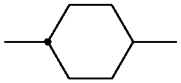 | — | 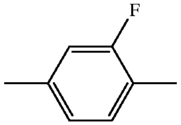 | 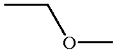 |
| 969 | n-$C_3H_7$ | 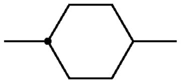 | — | 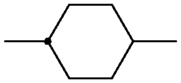 | 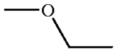 | 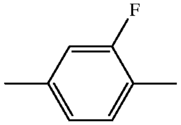 | — |
| 970 | n-$C_3H_7$ | 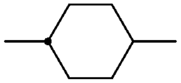 | — | 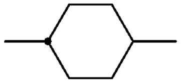 | 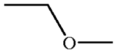 | 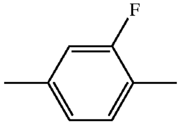 | — |
| 971 | $CH_3$ | 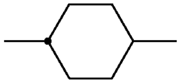 | 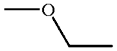 | 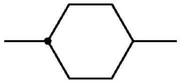 | — | 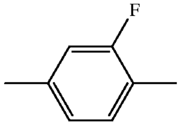 | — |
| 972 | n-$C_5H_{11}$ | 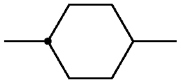 | 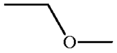 | 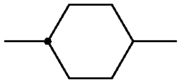 | — | 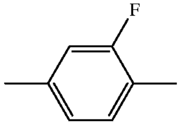 | — |

-continued
| | | |
|---|---|---|
| 973 | n-$C_3H_7$ | 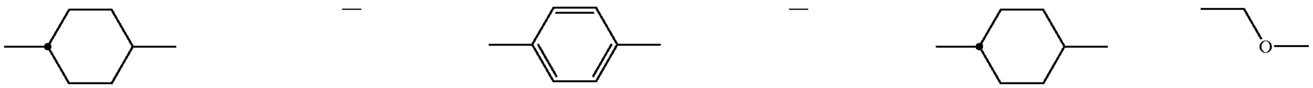 |
| 974 | $CH_3$ | 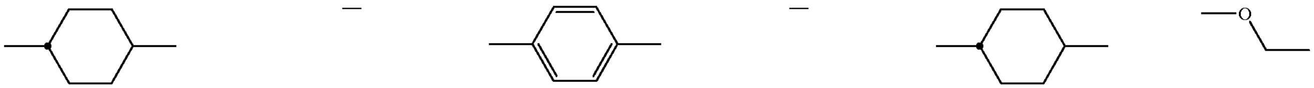 |
| 975 | n-$C_3H_7$ | 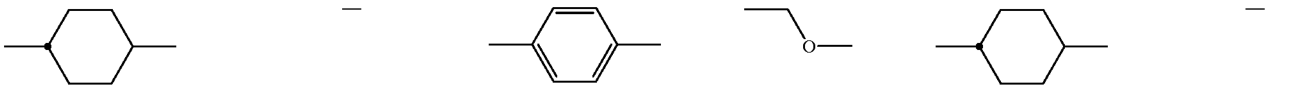 |
| 976 | n-$C_5H_{11}$ | 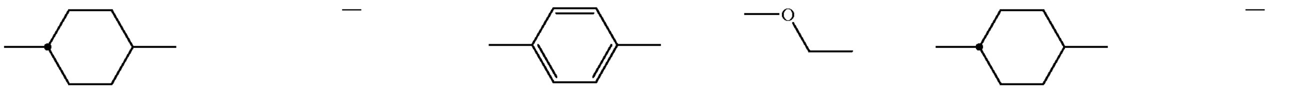 |
| 977 | n-$C_3H_7$ | 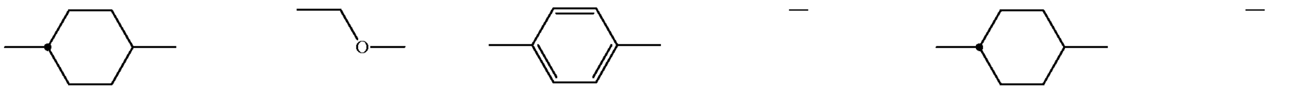 |
| 978 | n-$C_3H_7$ | 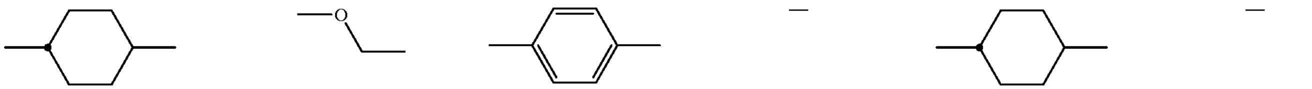 |
| 979 | $CH_3$ | 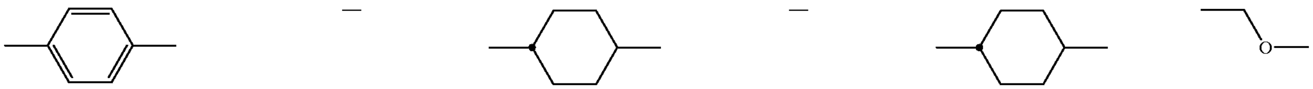 |
| 980 | n-$C_3H_7$ | 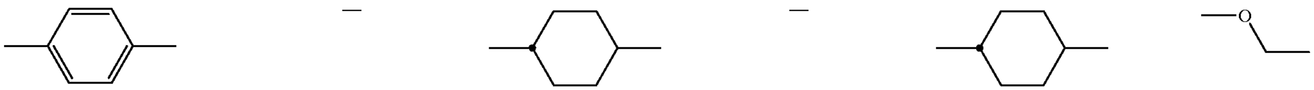 |
| 981 | n-$C_3H_7$ | 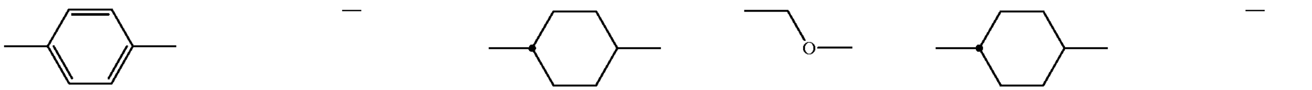 |

-continued
| | | |
|---|---|---|
| 982 | n-$C_5H_{11}$ | 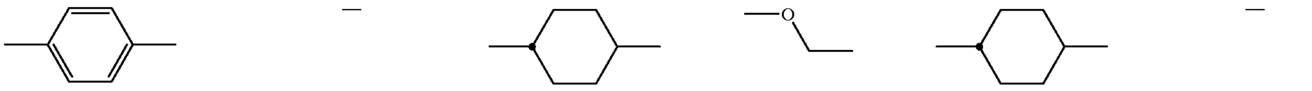 |
| 983 | n-$C_5H_{11}$ | 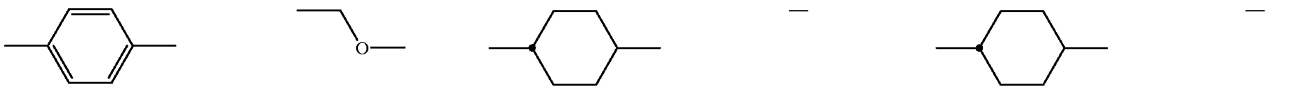 |
| 984 | $CH_3$ | 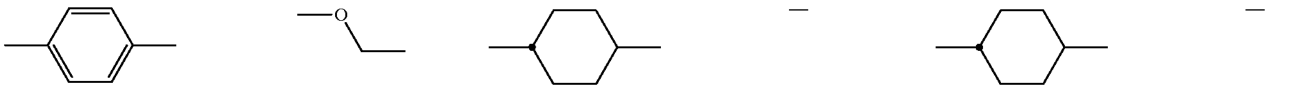 |
| 985 | n-$C_3H_7$ | 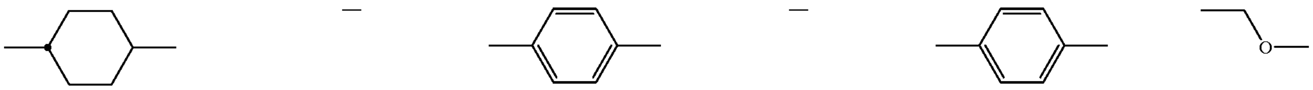 |
| 986 | n-$C_5H_{11}$ | 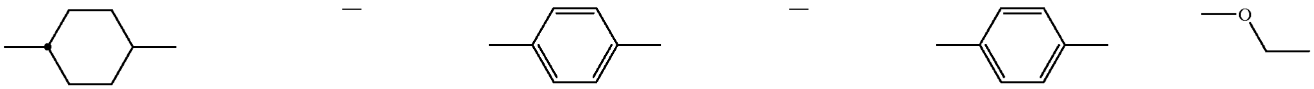 |
| 987 | n-$C_3H_7$ | 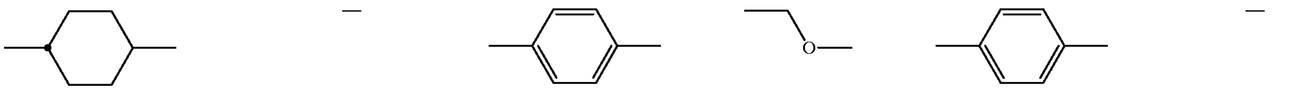 |
| 988 | n-$C_5H_{11}$ | 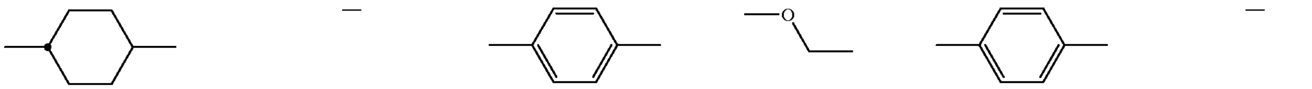 |
| 989 | n-$C_5H_{11}$ | 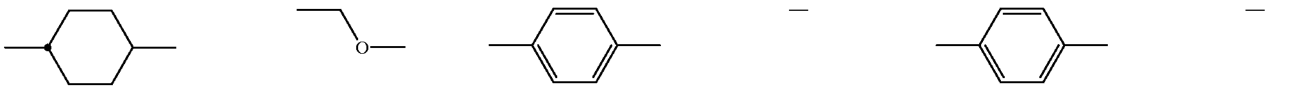 |
| 990 | $CH_3$ | 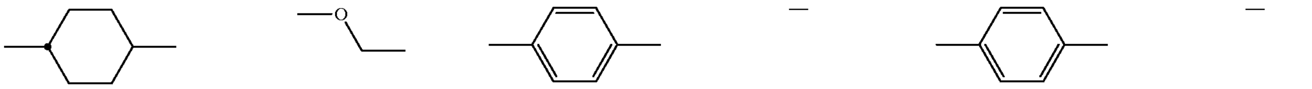 |

-continued
| | | | | | | | |
|---|---|---|---|---|---|---|---|
| 991 | $n-C_3H_7$ | 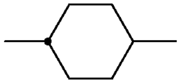 | — | 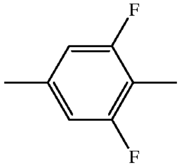 | — | 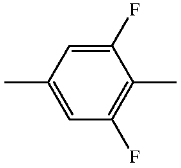 | 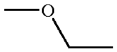 |
| 992 | $n-C_5H_{11}$ | 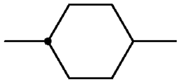 | — | 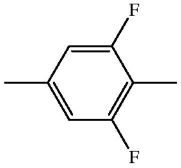 | — | 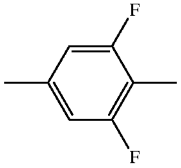 | 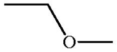 |
| 993 | $CH_3$ | 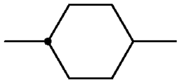 | — | 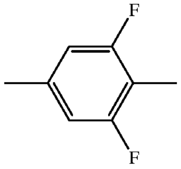 | 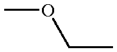 | 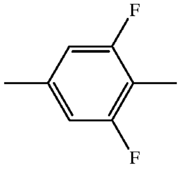 | — |
| 994 | $n-C_3H_7$ | 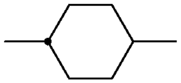 | — | 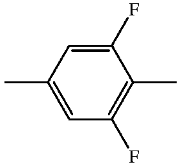 | 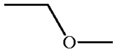 | 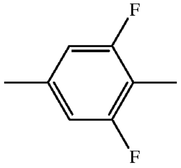 | — |
| 995 | $n-C_3H_7$ | 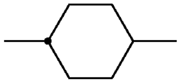 | 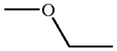 | 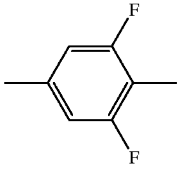 | — | 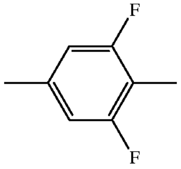 | — |

-continued
| | | | | | | | |
|---|---|---|---|---|---|---|---|
| 996 | $CH_3$ | 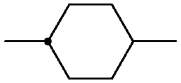 | 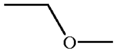 | 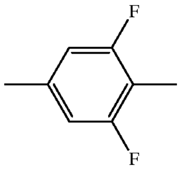 | — | 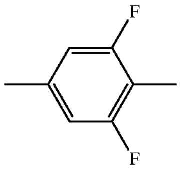 | — |
| 997 | n-$C_3H_7$ | 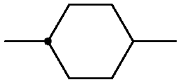 | — | 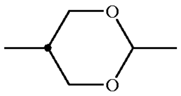 | — | 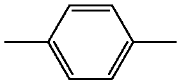 | 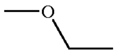 |
| 998 | n-$C_5H_{11}$ | 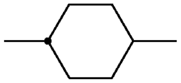 | — | 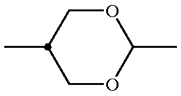 | — | 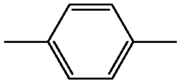 | 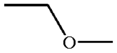 |
| 999 | n-$C_3H_7$ | 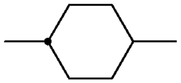 | — | 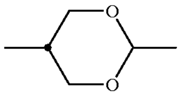 | 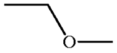 | 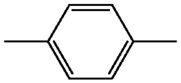 | — |
| 1000 | n-$C_3H_7$ | 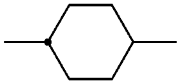 | 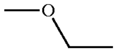 | 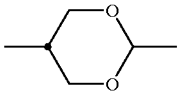 | — | 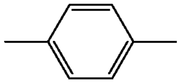 | — |
| 1001 | $CH_3$ | 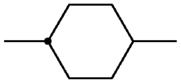 | 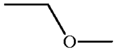 | 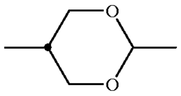 | — | 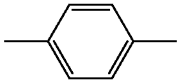 | — |
| 1002 | n-$C_3H_7$ | 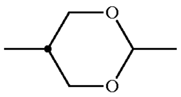 | — | 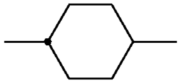 | — | 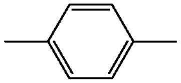 | 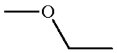 |
| 1003 | n-$C_5H_{11}$ | 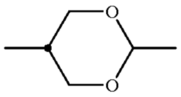 | — | 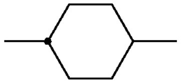 | — | 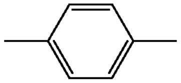 | 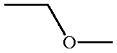 |

-continued
| | | | | | | | |
|---|---|---|---|---|---|---|---|
| 1004 | n-$C_3H_7$ | 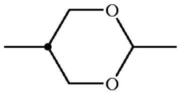 | — | 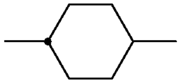 | 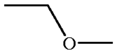 | 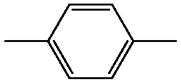 | — |
| m = n = 1, $CF_2CFHCF_3$ | | | | | | | |
| 1005 | $CH_3$ | 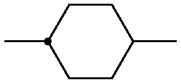 | — | 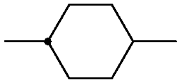 | — | 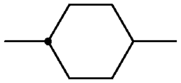 | 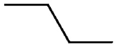 |
| 1006 | $CH_3$ | 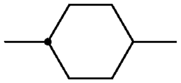 | — | 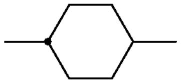 | 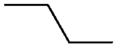 | 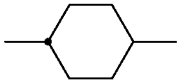 | — |
| 1007 | n-$C_3H_7$ | 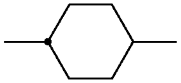 | — | 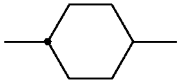 | 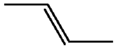 | 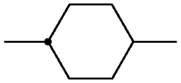 | — |
| 1008 | $CH_3$ | 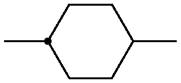 | 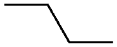 | 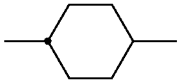 | — | 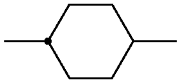 | — |
| 1009 | n-$C_3H_7$ | 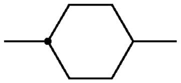 | 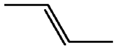 | 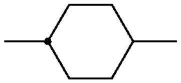 | — | 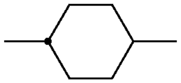 | — |
| 1010 | $CH_3$ | 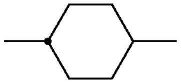 | — | 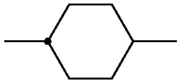 | — | 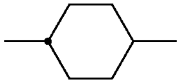 | $—CO_2—$ |
| 1011 | n-$C_3H_7$ | 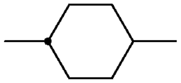 | — | 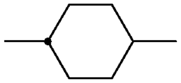 | $—CO_2—$ | 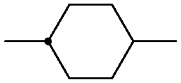 | — |
| 1012 | $CH_3$ | 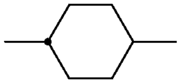 | $—CO_2—$ | 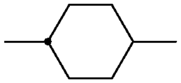 | — | 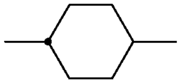 | — |

-continued
| | | |
|---|---|---|
| 1013 | $CH_3$ | 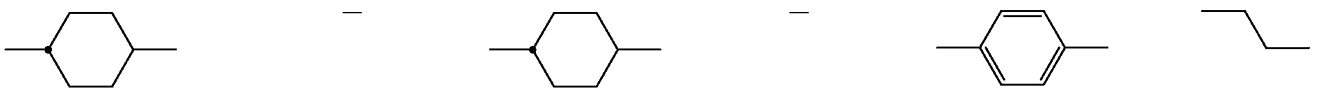 |
| 1014 | $CH_3$ | 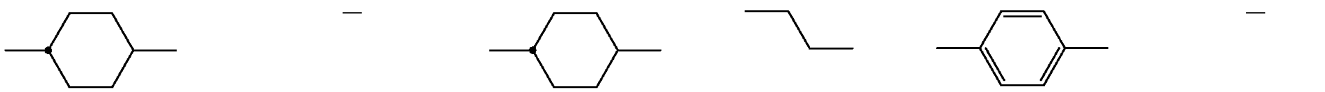 |
| 1015 | $n\text{-}C_3H_7$ | 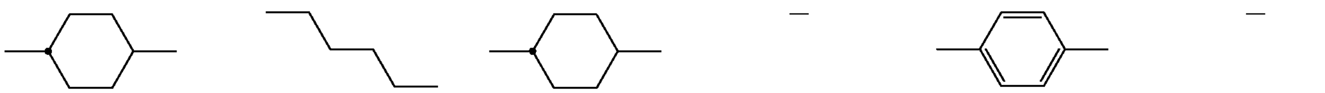 |
| 1016 | $CH_3$ | 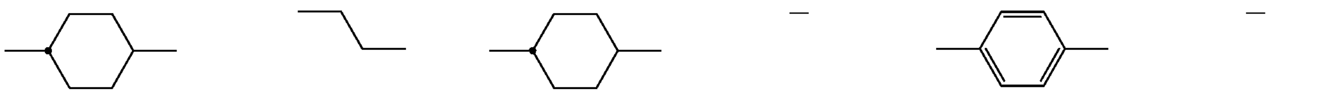 |
| 1017 | $n\text{-}C_3H_7$ | 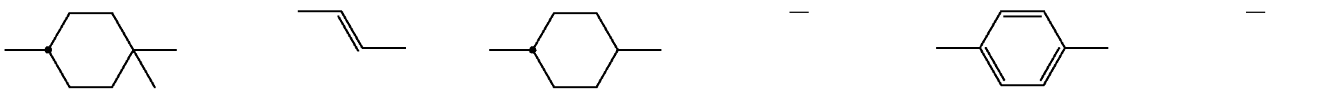 |
| 1018 | $CH_3$ | 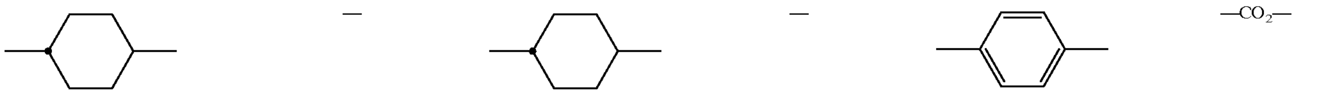 |
| 1019 | $n\text{-}C_3H_7$ | 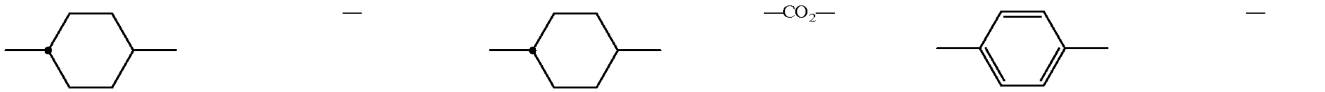 |
| 1020 | $CH_3$ | 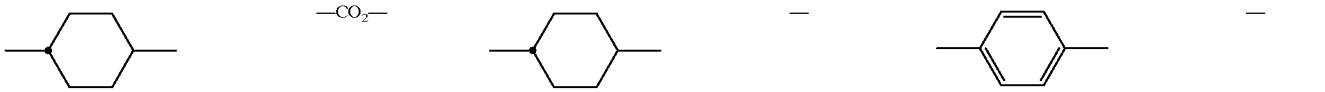 |
| 1021 | $CH_3$ | 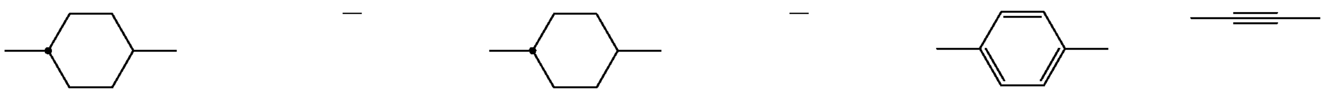 |

-continued
| | | | | | | | |
|---|---|---|---|---|---|---|---|
| 1022 | $CH_3$ | 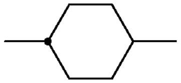 | | 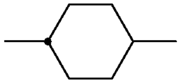 | — | 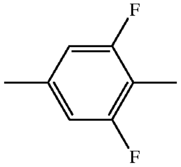 | $-CO_2-$ |
| 1023 | $CH_3$ | 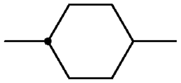 | — | 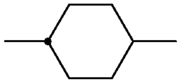 | $-CO_2-$ | 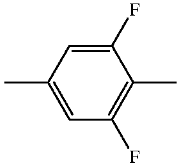 | — |
| 1024 | $CH_3$ | 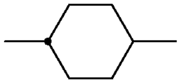 | $-CO_2-$ | 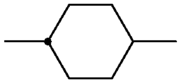 | $-CO_2-$ | 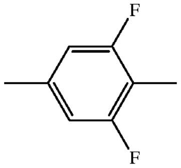 | — |
| 1025 | $CH_3$ | 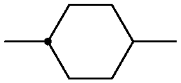 | — | 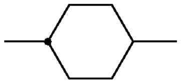 | — | 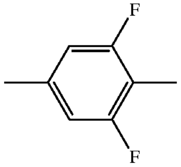 | 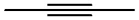 |
| 1026 | $CH_3$ | 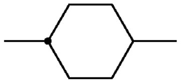 | — | 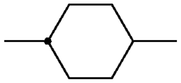 | — | 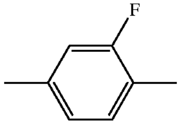 | 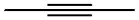 |
| 1027 | $CH_3$ | 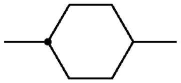 | — | 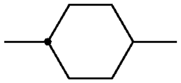 | — | 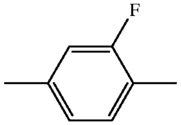 | $-CO_2-$ |

-continued
| | | | | | | | |
|---|---|---|---|---|---|---|---|
| 1028 | $CH_3$ | 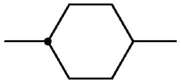 | — | 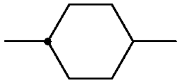 | —$CO_2$— | 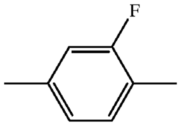 | — |
| 1029 | $CH_3$ | 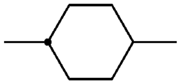 | —$CO_2$— | 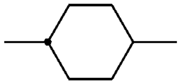 | — | 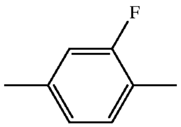 | — |
| 1030 | $CH_3$ | 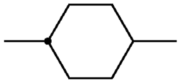 | — | 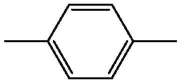 | — | 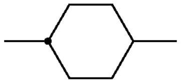 | — |
| 1031 | $CH_3$ | 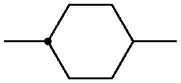 | — | 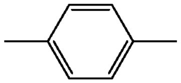 | — | 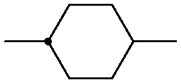 | 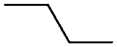 |
| 1032 | $CH_3$ | 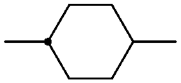 | — | 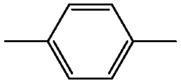 | 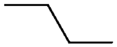 | 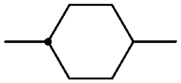 | — |
| 1033 | $CH_3$ | 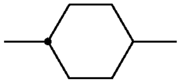 | 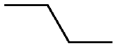 | 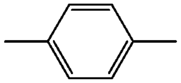 | — | 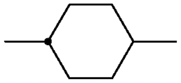 | — |
| 1034 | $CH_3$ | 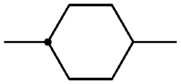 | — | 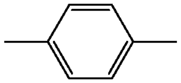 | — | 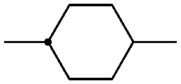 | —$CO_2$— |
| 1035 | n-$C_3H_7$ | 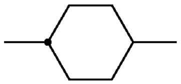 | — | 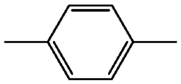 | —$CO_2$— | 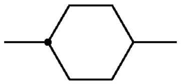 | — |
| 1036 | $CH_3$ | 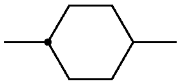 | —$CO_2$— | 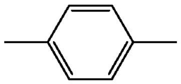 | — | 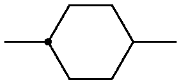 | — |

-continued
| | | | | | | | |
|---|---|---|---|---|---|---|---|
| 1037 | $CH_3$ | 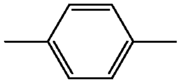 | — | 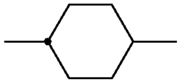 | — | 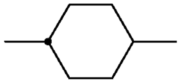 | 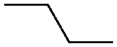 |
| 1038 | $CH_3$ | 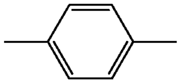 | — | 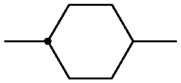 | 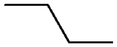 | 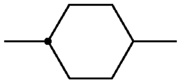 | — |
| 1039 | n-$C_3H_7$ | 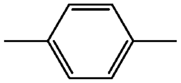 | — | 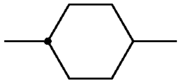 | 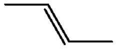 | 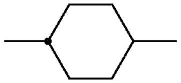 | — |
| 1040 | n-$C_3H_7$ | 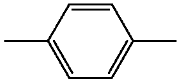 | 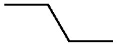 | 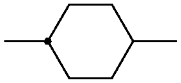 | — | 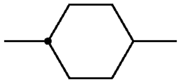 | — |
| 1041 | n-$CH_3$ | 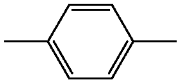 | 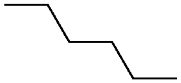 | 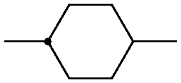 | — | 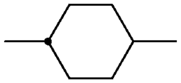 | — |
| 1042 | $CH_3$ | 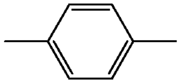 | — | 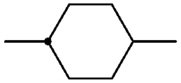 | — | 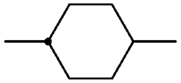 | —$CO_2$— |
| 1043 | n-$C_3H_7$ | 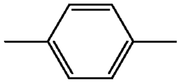 | — | 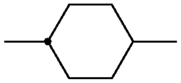 | —$CO_2$— | 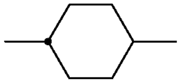 | — |
| 1044 | $CH_3$ | 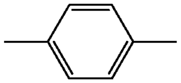 | —$CO_2$— | 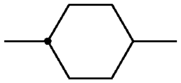 | — | 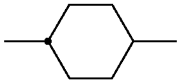 | — |
| 1045 | n-$C_3H_7$ | 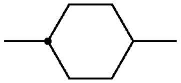 | — | 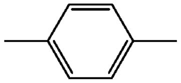 | — | 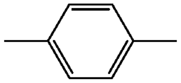 | 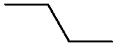 |

-continued
| | | | | | | | |
|---|---|---|---|---|---|---|---|
| 1046 | $CH_3$ | 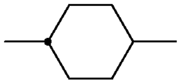 | — | 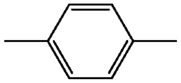 | 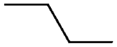 | 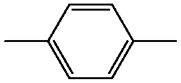 | — |
| 1047 | $CH_3$ | 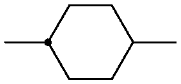 | 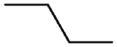 | 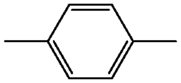 | — | 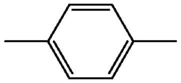 | — |
| 1048 | $CH_3$ | 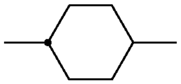 | — | 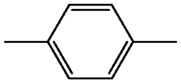 | — | 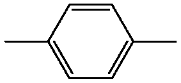 | $—CO_2—$ |
| 1049 | $CH_3$ | 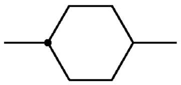 | — | 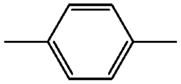 | $—CO_2—$ | 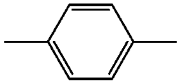 | — |
| 1050 | $CH_3$ | 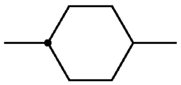 | $—CO_2—$ | 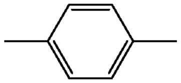 | — | 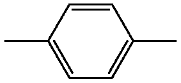 | — |
| 1051 | $CH_3$ | 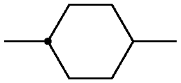 | | 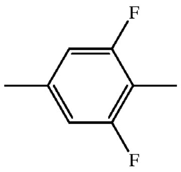 | — | 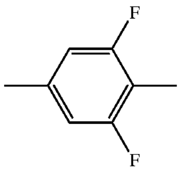 | $—CO_2—$ |
| 1052 | $CH_3$ | 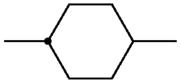 | — | 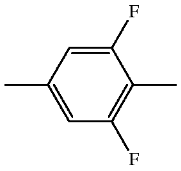 | $—CO_2—$ | 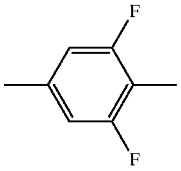 | — |

-continued
| | | | | | | | |
|---|---|---|---|---|---|---|---|
| 1053 | $CH_3$ | 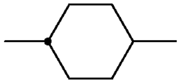 | $—CO_2—$ | 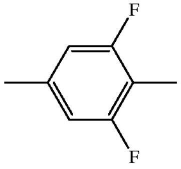 | $—CO_2—$ | 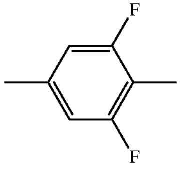 | — |
| 1054 | $CH_3$ | 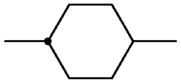 | — | 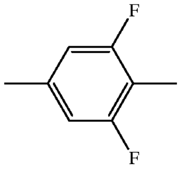 | — | 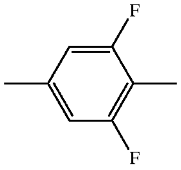 | 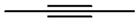 |
| 1055 | $CH_3$ | 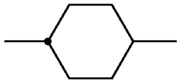 | — | 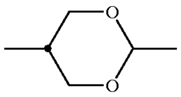 | — | 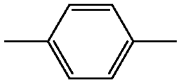 | — |
| 1056 | $CH_3$ | 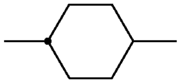 | — | 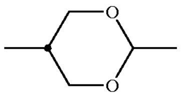 | — | 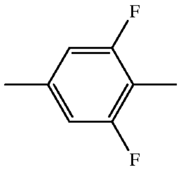 | — |
| 1057 | $CH_3$ | 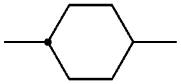 | — | 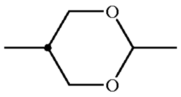 | — | 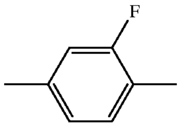 | — |
| 1058 | $CH_3$ | 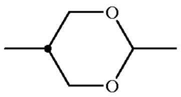 | — | 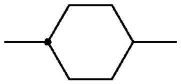 | — | 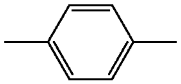 | — |

-continued
| | | | | | | | |
|---|---|---|---|---|---|---|---|
| 1059 | $CH_3$ | 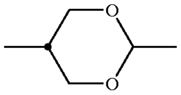 | — | 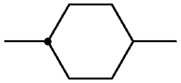 | — | 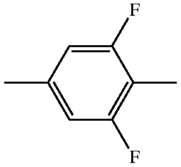 | — |
| 1060 | n-$C_3H_7$ | 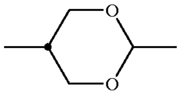 | — | 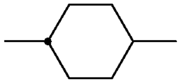 | — | 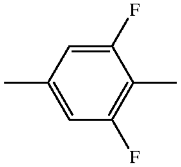 | — |
| 1061 | $CH_3$ | 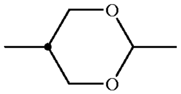 | — | 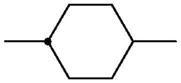 | — | 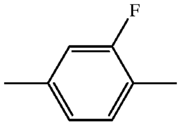 | — |
| 1062 | $CH_3$ | 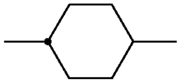 | — | 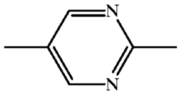 | — | 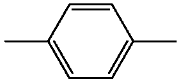 | — |
| 1063 | $CH_3$ | 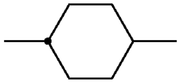 | — | 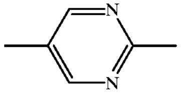 | — | 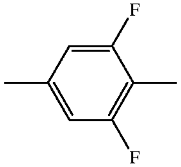 | — |
| 1064 | $CH_3$ | 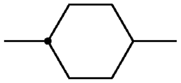 | — | 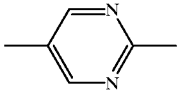 | — | 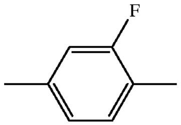 | — |

-continued
| | | | | | | | |
|---|---|---|---|---|---|---|---|
| 1065 | $CH_3$ | 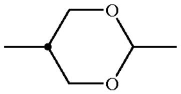 | — | 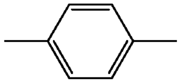 | — | 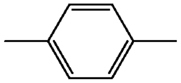 | — |
| 1066 | $n-C_3H_7$ | 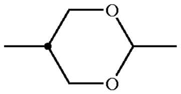 | — | 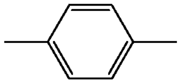 | — | 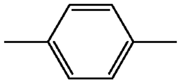 | — |
| 1067 | $CH_3$ | 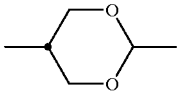 | — | 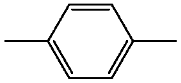 | — | 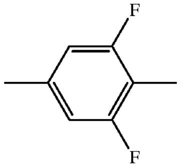 | — |
| 1068 | $n-C_3H_7$ | 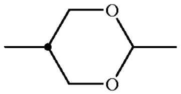 | — | 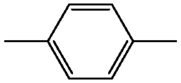 | — | 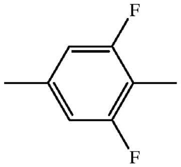 | — |
| 1069 | $CH_3$ | 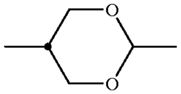 | 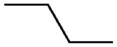 | 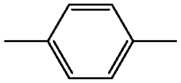 | — | 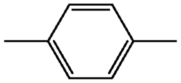 | — |
| 1070 | $n-C_3H_7$ | 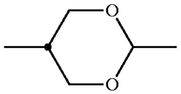 | 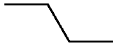 | 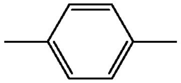 | — | 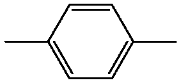 | — |
| 1071 | $CH_3$ | 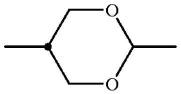 | 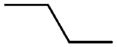 | 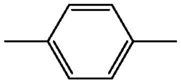 | — | 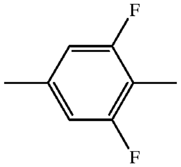 | — |

-continued
| | | |
|---|---|---|
| 1072 | $CH_3$ | 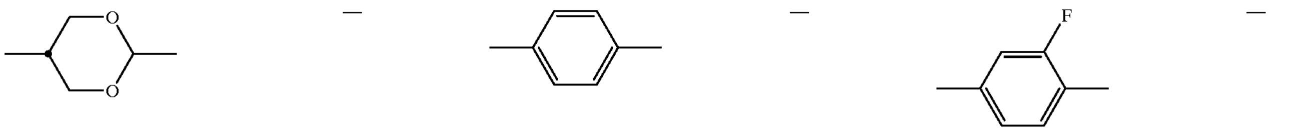 |
| 1073 | n-$C_3H_7$ | 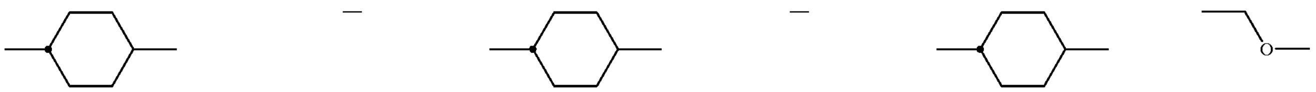 |
| 1074 | n-$C_5H_{11}$ | 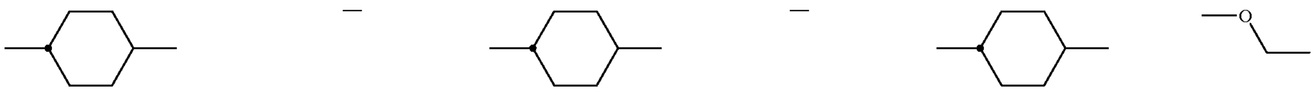 |
| 1075 | $CH_3$ | 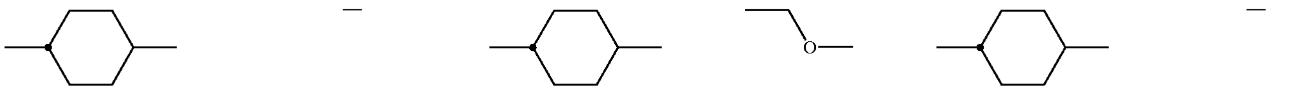 |
| 1076 | n-$C_5H_{11}$ | 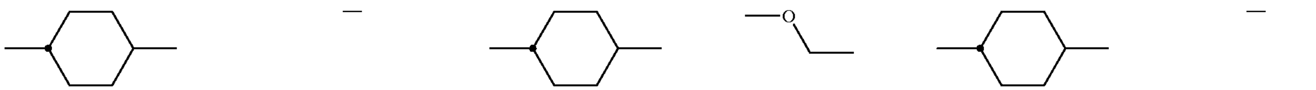 |
| 1077 | n-$C_5H_{11}$ | 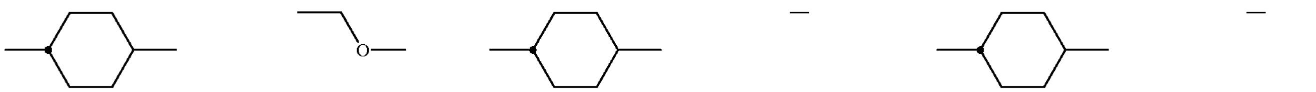 |
| 1078 | n-$C_3H_7$— | 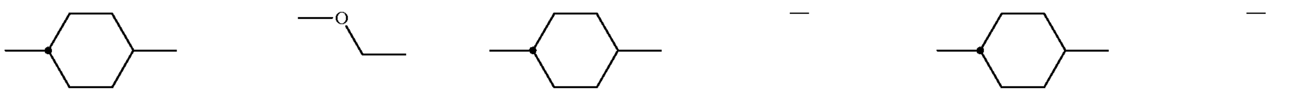 |
| 1079 | n-$C_3H_7$ | 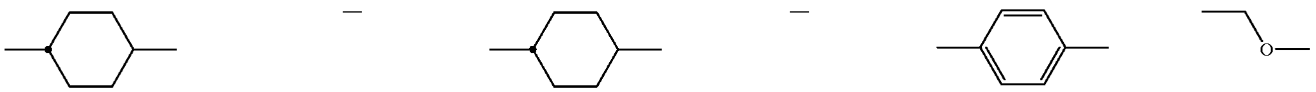 |
| 1080 | $CH_3$ | 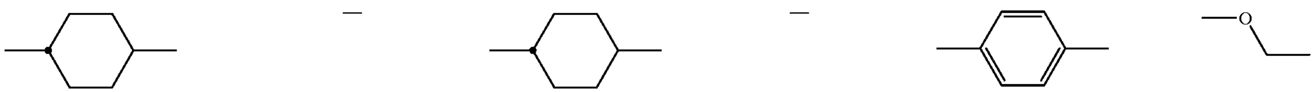 |

-continued
| | | |
|---|---|---|
| 1081 | n-$C_3H_7$ | 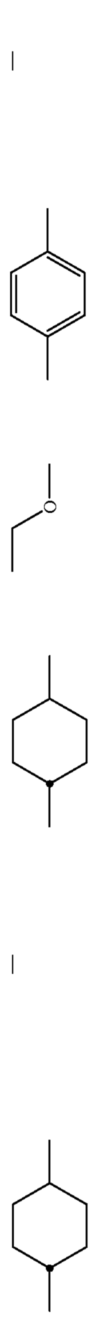 |
| 1082 | n-$C_5H_{11}$ | 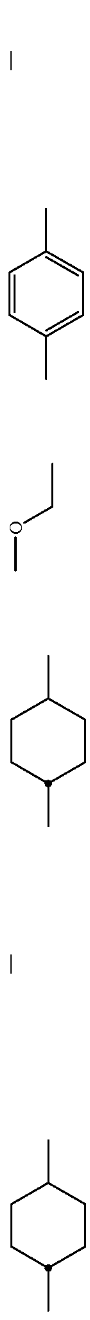 |
| 1083 | n-$C_5H_{11}$ | 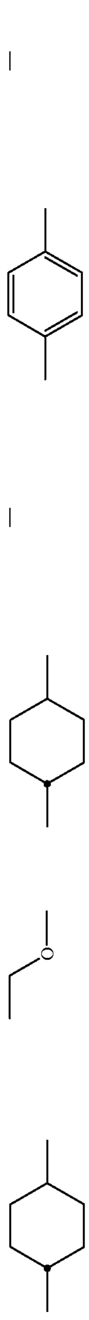 |
| 1084 | n-$C_3H_7$ | 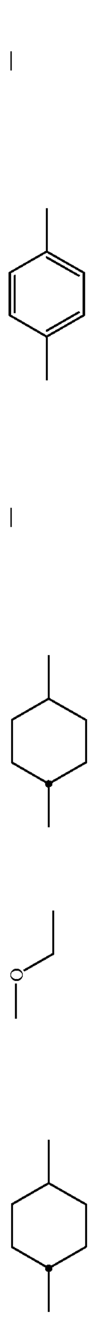 |
| 1085 | n-$C_3H_7$ | 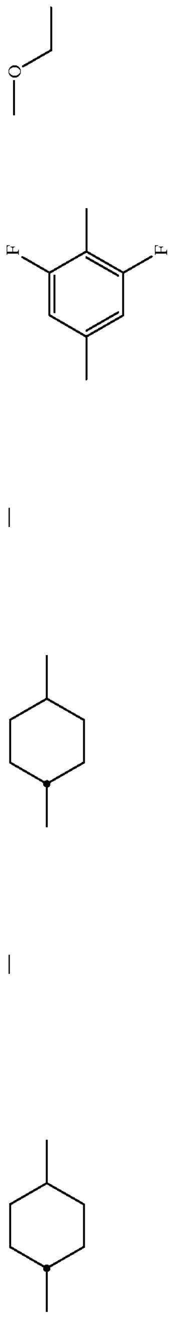 |
| 1086 | n-$C_5H_{11}$ | 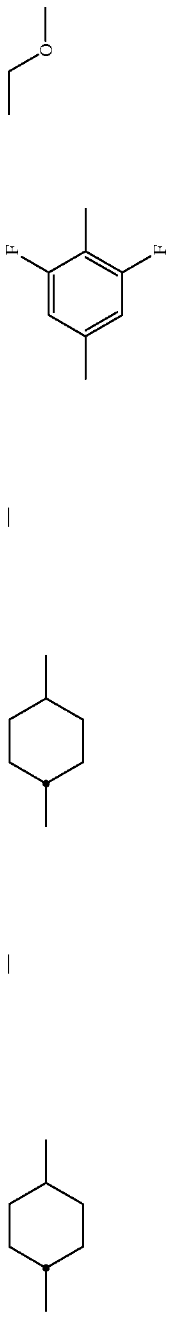 |
| 1087 | n-$C_3H_7$ | 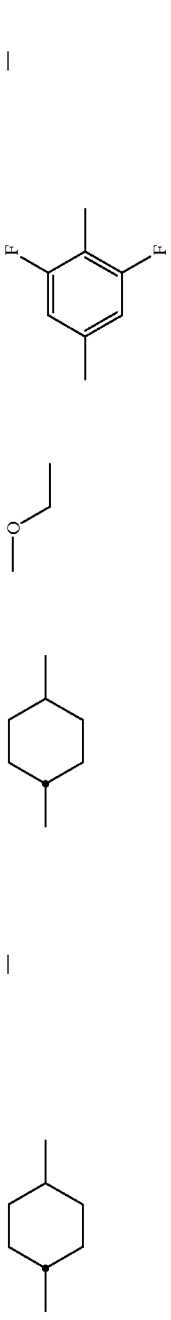 |

-continued
| | | |
|---|---|---|
| 1088 | n-$C_3H_7$ | 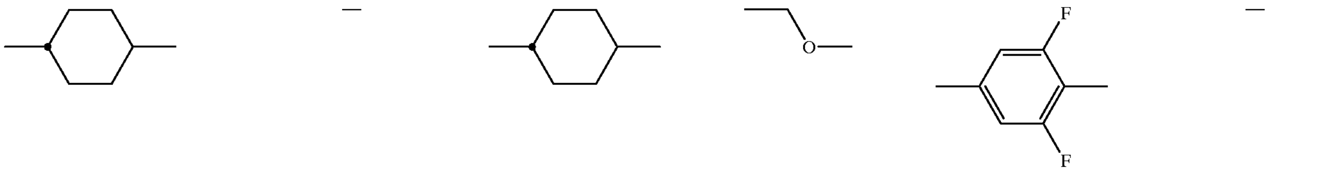 |
| 1089 | n-$C_3H_7$ | 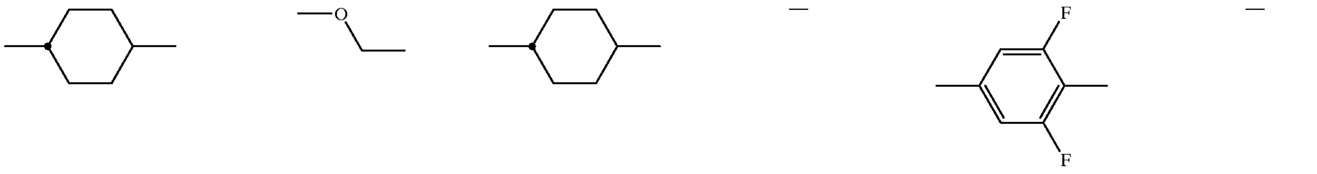 |
| 1090 | n-$C_5H_{11}$ | 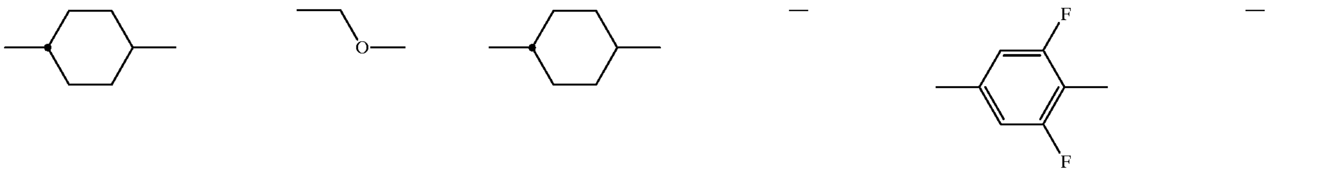 |
| 1091 | n-$C_3H_7$ | 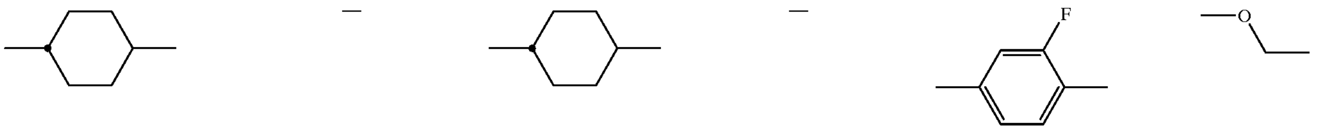 |
| 1092 | n-$C_5H_{11}$ | 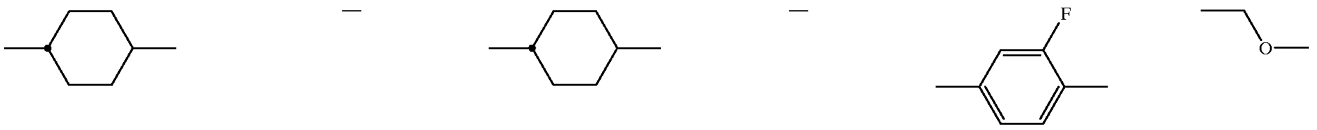 |
| 1093 | n-$C_3H_7$ | 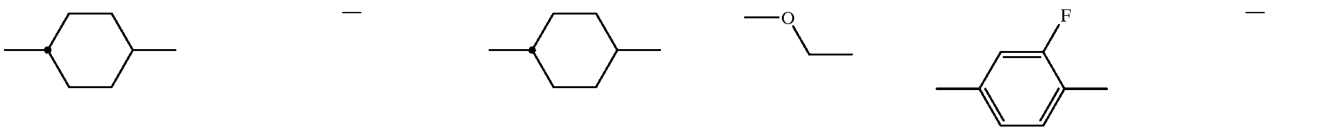 |

-continued
| | | |
|---|---|---|
| 1094 | n-$C_3H_7$ | 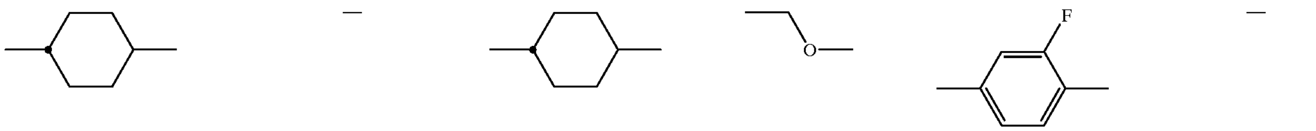 |
| 1095 | $CH_3$ | 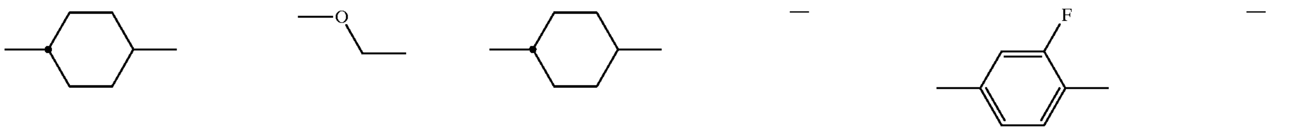 |
| 1096 | n-$C_5H_{11}$ | 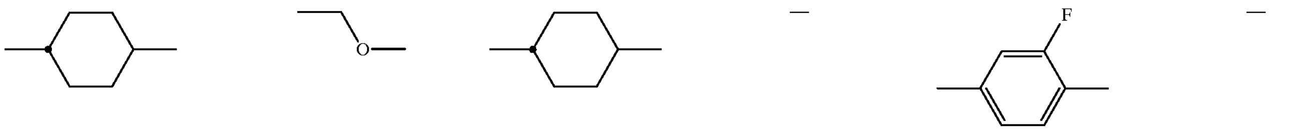 |
| 1097 | n-$C_3H_7$ | 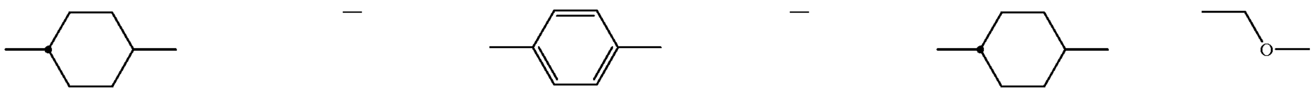 |
| 1098 | $CH_3$ | 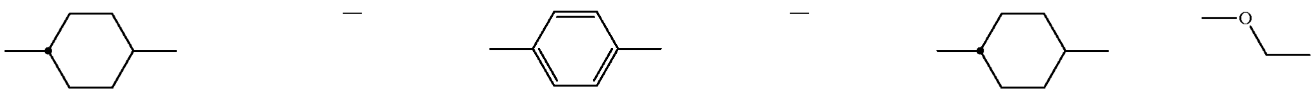 |
| 1099 | n-$C_3H_7$ | 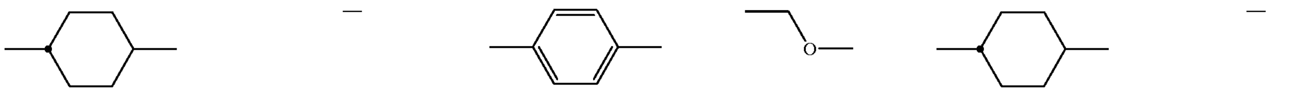 |
| 1100 | n-$C_5H_{11}$ | 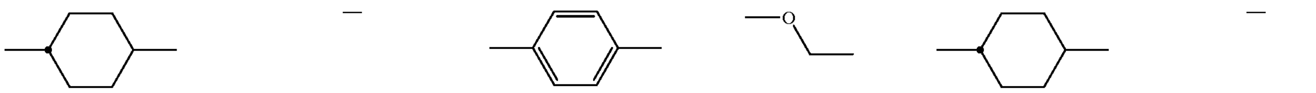 |
| 1101 | n-$C_3H_7$ | 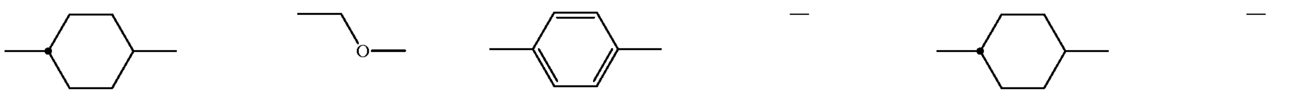 |

-continued
| | | |
|---|---|---|
| 1102 | n-$C_3H_7$ | 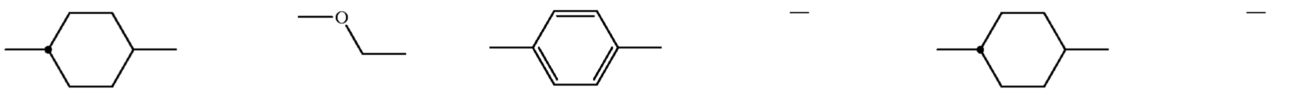 |
| 1103 | $CH_3$ | 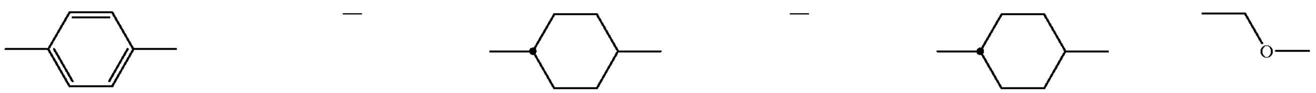 |
| 1104 | n-$C_3H_7$ | 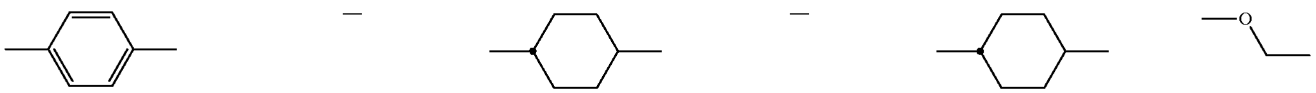 |
| 1105 | n-$C_3H_7$ | 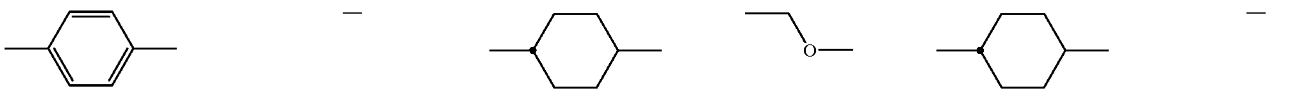 |
| 1106 | n-$C_5H_{11}$ | 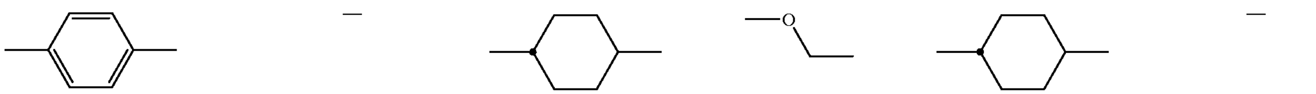 |
| 1107 | n-$C_5H_{11}$ | 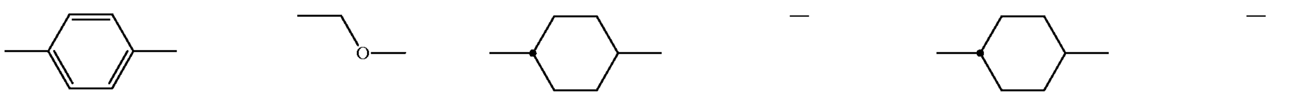 |
| 1108 | $CH_3$ | 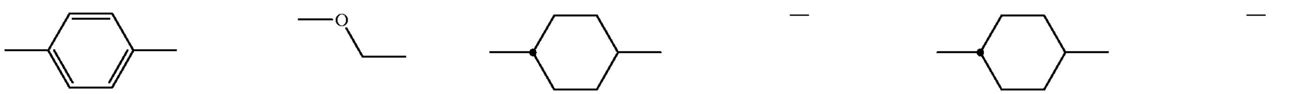 |
| 1109 | n-$C_3H_7$ | 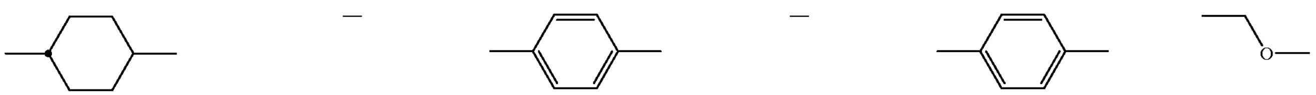 |
| 1110 | n-$C_5H_{11}$ | 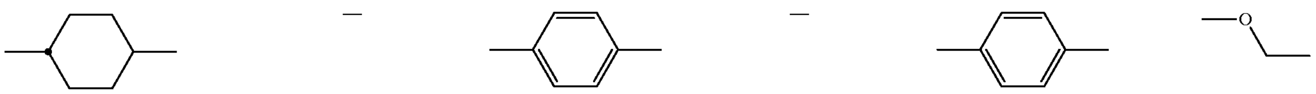 |

-continued
| | | | | | | | |
|---|---|---|---|---|---|---|---|
| 1111 | n-$C_3H_7$ | 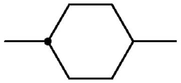 | — | 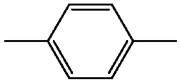 | 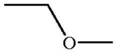 | 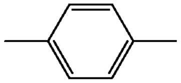 | — |
| 1112 | n-$C_5H_{11}$ | 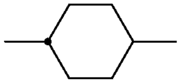 | — | 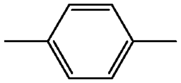 | 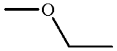 | 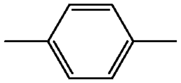 | — |
| 1113 | n-$C_5H_{11}$ | 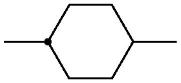 | 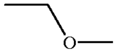 | 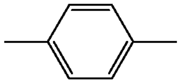 | — | 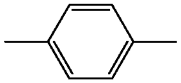 | — |
| 1114 | $CH_3$ | 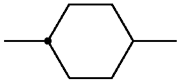 | 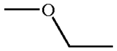 | 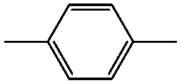 | — | 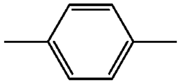 | — |
| 1115 | n-$C_3H_7$ | 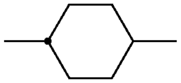 | — | 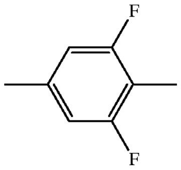 | — | 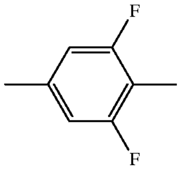 | 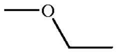 |
| 1116 | n-$C_5H_{11}$ | 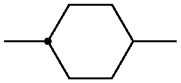 | — | 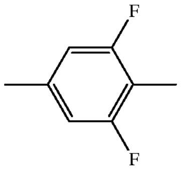 | — | 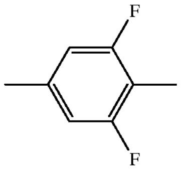 | 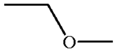 |
| 1117 | $CH_3$ | 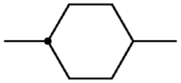 | — | 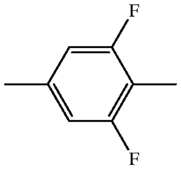 | 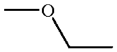 | 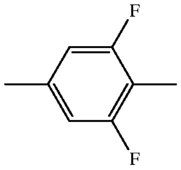 | — |

-continued
| | | | | | | | |
|---|---|---|---|---|---|---|---|
| 1118 | n-$C_3H_7$ | 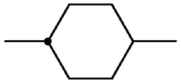 | — | 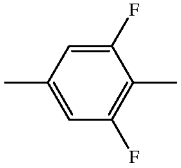 | 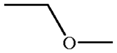 | 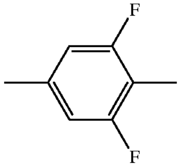 | — |
| 1119 | n-$C_3H_7$ | 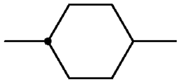 | 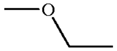 | 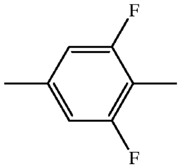 | — | 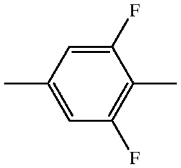 | — |
| 1120 | $CH_3$ | 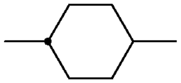 | 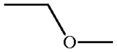 | 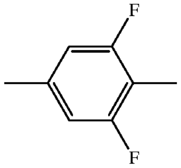 | — | 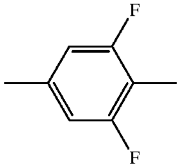 | — |
| 1121 | n-$C_3H_7$ | 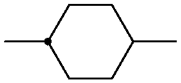 | — | 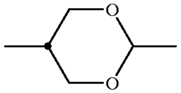 | — | 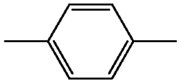 | 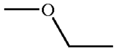 |
| 1122 | n-$C_5H_{11}$ | 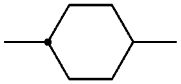 | — | 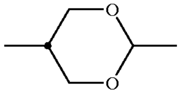 | — | 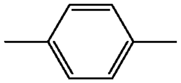 | 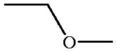 |
| 1123 | n-$C_3H_7$ | 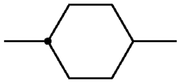 | — | 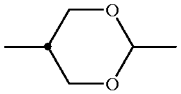 | 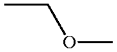 | 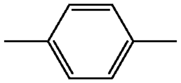 | — |
| 1124 | n-$C_3H_7$ | 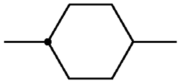 | 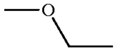 | 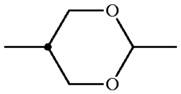 | — | 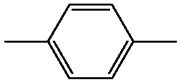 | — |

-continued
| | | |
|---|---|---|
| 1125 | $CH_3$ | 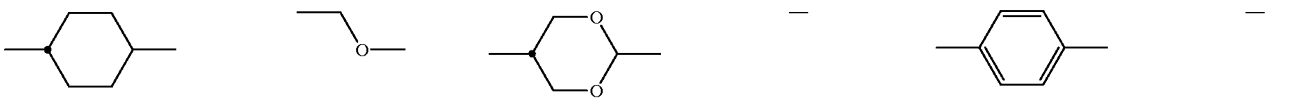 |
| 1126 | n-$C_3H_7$ | 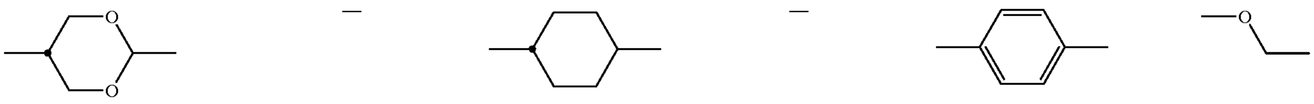 |
| 1127 | n-$C_5H_{11}$ | 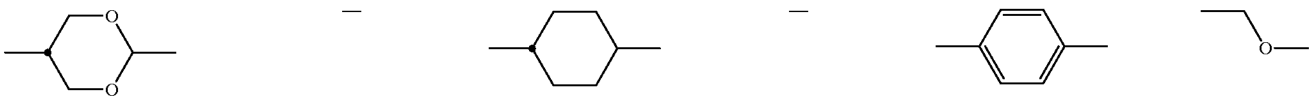 |
| 1128 | n-$C_3H_7$ | 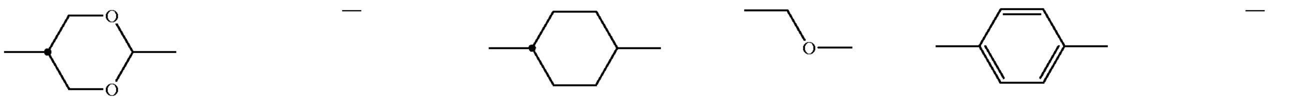 |
= m = n = 1, = $CH_2CF_2CF_3$
| | | |
|---|---|---|
| 1129 | $CH_3$ | 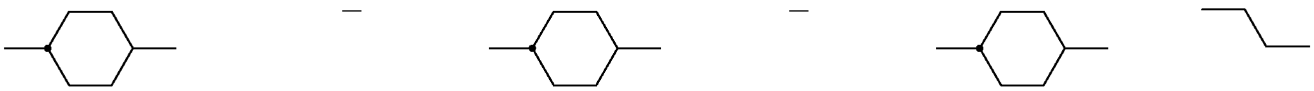 |
| 1130 | $CH_3$ | 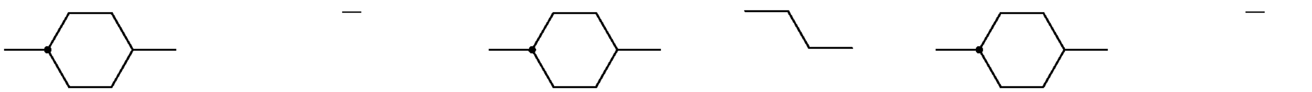 |
| 1131 | n-$C_3H_7$ | 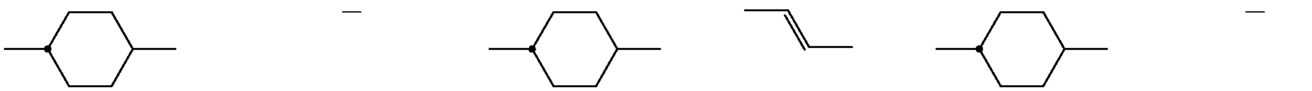 |
| 1132 | $CH_3$ | 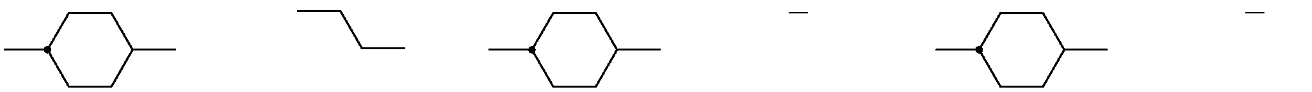 |
| 1133 | n-$C_3H_7$ | 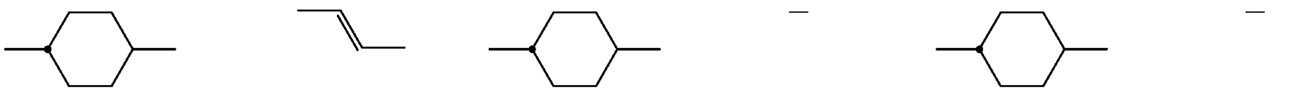 |

-continued
| | | | | | | | |
|---|---|---|---|---|---|---|---|
| 1134 | $CH_3$ | 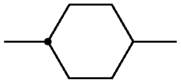 | — | 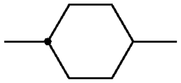 | — | 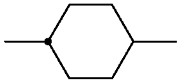 | —$CO_2$— |
| 1135 | n-$C_3H_7$ | 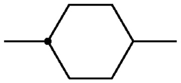 | — | 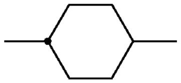 | —$CO_2$— | 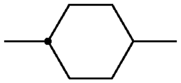 | — |
| 1136 | $CH_3$ | 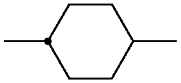 | —$CO_2$— | 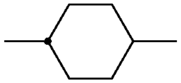 | — | 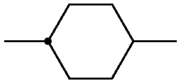 | — |
| 1137 | $CH_3$ | 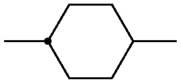 | — | 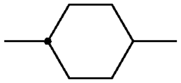 | — | 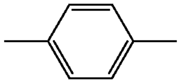 | 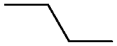 |
| 1138 | $CH_3$ | 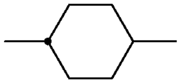 | — | 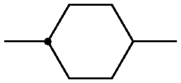 | 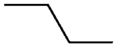 | 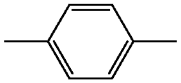 | — |
| 1139 | n-$C_3H_7$ | 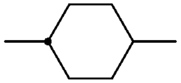 | 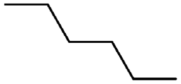 | 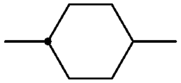 | — | 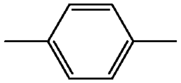 | — |
| 1140 | $CH_3$ | 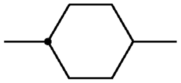 | 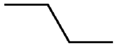 | 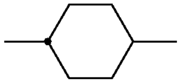 | — | 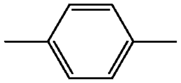 | — |
| 1141 | n-$C_3H_7$ | 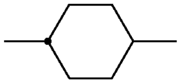 | 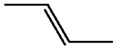 | 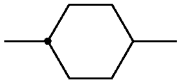 | — | 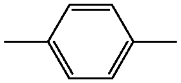 | — |
| 1142 | $CH_3$ | 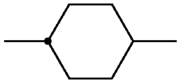 | — | 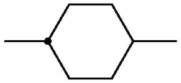 | — | 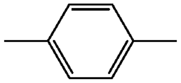 | —$CO_2$— |

-continued
| | | | | | | | |
|---|---|---|---|---|---|---|---|
| 1143 | n-$C_3H_7$ | 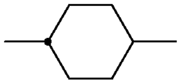 | — | 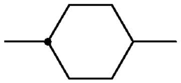 | —$CO_2$— | 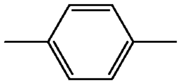 | — |
| 1144 | $CH_3$ | 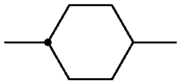 | —$CO_2$— | 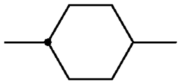 | — | 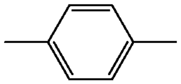 | — |
| 1145 | $CH_3$ | 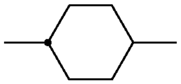 | — | 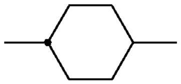 | — | 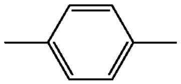 | 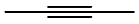 |
| 1146 | $CH_3$ | 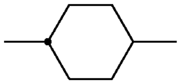 | | 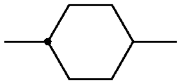 | — | 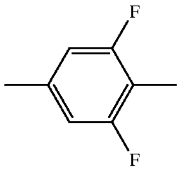 | —$CO_2$— |
| 1147 | $CH_3$ | 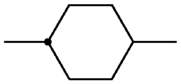 | — | 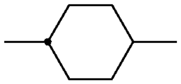 | —$CO_2$— | 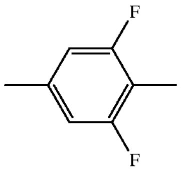 | — |
| 1148 | $CH_3$ | 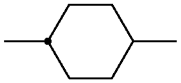 | —$CO_2$— | 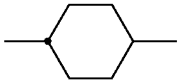 | —$CO_2$— | 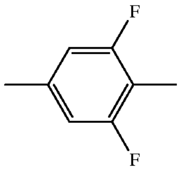 | — |

-continued
| | | | | | | | |
|---|---|---|---|---|---|---|---|
| 1149 | $CH_3$ | 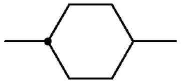 | — | 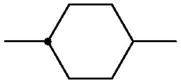 | — | 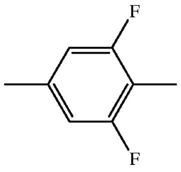 | 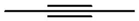 |
| 1150 | $CH_3$ | 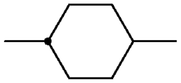 | — | 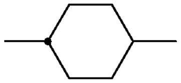 | — | 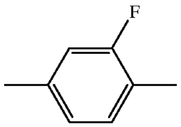 | 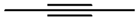 |
| 1151 | $CH_3$ | 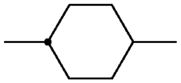 | — | 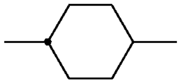 | — | 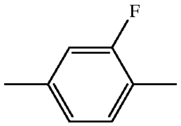 | $—CO_2—$ |
| 1152 | $CH_3$ | 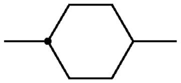 | — | 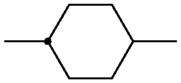 | $—CO_2—$ | 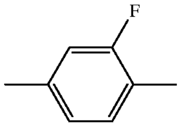 | — |
| 1153 | $CH_3$ | 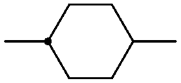 | $—CO_2—$ | 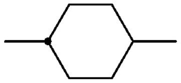 | — | 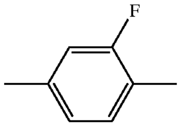 | — |
| 1154 | $CH_3$ | 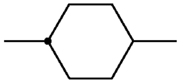 | — | 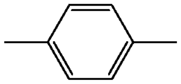 | — | 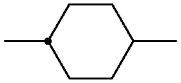 | — |
| 1155 | $CH_3$ | 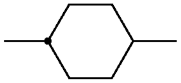 | — | 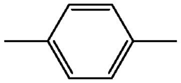 | — | 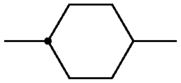 | 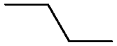 |

-continued
| | | | | | | | |
|---|---|---|---|---|---|---|---|
| 1156 | $CH_3$ | 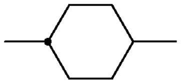 | — | 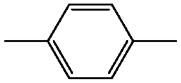 | 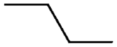 | 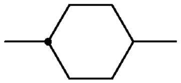 | — |
| 1157 | $CH_3$ | 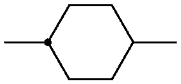 | 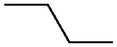 | 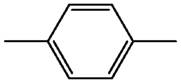 | — | 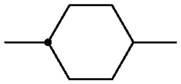 | — |
| 1158 | $CH_3$ | 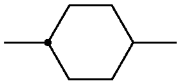 | — | 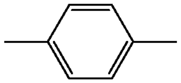 | — | 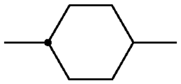 | $—CO_2—$ |
| 1159 | n-$C_3H_7$ | 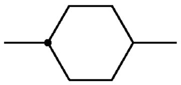 | — | 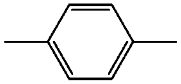 | $—CO_2—$ | 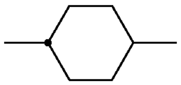 | — |
| 1160 | $CH_3$ | 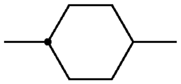 | $—CO_2—$ | 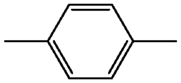 | — | 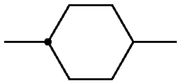 | — |
| 1161 | $CH_3$ | 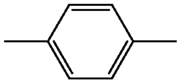 | — | 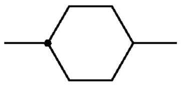 | — | 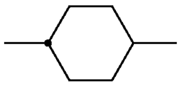 | 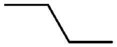 |
| 1162 | $CH_3$ | 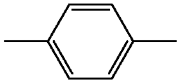 | — | 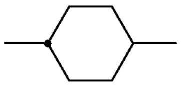 | 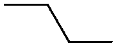 | 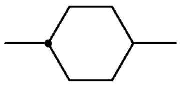 | — |
| 1163 | n-$C_3H_7$ | 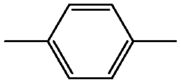 | — | 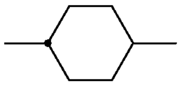 | 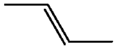 | 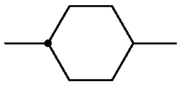 | — |
| 1164 | n-$C_3H_7$ | 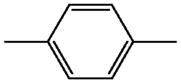 | 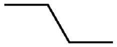 | 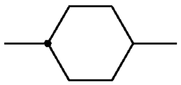 | — | 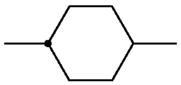 | — |

-continued
| | | | | | | | |
|---|---|---|---|---|---|---|---|
| 1165 | n-$CH_3$ | 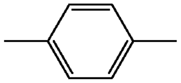 | 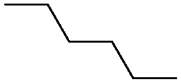 | 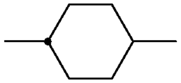 | — | 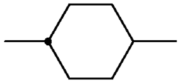 | — |
| 1166 | $CH_3$ | 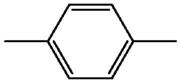 | — | 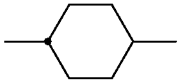 | — | 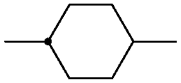 | —$CO_2$— |
| 1167 | n-$C_3H_7$ | 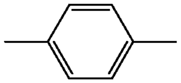 | — | 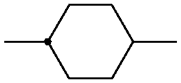 | —$CO_2$— | 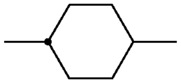 | — |
| = m = n = 1, = $CH_2CF_3$ | | | | | | | |
| 1168 | $CH_3$ | 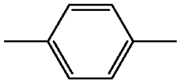 | —$CO_2$— | 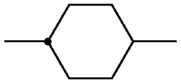 | — | 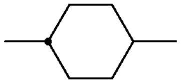 | — |
| 1169 | n-$C_3H_7$ | 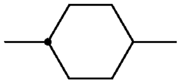 | — | 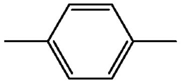 | — | 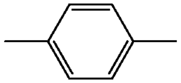 | 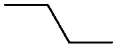 |
| 1170 | $CH_3$ | 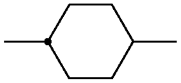 | — | 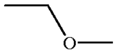 | 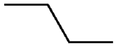 | 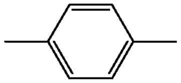 | — |
| 1171 | $CH_3$ | 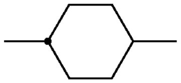 | 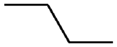 | 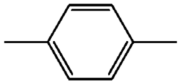 | — | 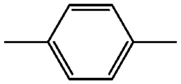 | — |
| 1172 | $CH_3$ | 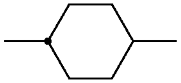 | — | 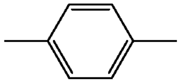 | — | 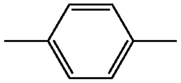 | —$CO_2$— |
| 1173 | $CH_3$ | 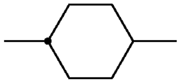 | — | 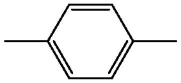 | —$CO_2$— | 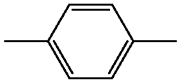 | — |

-continued
| | | | | | | | |
|---|---|---|---|---|---|---|---|
| 1174 | $CH_3$ | 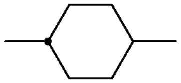 | —$CO_2$— | 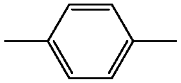 | — | 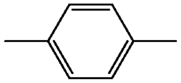 | — |
| 1175 | $CH_3$ | 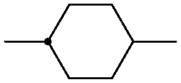 | | 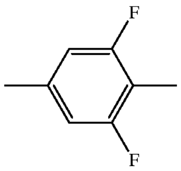 | — | 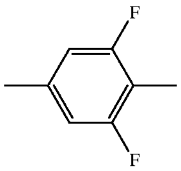 | —$CO_2$— |
| 1176 | $CH_3$ | 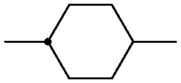 | — | 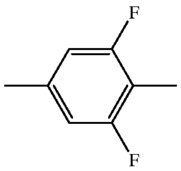 | —$CO_2$— | 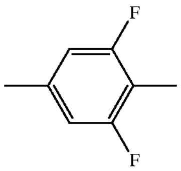 | — |
| 1177 | $CH_3$ | 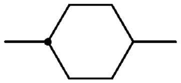 | —$CO_2$— | 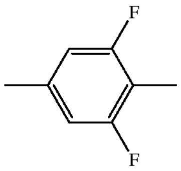 | —$CO_2$— | 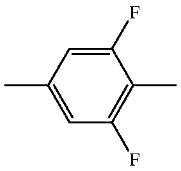 | — |
| 1178 | $CH_3$ | 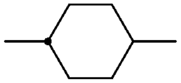 | — | 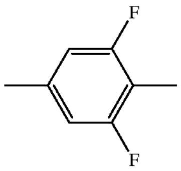 | — | 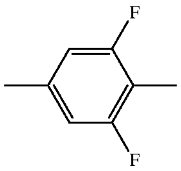 | 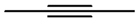 |
| 1179 | $CH_3$ | 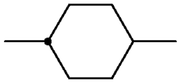 | — | 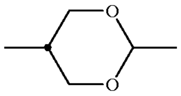 | — | 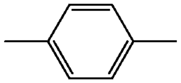 | — |

-continued
| | | | | | | | |
|---|---|---|---|---|---|---|---|
| 1180 | $CH_3$ | 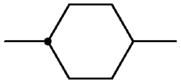 | — | 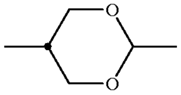 | — | 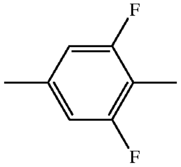 | — |
| 1181 | $CH_3$ | 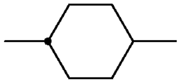 | — | 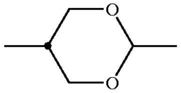 | — | 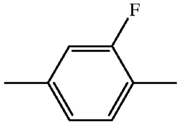 | — |
| 1182 | $CH_3$ | 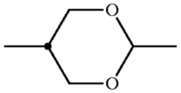 | — | 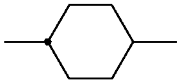 | — | 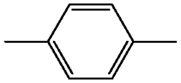 | — |
| 1183 | $CH_3$ | 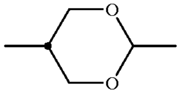 | — | 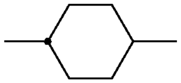 | — | 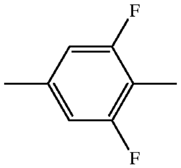 | — |
| $K = 0$, $m = n = 1$, $R_f = CH_2CF_2CF_3$ | | | | | | | |
| 1184 | n-$C_3H_7$ | 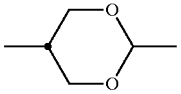 | — | 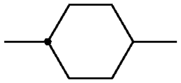 | — | 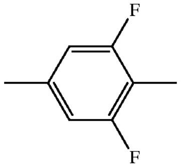 | — |
| 1185 | $CH_3$ | 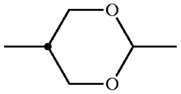 | — | 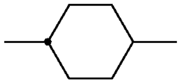 | — | 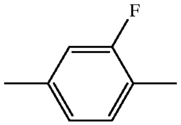 | — |

-continued
| | | | | | | | |
|---|---|---|---|---|---|---|---|
| 1186 | $CH_3$ | 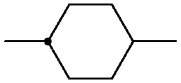 | — | 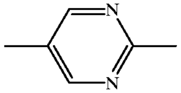 | — | 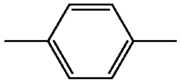 | — |
| 1187 | $CH_3$ | 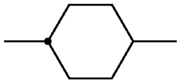 | — | 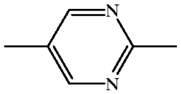 | — | 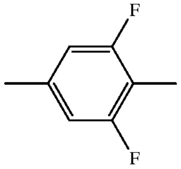 | — |
| 1188 | $CH_3$ | 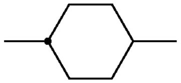 | — | 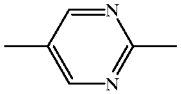 | — | 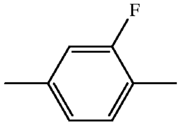 | — |
| 1189 | $CH_3$ | 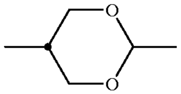 | — | 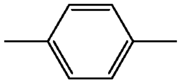 | — | 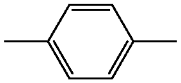 | — |
| 1190 | n-$C_3H_7$ | 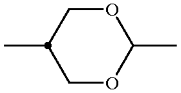 | — | 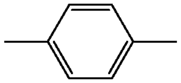 | — | 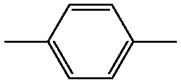 | — |
| 1191 | $CH_3$ | 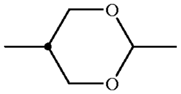 | — | 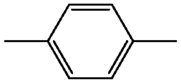 | — | 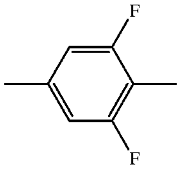 | — |
| 1192 | n-$C_3H_7$ | 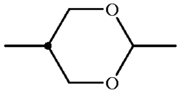 | — | 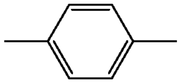 | — | 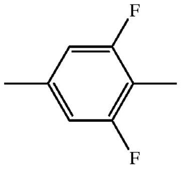 | — |

-continued
| | | |
|---|---|---|
| 1193 | $CH_3$ | 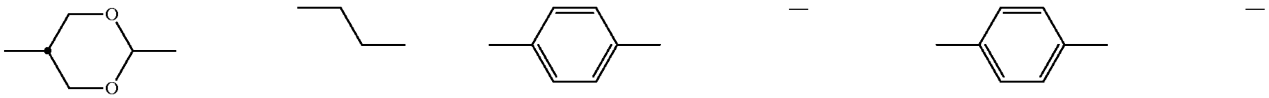 |
| 1194 | $n\text{-}C_3H_7$ | 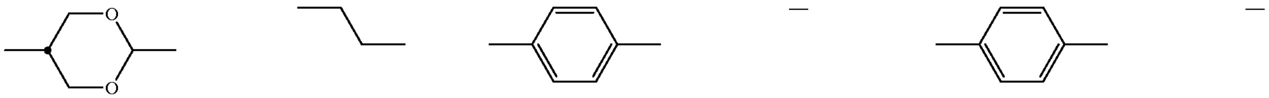 |
| 1195 | $CH_3$ | 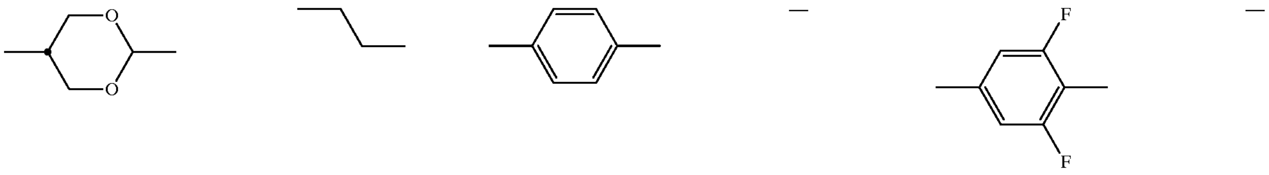 |
| 1196 | $CH_3$ | 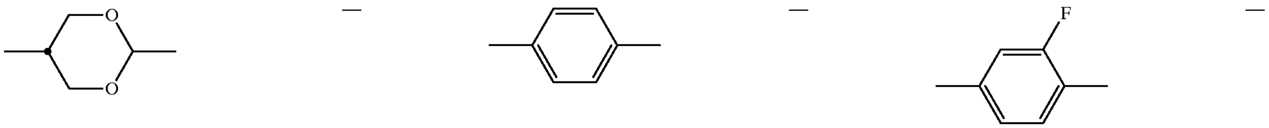 |
| 1197 | $n\text{-}C_3H_7$ | 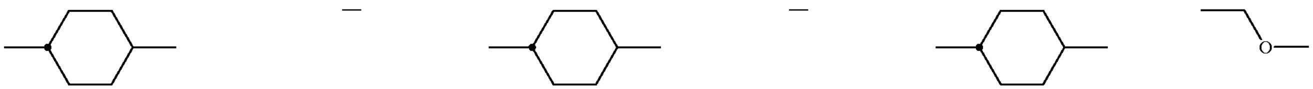 |
| 1198 | $n\text{-}C_5H_{11}$ | 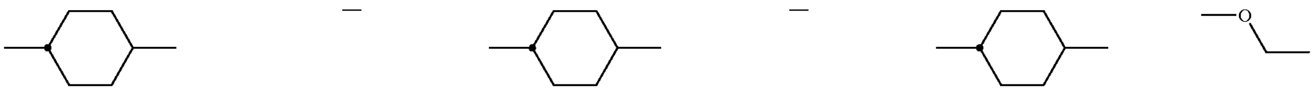 |
| 1199 | $CH_3$ | 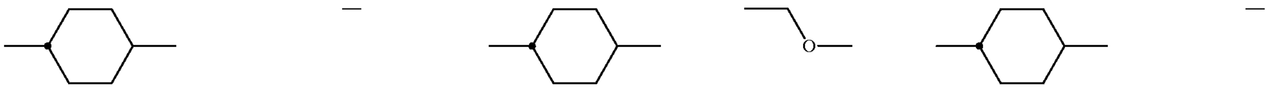 |
| 1200 | $n\text{-}C_5H_{11}$ | 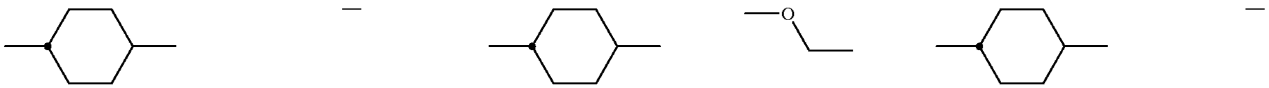 |

-continued
| | | |
|---|---|---|
| 1201 | n-$C_5H_{11}$ | 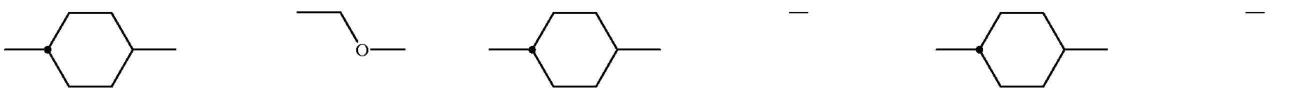 |
| 1202 | n-$C_3H_7$ | 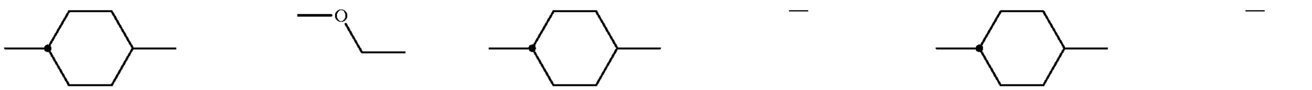 |
| 1203 | n-$C_3H_7$ | 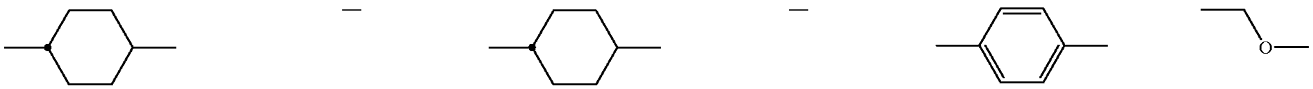 |
| 1204 | $CH_3$ | 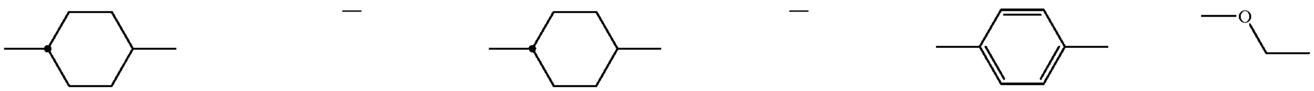 |
| 1205 | n-$C_3H_7$ | 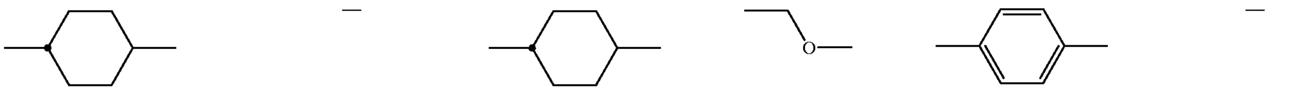 |
| 1206 | n-$C_5H_{11}$ | 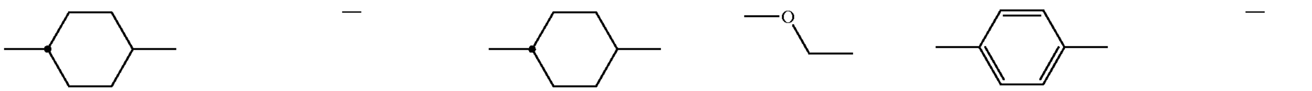 |
| 1207 | n-$C_5H_{11}$ | 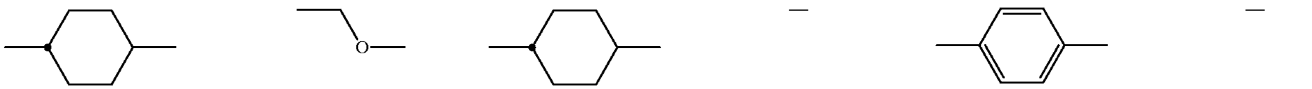 |
| 1208 | n-$C_3H_7$ | 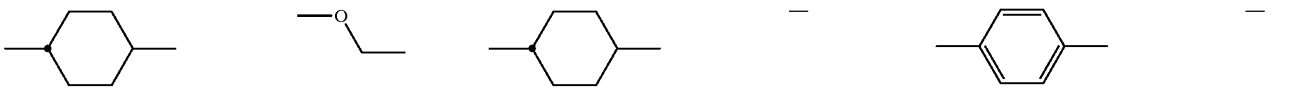 |
| 1209 | n-$C_3H_7$ | 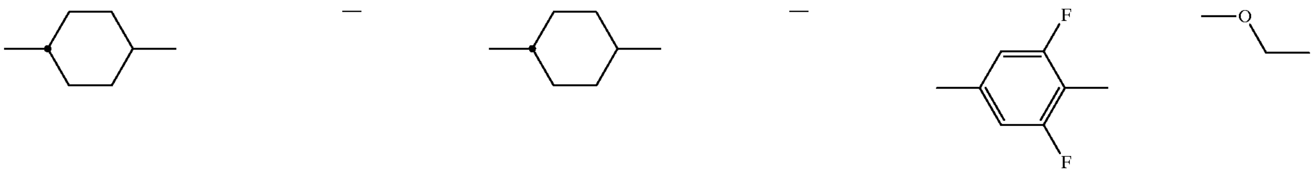 |

-continued
| | | |
|---|---|---|
| 1210 | n-$C_5H_{11}$ | 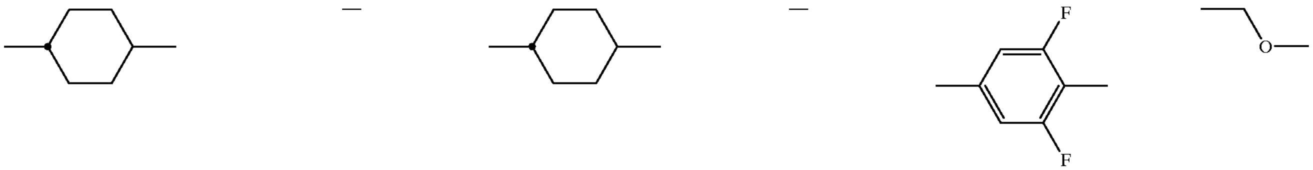 |
| 1211 | n-$C_3H_7$ | 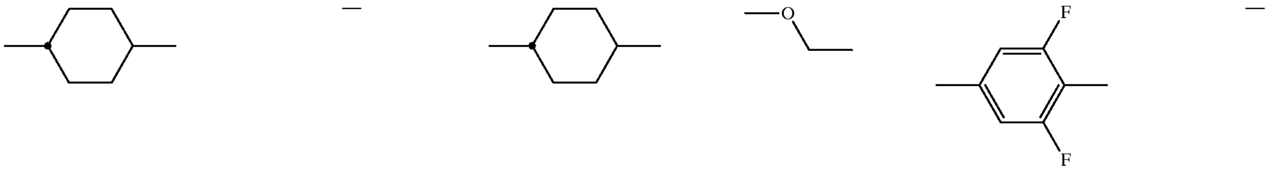 |
| 1212 | n-$C_3H_7$ | 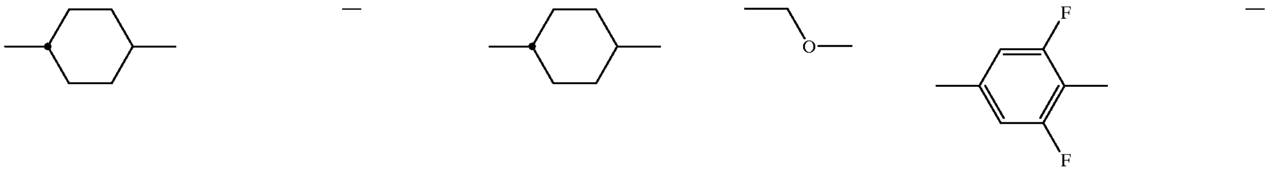 |
| 1213 | n-$C_3H_7$ | 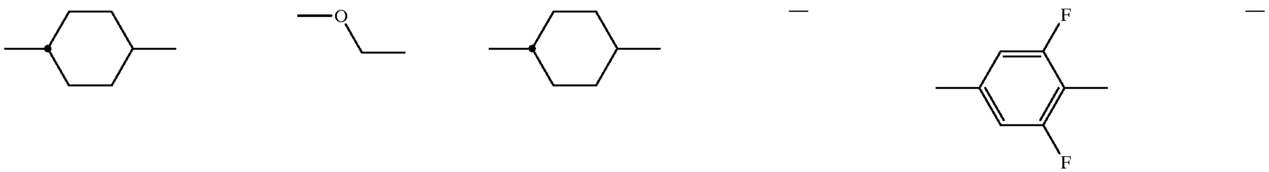 |
| 1214 | n-$C_5H_{11}$ | 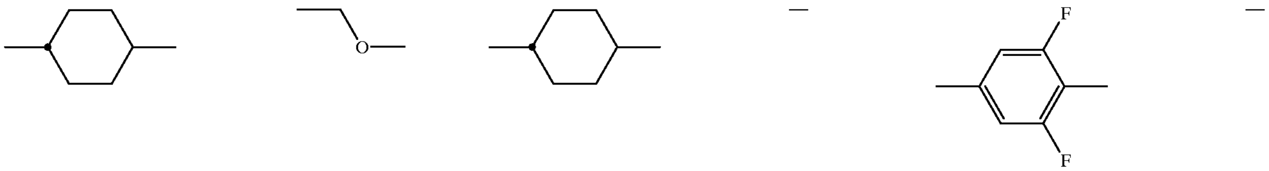 |

-continued
| | | |
|---|---|---|
| 1215 | n-$C_3H_7$ | 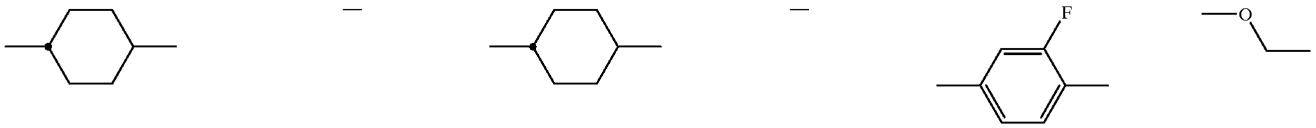 |
| 1216 | n-$C_5H_{11}$ | 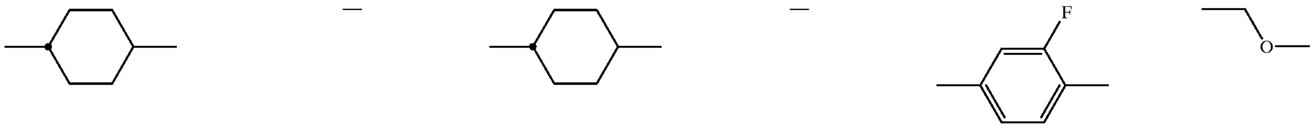 |
| 1217 | n-$C_3H_7$ | 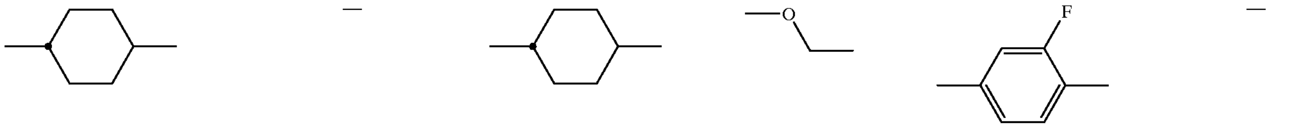 |
| 1218 | n-$C_3H_7$ | 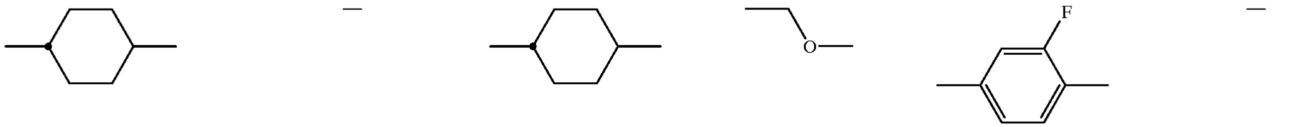 |
| 1219 | $CH_3$ | 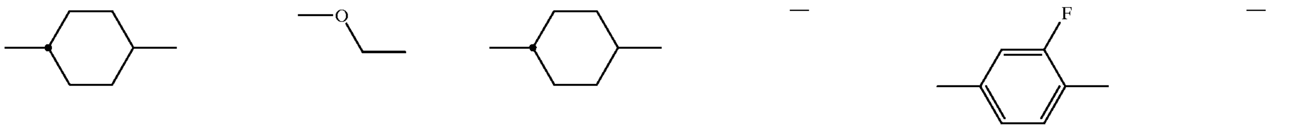 |
| 1220 | n-$C_5H_{11}$ | 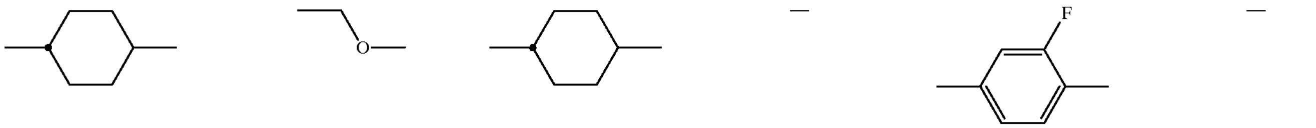 |
| 1221 | n-$C_3H_7$ | 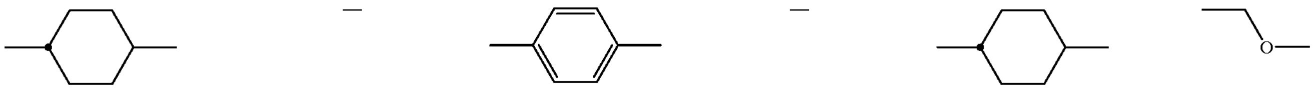 |

-continued
| | | |
|---|---|---|
| 1222 | $CH_3$ | 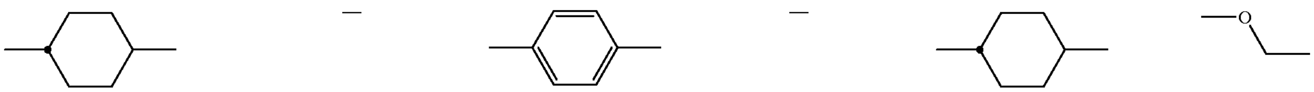 |
| 1223 | n-$C_3H_7$ | 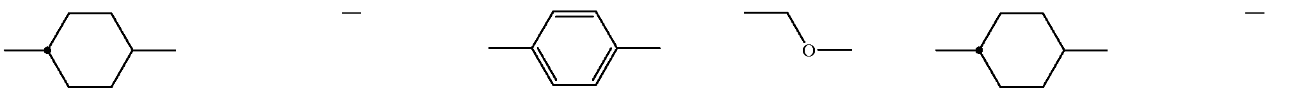 |
| 1224 | n-$C_5H_{11}$ | 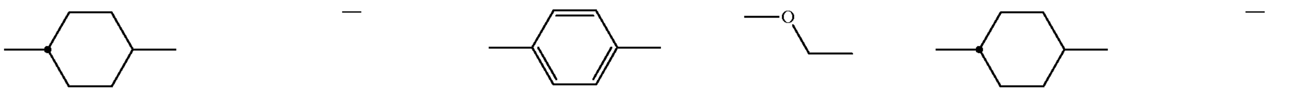 |
| 1225 | n-$C_3H_7$ | 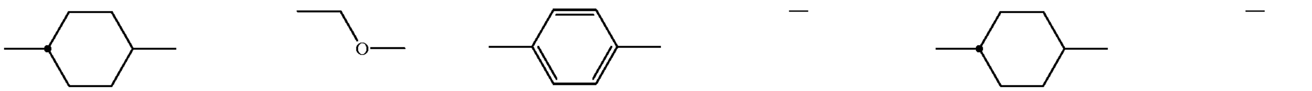 |
| 1226 | n-$C_3H_7$ — | 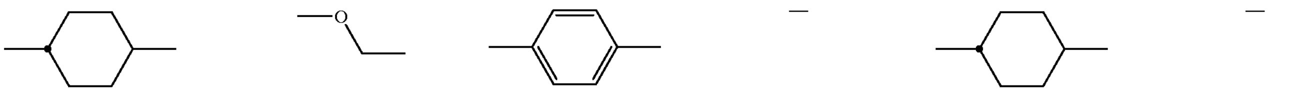 |
| 1227 | $CH_3$ | 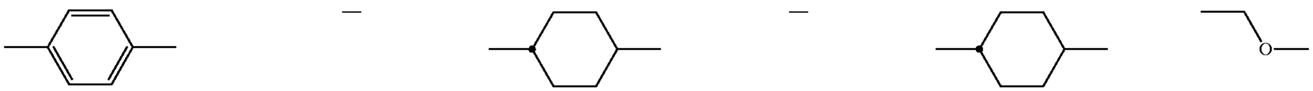 |
| 1228 | n-$C_3H_7$ | 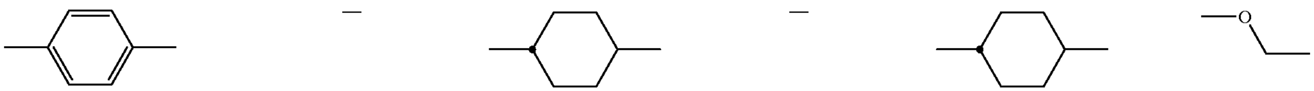 |
| 1229 | n-$C_3H_7$ | 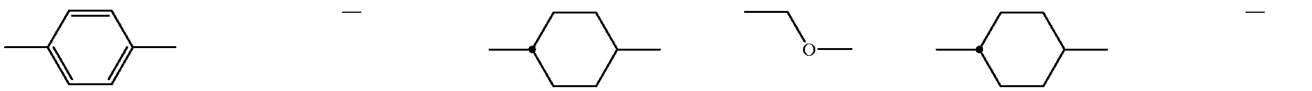 |
| 1230 | n-$C_5H_{11}$ | 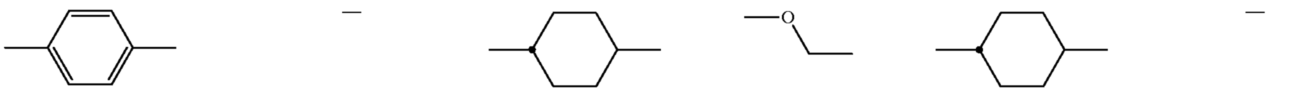 |

-continued
| | | |
|---|---|---|
| 1231 | n-$C_5H_{11}$ | 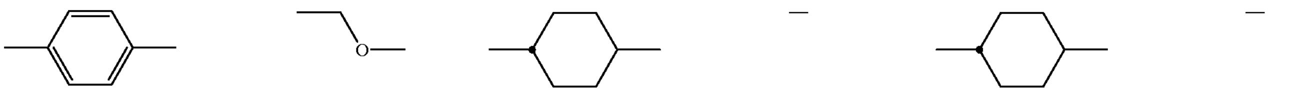 |
| 1232 | $CH_3$ | 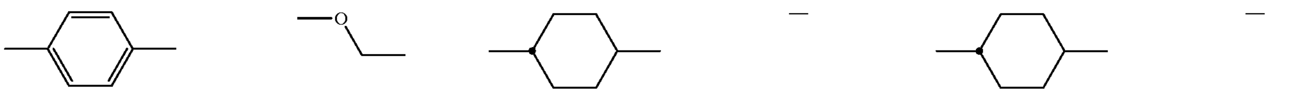 |
| 1233 | n-$C_3H_7$ | 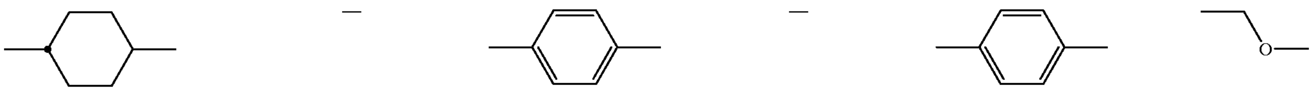 |
| 1234 | n-$C_5H_{11}$ | 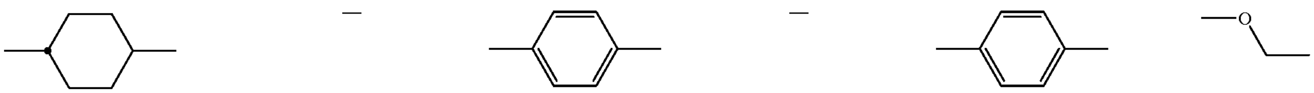 |
| 1235 | n-$C_3H_7$ | 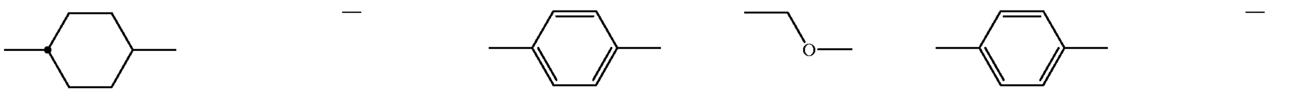 |
| 1236 | n-$C_5H_{11}$ | 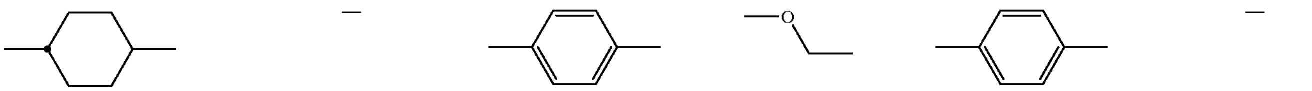 |
| 1237 | n-$C_5H_{11}$ | 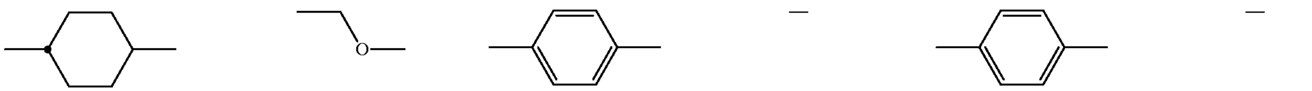 |
| 1238 | $CH_3$ | 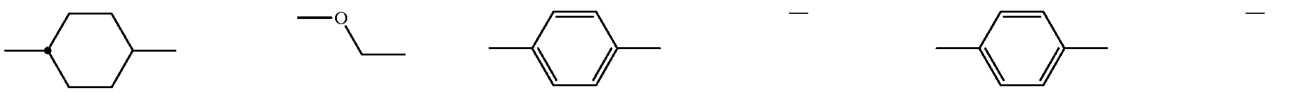 |
| 1239 | n$C_3H_7$ | 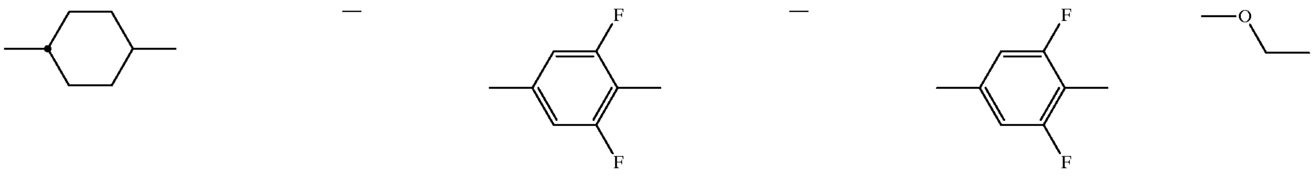 |

-continued
| | | | | | | | |
|---|---|---|---|---|---|---|---|
| 1240 | n-$C_5H_{11}$ | 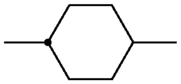 | — | 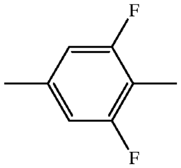 | — | 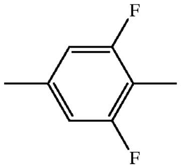 | 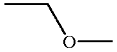 |
| 1241 | $CH_3$ | 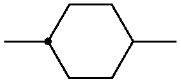 | — | 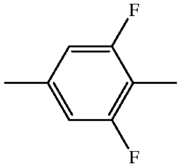 | 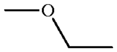 | 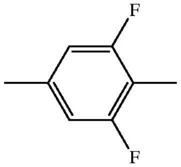 | — |
| 1242 | n-$C_3H_7$ | 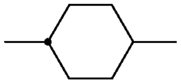 | — | 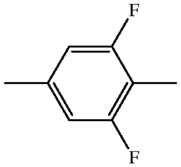 | 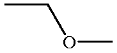 | 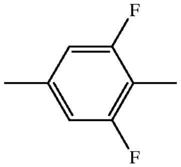 | — |
| 1243 | n-$C_7H_7$ | 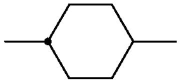 | 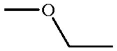 | 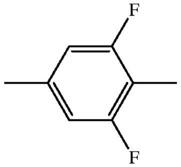 | — | 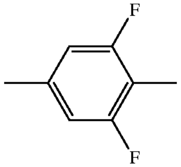 | — |
| 1244 | $CH_3$ | 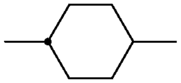 | 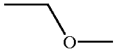 | 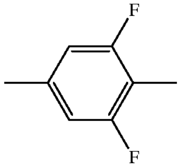 | — | 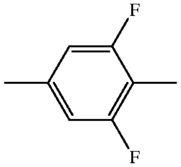 | — |
| 1245 | n-$C_3H_7$ | 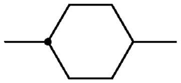 | — | 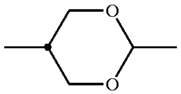 | — | 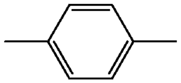 | 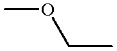 |

-continued
| | | |
|---|---|---|
| 1246 | n-$C_5H_{11}$ | 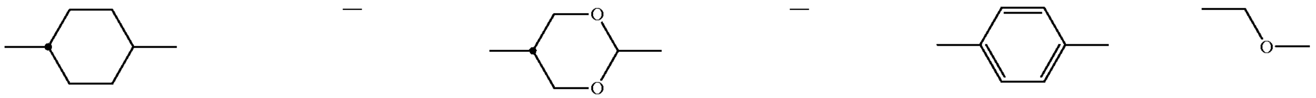 |
| 1247 | n-$C_3H_7$ | 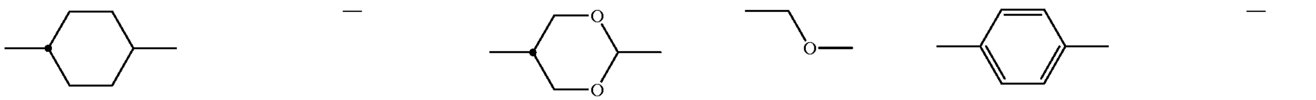 |
| 1248 | n-$C_3H_7$ | 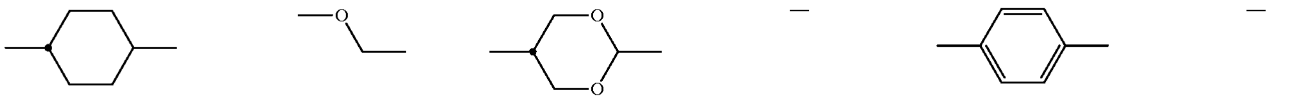 |
| 1249 | $CH_3$ | 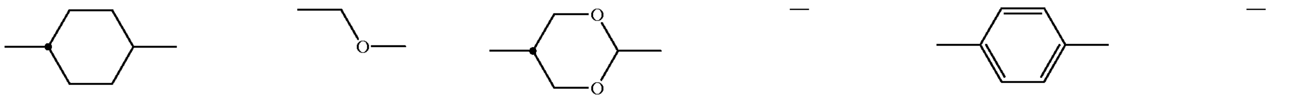 |
| 1250 | n-$C_3H_7$ | 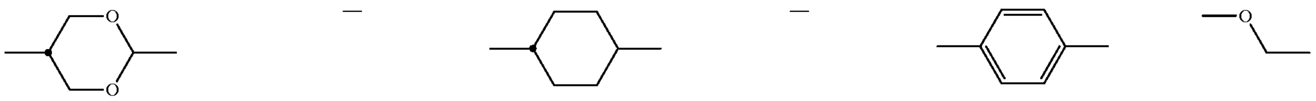 |
| 1251 | n-$C_5H_{11}$ | 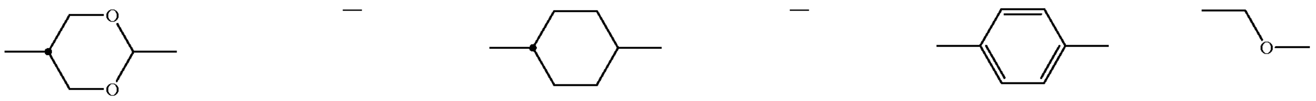 |
| 1252 | n-$C_3H_7$ | 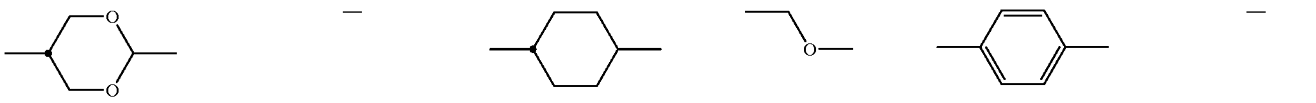 |

Example 6 (Use Example 1)

A nematic liquid cystal composition (hereinaftlrxeferred to as liquid crystal composition A1) containing of the components: 4-(trans-4-propylcyclohexy) benzonitrfle 24% by weight, 4-(trans-4-pentylcyclohexyl) benzonitrile 36% by weight, 4-(trans-4-heptylcyclohexyl) benzonitrile 25% by weight and 4-(trans-4-propylphenyl) benzonitrile 15% by weight has the following characteristics:

Clearing point ($T_{NI}$): 71.7° C., threshold voltage at cell thickness of 9 $\mu$($V_{th}$); 1.78V, $\Delta\epsilon$: 11.0, $\Delta n$: 0.137, viscosity at 20° C.: 26.3 mPa.s.

85% by weight of the liquid crystal composition A1 was mixed with 15% by weight of 2,6-difluoro-4-(trans-4-(trans-4-methoxymethylcyclohexyl) (cyclohexyl) trifluoromethoxybenzene (Compound No. 153) obtained in Example 1 to prepare a liquid crystal composition B1. The physical properties of the composition B1 was determined as follows:

$T_{NI}$: 71.0° C., $V_{th}$: 1.57V, $\Delta\epsilon$: 12.3, $\Delta n$: 0.129, $\eta$20: 32.2 mPa.s This composition was allowed to stand in a freezer at −20° C. for 30 days, but both deposition of crystals and smectic phase were not observed.

Example 7 (Use Example 2)

Liquid crystal composition B2 was prepared in the same manner as Example 6 except that 2,6-difluoro-4-(4-(trans-4-methoxymethylcyclohexyl)-2,6-difluorophenyl) trifluoromethoxybenzene (Compound No. 187) obtained in Example 2 was mixed with A1 in place of Compound No. 153. The physical properties of the composition B2 was determined as follows:

$T_{NI}$: 63.0° C., $V_{th}$: 1.49V, $\Delta\epsilon$: 14.1, $\Delta n$: 0.132, $\eta$20: 35.5 mPa.s Example 8 (Use Example 3)

Liquid crystal composition B3 was prepared in the same manner as Example 6 except that 2,6-difluoro-4-(4-(trans-4-pentylcyclohexyl) methoxyphenyl) trifluoromethoxybenzene (Compound No. 239) obtained in Example 3 was mixed with A1 in place of Compound No. 153. The physical properties of the composition B3 was determined as follows:

$T_{NI}$: 71.4° C., V: 1.73V, $\Delta\epsilon$: 10.9, $\Delta n$: 0.135, $\eta$20: 37.6 mPa.s Example 9 (Use Example 4)

Liquid crystal composition B4 was prepared in the same manner as Example 6 except that 2,6-difluoro-4-(trans-4-(trans-4-methoxymethylcyclohexyl) cyclohexyl) difluoromethoxybenzene (Compound No. 269) obtained in Example 4 was mixed with A1 in place of Compound No. 153. The physical properties of the composition B4 was determined as follows:

$T_{NI}$: 72.4° C., $V_{th}$: 1.69V, $\Delta\epsilon$: 12.2, $\Delta n$: 0.131, $\eta$20: 31.6 mPa.s Further, the compositions prepared by Example 7 to 9 were allowed to stand in a freezer at −20 ° C. for 30 days, but both deposition of crystals and smectic phase were not observed from all the compositions.

Comparative Example 1

Physical properties of the compounds of the present invention were determined based on the data in the above-mentioned Examples and were summarized in Table 2.

Furthermore, compounds (50) to (53) which are identical to compounds expressed by the above-mentioned formulae (10), (12), (13) and (14) wherein R is specified as propyl group were practically synthesized and their physical properties were determined in the same manner as above-mentioned Examples. Amongst of the respective physical properties, $\Delta\epsilon$ and $\eta$20 are shown by extrapolated values. [Table 2]

TABLE 2

| Compounds | | $T_{NI}$ (° C.) | $\Delta_E$ | $\eta_{20}$ (mPa·s) | Vth (V) |
|---|---|---|---|---|---|
| Liquid Crystal Composition A1 | | 71.1 | 11.0 | 27.0 | 1.78 |
| 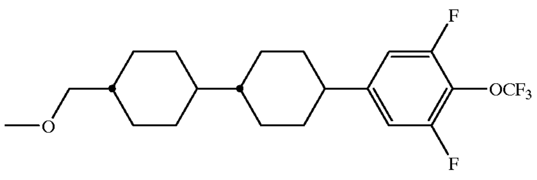 | No. 153 | 71.0 | 19.7 | 65.6 | 1.57 |
| 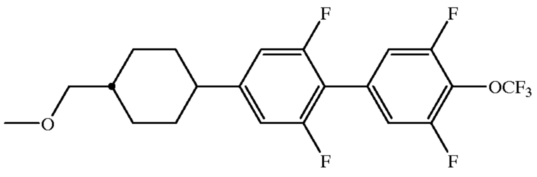 | No. 187 | 63.0 | 31.7 | 88.2 | 1.49 |
| 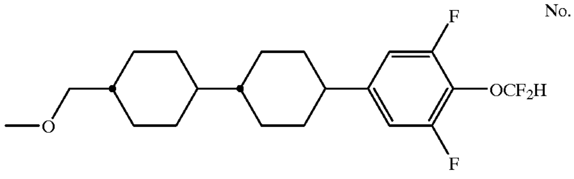 | No. 269 | 72.4 | 19.0 | 62.2 | 1.69 |

TABLE 2-continued

| Compounds | | $T_{NI}$ (° C.) | $\Delta_E$ | $\eta_{20}$ (mPa·s) | Vth (V) |
|---|---|---|---|---|---|
| 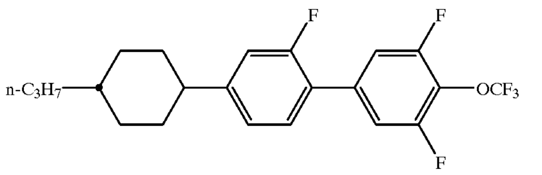 | (50) | 66.7 | 19.7 | 58.3 | 1.59 |
| 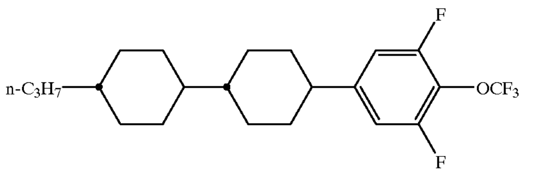 | (51) | 72.0 | 15.0 | 46.2 | 1.70 |
| 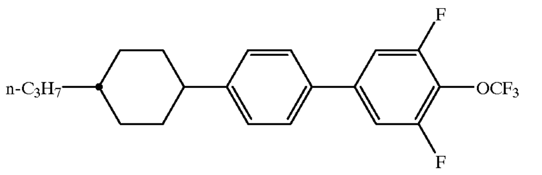 | (52) | 72.0 | 15.0 | 61.7 | 1.66 |
| 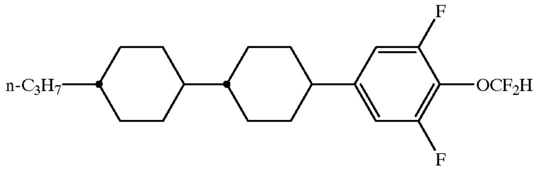 | (53) | 74.0 | 11.0 | 47.2 | 1.72 |

As is shown in Table 2, it is apparent that the compounds of the present invention exhibit high dielectric anisotropy ($\Delta\epsilon$) valueas.

For instance, Compounds No. 153 and 269 have as higher $\Delta\epsilon$ values of 19.7 and 19.0, respectively, while the known reference compounds (51) and (53) wherein propyl group is only replaced from methoxymethyl group have the values of 15.0 and 11.0, respectively. Further, Compound No. 187 was found to have as very high $\Delta\epsilon$ value of 31.7. Although the compounds of the present invention exhibit somewhat higher viscosity values than those of the reference compounds, the compounds are found to have capability so that they let liquid crystal cells drive at lower threshold voltage than those of the reference compounds due to their very high $\Delta\epsilon$ values.

Furthermore, it was found that $T_{NI}$ values of liquid crystals, which were obtained from the mother liquid crystal by adding thereto the compounds of the invention, were only either somewhat increased (No. 269) or unchanged (No. 153, 187).

From these results, it was found that the compounds of the present invention could contribute to lower threshold voltages of mother liquid crystals without lowering clearing points of liquid crystal compositions, and also recognized that the compounds have a superior miscibility at a low temperature as described before.

Thus, by using the compounds of the present invention, liquid crystal compositions having properties such as (1) lowering threshold voltages without lowering clearing points of mother liquid crystals and (2) being superior in miscibility, especially in miscibility at a low temperature can be first prepared. And, by using the compositions, liquid crystal display elements having properties of high response speed and low voltage drive-ability can be provided

EFFECT OF THE INVENTION

As described above, the compounds of the present invention expressed by the general formula (1) are the ones having a very high dielectric anisotropy value, being stable against outer environment and being superior in miscibility with other liquid crystal compounds, especially at a low temperature.

Thus, by using the liquid crystalline compounds of the present invention as constitutional components of liquid crystal compositions, there can be provided liquid crystal compositions and display elements having properties of high response speed and low voltage drive-ability.

What is claimed is:

1. A fluoroalkoxybenzene derivative expressed by the general formula (1)

(1)

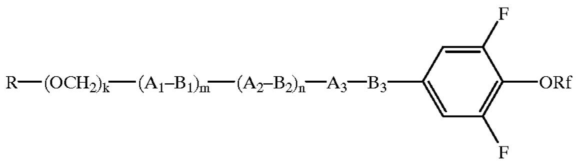

wherein $A_1$, $A_2$ and $A_3$ each independently denote trans-1,4-cyclohexylene, 1,4-phenylene in which one or more hydrogen atoms may optionally be substituted with a fluorine atom(s), 1,3-dioxane-2,5-diyl, pyrimidine-2,5-diyl or 1-sila-1,4-cyclohexylene; $B_1$, $B_2$ and $B_3$ each independently denote a single bond, 1,2- ethylene, 1,2-cethenylene, 1,2-ethynylene, oxymethylene, methyleneoxy, carbonyloxy or 1,4-butylene group; R denotes an alkyl croup having 1 to 15 carbon atoms optionally substitutable with a halogen atom(s), wherein one or more non-adjacent ethylene groups may be replaced by 1,2-ethenylene group(s);

RE denotes a fluoroalLyl group having 1 to 3 carbon atoms substitutable with two or more fluorine atoms; k, m, and n each independentiy denote 0 or 1, with the proviso that when k=0 is a case, then one of $B_1$, $B_2$ and $B_3$ is a methyleneoxy or oxymethylene bond, that when k=1 and Rf denotes $CF_3$ or $CF_2H$, then both $B_1$ and $B_3$, or both $B_2$ and $B_3$ are never carbonyloxy groups, that when m+n=2 is a case, then both $A_1$ and $A_3$, or both $A_2$ and $A_3$ are not 1,4-phenylene at the same time, respectively, and further when both $A_1$ and $A_3$, or both $A_2$ and $A_3$ are trans-1, 4-cyclohexylene or 1,4-phenylene and both $B_1$ and $B_3$, or both $B_2$ and B3 are all single bonds, then Rf is never $C_2F_5$, $CH_2CF_3$ or $CH_2CF_2CF_3$, that when m+n=1 is a case, both $A_1$ and $A_3$, or both $A_2$ and $A_3$ are trans-1,4-cyclohexylene at the same time, respectively, $B_1$ or $B_2$ is a single bond and $B_3$ is 1,2-ethylene, then Rf is never $CH_2CF_2CF_3$, and that when m+n=0 is a case and $A_3$ is 1-sila-1,4-cyclohexylene, then B3 is never methyleneoxy group.

2. A compound according to claim 1 wherein k=1.

3. A compound according to claim 1 wherein one of $B_1$, $B_2$ or $B_3$ is a methyleneoxy or oxymethylene bond.

4. A compound according to claim 2 wherein m=0, n=1, $A_2$ and $A_3$ are 1, 4-cyclohexylene, and $B_2$ and $B_3$ are single bonds.

5. A compound according to claim 2 wherein m=0, n=1, $A_2$ is 1, 4-cyclohexylene, $A_3$ is 1, 4-cyclohexylene optionally substitutable with a fluorine atom(s), and $B_2$ and $B_3$ are both single bonds.

6. A compound according to claim 2 wherein m+n=1, $A_1$ or $A_2$ and $A_3$ are both trans-1, 4-cyclohexylenes, $B_1$ or $B_2$ is 1, 2-ethylene, and $B_3$ is a single bond.

7. A compound according to claim 2 wherein m+n=1, $A_1$ or $A_2$ and $A_3$ are both trans-1, 4-cyclohexylenes, $B_1$ or $B_2$ is a single bond, and $B_3$ is 1,2-ethylene.

8. A compound according to claim 2 wherein m=n=1, and $A_1$ and $A_2$ are both trans-1, 4-cyclohexylenes.

9. A compound according to claim 8 wherein m=n=1, $A_1$ and $A_2$ are both trans-1, 4-cyclohexylenes, $A_3$ is 1, 4-phenylene one or two hydrogen atoms of which may be optionally substituted with a fluorine atom(s), $B_1$ and $B_3$ are single bonds, and $B_2$ is 1,2-ethylene.

10. A liquid crystal composition comprising at least one liquid crystalline compound defined in any one of claims 1 to 9.

11. A liquid crystal composition comprising, as a first component, at least one liquid crystalline compound defined in any one of claims 1 to 9, and as a second component, at least one compound selected from the group of compounds expressed by any one of general formulae (2), (3), and (4)

(2)

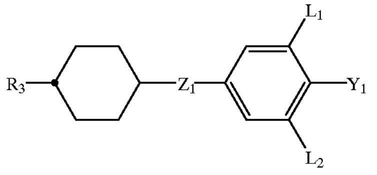

(3)

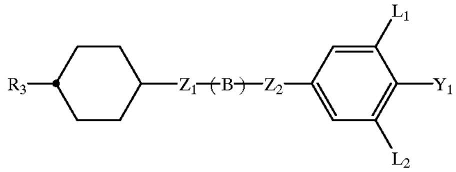

(4)

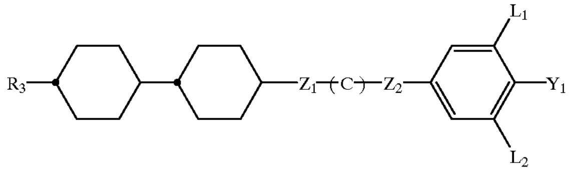

wherein $R_3$ denotes an alkyl group having 1 to 10 carbon atom(s) in which alkyl group any non-adjacent methylene group may be replaced by an oxygen atom or —CH═CH—, and any hydrogen atom may be replaced by a fluorine atom; Y1 denotes a fluorine atom, a chlorine atom, $OCF_3$, $OCF_2H$, $CF_3$, $CF_2H$, $CFH_2$, $OCF_2CF_2H$ or $OCF_2CFHCF_3$; $L_1$ and $L_2$ each independently denote a hydrogen atom or a fluorine atom; Z, and $Z_2$ each independently denote 1,2-ethylene group, 1,4-butylene group, —COO—, —$CF_2O$—, —$OCF_2$—, —CH═CH—, or a single bond; B denotes trans-1,4-cyclohexylene, 1,3-dioxane-2,5-diyl or 1,4-phenylene any hydrogen atom of which may be replaced by a fluorine atom; and C denotes trans-1,4-cyclohexylene or 1,4-phenylene any hydrogen atom of which may be replaced by a fluorine atom.

12. A liquid crystal composition comprising, as a first component, at least one liquid crystalline compound defined in any one of claims 1 to 9, and as a second component, at least one compound selected from a group of compounds expressed by any one general formulae (5) and (6)

(5)

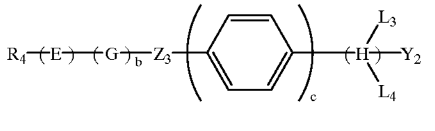

-continued (6)

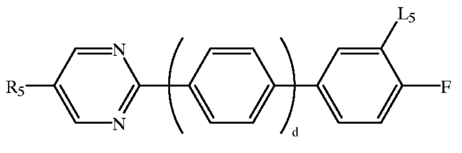

wherein $R_4$ and $R_5$ each independently denote an alkyl group having 1 to 10 carbon atoms in which alkyl group any non-adjacent methylene group may be replaced by an oxygen atom or —CH═CH— and any hydrogen atom of which may be replaced by a fluorine atom; $Y_2$ denotes —CN group or —C═C—CN group; E denotes trans-1,4-cyclohexylene, 1,4-phenylene, 1,3-dioxane-2,5-diyl or pyrimidine-2,5-diyl; G denotes trans-1,4-cyclohexylene, 1,4-phenylene any hydrogen atom of which may be replaced by a fluorine atom or pyrirnidine-2,5-diyl; H denotes trans-1,4-cyclohexylene or 1,4-phenylene; $Z_3$ denotes 1,2-ethylene group, —COO— or a single bond; $L_3$, $L_4$ and $L_5$ each independently denote a hydrogen atom or fluorine atom, and b, c and d each independently denote 0 or 1.

13. A liquid crystal composition according to claim 10 wherein the liquid crystal composition further comprises one or more optically active compounds.

14. A liquid crystal display element comprising a liquid crystal composition defined in claim 10.

15. A liquid crystal composition comprising, as a first component, at least one liquid crystalline compound defined in any one of claims 1 to 9, as a second component, at least one compound selected from the group of compounds expressed by any one of general formulae (2), (3), and (4), and as a third component, at least one compound selected from the group of compounds expressed by any one of the general formulae (7), (8) and (9)

(2)

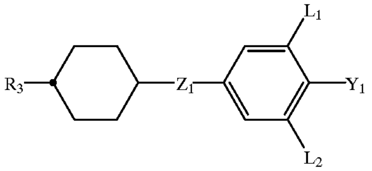

(3)

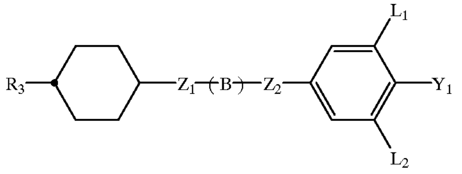

(4)

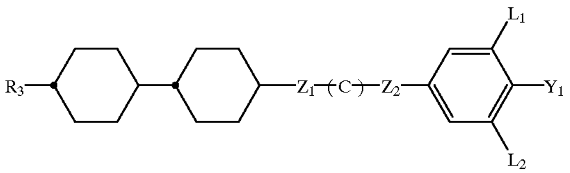

wherein $R_3$ denotes an alkyl group having 1 to 10 carbon atom(s) in which alkyl group any non-adjacent methylene group may be replaced by an oxygen atom or —CH═CH—, and any hydrogen atom may be replaced by a fluorine atom; $Y_1$ denotes a fluorine atom, a chlorine atom, $OCF_3$, $OCF_2H$, $CF_3$, $CF_2H$, $CFH_2$, $OCF_2CF_2H$ or $OCF_2CFHCF_3$; $L_1$ and $L_2$ each independently denote a hydrogen atom or a fluorine atom; $Z_1$ and $Z_2$ each independently denote 1,2-ethylene group, 1,4-butylene group, —COO—, —$CF_2$O—, —O$CF_2$—, —CH═CH—, or a single bond; B denotes trans-1,4-cyclohexylene, 1,3-dioxane-2,5-diyl or 1,4-phenylene any hydrogen atom of which may be replaced by a fluorine atom; and C denotes trans-1,4-cyclohexylene or 1,4-phenylene any hydrogen atom of which may be replaced by a fluorine atom, (7)

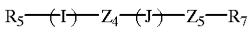

(8)

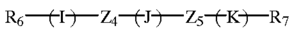

(9)

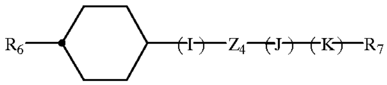

wherein $R_6$ and $R_7$ each independently denote an alkyl group having 1 to 10 carbon atoms in which alkyl group any non-adjacent methylene group may be replaced by an oxygen atom or —CH═CH— and any hydrogen atom of which may be replaced by a fluorine atom; I, J and K each independently denote trans-1,4,-cyclohexylene, pyrimidine-2,5-diyl or 1 ,4-phenylene any hydrogen atom of which may be replaced by a fluorine atom; and $Z_4$ and $Z_5$ each independently denote —C≡C—, —COO—, —$CH_2CH_2$—, —CH═CH— or a single bond.

16. A liquid crystal composition comprising, as a first component, at least one liquid crystalline compound defined in any one of claims 1 to 9, as a second component, at least one compound selected from the group of compounds expressed by any one of general formulae (5) and (6); and as a third component, at least one compound selected from the group of compounds expressed by any one of the general formulae (7), (8) and (9)

(5)

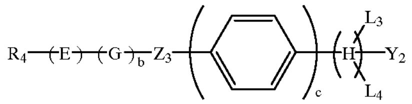

(6)

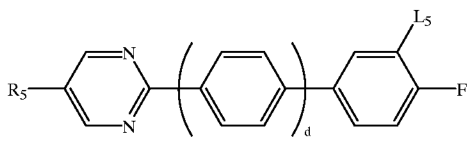

wherein $R_4$ and $R_5$ each independently denote an alkyl group having 1 to 10 carbon atoms in which alkyl group any non-adjacent methylene group may be replaced by an oxygen atom or —CH═CH— and any hydrogen atom of which may be replaced by a fluorine atom; $Y_2$ denotes —CN group or —C—C—CN group; E denotes trans-1,4-cyclohexylene, 1,4-phenylene, 1,3-dioxane-2,5-diyl or pyrimidine-2,5-diyl; G denotes trans-1,4-cyclohexylene, 1,4-phenylene any hydrogen atom of which may be replaced by a fluorine atom or pyrimidine-2,5-diyl; H denotes trans-1, 4-cyclohexylene or 1,4-phenylene; $Z_3$ denotes 1,2-ethylene group, —COO— or a single bond; $L_3$, $L_4$ and $L_5$ each independently denote a hydrogen atom or fluorine atom, and b, c and d each independently denote 0 or 1,

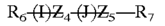

(7)

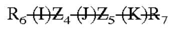

(9)

(7)

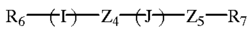

(8)

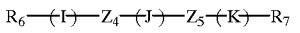

(9)

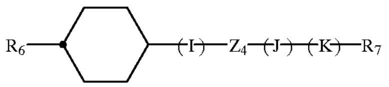

wherein $R_6$ and $R_7$ each independently denote an alkyl group having 1 to 10 carbon atoms in which alkyl group any non-adjacent methylene group may be replaced by an oxygen atom or —CH═CH— and any hydrogen atom of which may be replaced by a fluorine atom; I, J and K each independently denote trans-1,4,-cyclohexylene, pyrimidine-2,5-diyl or 1,4-phenylene any hydrogen atom of which may be replaced by a fluorine atom; and $Z_4$ and $Z_5$ each independently denote —C≡—C—, —COO—, —$CH_2CH_2$—, —CH═CH— or a single bond.

17. A liquid crystal composition comprising, as a first component, at least one liquid crystalline compound defined in any one of claims 1 to 9, as a second component, at least one compound selected from the group of compounds expressed by any one of general formulae (2), (3), and (4), as a third component, at least one compound selected from the group of compounds expressed by any one of the general formulae (5) and (6), and as a fourth component, at least one compound selected from the group of compounds expressed by any one of the general formulae (7), (8) and (9)

(2)

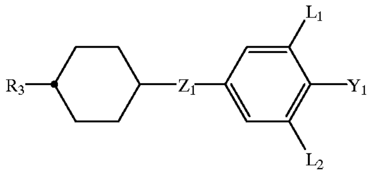

(3)

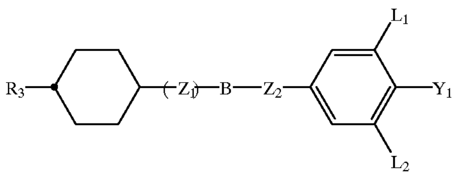

(4)

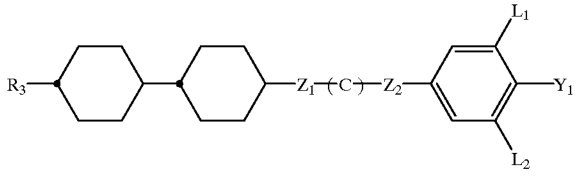

wherein $R_3$ denotes an alkyl group having 1 to 10 carbon atom(s) in which alkyl group any non-adjacent methylene group may be replaced by an oxygen atom or —CH═CH—, and any hydrogen atom may be replaced by a fluorine atom; $Y_1$ denotes a fluorine atom, a chlorine atom, $OCF_3$, $OCF_2H$, $CF_3$, $CF_2H$, CFH2, $OCF_2CF_2H$ or $OCF_2CFHCF_3$; $L_1$ and $L_2$ each independently denote a hydrogen atom or a fluorine atom; $Z_1$ and $Z_2$ each independently denote 1,2-ethylene group, 1,4-butylene group, —COO—, —$CF_2O$—, —$OCF_2$—, —CH═CH—, or a single bond; B denotes trans-1,4-cyclohexylene, 1,3-dioxane-2,5-diyl or 1,4-phenylene any hydrogen atom of which may be replaced by a fluorine atom; and C denotes trans-1,4-cyclohexylene or 1,4-phenylene any hydrogen atom of which may be replaced by a fluorine atom, (5)

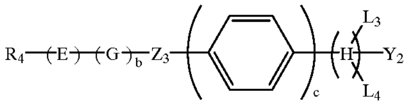

(6)

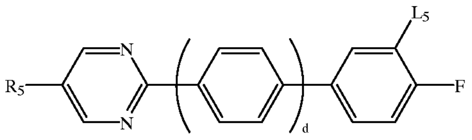

wherein $R_4$ and $R_5$ each independently denote an alkyl group having 1 to 10 carbon atoms in which alkl group any non-adjacent methylene group may be replaced by an oxygen atom or —CH═CH— and any hydrogen atom of which may be replaced by a fluorine atom; $Y_2$ denotes —CN group or —C≡C—CN group; E denotes trans-1,4-cyclohexylene, 1,4-phenylene, 1,3-dioxane-2,5-diyl or pyrimidine-2,5-diyl; G denotes trans-1,4-cyclohexylene, 1,4-phenylene any hydrogen atom ofwhich may be replaced by a fluorine atom or pyrimidine-2,5-diyl; H denotes trans-1,4-cyclohexylene or 1,4-phenylene; $Z_3$ denotes 1,2-ethylene group, —COO— or a single bond; $L_3$, $L_4$ and $L_5$ each independently denote a hydrogen atom or fluorine atom, and b, c and d each independently denote 0 or 1, (7)

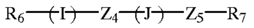

(8)

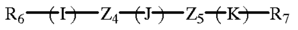

(9)

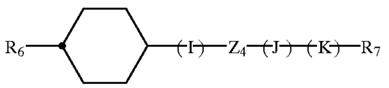

wherein $R_6$ and $R_7$ each independently denote an alkyl group having 1 to 10 carbon atoms in which alkyl group any non-adjacent methylene group may be replaced by an oxygen atom or —CH═CH— and any hydrogen atom of which may be replaced by a fluorine atom; I, J and K each independently denote trans-1,4,-cyclohexylene, pyrimnidine-2,5-diyl or 1,4-phenylene any hydrogen atom of which may be replaced by a fluorine atom; and $Z_4$ and $Z_5$ each independently denote —C≡C—, —COO—, —$CH_2CH_2$—, —CH═CH— or a single bond.

* * * * *